US008865881B2

(12) United States Patent
Balazs et al.

(10) Patent No.: US 8,865,881 B2
(45) Date of Patent: Oct. 21, 2014

(54) DELIVERY OF PROTEINS USING ADENO-ASSOCIATED VIRUS (AAV) VECTORS

(75) Inventors: Alejandro Benjamin Balazs, Berkeley, CA (US); David Baltimore, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/400,945

(22) Filed: Feb. 21, 2012

(65) Prior Publication Data

US 2012/0232133 A1 Sep. 13, 2012

Related U.S. Application Data

(60) Provisional application No. 61/598,728, filed on Feb. 14, 2012, provisional application No. 61/550,123, filed on Oct. 21, 2011, provisional application No. 61/445,449, filed on Feb. 22, 2011.

(51) Int. Cl.
| | |
|---|---|
| C07H 21/04 | (2006.01) |
| C12N 15/63 | (2006.01) |
| C07K 16/10 | (2006.01) |
| A61K 48/00 | (2006.01) |

(52) U.S. Cl.
CPC ... C07K 16/1045 (2013.01); *C12N 2750/14143* (2013.01)
USPC ...................................... 536/24.1; 435/320.1

(58) Field of Classification Search
USPC ...................................... 536/24.1; 435/320.1
See application file for complete search history.

(56) References Cited

U.S. PATENT DOCUMENTS

| | | | | |
|---|---|---|---|---|
| 4,937,190 | A | 6/1990 | Palmenberg et al. | |
| 7,378,273 | B2 * | 5/2008 | Bleck | 435/320.1 |
| 7,662,623 | B2 | 2/2010 | Fang et al. | |
| 7,714,119 | B2 | 5/2010 | Fang et al. | |
| 7,863,041 | B2 * | 1/2011 | Rupprecht et al. | 435/320.1 |
| 7,943,374 | B2 * | 5/2011 | Hildinger | 435/320.1 |
| 2002/0136710 | A1 | 9/2002 | Samulski et al. | |
| 2002/0173477 | A1 * | 11/2002 | Liou et al. | 514/44 |
| 2004/0156828 | A1 | 8/2004 | Xu et al. | |
| 2006/0034805 | A1 | 2/2006 | Fang et al. | |
| 2007/0098690 | A1 * | 5/2007 | Ostedgaard et al. | 424/93.2 |
| 2007/0116690 | A1 | 5/2007 | Yang et al. | |
| 2011/0201088 | A1 | 8/2011 | Beall et al. | |
| 2013/0209410 | A1 * | 8/2013 | Caboche et al. | 424/93.2 |

FOREIGN PATENT DOCUMENTS

| | | |
|---|---|---|
| EP | 2 108 706 * | 10/2009 |
| WO | WO 03/087324 | 10/2003 |
| WO | WO 2006/017325 | 2/2006 |
| WO | WO 2006/047250 A2 | 5/2006 |
| WO | WO 2012/115980 | 8/2012 |

OTHER PUBLICATIONS

Xu et al. CMV-beta-Actin promoter directs higher expression from an adeno-associated viral vector in the liver than the *Cytomegalovirus* or Elongation factor 1alpha promoter an results in therapeutic levies of human Factor X in mice. Hum. Gene Ther. 12:563-573, 2001.*
Alam et al. Lung surfactant protein B promoter function is dependent on the helical phasing, orientation and combinatorial actions of cis-DNA elements. Gene 282:103-111, 2002.*
Muller et al. repression of lac promoter as a function of distance, phase and qulaity of an auxiliary lac operator. J. Mol. Biol. 257:21-29, 1996.*
Xie et al. Domains of the rat rDNA promoter must be aligned stereospecifically. Mol. Cell. Biol. 12:1266-1275, 1992.*
Adachi et al., Production of acquired immunodeficiency syndrome-associated retrovirus in human and nonhuman cells transfected with an infectious molecular clone. J. Virol., 59:284-291 (1986).
Ayuso et al., High AAV vector purity results in serotype- and tissue-independent enhancement of transduction efficiency. Gene therapy 17:503-510 (2010).
Balazs et al. Antibody-based protection against HIV infection by vectored immunoprophylaxis, Nature, 481:81-84 (2012).
Barouch et al., Eventual AIDS vaccine failure in a rhesus monkey by viral escape from cytotoxic T lymphocytes. Nature 415:335-339 (2002).
Binley et al., Comprehensive cross-clade neutralization analysis of a panel of anti-human immunodeficiency virus type 1 monoclonal antibodies. J. Virol. 78:13232-13252 (2004).
Breous et al., BALB/c mice show impaired hepatic tolerogenic response following AAV gene transfer to the liver, Mol. Ther., 18:766-774 (2010).
Brisson et al., Expression of a bacterial gene in plants by using a viral vector, Nature, 310:511-514 (1984).
Buchbinder et al., Efficacy assessment of a cell-mediated immunity HIV-1 vaccine (the Step Study): a double-blind, randomised, placebo-controlled, test-of-concept trial. Lancet, 372:1881-1893 (2008).
Burton, Antibodies, viruses and vaccines. Nature reviews. Immunology, 2:706-713 (2002).
Burton et al., Efficient neutralization of primary isolates of HIV-1 by a recombinant human monoclonal antibody. Science, 266:1024-1027 (1994).
Burton et al., HIV vaccine design and the neutralizing antibody problem. Nature immunology, 5:233-236 (2004).
Crystal et al. Clinical Protocol: Administration of a Replication-Deficient Adeno-Associated Virus Gene Transfer Vector Expressing the Human CLN2 cDNA to the Brain of Children with Late Infantile Neuronal Ceroid Lipofuscinosis, Human Gene Therapy, 15:1131-1154 (2004).
de Felipe et al., Targeting of Proteins Derived from Self-Processing Polyproteins Containing Multiple Signal Sequences, Traffic, 5:616-626 (2004).
Diskin et al., Increasing the potency and breadth of an HIV antibody using structure-based rational design. Science, 334(6060):1289-1293 (2011).

(Continued)

*Primary Examiner* — Quang Nguyen
(74) *Attorney, Agent, or Firm* — Knobbe, Martens, Olson & Bear LLP

(57) ABSTRACT

Disclosed herein are compositions, systems and methods for delivery of proteins of interest using adeno-associated virus (AAV) vectors.

29 Claims, 31 Drawing Sheets

(56) References Cited

OTHER PUBLICATIONS

Dong et al., Quantitative analysis of the packaging capacity of recombinant adeno-associated virus, Human Gene Therapy, 7:2101-2112 (1996).
Dormitzer et al., Structure-based antigen design: a strategy for next generation vaccines. Trends Biotechnol., 26:659-667 (2008).
D'Souza et al., Evaluation of monoclonal antibodies to human immunodeficiency virus type 1 primary isolates by neutralization assays: performance criteria for selecting candidate antibodies for clinical trials. AIDS Clinical Trails Group Antibody Selection Working Group. J. Infect. Dis., 175:1056-1062 (1997).
Fang et al., Stable antibody expression at therapeutic levels using the 2A peptide, Nature Biotechnol., 23: 584-590 (2005).
Fang et al., An antibody delivery system for regulated expression of therapeutic levels of monoclonal antibodies in vivo. Mol. Ther., 15:153-1159 (2007).
Flynn et al., Placebo-controlled phase 3 trial of a recombinant glycoprotein 120 vaccine to prevent HIV-1 infection, J. Infect. Dis., 191:654-665 (2005).
Gao et al., Novel adeno-associated viruses from rhesus monkeys as vectors for human gene therapy. Proceedings of the National Academy of Sciences of the United States of America, 99:11854-11859, (2002).
Gurley et al., Upstream sequences required for efficient expression of a soybean heat shock gene, Mol. Cell. Biol., 6:559-565 (1986).
Halbert et al., "High-Efficiency Promoter-Dependent Transduction by Adeno-Associated Virus Type 6 Vectors in Mouse Lung", Human Gene Therapy, 18:344-354 (2007).
Haynes et al., Cardiolipin polyspecific autoreactivity in two broadly neutralizing HIV-1 antibodies. Science, 308:1906-1908 (2005).
Jiang et al., Evidence of multiyear factor IX expression by AAV-mediated gene transfer to skeletalmuscle in an individual with severe hemophilia B. Mol. Ther., 14:452-455 (2006).
Johnson et al., Vector-mediated gene transfer engenders long-lived neutralizing activity and protection against SIV infection in monkeys. Nature Med. 15:901-906 (2009).
Kaluza et al., A monoclonal antibody that recognizes a formalin-resistant epitope on the p 24 core protein of HIV-1. Pathology, research and practice, 188:91-96 (1992).
Kumar, P. et al. T cell-specific siRNA delivery suppresses HIV-1 infection in humanized mice. Cell 134:577-586 (2008).
Kwong & Wilson, HIV-1 and influenza antibodies: seeing antigens in new ways. Nature Immunol., 10:573-578 (2009).
Lewin, "Genes V" (Oxford University Press, Oxford) pp. 847-873 (1994).
Lewis et al., Generation of neutralizing activity against human immunodeficiency virus type 1 in serum by antibody gene transfer. J. Virol., 76:8769-8775 (2002).
Lock et al., Rapid, simple, and versatile manufacturing of recombinant adeno-associated viral vectors at scale. Human gene therapy, 21:1259-1271 (2010).
Maguire et al. Safety and efficacy of gene transfer for Leber's congenital amaurosis. N. Engl. J. Med., 358:2240-2248 (2008).
Manno et al., Successful transduction of liver in hemophilia by AAV-Factor IX and limitations imposed by the host immune response. Nature Med. 12:342-347 (2006).
Matsushita et al., Adeno-associated virus vectors can be efficiently produced without helper virus. Gene therapy, 5:938-945 (1998).
McCarty, Self-complementary AAV vectors; advances and applications. Mol. Ther., 16:1648-1656 (2008).
McCarty et al., Self-complementary recombinant adenoassociated virus (scAAV) vectors promote efficient transduction independently of DNA synthesis. Gene therapy 8:1248-1254 (2001).
Morell et al., Metabolic properties of IgG subclasses in man. The Journal of clinical investigation, 49:673-680 (1970).
Muster et al., A conserved neutralizing epitope on gp41 of human immunodeficiency virus type 1. J. Virol., 67:6642-6647 (1993).

Pancera et al., Crystal structure of PG16 and chimeric dissection with somatically related PG9: structure-function analysis of two quaternary-specific antibodies that effectively neutralize HIV-1. J. Virol., 84:8098-8110 (2010).
Petkova et al., Enhanced half-life of genetically engineered human IgG1 antibodies in a humanized FcRn mouse model: potential applications in humorally mediated autoimmune disease. International immunology, 18:1759-1769 (2006).
Reese et al., Improved splice site detection in Genie. Journal of computational biology : a journal of computational molecular cell biology, 4:311-323 (1997).
Rerks-Ngarm et al., Vaccination with ALVAC and AIDSVAX to prevent HIV-1 infection in Thailand. The New England journal of medicine, 361:2209-2220 (2009).
Rohr et al., Fast and reliable titration of recombinant adeno-associated virus type-2 using quantitative real-time PCR. Journal of virological methods, 106:81-88 (2002).
Salazar-Gonzalez et al., Deciphering human immunodeficiency virus type 1 transmission and early envelope diversification by single-genome amplification and sequencing. J. Virol., 82:3952-3970 (2008).
Scheid et al., Broad diversity of neutralizing antibodies isolated from memory B cells in HIVinfected individuals. Nature 458:636-640, (2009).
Scheid et al., Sequence and structural convergence of broad and potent HIV antibodies that mimic CD4 binding. Science 333:1633-1637 (2011).
Schmitz et al., Control of viremia in simian immunodeficiency virus infection by CD8+ lymphocytes. Science 283:857-860 (1999).
Shiver et al., Replication-incompetent adenoviral vaccine vector elicits effective antiimmunodeficiency-virus immunity. Nature 415:331-335 (2002).
Szymczak et al., Correction of multi-gene deficiency in vivo using a single 'self-cleaving' 2A peptide-based retroviral vector. Nat. Biotechnol., 22:589-594 (2004).
Trkola et al., Human monoclonal antibody 2G12 defines a distinctive neutralization epitope on the gp120 glycoprotein of human immunodeficiency virus type 1. J. Virol., 70:1100-1108 (1996).
Vandenberghe et al., Heparin binding directs activation of T cells against adeno-associated virus serotype 2 capsid. Nature Med. 12:967-971 (2006).
Walker & Burton, Toward an AIDS vaccine. Science 320:760-764 (2008).
Walker et al., Broad and Potent Neutralizing Antibodies from an African Donor Reveal a New HIV-1 Vaccine Target. Science, 326:(5950):285-289 (2009).
Walker et al., Broad neutralization coverage of HIV by multiple highly potent antibodies. Nature 477:466-470 (2011).
Wawer et al., Rates of HIV-1 transmission per coital act, by stage of HIV-1 infection, in Rakai, Uganda. J. Infect, Dis., 191:1403-1409 (2005).
West et al., Single chain Fv-based anti-HIV proteins: potential and limitations. J. Virol., 86(1):195-202 (2011).
Wrammert et al., Rapid cloning of high-affinity human monoclonal antibodies against influenza virus. Nature 453:667-671 (2008).
Wright et al., Identification of factors that contribute to recombinant AAV2 particle aggregation and methods to prevent its occurrence during vector purification and formulation. Mol. Ther., 12:171-178 (2005).
Wu et al., Focused evolution of HIV-1 neutralizing antibodies revealed by structures and deep sequencing. Science 333:1593-1602 (2011).
Wu et al., Rational design of envelope identifies broadly neutralizing human monoclonal antibodies to HIV-1. Science 329:856-861 (2010).
Yang et al., Suppression of human immunodeficiency virus type 1 replication by CD8+ cells; evidence for HLA class I-restricted triggering of cytolytic and noncytolytic mechanisms. J. Virol., 71:3120-3128 (1997).
Zhou et al., Paratope diversity in the human antibody response to *Bacillus anthracis* protective antigen. Molecular immunology, 45:338-347 (2008).

(56) References Cited

OTHER PUBLICATIONS

Zhou et al., Structural basis for broad and potent neutralization of HIV-1 by antibody VRC01. Science 329:811-817 (2010).

Zufferey et al., Woodchuck hepatitis virus posttranscriptional regulatory element enhances expression of transgenes delivered by retroviral vectors. J. Virol., 73:2866-2892 (1999).

Zwick et al., Broadly neutralizing antibodies targeted to the membrane-proximal external region of human immunodeficiency virus type 1 glycoprotein gp41. J. Virol., 75:10892-10905 (2001).

Balazs et al., "Antibody-based protection against HIV infection by vectored immunoprophylaxis", Nature, 481 (7379):81-84, 2011.

Balazs et al., "Broad protection against influenza infection by vectored immunoprophylaxis in mice", Nature Biotechnology, 31(7):647-652, 2013.

Geng et al. Gene transfer of mutant mouse cholinesterase provides high lifetime expression and reduced cocaine responses with no evident toxicity, *PLoS One* 8(6):e67446 (2013).

Balazs et al., Vectored immunoprophylaxis protects humanized mice from mucosal HIV transmission, *Nature Medicine* 20(3):296-300 (2014) with supplemental material.

Alexopoulou et al., The CMV early enhancer/chicken β actin (CAG) promoter can be used to drive transgene expression during the differentiation of murine embryonic stem cells into vascular progenitors, *BMC Cell Biology*, 9:2 (2008), pp. 1-11.

de Felipe, Skipping the co-expression problem: the new 2A "CHYSEL" technology, *Genetic Vaccines and Therapy*, 2:13 (2004), pp. 1-6.

Montefiori, Evaluating neutralizing antibodies against HIV, SIV, and SHIV in luciferase reporter gene assays. *Current Protocols in Immunology*, Chapter 12, 12.11.1-12.11.17 (2004), 17 pages.

\* cited by examiner

A.

B.

A.

B.

C.

D.

A.

B.

C.

D.

A.

B.

C.

A.

B.

C.

D.

A.

B.

A.

B.

C.

C.

A.

B.

| Abbreviation | Description of Substitution |
|---|---|
| LO1 | 5' b12 (6aa) |
| LO2 | 5' b12 (22aa) |
| LO3 | 3' b12 (6aa) |
| LO4 | 3' 4E10 (6aa) |
| LO13 | 5' b12 (6aa) + 3' b12 (6aa) |
| LO14 | 5' b12 (6aa) + 3' 4E10 (6aa) |
| LO23 | 5' b12 (22aa) + 3' b12 (6aa) |
| LO24 | 5' b12 (22aa) + 3' 4E10 (6aa) |

C.

D.

D.

E.

E.

G.

A.

B.

C.

D.

E.

F.

G.

DELIVERY OF PROTEINS USING ADENO-ASSOCIATED VIRUS (AAV) VECTORS

RELATED APPLICATIONS

The present application claims priority under 35 U.S.C. §119(e) to U.S. Provisional Application Nos. 61/445,449, filed Feb. 22, 2011; 61/550,123, filed Oct. 21, 2011; and 61/598,728, filed Feb. 14, 2012. These priority applications are herein expressly incorporated by reference in their entireties.

STATEMENT REGARDING FEDERALLY SPONSORED R&D

This invention was made with government support under HHSN266200500035C awarded by the National Institutes of Health. The government has certain rights in the invention.

REFERENCE TO SEQUENCE LISTING

The present application is being filed along with a Sequence Listing in electronic format. The Sequence Listing is provided as a file entitled SEQLISTING.TXT, created Feb. 21, 2012, which is 148 Kb in size. The information in the electronic format of the Sequence Listing is incorporated herein by reference in its entirety.

BACKGROUND

1. Field of the Invention

The present application relates generally to the fields of immunology and gene delivery. More particularly, the application relates to compositions, systems and methods for producing proteins of interest, such as antibodies.

2. Description of the Related Art

Despite tremendous efforts, no effective vaccine has been developed for human immunodeficiency virus (HIV) so far. Many antibodies have been identified as capable of neutralizing most circulating HIV strains. Although substantial effort has focused on the design of immunogens capable of eliciting antibodies de novo that would target similar epitopes, it remains uncertain whether a conventional vaccine will be able to elicit analogues of the existing broadly neutralizing antibodies. As an alternative to immunization, the vector-mediated gene transfer described herein can be used to engineer secretion of the existing broadly neutralizing antibodies into the circulation.

Existing methods aimed at producing genetically encoded therapeutic proteins result in only limited levels of gene expression. For example, previous efforts to engineer humoral immunity using adeno-associated virus (AAV)-based vectors resulted in modest antibody production (Lewis et al., J. Virol. 76: 8769-8775 (2002)), which was subsequently improved through the use of alternative capsids (Fang et al. Nature Biotechnol., 23: 584-590 (2005)) and self-complementary AAV (scAAV) vectors (McCarty., Mol. Ther., 16: 1648-1656 (2008)) that increase expression at the expense of carrying capacity. Recently, scAAV vectors were used to direct expression of simian immunodeficiency virus (SIV)-neutralizing immunoadhesins consisting of small, artificially fused antibody fragments (Johnson et al., Nature Med., 15(8): 901-906 (2009)). However, the efficacy of this prophylaxis was limited by an endogenous immune response directed against the immunoadhesin proteins. In addition, the lack of effectiveness of the existing AAV-based methods can be traced to the inability of AAV vectors to transmit sequences greater than approximately 4800 base pairs in length. Dong et al., Human Gene Therapy, 7:2101-2112 (1996). This limitation of AAV vectors has made it difficult to design vectors containing both a gene encoding a therapeutic protein as well as expression promoting elements to allow for high levels of production, particularly in vivo. Therefore, there is a pressing need for the development of compact vectors and systems capable of efficiently expressing genes.

SUMMARY

Some embodiments disclosed herein provide a viral vector, where the viral vector comprises: a 5' inverted terminal repeat (ITR) of adeno-associated virus (AAV) and a 3' AAV ITR; a promoter; a restriction site downstream of the promoter to allow insertion of a polynucleotide encoding one or more proteins of interest, and a posttranscriptional regulatory element downstream of the restriction site, where the promoter, the restriction site and the posttranscription regulatory element are located downstream of the 5' AAV ITR and upstream of the 3' AAV ITR.

In some embodiments, the viral vector further comprises a polynucleotide inserted at the restriction site and operably linked with the promoter, where the polynucleotide comprises a coding region of a protein of interest.

In some embodiments, the polynucleotide comprises a signal peptide sequence immediately upstream of the coding region of the protein of interest. In some embodiments, the signal peptide is selected from the group consisting of a signal peptide of interferon, a signal peptide of human growth hormone, a signal peptide of erythropoietin (EPO), a signal peptide of granulocyte colony-stimulating factor (G-CSF), a signal peptide of insulin, and any combination thereof.

In some embodiments, the viral vector comprises a nucleotide sequence having at least about 70%, at least about 80%, at least about 90% sequence identity, or more to the Kozak consensus sequence.

In some embodiments, the protein of interest is selected from the group consisting of full-length antibodies, growth hormones (GHs), insulin-like growth factors (IGFs), G-CSFs, erythropoietins (EPOs), insulins, antibody Fab fragments, antibody scFV fragments, hemophilia related clotting proteins, dystrophin, lysosomal acid lipase, phenylalanine hydroxylase (PAH), glycogen storage disease-related enzymes, and any variants thereof.

In some embodiments, the protein of interest is a virus neutralizing antibody. In some embodiments, the virus neutralizing antibody is a neutralizing antibody for a human immunodeficiency virus (HIV), a hepatitis C virus (HCV), or an influenza virus. In some embodiments, the neutralizing antibody for HIV is selected from the group consisting of b12 anti-HIV antibody, 2G12 anti-HIV antibody, 4E10 anti-HIV antibody, 2F5 anti-HIV antibody, and any variant thereof. In some embodiments, the neutralizing antibody for HCV is selected from the group consisting AR3A anti-HCV antibody, AR3B anti-HCV antibody, AR4A anti-HCV antibody, and any variant thereof. In some embodiments, the neutralizing antibody for influenza virus is selected from the group consisting F10 anti-influenza antibody, CR6261 anti-influenza antibody, FI6 anti-influenza antibody, TCN32 anti-influenza antibody, and any variant thereof.

In some embodiments, the protein of interest is a neutralizing antibody for malaria.

In some embodiments, the promoter comprises cytomegalovirus (CMV) immediate early promoter, chicken beta-actin (CAG) promoter, ubiquitin C (UBC) promoter, or any variant thereof. In some embodiments, the promoter comprises a splice donor, a splice acceptor, or any variant thereof. In some embodiments, the splice donor comprises a nucleotide sequence having at least 90% sequence identity to SEQ ID NO: 5. In some embodiments, the splice acceptor comprises a nucleotide sequence having at least 90% sequence identity to SEQ ID NO: 6. In some embodiments, the promoter comprises a nucleotide sequence having at least 90% sequence identity to SEQ ID NO: 1. In some embodiments, the promoter comprises a nucleotide sequence having at least 90% sequence identity to any one of SEQ ID NOs: 2-4.

In some embodiments, the posttranscriptional regulatory element is a viral posttranscriptional regulatory element. In some embodiments, the viral posttranscriptional regulatory element is woodchuck hepatitis virus posttranscriptional regulatory element (WPRE), hepatitis B virus posttranscriptional regulatory element (HBVPRE), RNA transport element (RTE), or any variant thereof.

In some embodiments, the viral vector further comprises a transcription termination region downstream of the posttranscriptional regulatory element. In some embodiments, the transcription termination region comprises an SV40 late poly (A) sequence, a rabbit beta-globin poly(A) sequence, a bovine growth hormone poly(A) sequence, or any variant thereof.

In some embodiments, the promoter comprises an intron. In some embodiments, the intron is a synthetic intron comprising a nucleotide sequence having at least 90% sequence identity to SEQ ID NO: 8.

In some embodiments, the polynucleotide comprises a first coding region for the heavy chain variable region of an immunoglobulin and a second coding region for the light chain variable region of the immunoglobulin. In some embodiments, the first coding region and the second coding region are separated by a 2A sequence. In some embodiments, the 2A sequence is an F2A sequence.

In some embodiments, 5' of the first coding region is fused with a first signal peptide sequence and 5' of the second coding region is fused with a second signal peptide sequence. In some embodiments, the first signal peptide sequence and the second signal peptide sequence are different.

In some embodiments, the region starting from the 5' ITR and ending at the 3' ITR is at least about 2.5 kb.

Some embodiments herein provide a method for producing a protein of interest in vivo, where the method comprises: providing a recombinant adeno-associated virus (AAV) comprising a nucleotide sequence encoding the protein of interest; and administering the recombinant AAV to the subject, whereby the recombinant AAV expresses the antibody in the subject, wherein the nucleotide is at least about 1.4 kb.

In some embodiments, the protein of interest is an antibody. In some embodiments, the antibody is a full length antibody. In some embodiments, the antibody is selected from the group consisting of b12 anti-HIV antibody, 2G12 anti-HIV antibody, 4E10 anti-HIV antibody, 2F5 anti-HIV antibody, F10 anti-influenza antibody, FI6 anti-influenza antibody, TCN32 influenza antibody, CR6261 anti-influenza antibody, AR3A anti-HCV antibody, AR3B anti-HCV antibody, AR4A anti-HCV antibody, anti-malaria antibody, and any variant thereof.

In some embodiments, the protein of interest is expressed in the serum of the subject in the amount of at least about 9 μg/ml. In some embodiments, the protein of interest is expressed in the serum of the subject in the amount of at least about 100 μg/ml. In some embodiments, the protein of interest is expressed in the serum of the subject in the amount of at least about 500 μg/ml.

In some embodiments, the recombinant AAV is produced by providing a packaging cell line with a viral vector, helper functions for generating a productive AAV infection, and AAV cap genes, where the viral vector comprises a 5' AAV inverted terminal repeat (ITR), a 3' AAV ITR and a nucleotide sequence encoding the protein of interest; and recovering a recombinant AAV virus from the supernatant of the packaging cell line.

In some embodiments, the viral vector is the viral vector of any one of viral vectors disclosed herein.

Some embodiments disclosed herein provide a method for reducing or inhibiting the infection risk of a virus in a subject, where the method comprises: providing a recombinant adeno-associated virus (AAV) comprising a nucleotide sequence encoding a neutralizing antibody for the virus; and administering the recombinant AAV to the subject, whereby the recombinant AAV expresses the antibody in the subject.

In some embodiments, the method further comprises providing a second recombinant AAV comprising a nucleotide sequence encoding a second neutralizing antibody for the virus.

In some embodiments, the subject is a mammal. In some embodiments, the subject is a human.

In some embodiments, the neutralizing antibody is a full-length antibody.

In some embodiments, the method reduces the infection risk in the subject by at least about 5 fold as compared to the subjects without the viral vector treatment. In some embodiments, the method reduces the infection risk in the subject by at least about 20 fold as compared to the subjects without the viral vector treatment. In some embodiments, the method inhibits the viral infection in the subject.

In some embodiments, the antibody is expressed in the serum of the subject in the amount of at least about 9 μg/ml. In some embodiments, the antibody is expressed in the serum of the subject in the amount of at least about 100 μg/ml. In some embodiments, the antibody is expressed in the serum of the subject in the amount of at least about 500 μg/ml In some embodiments, the virus is a human immunodeficiency virus (HIV), a hepatitis C virus (HCV), or an influenza virus.

In some embodiments, the neutralizing antibody is selected from the group consisting of b12 anti-HIV antibody, 2G12 anti-HIV antibody, 4E10 anti-HIV antibody, 2F5 anti-HIV antibody, F10 anti-influenza antibody, CR6261 anti-influenza antibody, TCN32 influenza antibody, FI6 anti-influenza antibody, AR3A anti-HCV antibody, AR3B anti-HCV antibody, AR4A anti-HCV antibody, and any variant thereof.

In some embodiments, the recombinant AAV is administered to the subject by intramuscular injection, intravaginal injection, intravenous injection, intraperitoneal injection, subcutaneous injection, epicutaneous administration, intradermal administration, or nasal administration.

In some embodiments, the recombinant AAV is administered to the subject at most once every year. In some embodiments, the recombinant AAV is administered to the subject at most once every 5 years. In some embodiments, the recombinant AAV is administered to the subject at most once every 10 years.

Some embodiments disclosed herein provide a method of producing a recombinant adeno-associated virus (AAV), where the method comprises: providing a packaging cell line with a viral construct comprising 5' AAV inverted terminal repeat (ITR) and 3' AAV ITR, helper functions for generating a productive AAV infection, and AAV cap genes; and recovering a recombinant AAV virus from the supernatant of the packaging cell line.

In some embodiments, the AAV cap genes encode a capsid from serotype 1, serotype 2, serotype 4, serotype 5, serotype 6, serotype 7, serotype 8, serotype 9, or a variant thereof.

In some embodiments, the viral construct is any of the viral vectors disclosed herein.

In some embodiments, the recombinant AAV is not a self-complementary AAV (scAAV).

Some embodiments disclosed herein provide an isolated, synthetic or recombinant polynucleotide, where the polynucleotide comprises: a nucleic acid sequence having at least about 90% or more sequence identity to SEQ ID NO: 1. In some embodiments, the polynucleotide comprises a nucleotide sequence selected from SEQ ID NOs: 2-4.

BRIEF DESCRIPTION OF THE DRAWINGS

FIG. 9A shows concentration of antibody in circulation as measured by total human IgG ELISA on serum samples taken after intramuscular injection of vectors expressing four broadly neutralizing HIV antibodies (n=8). FIG. 9B shows comparison of the relative effectiveness of four broadly neutralizing HIV antibodies in protecting huPBMC-NSG humanized mice against CD4 cell depletion after intravenous HIV challenge with 5 ng p24 NL4-3 (n=8). FIG. 9C shows HIV p24 detection by immunohistochemical staining of sections taken from spleens 8 weeks after challenge. Arrows indicate cells scored as positive for p24 expression. Scale bar, 40 mm. FIG. 9D shows quantification of immunohistochemical staining of spleen denoting the relative frequency of p24-expressing cells in spleens of infected animals. ND, not detected. Asterisks indicate outcomes significantly different from luciferase control mice versus mice expressing antibodies by two-tailed t-test (n=4-6) P, 0.01, *P, 0.0001. FIGS. 9A-B show mean and s.e.m.; FIG. 9D shows mean and s.d.

FIG. 10A is a graph showing concentration of total human antibody produced by engrafted cells and VIP as measured by human IgG ELISA on serum samples taken 5 weeks after intramuscular injection of vectors expressing either luciferase or b12 antibody and 3 weeks after adoptive transfer of human PBMCs and the day prior to IV HIV challenge (n=8). FIG. 10B is a graph showing concentration of antibody at the same time point quantified using a gp120-specific ELISA to measure the concentration of antibody specific for HIV (n=8).

FIGS. 12A and 12C show mean and standard error, and FIG. 12B shows individual animals and mean (n=8-12).

FIGS. 13A and 13C show mean and standard error, and FIG. 13B shows individual animals and mean (n=8-12).

FIG. 15A is a bar graph comparing b12 antibody with F10 and CR6261 WT sequences as compared to chimeric constructs consisting of F10 or CR6261 heavy chain with b12 light chain. FIG. 15B is a table listing various modified b12 and/or 4E10 antibody light chain used in the AAV vector. FIG. 15C is bar graph comparing the expression level of F10 antibody light chain variants consisting of F10 VL sequences fused to b12 and/or 4E10 antibody light chain sequences. FIG. 15D is bar graph comparing the expression level of CR6261 antibody light chain variants consisting of CR6261 VL sequences fused to b12 and/or 4E10 antibody light chain sequences.

DETAILED DESCRIPTION

Figure 1:
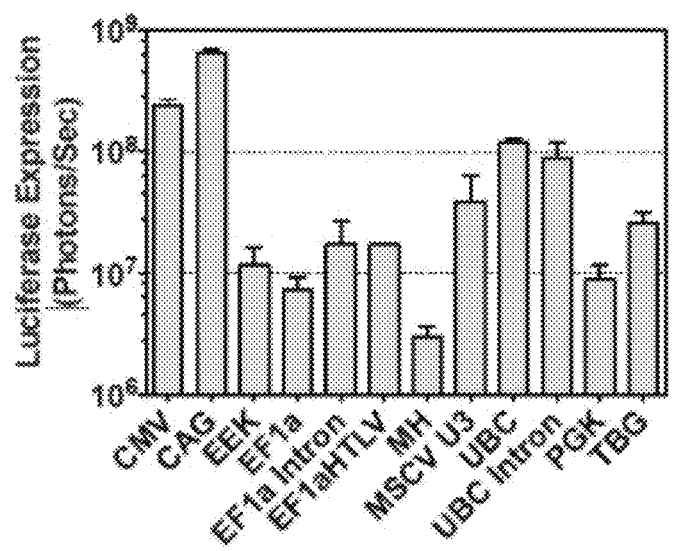
FIG. 1A is a graph showing luciferase activities 15 weeks after intramuscular injection of $2 \times 10^9$ GC of AAV2/8 vectors expressing luciferase from a panel of promoters (n=2).
FIG. 1B is a schematic presentation of an embodiment of the CASI promoter combining the CMV enhancer and chicken β-actin promoter followed by a splice donor (SD) and splice acceptor (SA) flanking the ubiquitin enhancer region.
FIG. 1C is a graph showing luciferase activities from AAV vectors driven by CASI as compared to conventional CMV and CAG promoters 8 weeks after intramuscular injection of $1 \times 10^9$ GC of AAV2/8 encoding luciferase driven by the indicated promoter (n=2).
FIG. 1D is a graph showing luciferase activities 6 weeks post-administration of CMV-driven AAV vectors with or without WPRE, terminated by the indicated polyadenylation signal (n=2).
FIG. 1E is a schematic presentation of an expression cassette for antibody expression comprising the inverted terminal repeats (ITR), the CASI promoter, an IgG1 heavy chain linked to kappa light chain separated by a self-processing 2A sequence, a WPRE for improved expression, and SV40 late-polyadenylation signal. Antibody V-regions of heavy and light chains are cloned into the vector at positions indicated in filled boxes.
Figure 1:
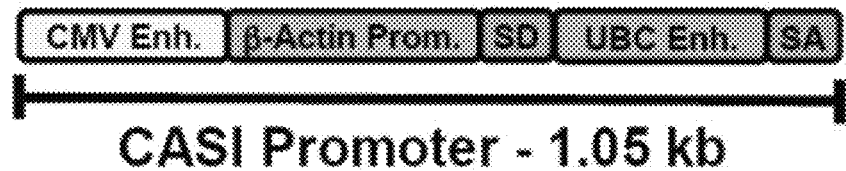
Figure 1:
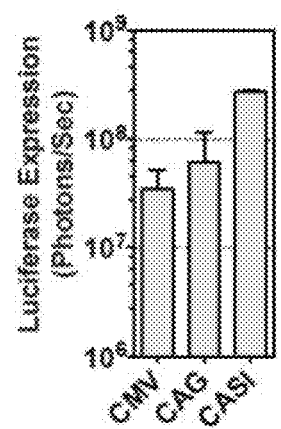
Figure 1:
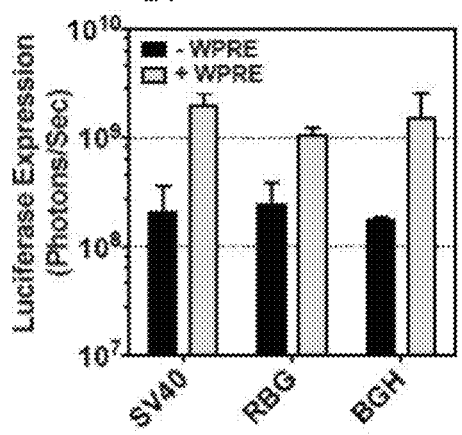
Figure 1:
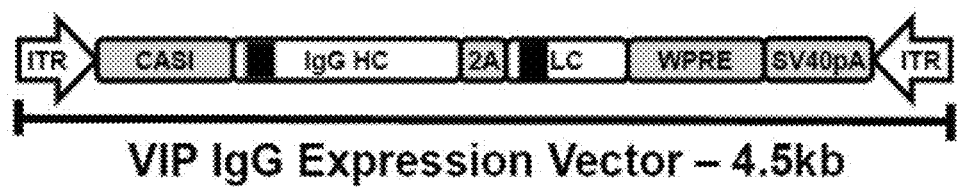

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

The present application provides viral vectors useful in producing recombinant adeno-associated viruses (AAVs), and recombinant AAVs capable of expressing one or more proteins of interest in an appropriate environment, for example, in a cell, a tissue, an organ, or a subject transfected with the recombinant AAVs. Also disclosed herein are the methods for making and using the recombinant AAVs. For example, the recombinant AAVs can be used to produce a protein of interest in vivo, ex vivo, or in vitro. In some embodiments, the expression of the protein of interest can be used to diagnose, prevent, or treat one or more diseases or disorders, such as to reduce or inhibit the risk of viral infections.

In some embodiments, the viral vector comprises a 5' inverted terminal repeat (ITR) of AAV and a 3' AAV ITR, a promoter, a restriction site downstream of the promoter to allow insertion of a polynucleotide encoding one or more proteins of interest, and a posttranscriptional regulatory element downstream of the restriction site, where the promoter, the restriction site and the posttranscription regulatory element are located downstream of the 5' AAV ITR and upstream of the 3' AAV ITR. The viral vector can be used, for example, to express one or more proteins of interest (e.g., antibodies). For example, the viral vector can include a polynucleotide encoding one or more anti-HIV antibodies, anti-HCV antibodies, anti-influenza antibodies, or combinations thereof. The viral vector can, for example, be used to produce high level of the protein(s) of interest (e.g., antibodies) in a subject for diagnostic or therapeutic purposes.

DEFINITIONS

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below.

As used herein, the term "vector" refers to a polynucleotide construct, typically a plasmid or a virus, used to transmit genetic material to a host cell. Vectors can be, for example, viruses, plasmids, cosmids, or phage. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "construct," as used herein, refers to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, 2A sequences or elements refer to small peptides introduced as a linker between two proteins, allowing autonomous intraribosomal self-processing of polyproteins (See e.g., de Felipe. Genetic Vaccines and Ther. 2:13 (2004); deFelipe et al. Traffic 5:616-626 (2004)). These short peptides allow co-expression of multiple proteins from a single vector. Many 2A elements are known in the art.

Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A) as described in U.S. Patent Publication No. 20070116690.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "enhancer" refers to a type of regulatory element that can increase the efficiency of transcription, regardless of the distance or orientation of the enhancer relative to the start site of transcription.

As used herein, the term "antibody" is used in the broadest sense and specifically covers human, non-human (e.g., murine) and humanized monoclonal antibodies (including full-length monoclonal antibodies), polyclonal antibodies, multi-specific antibodies (e.g., bispecific antibodies), and antibody fragments so long as they exhibit the desired biological activity. Various antibodies can be expressed using the system and method disclosed herein. "Antibodies" and "immunoglobulins" are usually heterotetrameric glycoproteins, composed of two identical light (L) chains and two identical heavy (H) chains. Each light chain is linked to a heavy chain by a disulfide bond. The number of disulfide linkages varies among the heavy chains of different immunoglobulin isotypes. Each heavy chain comprises a variable domain ($V_H$) followed by a number of constant domains. Each light chain comprises a variable domain at one end ($V_L$) and a constant domain at its other end. The constant domain of the light chain is aligned with the first constant domain of the heavy chain, and the light-chain variable domain is aligned with the variable domain of the heavy chain. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "transfection" refers to the introduction of a nucleic acid into a host cell, such as by contacting the cell with a recombinant AAV virus as described below.

As used herein, the term "transgene" refers to any nucleotide or DNA sequence that is integrated into one or more chromosomes of a target cell by human intervention. In some embodiment, the transgene comprises a polynucleotide that encodes a protein of interest. The protein-encoding polynucleotide is generally operatively linked to other sequences that are useful for obtaining the desired expression of the gene of interest, such as transcriptional regulatory sequences. In some embodiments, the transgene can additionally comprise a nucleic acid or other molecule(s) that is used to mark the chromosome where it has integrated.

As used herein, "treatment" refers to a clinical intervention made in response to a disease, disorder or physiological condition manifested by a patient or to which a patient may be susceptible. The aim of treatment includes, but is not limited to, the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Subjects in need of treatment include those already affected by a disease or disorder or undesired physiological condition as well as those in which the disease or disorder or undesired physiological condition is to be prevented.

As used herein, the term "effective amount" refers to an amount sufficient to effect beneficial or desirable biological and/or clinical results.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human.

Adeno-Associated Virus (AAV) Vector

Adeno-associated virus (AAV) is a replication-deficient parvovirus, the single-stranded DNA genome of which is about 4.7 kb in length including 145 nucleotide inverted terminal repeat (ITRs). The ITRs play a role in integration of the AAV DNA into the host cell genome. When AAV infects a host cell, the viral genome integrates into the host's chromosome resulting in latent infection of the cell. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced. In the instances of recombinant AAV vectors having no Rep and/or Cap genes, the AAV can be non-integrating.

AAV vectors that comprise coding regions of one or more proteins of interest, for example proteins that are more than 500 amino acids in length, are provided. The AAV vector can include a 5' inverted terminal repeat (ITR) of AAV, a 3' AAV ITR, a promoter, and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the recombinant AAV vector includes a posttranscriptional regulatory element downstream of the restriction site and upstream of the 3' AAV ITR. In some embodiments, the AAV vectors disclosed herein can be used as AAV transfer vectors carrying a transgene encoding a protein of interest for producing recombinant AAV viruses that can express the protein of interest in a host cell.

Generation of the viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

The viral vector can incorporate sequences from the genome of any known organism. The sequences can be incorporated in their native form or can be modified in any way to obtain a desired activity. For example, the sequences can comprise insertions, deletions or substitutions.

Promoter

Various promoters can be operably linked with a nucleic acid comprising the coding region of the protein of interest in the viral vector disclosed herein. In some embodiments, the promoter can drive the expression of the protein of interest in a cell infected with a virus derived from the viral vector, such as a target cell. The promoter can be naturally-occurring or non-naturally occurring.

Examples of promoters, include, but are not limited to, viral promoters, plant promoters and mammalian promoters. Examples of viral promoters include, but are not limited to cytomegalovirus (CMV) immediate early promoter, CAG promoter (which is a combination of the CMV early enhancer element and chicken beta-actin promoter, described in Alexopoulou et al. BMC Cell Biology 9:2, (2008)), simian virus 40 (SV40) promoter, the $^{35}$S RNA and 19S RNA promoters of cauliflower mosaic virus (CaMV) described in Brisson et al., Nature 1984, 310:511-514, the coat protein promoter to tobacco mosaic virus (TMV), and any variants thereof. Examples of plant promoters include, but are not limited to, heat shock promoters, such as soybean hsp17.5-E or hsp17.3-B described in Gurley et al., Mol. Cell. Biol. 1986, 6:559-565, and any variants thereof. Examples of mammalian promoters include, but are not limited to, human elongation factor 1α-subunit (EF1-1a) promoter, human ubiquitin C (UCB) promoter, murine phosphoglycerate kinase-1 (PGK) promoter, and any variants thereof.

In some embodiments, the promoter is a synthetic promoter comprising at least a portion of the CAG promoter. The portion of the CAG promoter can comprise a nucleic acid sequence having at least about 90%, at least about 95%, at least about 96%, at least about 97%, at least about 98%, at least about 99%, or more, sequence identity to SEQ ID NO: 3.

In some embodiments, the promoter comprises a CMV enhancer. In some embodiments, the promoter comprises a UBC enhancer. In some embodiments, the promoter comprises at least a portion of the CMV enhancer. For example, the CMV enhancer can comprise a nucleic acid sequence having at least about 90%, at least about 95%, at least about 96%, at least about 97%, at least about 98%, at least about 99%, or more, sequence identity to SEQ ID NO: 2. In some embodiments the promoter comprises at least a portion of the UCB enhancer. The UCB enhancer can comprise a nucleic acid sequence having at least about 90%, at least about 95%, at least about 96%, at least about 97%, at least about 98%, at least about 99%, or more, sequence identity to SEQ ID NO: 4.

In some embodiments, the promoter is a synthetic CASI promoter having a nucleotide sequence of SEQ ID NO: 1. The synthetic CASI promoter contains a portion of the CMV enhancer, a portion of the chicken beta-actin promoter, and a portion of the UBC enhancer. In some embodiments, the promoter can include a nucleic acid sequence having at least about 90%, at least about 95%, at least about 96%, at least about 97%, at least about 98%, at least about 99%, or more, sequence identity to SEQ ID NO: 1. In some embodiments, the promoter comprises a nucleic acid sequence that is at least about 90% identical to SEQ ID NO: 1. In some embodiments, the promoter comprises a nucleic acid sequence that is at least about 95% identical to SEQ ID NO: 1. In some embodiments, the promoter comprises a nucleic acid sequence of SEQ ID NO: 1.

In some embodiments, the vector can include one or more introns to facilitate processing of the RNA transcript in mammalian host cells. A non-limiting example of such an intron is the rabbit β-globin intron. In some embodiments, the intron is a synthetic intron. For example, the synthetic intron can include a nucleotide sequence having at least about 90%, at least about 95%, at least about 96%, at least about 97%, at least about 98%, at least about 99%, or more, sequence identity to SEQ ID NO: 8. The location of the intron in the vector can vary. In some embodiments, the intron is located between the promoter and the restriction site. In some embodiments, the intron is located within the promoter. In some embodiments, the intron includes a UCB enhancer. The UCB enhancer can comprise a nucleotide sequence having at least about 90%, at least about 95%, at least about 96%, at least about 97%, at least about 98%, at least about 99%, or more, sequence identity to SEQ ID NO: 4.

In some embodiments, the promoter is operably linked with a polynucleotide encoding one or more proteins of interest. In some embodiments, the promoter is operably linked with a polynucleotide encoding the heavy chain and/or the light chain of an antibody of interest (such as the heavy and light variable region of the antibody). In some embodiments, the promoter is operably linked with a polynucleotide encoding the heavy chain and the light chain of an antibody of interest to allow multicistronic expression of the heavy and light chain genes. In some embodiments, a 2A sequence or IRES element is located between the coding region of the heavy chain variable region and the coding region of the light chain variable region in the vector to facilitate equivalent expression of each subunit. Alternatively, polynucleotides encoding the heavy and light chains can be introduced separately into the target cell, each in an appropriate viral vector.

The size of the promoter can vary. Because of the limited packaging capacity of AAV, it is preferred to use a promoter that is small in size, but at the same time allows high level production of the protein(s) of interest in host cells. For example, in some embodiments the promoter is at most about 1.5 kb, at most about 1.4 kb, at most about 1.35 kb, at most about 1.3 kb, at most about 1.25 kb, at most about 1.2 kb, at most about 1.15 kb, at most about 1.1 kb, at most about 1.05 kb, at most about 1 kb, at most about 800 base pairs, at most about 600 base pairs, at most about 400 base pairs, at most about 200 base pairs, or at most about 100 base pairs.

The nucleotide sequence of the promoter can also be modified for improving expression efficiency. For example, the promoter can include one or more splice donors, one or more splice acceptors, and/or combination thereof. In some embodiments, the promoter includes a splice donor and a splice acceptor. In some embodiments, the promoter includes one or more splice donors, and no splice acceptor. In some embodiments, the promoter includes no splice donor, and one or more splice acceptors. For example, in some embodiments the splice donor can comprise a nucleic acid sequence having at least about 90%, at least about 95%, at least about 96%, at least about 97%, at least about 98%, at least about 99%, or more, sequence identity to SEQ ID NO: 5. In some embodiments the splice acceptor can comprise a nucleic acid sequence having at least about 90%, at least about 95%, at least about 96%, at least about 97%, at least about 98%, at least about 99%, or more, sequence identity to SEQ ID NO: 6.

Regulatory Elements

Various posttranscriptional regulatory elements can be used in the viral vectors, for example to increase expression level of the protein of interest in a host cell. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element (RTE), and any variants thereof. The WPRE can comprise a nucleic acid sequence having at least about 90%, at least about 95%, at least about 96%, at least about 97%, at least about 98%, at least about 99%, or more, sequence identity to SEQ ID NO: 7. The RTE can be a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

The viral vector described herein can include a prokaryotic replicon (that is, a DNA sequence having the ability to direct autonomous replication and maintenance of the recombinant DNA molecule extrachromosomally in a prokaryotic host cell), such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

In some embodiments, the AAV vector can include a gene for a selectable marker that is effective in a eukaryotic cell, such as a drug resistance selection marker. This selectable marker gene can encode a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

The viral vectors disclosed herein can include various regulatory elements, such as a transcription initiation region and/or a transcriptional termination region. Examples of transcription termination region include, but are not limited to, polyadenylation signal sequences. Examples of polyadenylation signal sequences include, but are not limited to, Bovine growth hormone (BGH) poly(A), SV40 late poly(A), rabbit beta-globin (RBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence. In some embodiments, the transcriptional termination region is SV40 late poly(A) sequence.

The viral vectors disclosed herein can also include one or more A nucleotides immediately after a restriction site downstream of the promoter, where the restriction site allows the insertion of a polynucleotide encoding the protein(s) of interest. For example, one or more A nucleotides are located immediately after the TAA stop codon of the protein of interest after the insertion of the polynucleotide encoding the protein of interest into the vector. In some embodiments, one A nucleotide, two A nucleotides, three A nucleotides, or more are located immediately after the restriction site. In some embodiments, one A nucleotide, two A nucleotides, three A nucleotides, or more are located immediately after the TAA stop codon of the protein of interest.

In some embodiments, the viral vectors can include additional sequences that make the vectors suitable for replication and integration in eukaryotes. In other embodiments, the viral vectors disclosed herein can include a shuttle element that makes the vectors suitable for replication and integration in both prokaryotes and eukaryotes. In some embodiments, the viral vectors can include additional transcription and translation initiation sequences, such as promoters and enhancers; and additional transcription and translation terminators, such as polyadenylation signals.

In some embodiment, the viral vectors can include a regulatory sequence that allows, for example, the translation of multiple proteins from a single mRNA. Non-limiting examples of such regulatory sequences include internal ribosome entry site (IRES) and 2A self-processing sequence. In some embodiments, the 2A sequence is a 2A peptide site from foot-and-mouth disease virus (F2A sequence). In some embodiments, the F2A sequence has a standard furin cleavage site. For example, the F2A sequence having a standard furin cleavage site can include a nucleotide sequence having at least about 90%, at least about 95%, at least about 96%, at least about 97%, at least about 98%, at least about 99%, or more, sequence identity to SEQ ID NO: 9. In some embodiments, the F2A sequence has a modified furin cleavage site. For example, the F2A sequence having a modified furin cleavage site can include a nucleotide sequence having at least about 90%, at least about 95%, at least about 96%, at least about 97%, at least about 98%, at least about 99%, or more, sequence identity to SEQ ID NO: 10.

The viral vectors can also, in some embodiments, have one or more restriction site(s) located near the promoter sequence to provide for the insertion of nucleic acid sequences encoding one or more proteins of interest and other protein(s).

Protein of Interest

As used herein, a "protein of interest" can be any protein, including naturally-occurring and non-naturally occurring proteins. In some embodiments, a polynucleotide encoding one or more proteins of interest can be inserted into the viral vectors disclosed herein, wherein the polynucleotide is operably linked with the promoter. In some instances, the promoter can drive the expression of the protein(s) of interest in a host cell (e.g., a human muscle cell).

Examples of protein of interest include, but are not limited to, luciferases; fluorescent proteins (e.g., GFP); growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like; antibodies and variants thereof, such as hybrid antibodies, chimeric antibodies, humanized antibodies, monoclonal antibodies; antigen binding fragments of an antibody (Fab fragments), single-chain variable fragments of an antibody (scFV fragments); dystrophin and variants thereof; clotting factors and variants thereof; cystic fibrosis transmembrane conductance regulator (CFTR) and variants thereof; and interferons and variants thereof.

In some embodiments, the protein of interest is a therapeutic protein or variant thereof. Non-limiting examples of therapeutic proteins include blood factors, such as β-globin, hemoglobin, tissue plasminogen activator, and coagulation factors; colony stimulating factors (CSF); interleukins, such as IL-1, IL-2, IL-3, IL-4, IL-5, IL-6, IL-7, IL-8, IL-9, etc.; growth factors, such as keratinocyte growth factor (KGF), stem cell factor (SCF), fibroblast growth factor (FGF, such as basic FGF and acidic FGF), hepatocyte growth factor (HGF), insulin-like growth factors (IGFs), bone morphogenetic protein (BMP), epidermal growth factor (EGF), growth differentiation factor-9 (GDF-9), hepatoma derived growth factor (HDGF), myostatin (GDF-8), nerve growth factor (NGF), neurotrophins, platelet-derived growth factor (PDGF), thrombopoietin (TPO), transforming growth factor alpha (TGF-α), transforming growth factor beta (TGF-β), and the like; soluble receptors, such as soluble TNF-α receptors, soluble VEGF receptors, soluble interleukin receptors (e.g., soluble IL-1 receptors and soluble type II IL-1 receptors), soluble γ/δ T cell receptors, ligand-binding fragments of a soluble receptor, and the like; enzymes, such as α-glucosidase, imiglucarase, β-glucocerebrosidase, and alglucerase; enzyme activators, such as tissue plasminogen activator; chemokines, such as IP-10, monokine induced by interferon-gamma (Mig), Groα/IL-8, RANTES, MIP-1α, MIP-1β, MCP-1, PF-4, and the like; angiogenic agents, such as vascular endothelial growth factors (VEGFs, e.g., VEGF121, VEGF165, VEGF-C, VEGF-2), transforming growth factor-beta, basic fibroblast growth factor, glioma-derived growth factor, angiogenin, angiogenin-2; and the like; anti-angiogenic agents, such as a soluble VEGF receptor; protein vaccine; neuroactive peptides, such as nerve growth factor (NGF), bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, warfarin, neurotensin, motilin, thyrotropin, neuropeptide Y, luteinizing hormone, calcitonin, insulin, glucagons, vasopressin, angiotensin II, thyrotropin-releasing hormone, vasoactive intestinal peptide, a sleep peptide, and the like; thrombolytic agents; atrial natriuretic peptide; relaxin; glial fibrillary acidic protein; follicle stimulating hormone (FSH); human alpha-1 antitrypsin; leukemia inhibitory factor (LIF); transforming growth factors (TGFs); tissue factors, luteinizing hormone; macrophage activating factors; tumor necrosis factor (TNF); neutrophil chemotactic factor (NCF); nerve growth factor; tissue inhibitors of metalloproteinases; vasoactive intestinal peptide; angiogenin; angiotropin; fibrin; hirudin; IL-1 receptor antagonists; and the like. Some other non-limiting examples of protein of interest include ciliary neurotrophic factor (CNTF); brain-derived neurotrophic factor (BDNF); neurotrophins 3 and 4/5 (NT-3 and 4/5); glial cell derived neurotrophic factor (GDNF); aromatic amino acid decarboxylase (AADC); hemophilia related clotting proteins, such as Factor VIII, Factor IX, Factor X; dystrophin or nini-dystrophin; lysosomal acid lipase; phenylalanine hydroxylase (PAH); glycogen storage disease-related enzymes, such as glucose-6-phosphatase, acid maltase, glycogen debranching enzyme, muscle glycogen phosphorylase, liver glycogen phosphorylase, muscle phosphofructokinase, phosphorylase kinase (e.g., PHKA2), glucose transporter (e.g., GLUT2), aldolase A, β-enolase, and glycogen synthase; lysosomal enzymes (e.g., beta-N-acetylhexosaminidase A); and any variants thereof.

In some embodiments, the protein of interest is an active fragment of a protein, such as any of the aforementioned proteins. In some embodiments, the protein of interest is a fusion protein comprising some or all of two or more proteins. In some embodiments a fusion protein can comprise all or a portion of any of the aforementioned proteins.

In some embodiments, the viral vector comprises a polynucleotide comprising coding regions for two or more proteins of interest. The two or more proteins of interest can be the same or different from each other. In some embodiments, the two or more proteins of interest are related polypeptides, for example neutralizing antibodies for the same virus.

In some embodiments, the protein of interest is a multi-subunit protein. For examples, the protein of interest can comprise two or more subunits, or two or more independent polypeptide chains. In some embodiments, the protein of interest can be an antibody. Examples of antibodies include, but are not limited to, antibodies of various isotypes (for example, IgG1, IgG2, IgG3, IgG4, IgA, IgD, IgE, and IgM); monoclonal antibodies produced by any means known to those skilled in the art, including an antigen-binding fragment of a monoclonal antibody; humanized antibodies; chimeric antibodies; single-chain antibodies; antibody fragments such as Fv, F(ab')2, Fab', Fab, Facb, scFv and the like; provided that the antibody is capable of binding to antigen. In some embodiments, the antibody is a full-length antibody. In some embodiments, the protein of interest is not an immunoadhesin.

In some embodiments, the antibody is an anti-Malaria antibody. Non-limiting examples of anti-Malaria include 2A10 anti-Malaria antibody and 2C11 anti-Malaria antibody.

In some embodiments, the antibody is a viral neutralizing antibody. For example, the antibody can be a neutralizing antibody for HIV, HCV or influenza viruses. In some embodiments, the antibody is a neutralizing anti-HIV antibody. In some embodiments, a neutralizing anti-HIV antibody may be, for example, a human monoclonal neutralizing antibody that neutralizes many primary isolates of different genetic subtypes of HIV-1.

In some embodiments, the antibody is a neutralizing anti-HCV antibody.

In some embodiments, the antibody is a neutralizing anti-influenza antibody. Non-limiting examples of neutralizing viral antibodies include b12 anti-HIV antibody, 2G12 anti-HIV antibody, 4E10 anti-HIV antibody, 2F5 anti-HIV antibody, VRC01 anti-HIV antibody, 3BNC60 anti-HIV antibody, 3BNC117 anti-HIV antibody, NIH45-46 anti-HIV antibody, NIH45-46W anti-HIV antibody, VRC-PG04 anti-HIV antibody, VRC-CH31 anti-HIV antibody, PGT121 anti-HIV antibody, PGT128 anti-HIV antibody, F10 anti-influenza antibody, CR6261 anti-influenza antibody, TCN32 influenza antibody, FI6 anti-influenza antibody, FI6v3 anti-influenza antibody, AR3A anti-HCV antibody, AR3B anti-HCV antibody, AR4A anti-HCV antibody, and any variants thereof.

As described herein, the nucleotide sequence encoding the protein of interest can be modified to improve expression efficiency of the protein. The methods that can be used to improve the transcription and/or translation of a gene herein are not particularly limited. For example, the nucleotide sequence can be modified to better reflect host codon usage to increase gene expression (e.g., protein production) in the host (e.g., a mammal). As another non-limiting example for the modification, one or more of the splice donors and/or splice acceptors in the nucleotide sequence of the protein of interest is modified to reduce the potential for extraneous splicing.

The protein of interest can be of various lengths. For example, the protein of interest can be at least about 200 amino acids, at least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer in length. In some embodiments, the protein of interest is at least about 480 amino acids in length. In some embodiments, the protein of interest is at least about 500 amino acids in length. In some embodiments, the protein of interest is about 750 amino acids in length.

When it is desired to include coding regions for two or more proteins of interest, two or more individual polypeptide chains, or two or more subunits of a protein of interest in one viral vector, each additional coding region beyond the first is preferably linked to an element that facilitates co-expression of the proteins in host cells, such as an internal ribosomal entry sequence (IRES) element (U.S. Pat. No. 4,937,190), or a 2A element. For example, IRES or 2A elements are preferably used when a single vector comprises sequences encoding each subunit of a multi-subunit protein. In the case of that the protein of interest is immunoglobulin with a desired specificity, for example, the first coding region (encoding either the heavy or light chain of immunoglobulin) is located downstream from the promoter. The second coding region (encoding the remaining chain of immunoglobulin) can be located downstream from the first coding region, and an IRES or 2A element can be disposed between the two coding regions, preferably immediately preceding the second coding region. The incorporation of an IRES or 2A element between the sequences of a first and second gene (encoding the heavy and light chains, respectively) can allow both chains to be expressed from the same promoter at about the same level in the cell.

In some embodiments, the protein of interest comprises two or more subunits, for example an immunoglobulin (Ig). The viral vector can include a coding region for each of the subunits. For example, the viral vector can include both the coding region for the Ig heavy chain (or the variable region of the Ig heavy chain) and the coding region for the Ig light chain (or the variable region of the Ig light chain). In some embodiments, the vectors include a first coding region for the heavy chain variable region of an antibody, and a second coding region for the light chain variable region of the antibody. The two coding regions can be separated, for example, by a 2A self-processing sequence to allow multi-cistronic transcription of the two coding regions.

The viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

The Kozak consensus sequence, Kozak consensus or Kozak sequence, is known as a sequence which occurs on eukaryotic mRNA and has the consensus (gcc)gccRccAUGG, where R is a purine (adenine or guanine) three bases upstream of the start codon (AUG), which is followed by another "G." In some embodiments, the vector comprises a nucleotide sequence having at least about 70%, at least about 80%, at least about 90% sequence identity, or more to the Kozak consensus sequence. In some embodiments, the vector comprises a Kozak consensus sequence. In some embodiments, the vector includes a Kozak consensus sequence after the polynucleotide encoding one or more proteins of interest is inserted into the vector, e.g., at the restrict site downstream of the promoter. For example, the vector can include a nucleotide sequence of GCCGCCATG (SEQ ID NO: 41), where the ATG is the start codon of the protein of interest. In some embodiments, the vector comprises a nucleotide sequence of GCGGCCGCCATG (SEQ ID NO: 42), where the ATG is the start codon of the protein of interest.

The protein of interest can be isolated and purified, if desired, in accordance with conventional methods known to those skilled in the art. For example, a lysate can be prepared of the expression host cells and the lysate can be purified using HPLC, hydrophobic interaction chromatography (HIC), anion exchange chromatography, cation exchange chromatography, size exclusion chromatography, ultrafiltration, gel electrophoresis, affinity chromatography, and/or other purification techniques.

Signal Peptide Sequence

Various signal peptide sequences can be used in the viral vector disclosed herein. The signal peptide sequence can be naturally-occurring or non-naturally occurring.

In some embodiments, a signal peptide can provide for secretion from a mammalian cell. Examples of signal peptides include, but are not limited to, the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. In some embodiments, the signal peptide is a modified HGH signal peptide. In some embodiments, the nucleotide sequence encoding the signal peptide comprises a nucleotide sequence having at least about 90%, at least about 95%, at least about 96%, at least about 97%, at least about 98%, at least about 99%, or more, sequence identity to SEQ ID NO: 11. In some embodiments, the nucleotide sequence encoding the signal peptide comprises a nucleotide sequence having at least about 90%, at least about 95%, at least about 96%, at least about 97%, at least about 98%, at least about 99%, or more, sequence identity to SEQ ID NO: 12.

In some embodiments, the signal polypeptide for a protein that is different from the protein of interest can be used. In some embodiments, the native signal polypeptide for the protein of interest is used. In some instances, a non-naturally occurring signal peptide can be used.

Typically, the nucleotide sequence of the signal peptide is located immediately upstream of the coding region of the protein of interest (e.g., fused at the 5' of the coding region of the protein of interest) in the vector. In the instances where the viral vector includes the coding regions of two or more proteins of interest, signal peptide sequence can be inserted immediately upstream of one or more of the coding regions. In some embodiments, each of the coding regions has a signal peptide sequence fused at the 5' end. The signal peptide sequence added to each of the coding region can be the same or different. For example, when the protein of interest has two subunits, the viral vector can include a coding region for one of the subunits and a coding region for the other subunit, and a signal peptide sequence can be inserted immediately upstream of either one of the coding regions, or both of the coding regions. As another non-limiting example, the viral vector can include a coding region for the heavy chain vari- As disclosed above, the viral vectors can include various elements, for example, but not limited to, a promoter, a transgene encoding the protein of interest, a signal peptide sequence, a posttranscriptional regulatory element, a transcriptional terminal element, and a regulatory sequence allowing translation of multiple proteins from a single mRNA. A skilled artisan will appreciate that a viral vector can include one of these elements, or any combinations of two or more of these elements. For example, the viral vector can include at least one element or a combination of elements listed in Table 1. The convention used in Table 1 is as follows:

A=promoter
B=transgene
C=signal peptide sequence
D=posttranscriptional regulatory element
E=transcriptional terminal element
F=regulatory sequence allowing translation of multiple proteins from a single mRNA
G=Kozak consensus sequence

TABLE 1

| \multicolumn{5}{c}{Element or combination of elements included in some embodiments of the viral vector} | | | | |
|---|---|---|---|---|
| A | B | C | D | E |
| F | G | A + B | A + C | A + D |
| A + E | A + F | A + G | B + C | B + D |
| B + E | B + F | B + G | C + D | C + E |
| C + F | C + G | D + E | D + F | D + G |
| E + F | E + G | F + G | A + B + C | A + B + D |
| A + B + E | A + B + F | A + B + G | A + C + D | A + C + E |
| A + C + F | A + C + G | A + D + E | A + D + F | A + D + G |
| A + E + F | A + E + G | A + F + G | B + C + D | B + C + E |
| B + C + F | B + C + G | B + D + E | B + D + F | B + D + G |
| B + E + F | B + E + G | C + D + E | C + D + F | C + D + G |
| C + E + F | C + E + G | C + F + G | D + E + F | D + E + G |
| E + F + G | A + B + C + D | A + B + C + E | A + B + C + F | A + B + C + G |
| A + B + D + E | A + B + D + F | A + B + D + G | A + B + E + F | A + B + E + G |
| A + B + F + G | A + C + D + E | A + C + D + F | A + C + D + G | A + C + E + F |
| A + C + E + G | A + C + F + G | A + D + E + F | A + D + E + G | A + D + F + G |
| A + E + F + G | B + C + D + E | B + C + D + F | B + C + D + G | B + C + E + F |
| B + C + E + G | B + C + F + G | B + D + E + F | B + D + E + G | B + D + F + G |
| B + E + F + G | C + D + E + F | C + D + E + G | C + D + F + G | C + E + F + G |
| D + E + F + G | A + B + C + D + E | A + B + C + D + F | A + B + C + D + G | A + B + C + E + F |
| A + B + C + E + G | A + B + C + F + G | A + B + D + E + F | A + B + D + E + G | A + B + D + F + G |
| A + B + E + F + G | A + C + D + E + F | A + C + D + E + G | A + C + D + F + G | A + C + E + F + G |
| A + D + E + F + G | B + C + D + E + F | B + C + D + E + G | B + C + D + F + G | B + C + E + F + G |
| B + D + E + F + G | C + D + E + F + G | A + B + C + D + E + F | A + B + C + D + E + G | A + B + C + D + F + G |
| A + B + C + E + F + G | A + B + D + E + F + G | A + C + D + E + F + G | B + C + D + E + F + G | A + B + C + D + E + F + G | able region of an immunoglobulin and a coding region for the light chain variable region of the immunoglobulin, and each of the coding regions is fused with a signal peptide sequence at the 5' end. In some embodiments, the two signal peptide sequences are the same. In some embodiments, the two signal peptide sequences are different.

In some embodiments, following protein expression and/or secretion, the signal peptides can be cleaved from the precursor proteins resulting in mature proteins.

In some embodiments, the region in the viral vector starting from the 5' AAV ITR and ending at the 3' AAV ITR can be delivered to a host cell and integrate into the host cell genome. The length of this region can vary. For example, the length of this region can be at least about 2 kb, at least about 2.25 kb, at least about 2.5 kb, at least about 2.75 kb, at least about 3 kb, at least about 3.25 kb, at least about 3.5 kb, at least about 3.75 kb, at least about 4 kb, at least about 4.25 kb, or at least about 4.5 kb. In some embodiments, this region is at least about 2.5 kb. In some embodiments, this region is about 4.5 kb. In some embodiments, the viral vector is not a self-complementary AAV (scAAV) vector.

As described above, the nucleotide sequence of each of the above-listed elements can be modified to increase the expression efficiency of the protein of interest in a host cell. In some embodiments wherein more than one transgenes are present in the viral vector, a sequence that can facilitate the co-expression of the transgenes can be used. Non-limiting examples of such sequence include IRES, 2A sequence, and variants thereof.

Sequences of non-limiting examples of the AAV vectors are provided in SEQ ID NOs: 13-30. For example, the nucleotide sequence for an AAV vector including the CMV promoter, coding sequences for b12 anti-HIV antibody and SV40 late poly(A) sequence is set forth in SEQ ID NO: 13; the nucleotide sequence for an AAV vector including the CASI synthetic promoter, coding sequences for luciferase protein, WPRE, and SV40 late poly(A) sequence is set forth in SEQ ID NO: 14; the nucleotide sequence for an AAV vector including the CASI synthetic promoter, coding sequences for luciferase protein, WPRE, and rabbit beta-globin (RBG) poly (A) sequence is set forth in SEQ ID NO: 15; the nucleotide sequence for an AAV vector including the CASI synthetic promoter, coding sequences for luciferase protein, WPRE, and bovine growth hormone (BGH) poly(A) sequence is set forth in SEQ ID NO: 16; the nucleotide sequence for an AAV vector including the CASI synthetic promoter, coding sequences for b12 anti-HIV antibody, WPRE, and SV40 poly(A) sequence is set forth in SEQ ID NO: 17; the nucleotide sequence for an AAV vector including the CASI synthetic promoter, coding sequences for 4E10AB anti-HIV antibody, WPRE, and SV40 poly(A) sequence is set forth in SEQ ID NO: 18; the nucleotide sequence for an AAV vector including the CASI synthetic promoter, coding sequences for 2G12 anti-HIV antibody, WPRE, and SV40 poly(A) sequence is set forth in SEQ ID NO: 19; the nucleotide sequence for an AAV vector including the CASI synthetic promoter, coding sequences for 2F5AB anti-HIV antibody, WPRE, and SV40 poly(A) sequence is set forth in SEQ ID NO: 20; the nucleotide sequence for an AAV vector including the CASI synthetic promoter, coding sequences for b12 anti-HIV antibody, WPRE, and SV40 poly(A) sequence is set forth in SEQ ID NO: 21; the nucleotide sequence for an AAV vector including the CASI synthetic promoter, coding sequences for AR3 antibody, WPRE, and SV40 poly(A) sequence is set forth in SEQ ID NO: 22; the nucleotide sequence for an AAV vector including the CASI synthetic promoter, coding sequences for AR3 antibody, WPRE, and SV40 poly(A) sequence is set forth in SEQ ID NO: 23; the nucleotide sequence for an AAV vector including the CASI synthetic promoter, coding sequences for VRC01 anti-HIV antibody, WPRE, and SV40 poly(A) sequence is set forth in SEQ ID NO: 24; the nucleotide sequence for an AAV vector including the CASI synthetic promoter, coding sequences for TCN32 anti-influenza antibody, WPRE, and SV40 poly(A) sequence is set forth in SEQ ID NO: 25; the nucleotide sequence for an AAV vector including the CASI synthetic promoter, coding sequences for CR6261 antibody, WPRE, and SV40 poly(A) sequence is set forth in SEQ ID NO: 26; the nucleotide sequence for an AAV vector including the CASI synthetic promoter, coding sequences for F10 antibody, WPRE, and SV40 poly(A) sequence is set forth in SEQ ID NO: 27; the nucleotide sequence for an AAV vector including the CASI synthetic promoter, coding sequences for AR4 antibody, WPRE, and SV40 poly(A) sequence is set forth in SEQ ID NO: 28; the nucleotide sequence for an AAV vector including the CASI synthetic promoter, coding sequences for FI6 antibody, WPRE, and SV40 poly(A) sequence is set forth in SEQ ID NO: 29; and the nucleotide sequence for an AAV vector including the CASI synthetic promoter, coding sequences for FI6 antibody, WPRE, and SV40 poly(A) sequence is set forth in SEQ ID NO: 30. In some embodiments, the coding sequences of the antibody are variants of the wildtype coding sequence of the antibody. As another example, the nucleotide sequence for an AAV vector including the CASI promoter, WPRE, and SV40 poly(A) sequence is set forth in SEQ ID NO: 40. A skilled artisan will appreciate that in each of the viral vectors described above, the nucleotide sequence encoding the antibody can be replaced with any other nucleic acid sequence encoding a protein of interest, such as any other nucleic acid sequence encoding an antibody, for example any known anti-HIV, anti-HCV, and/or anti-influenza antibody.

In some embodiments, the AAV vector comprises a nucleotide sequence having at least about 90%, at least about 95%, at least about 96%, at least about 97%, at least about 98%, at least about 99%, or more, sequence identity to SEQ ID NOs: 13-30. In some embodiments, the AAV vector comprises a nucleotide sequence having at least about 90%, at least about 95%, at least about 96%, at least about 97%, at least about 98%, at least about 99%, or more, sequence identity to SEQ ID NO: 40.

In some embodiments, the viral vector includes the CMV promoter and SV40 late poly(A) sequence. In some embodiments, the AAV vector includes the CASI synthetic promoter, WPRE and SV40 late poly(A) sequence. In some embodiments, the AAV vector includes the CASI synthetic promoter, WPRE and rabbit beta-globin (RBG) poly(A) sequence. In some embodiments, the AAV vector includes the CASI synthetic promoter, WPRE and bovine growth hormone (BGH) poly(A) sequence. In some embodiments, the AAV vector includes. In some embodiments, the viral vector includes the CAG promoter and SV40 late poly(A) sequence. In some embodiments, the viral vector includes the CAG promoter, WPRE and SV40 late poly(A) sequence.

Method for Producing Recombinant AAVs

The present application provides methods and materials for producing recombinant AAVs that can express one or more proteins of interest in a host cell. As described herein, the methods and materials disclosed herein allow for high production of the proteins of interest, for example, an antibody, such as a full-length antibody.

In some embodiments, methods for producing a recombinant AAV include providing a packaging cell line with a viral construct comprising a 5' inverted terminal repeat (ITR) of AAV and a 3' AAV ITR, such as described herein, helper functions for generating a productive AAV infection, and AAV cap genes; and recovering a recombinant AAV from the supernatant of the packaging cell line. Various types of cells can be used as the packaging cell line. For example, packaging cell lines that can be used include, but are not limited to, HEK 293 cells, HeLa cells, and Vero cells, for example as disclosed in US Patent Publication No. 20110201088.

In some embodiments, the supernatant of the packaging cell line is treated by PEG precipitation for concentrating the virus. In some embodiments, the precipitation occurs at no more than about 4° C. (for example about 3° C., about 2° C., about 1° C., or about 1° C.) for at least about 2 hours, at least about 3 hours, at least about 4 hours, at least about 6 hours, at least about 9 hours, at least about 12 hours, or at least about 24 hours. In some embodiments, the recombinant AAV is isolated from the PEG-precipitated supernatant by low-speed centrifugation followed by CsCl gradient. The low-speed centrifugation can be at about 4000 rpm, about 4500 rpm, about 5000 rpm, or about 6000 rpm for about 20 minutes, about 30 minutes, about 40 minutes, about 50 minutes or about 60 minutes. In some embodiments, the recombinant AAV is isolated from the PEG-precipitated supernatant by centrifugation at about 5000 rpm for about 30 minutes followed by CsCl gradient In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral helper genes. Non-limiting examples of the adenoviral helper genes include E1A, E1B, E2A, E4 and VA, which can provide helper functions to AAV packaging.

In some embodiments, the AAV cap genes are present in a plasmid. The plasmid can further comprise an AAV rep gene. It is contemplated by the present application that the cap genes and/or rep gene from any AAV serotype (including, but not limited to, AAV1, AAV2, AAV4, AAV5, AAV6, AAV7, AAV8, AAV9, and any variants thereof) can be used herein to produce the recombinant AAV disclosed herein to express one or more proteins of interest. In some embodiments, the AAV cap genes encode a capsid from serotype 1, serotype 2, serotype 4, serotype 5, serotype 6, serotype 7, serotype 8, serotype 9, or a variant thereof, In some embodiments, the packaging cell line can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088, helper vectors pHELP (Applied Viromics). A skilled artisan will appreciate that any helper virus or helper plasmid of AAV that can provide adequate helper function to AAV can be used herein.

The recombinant AAV viruses disclosed herein can also be produced using any convention methods known in the art suitable for producing infectious recombinant AAV. In some instances, a recombinant AAV can be produced by using a cell line that stably expresses some of the necessary components for AAV particle production. For example, a plasmid (or multiple plasmids) comprising AAV rep and cap genes, and a selectable marker, such as a neomycin resistance gene, can be integrated into the genome of a cell (the packaging cells). The packaging cell line can then be co-infected with a helper virus (e.g., adenovirus providing the helper functions) and the viral vector comprising the 5' and 3' AAV ITR and the nucleotide sequence encoding the protein(s) of interest. The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

In some embodiments, the recombinant AAV is not a self-complementary AAV (scAAV).

As will be appreciated with a skilled artisan, any conventional methods suitable for purifying AAV can be used in the embodiments described herein to purify the recombinant AAV. For example, the recombinant can be isolated and purified from packaging cells and/or the supernatant of the packaging cells. In some embodiments, the AAV can be purified by separation method using a CsCl gradient. Also, US Patent Publication No. 20020136710 describes another non-limiting example of method for purifying AAV, in which AAV was isolated and purified from a sample using a solid support that includes a matrix to which an artificial receptor or receptor-like molecule that mediates AAV attachment is immobilized.

Applications of the Viral Vectors and Recombinant AAV

The viral vectors disclosed herein can be used to generate recombinant AAV expressing the protein(s) of interest. The proteins produced by the recombinant AAV generated by the methods and systems described herein have a wide variety of utilities, for example, they can be useful in applications such as diagnostics, therapeutics, research, compound screening and drug discovery.

Production of Proteins In Vitro

As a non-limiting example, the recombinant AAV disclosed herein can be used to produce a protein of interest in vitro, for example, in a cell culture. As one non-limiting example, in some embodiments, a method for producing a protein of interest in vitro, where the method includes providing a recombinant AAV comprising a nucleotide sequence encoding the protein of interest; and contacting the recombinant AAV with a cell in a cell culture, whereby the recombinant AAV expresses the protein of interest in the cell. The size of the nucleotide sequence encoding the protein of interest can vary. For example, the nucleotide sequence can be at least about 1.4 kb, at least about 1.5 kb, at least about 1.6 kb, at least about 1.7 kb, at least about 1.8 kb, at least about 2.0 kb, at least about 2.2 kb, at least about 2.4 kb, at least about 2.6 kb, at least about 2.8 kb, at least about 3.0 kb, at least about 3.2 kb, at least about 3.4 kb, or at least about 3.5 kb in length. In some embodiments, the nucleotide is at least about 1.4 kb in length.

As disclosed above, the protein of interest is not in any way limited. For example, the protein of interest can be an antibody, for example a viral neutralizing antibody. The recombinant AAV disclosed here can produce high levels of the proteins of interest in vitro.

In some embodiments, the protein of interest is luciferase or a fluorescent protein (e.g., GFP). The recombinant AAV expressing the fluorescent protein can be used for labeling cells with fluorescent allowing visualization of the infected cells, for example muscle cells.

Production of Proteins In Vivo

As a non-limiting example, the recombinant AAV disclosed herein can be used to produce a protein of interest in vivo, for example in an animal such as a mammal. Some embodiments provide a method for producing a protein of interest in vivo, where the method includes providing a recombinant AAV comprising a nucleotide sequence encoding the protein of interest; and administering the recombinant AAV to the subject, whereby the recombinant AAV expresses the protein of interest in the subject. The subject can be, in some embodiments, a non-human mammal, for example, a monkey, a dog, a cat, a mouse, or a cow. The size of the nucleotide sequence encoding the protein of interest can vary. For example, the nucleotide sequence can be at least about 1.4 kb, at least about 1.5 kb, at least about 1.6 kb, at least about 1.7 kb, at least about 1.8 kb, at least about 2.0 kb, at least about 2.2 kb, at least about 2.4 kb, at least about 2.6 kb, at least about 2.8 kb, at least about 3.0 kb, at least about 3.2 kb, at least about 3.4 kb, or at least about 3.5 kb in length. In some embodiments, the nucleotide is at least about 1.4 kb in length.

As disclosed above, the protein of interest is not in any way limited. For example, the protein of interest can be an antibody, for example a viral neutralizing antibody. The recombinant AAV disclosed here can produce high levels of the proteins of interest in vivo. For example, the protein of interest can be expressed in the serum of the subject in the amount of at least about 9 μg/ml, at least about 10 μg/ml, at least about 50 µg/ml, at least about 100 µg/ml, at least about 200 µg/ml, at least about 300 µg/ml, at least about 400 µg/ml, at least about 500 µg/ml, at least about 600 µg/ml, at least about 700 µg/ml, at least about 800 µg/ml, at least about 900 µg/ml, or at least about 1000 µg/ml. In some embodiments, the protein of interest is expressed in the serum of the subject in the amount of about 9 µg/ml, about 10 µg/ml, about 50 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1500 µg/ml, about 2000 µg/ml, about 2500 µg/ml, or a range between any two of these values. In some embodiments, the protein of interest is expressed in the serum of the subject in the amount of at least about 9 µg/ml. In some embodiments, the protein of interest is expressed in the serum of the subject in the amount of at least about 100 µg/ml. In some embodiments, the protein of interest is expressed in the serum of the subject in the amount of at least about 500 µg/ml.

We might also want to have explicit support just for expression of antibodies in general in animals—want to make sure we have a section with a good description, and maybe something about level of expression? I was thinking that we might want to have claims to expression of, for example, HCV or HIV or Influenza antibodies in an animal (at a certain level?)—without mentioning therapy—just expression using a particular context (and possibly at a certain level) so it would be good to have specific description related to that.

Diagnostic Applications

In some embodiments, the viral vector can be used to generate recombinant AAV expressing one or more proteins of interest useful in detecting a disease or disorder and/or monitoring the progression of a disease or disorder. As used herein, the term "diagnostic" refers identifying the presence or absence of or nature of a disease or disorder. For example, when the protein of interest is an antibody, the recombinant AAV virus can be used to detect an antigen. The detection of an antigen (e.g., an antigen protein, an antigen nucleic acid sequence, an antigen peptide, an antigen lipid, an antigen carbohydrate, and an antigen small molecule) associated with a disease or disorder provides a means of diagnosing the disease or disorder. Such detection methods can be used, for example, for early diagnosis of the condition, to determine whether a subject is predisposed to a disease or disorder, to monitor the progress of the disease or disorder or the progress of treatment protocols, to assess the severity of the disease or disorder, to forecast the an outcome of a disease or disorder and/or prospects of recovery, or to aid in the determination of a suitable treatment for a subject. The detection can occur in vitro or in vivo.

Diseases contemplated for diagnosis in embodiments described herein include, but not limited to, any disease in which an antigen, such as an antigen associated with the disease, can bind specifically to the antibody of interest. For example, the antigen can be a tumor antigen, a viral antigen, a microbial antigen, an allergen, and an autoantigen. In some embodiments, the antigen is a viral antigen, such as an HIV antigen. In some embodiments, the antigen is a tumor associated antigen (TAA).

Many antibodies to diseases are known and can be used herein as the proteins of interest. For example, anti-cyclic citrullinated peptide antibodies (anti-CCP2) can be used as the protein of interest to detect rheumatoid arthritis.

In some embodiments, the disease to be diagnosed is a type of cancer, such as, for example, leukemia, carcinoma, lymphoma, astrocytoma, sarcoma and particularly Ewing's sarcoma, glioma, retinoblastoma, melanoma, Wilm's tumor, bladder cancer, breast cancer, colon cancer, hepatocellular cancer, pancreatic cancer, prostate cancer, lung cancer, liver cancer, stomach cancer, cervical cancer, testicular cancer, renal cell cancer, and brain cancer.

In some embodiments, the disease to be diagnosed is associated with infection by an intracellular parasite. For example, the intracellular parasite may be a virus such as, for example, an adenovirus, cytomegalovirus, Epstein-Barr virus, herpes simplex virus (HSV), human herpesvirus 6, varicella-zoster virus, hepatitis viruses, papilloma virus, parvovirus, polyomavirus, measles virus, rubella virus, human immunodeficiency virus (HIV), or human T cell leukemia virus. In some embodiments, the intracellular parasite may be a bacterium, protozoan, fungus, or a prion. More particularly, the intracellular parasite can be, for example, Chlamydia, Listeria, Salmonella, Legionella, Brucella, Coxiella, Rickettsia, Mycobacterium, Leishmania, Trypanasoma, Toxoplasma, and Plasmodium. In some embodiments, the disease is malaria.

In some embodiments, the method of detecting a disease in a subject comprises selecting an antibody for the disease to be detected, inserting a polynucleotide comprising the coding region of the antibody to the viral vector disclosed herein, producing a recombinant AAV from the viral vector, infect the recombinant AAV to the subject, and determining the presence or absence of the disease in the subject based on presence or absence of specific binding between the antibody and its specific antigen.

Many other uses for antibodies are well known in the art, including therapeutic, diagnostic, forensic, environmental, and commercial applications. For example, an antigen, either in vitro or in vivo, can bind to an antibody of interest. Thus, methods disclosed herein can be used for detecting the presence of an organisms and/or an antigen (for example, polypeptides, carbohydrates, lipids or nucleic acids), in a forensic/environmental sample or tissues/cells. In some embodiments, the methods can be used in producing antibody that can allow the detection of activated state of an enzyme.

In some embodiments, the methods can be used to purify proteins, e.g., in laboratory or industrial scales.

Therapeutic Applications

The recombinant AAV and methods described herein can be used to express one or more therapeutic proteins to prevent or treat one or more diseases or disorders in a subject.

The recombinant AAV and methods described herein can be used to inhibit or reduce the risk of various viral infections. Some embodiments disclose a method for reducing or inhibiting the infection risk of a virus in a subject, where the method include providing a recombinant AAV comprising a nucleotide sequence encoding a neutralizing antibody for the virus; and administering the recombinant AAV to the subject, whereby the recombinant AAV expresses the antibody in the subject. The recombinant AAV can produce high level of viral neutralizing antibody. For example, in some embodiments, the recombinant AAV can express in the serum of the subject in the amount of at least about 9 µg/ml, at least about 10 µg/ml, at least about 50 µg/ml, at least about 100 µg/ml, at least about 200 µg/ml, at least about 300 µg/ml, at least about 400 µg/ml, at least about 500 µg/ml, at least about 600 µg/ml, at least about 700 µg/ml, at least about 800 µg/ml, at least about 900 µg/ml, or at least about 1000 µg/ml of the viral neutralizing antibody. In some embodiments, the viral neutralizing antibody is expressed in the serum of the subject in the amount of about 9 µg/ml, about 10 µg/ml, about 50 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1500

µg/ml, about 2000 µg/ml, about 2500 µg/ml, or a range between any two of these values.

The method disclosed herein can, for example, reduce the infection risk in the subject by at least about 2 fold, at least about 3 fold, at least about 4 fold, at least about 5 fold, at least about 8 fold, at least about 10 fold, at least about 15 fold, at least about 20 fold, at least about 25 fold, or at least about 30 fold as compared to the subjects without the viral treatment. In some embodiments, the method can reduces the infection risk in the subject by about 2 fold, about 3 fold, about 4 fold, about 5 fold, about 8 fold, about 10 fold, about 15 fold, about 20 fold, about 25 fold, about 30 fold, or a range between any two of these values as compared to the subjects without the viral treatment. In some embodiments, the method reduces the infection risk in the subject with the viral treatment by at least about 5 fold as compared to the subjects without the viral treatment. In some embodiments, the method reduces the infection risk in the subject with the viral treatment by at least about 20 fold as compared to the subjects without the viral treatment. In some embodiments, the method prevents the viral infection from occurring in the subject. In some embodiments, the method inhibits the viral infection in the subject.

Non-limiting examples of the viral infection include infections caused by a virus selected from an adenovirus, an Alphaviridae, an Arbovirus, an Astrovirus, a Bunyaviridae, a Coronaviridae, a Filoviridae, a Flaviviridae, a Hepadnaviridae, a Herpesviridae, an Alphaherpesvirinae, a Betaherpesvirinae, a Gammaherpesvirinae, a Norwalk Virus, an Astroviridae, a Caliciviridae, an Orthomyxoviridae, a Paramyxoviridae, a Paramyxoviruses, a Rubulavirus, a Morbillivirus, a Papovaviridae, a Parvoviridae, a Picornaviridae, an Aphthoviridae, a Cardioviridae, an Enteroviridae, a Coxsackie virus, a Polio Virus, a Rhinoviridae, a Phycodnaviridae, a Poxyiridae, a Reoviridae, a Rotavirus, a Retroviridae, an A-Type Retrovirus, an Immunodeficiency Virus, a Leukemia Viruses, an Avian Sarcoma Viruses, a Rhabdoviruses, a Rubiviridae, a Togaviridae, and any combinations thereof. Non-limiting examples of the viral infections include human immunodeficiency virus (HIV) infection, hepatitis C virus (HCV(infection, hepatitis B virus (HBC) infection, Esptein Barr virus infection, influenza virus infection, respiratory syncytial virus infection. In some embodiments, the viral infection is a hepatitis C viral infection. In some embodiments, the viral infection is an HIV infection. In some embodiments, the viral infection is an influenza infection.

Some embodiments provide a method of reducing the risk of viral infection for a subject who has been exposed to a virus (for example, a subject who has come into contact with another subject infected with a virus). Some embodiments provide a method of reducing the risk of viral infection for a subject who will be exposed to a virus (for example, a subject who will come into contact with another subject infected with a virus). In some embodiments, a method of preventing the viral infection is provided.

The viral vectors, recombinant AAV and methods described herein can be used to express one or more therapeutic proteins to treat various diseases. Non-limiting examples of the diseases include cancer such as carcinoma, sarcoma, leukemia, lymphoma; and autoimmune diseases such as multiple sclerosis. Non-limiting examples of carcinomas include esophageal carcinoma; hepatocellular carcinoma; basal cell carcinoma, squamous cell carcinoma (various tissues); bladder carcinoma, including transitional cell carcinoma; bronchogenic carcinoma; colon carcinoma; colorectal carcinoma; gastric carcinoma; lung carcinoma, including small cell carcinoma and non-small cell carcinoma of the lung; adrenocortical carcinoma; thyroid carcinoma; pancreatic carcinoma; breast carcinoma; ovarian carcinoma; prostate carcinoma; adenocarcinoma; sweat gland carcinoma; sebaceous gland carcinoma; papillary carcinoma; papillary adenocarcinoma; cystadenocarcinoma; medullary carcinoma; renal cell carcinoma; ductal carcinoma in situ or bile duct carcinoma; choriocarcinoma; seminoma; embryonal carcinoma; Wilm's tumor; cervical carcinoma; uterine carcinoma; testicular carcinoma; osteogenic carcinoma; epithelieal carcinoma; and nasopharyngeal carcinoma. Non-limiting examples of sarcomas include fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas. Non-limiting examples of solid tumors include glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Non-limiting examples of leukemias include chronic myeloproliferative syndromes; acute myelogenous leukemias; chronic lymphocytic leukemias, including B-cell CLL, T-cell CLL prolymphocytic leukemia, and hairy cell leukemia; and acute lymphoblastic leukemias. Examples of lymphomas include, but are not limited to, B-cell lymphomas, such as Burkitt's lymphoma; Hodgkin's lymphoma; and the like. Other non-liming examples of the diseases that can be treated using the AAV vectors, recombinant viruses and methods disclosed herein include genetic disorders including sickle cell anemia, cystic fibrosis, lysosomal acid lipase (LAL) deficiency 1, Tay-Sachs disease, Phenylketonuria, Mucopolysaccharidoses, Glycogen storage diseases (GSD, e.g., GSD types I, II, III, IV, V, VI, VII, VIII, IX, X, XI, XII, XIII, and XIV), Galactosemia, muscular dystrophy (e.g., Duchenne muscular dystrophy), and hemophilia.

The amount of the protein of interest expressed in the subject (e.g., the serum of the subject) can vary. For example, in some embodiments the protein can be expressed in the serum of the subject in the amount of at least about 9 µg/ml, at least about 10 µg/ml, at least about 50 µg/ml, at least about 100 µg/ml, at least about 200 µg/ml, at least about 300 µg/ml, at least about 400 µg/ml, at least about 500 µg/ml, at least about 600 µg/ml, at least about 700 µg/ml, at least about 800 µg/ml, at least about 900 µg/ml, or at least about 1000 µg/ml. In some embodiments, the protein of interest is expressed in the serum of the subject in the amount of about 9 µg/ml, about 10 µg/ml, about 50 µg/ml, about 100 µg/ml, about 200 µg/ml, about 300 µg/ml, about 400 µg/ml, about 500 µg/ml, about 600 µg/ml, about 700 µg/ml, about 800 µg/ml, about 900 µg/ml, about 1000 µg/ml, about 1500 µg/ml, about 2000 µg/ml, about 2500 µg/ml, or a range between any two of these values. A skilled artisan will understand that the expression level in which a protein of interest is needed for the method to be effective can vary depending on non-limiting factors such as the particular protein of interest and the subject receiving the treatment, and an effective amount of the protein can be readily determined by a skilled artisan using conventional methods known in the art without undue experimentation.

A skilled artisan will appreciate the one or more of the viral vectors and recombinant AAV can be used together in the applications described herein. For example, recombinant AAV viruses expressing different proteins of interest or different subunit of a protein of interest can be administered to the same subject for diagnostic and/or therapeutic purposes. In some embodiments, the recombinant viruses are co-administered to the subject. In some embodiments, the recombinant viruses are administered to the subject separately. In some embodiments, a first recombinant AAV expressing a first protein of interest and a second recombinant AAV expressing a second protein of interest can be administered to the subject together or separately, wherein the first protein of interest and the second protein of interest can be the same or different. In some embodiments, the first protein of interest is an anti-HIV neutralizing antibody and the second protein of interest is a different anti-HIV neutralizing antibody. In some embodiments, the first protein of interest is an anti-influenza neutralizing antibody and the second protein of interest is a different anti-influenza neutralizing antibody. In some embodiments, a first recombinant AAV expressing a first subunit of the protein of interest and a second recombinant AAV expressing a second subunit of the protein of interest can be administered to the subject together or separately.

Pharmaceutical Composition and Method of Administration

Also disclosed herein are pharmaceutical compositions comprising the recombinant AAV viruses disclosed herein and a pharmaceutically acceptable carrier. The compositions can also comprise additional ingredients such as diluents, stabilizers, excipients, and adjuvants. As used herein, "pharmaceutically acceptable" carriers, excipients, diluents, adjuvants, or stabilizers are the ones nontoxic to the cell or subject being exposed thereto (preferably inert) at the dosages and concentrations employed or that have an acceptable level of toxicity as determined by the skilled practitioner.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Titers of the recombinant AAV virus to be administered will vary depending, for example, on the particular recombinant AAV virus, the mode of administration, the treatment goal, the individual, and the cell type(s) being targeted, and can be determined by methods standard in the art.

As will be readily apparent to one skilled in the art, the useful in vivo dosage of the recombinant virus to be administered and the particular mode of administration will vary depending upon the age, weight, the severity of the affliction, and animal species treated, the particular recombinant virus expressing the protein of interest tat is used, and the specific use for which the recombinant virus is employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

Although the exact dosage will be determined on a drug-by-drug basis, in most cases, some generalizations regarding the dosage can be made. In some embodiments, the recombinant AAV expressing a protein of interest can be administered via injection to a subject at a dose of between $1\times10^{11}$ genome copies (GC) of the recombinant virus per kg of the subject and $1\times10^{13}$ GC per kg, for example between $5\times10^{11}$ GC/kg and $5\times10^{12}$ GC/kg.

The recombinant viruses disclosed herein can be administered to a subject (e.g., a human) in need thereof. The route of the administration is not particularly limited. For example, a therapeutically effective amount of the recombinant viruses can be administered to the subject by via routes standard in the art. Non-limiting examples of the route include intramuscular, intravaginal, intravenous, intraperitoneal, subcutaneous, epicutaneous, intradermal, rectal, intraocular, pulmonary, intracranial, intraosseous, oral, buccal, or nasal. In some embodiments, the recombinant virus is administered to the subject by intramuscular injection. In some embodiments, the recombinant virus is administered to the subject by intravaginal injection. In some embodiments, the recombinant AAV is administered to the subject by the parenteral route (e.g., by intravenous, intramuscular or subcutaneous injection), by surface scarification or by inoculation into a body cavity of the subject. Route(s) of administration and serotype(s) of AAV components of the recombinant AAV virus can be readily determined by one skilled in the art taking into account the infection and/or disease state being treated and the target cells/tissue(s) that are to express the protein of interest. In some embodiments, the recombinant virus is administered to muscle cells.

Actual administration of the recombinant AAV virus can be accomplished by using any physical method that will transport the recombinant AAV virus into the target tissue of the subject. For example, the recombinant AAV virus can be injected into muscle, the bloodstream, and/or directly into the liver. Capsid proteins of the recombinant AAV virus may be modified so that the recombinant AAV virus is targeted to a particular target tissue of interest such as muscle and vagina. Pharmaceutical compositions can be prepared as injectable formulations or as topical formulations to be delivered to the muscles by transdermal transport.

For intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the recombinant AAV virus as a free acid (DNA contains acidic phosphate groups) or a pharmacologically acceptable salt can be prepared in water suitably mixed with a surfactant such as hydroxpropylcellulose. A dispersion of the recombinant AAV virus can also be prepared in glycerol, liquid polyethylene glycols and mixtures thereof and in oils. Under ordinary conditions of storage and use, these preparations contain a preservative to prevent the growth of microorganisms.

The recombinant virus to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of the recombinant virus expressing the therapeutic protein is administered to a host in need of such treatment. The use of the recombinant virus disclosed herein in the manufacture of a medicament for inducing immunity in, or providing gene therapy to, a host is within the scope of the present application.

In instances where human dosages for the recombinant AAV viruses have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

A therapeutically effective amount of the recombinant AAV can be administered to a subject at various points of time. For example, the recombinant AAV can be administered to the subject prior to, during, or after the infection by a virus. The recombinant AAV can also be administered to the subject prior to, during, or after the occurrence of a disease (e.g., cancer). In some embodiments, the recombinant AAV is administered to the subject during cancer remission. In some embodiments, the recombinant AAV is administered prior to infection by the virus for immunoprophylaxis.

The dosing frequency of the recombinant AAV virus can vary. For example, the recombinant AAV virus can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In some embodiments, the recombinant AAV virus is administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

EXAMPLE

Additional embodiments are disclosed in further detail in the following examples, which are not in any way intended to limit the scope of the claims.

Experimental Materials and Methods

The following experimental materials and methods were used for Examples 1-9 described below.

AAV Quantification and Functional Validation

Purified AAV was quantified by qPCR using the following general procedure. Frozen aliquots of AAV were thawed and diluted tenfold in digestion buffer containing 10 units of DNase I (Roche) and incubated at 37° C. for 30 minutes. DNase-digested virus was serially diluted and 5 ml of each dilution was used in a 15 µl qPCR reaction with PerfeCTa SYBR Green SuperMix, ROX (Quanta Biosciences) and primers designed against the CMV enhancer (5' CMV: AACGCCAATAGGGACTTTCC (SEQ ID NO: 31) and 3' CMV: GGGCGTACTTGGCATATGAT (SEQ ID NO: 32)) or the luciferase transgene (5' Luc: ACGTGCAAAAGAAGC-TACCG (SEQ ID NO: 33) and 3' Luc: AATGGGAAGTCAC-GAAGGTG (SEQ ID NO: 34). Samples were run in duplicate on an Applied Biosystems 7300 Real Time PCR System. The following cycling conditions were used: one cycle of 50° C. for 2 minutes, one cycle of 95° C. for 10 minutes, 40 cycles of 95° C. for 15 seconds and 60° C. for 60 seconds. Virus titre was determined by comparison with a standard curve generated using either a purified DNA fragment cut with XhoI/NheI from the pVIP luciferase-expressing vector or a reference standard consisting of purified AAV2/8 expressing 4E10 antibody previously titred against the DNA standard.

To validate the functional activity of each lot of the titred virus, in vitro infection assays were performed using 293T cells and the concentration of the antibody was measured in the cell supernatant. Twenty-four hours before infection, 12-well plates were seeded with 500K cells in 1 ml of media. Two hours before infection, media was replaced with 500 µl per well of fresh media. Genome copies (10") of each virus were added to each well and allowed to infect for 6 days. Supernatants were removed and quantified for total IgG production by ELISA.

Mouse Strains

Immunodeficient NOD/SCID/γc (NSG), immunocompetent C57BL/6 (B6) and Balb/C mice were obtained from the Jackson Laboratory. Immunodeficient Rag2/γc mice were obtained from A. Berns.

AAV Intramuscular Injection and Bioluminescent Imaging

Aliquots of previously titered viruses were thawed slowly on ice and diluted in TFB2 to achieve the predetermined dose in a 40 µl volume. Mice were anaesthetized by isofluorane inhalation and a single 40 µl injection was administered into the gastrocnemius muscle with a 28G insulin syringe. At various times after vector administration, mice were either bled to determine antibody concentration in serum or imaged using a Xenogen IVIS 200 Series imaging system (Caliper Lifesciences). To image, mice were anaesthetized by isofluorane inhalation and given 100 µl of 15 mg $ml^{-1}$ D-luciferin (Gold Biotechnology) by intraperitoneal injection. Images were taken between 5 and 10 minutes after D-luciferin injection.

Quantification of Antibody Production by ELISA

For detection of total human IgG, ELISA plates were coated with 1 µg per well of goat anti-human IgG-Fc antibody (Bethyl) for 1 hour. Plates were blocked with 1% BSA (KPL) in TBS for at least 2 hours. Samples were incubated for 1 hour at room temperature in TBST containing 1% BSA (KPL), then incubated for 30 minutes with HRP-conjugated goat anti-human kappa light chain antibody (Bethyl). Sample was detected with TMB Microwell Peroxidase Substrate System (KPL). A standard curve was generated using either Human Reference Serum (Lot 3, Bethyl) or purified Human IgG/Kappa (Bethyl).

For detection of gp120-binding IgG, ELISA plates were coated with 0.04-0.10 µg per well HIV-1 gp120MN protein (Protein Sciences) for 1 hour. Plates were blocked with 1% BSA (KPL) in TBS for at least 2 hours. Samples were incubated for 1 hour at room temperature in TBST containing 1% BSA (KPL), then incubated for 30 minutes with HRP-conjugated goat anti-human IgG-Fc antibody (Bethyl). Sample was detected with TMB Microwell Peroxidase Substrate System (KPL). A standard curve was generated using either purified b12 or VRC01 protein as appropriate for the samples.

HIV Virus Production and Titring 293T cells were maintained in DMEM medium supplemented with 10% fetal bovine serum, 1% penicillin-streptomycin mix (Mediatech), 1% glutamine (Mediatech) in a 5% $CO_2$ incubator at 37° C. Three days before transfection, two 15 cm plates were seeded with $3.75 \times 10^6$ cells each in 25 ml media. Two hours before transfection, media was changed to 15 ml of new media. Forty micrograms of the pNL4-3 plasmid36 encoding an infectious molecular clone of HIV was transfected using Trans-IT reagent (Minis) according to the manufacturer's instructions. Supernatant collections were performed at 24, 48 and 72 hours after transfection and 15 ml of fresh media was gently added back to plate after each harvest. Pooled supernatants were filtered using a 0.45 µm filter to remove cell debris and aliquoted for storage at −80° C. HIV was quantified following the manufacturer's instructions using an Alliance HIV-1 p24 antigen ELISA kit (Perkin-Elmer).

In Vitro HIV Protection Assay

In vitro neutralization assays in luciferase reporter cells were performed according to the typical procedure described as follows. TZM-bl cells from the National Institutes of Health AIDS Research and Reference Reagent Program were maintained in DMEM medium supplemented with 10% fetal bovine serum, 1% penicillin-streptomycin mix (Mediatech), 1% glutamine (Mediatech) in a 5% $CO_2$ incubator at 37° C. Before the assays, TZM-bl cells were trypsinzed, counted and re-suspended in a concentration of 105 cells per milliliter, in a total volume of 15 ml. Cells were mixed with 75 μg ml$^{-1}$ DEAE-dextran and varying concentrations of each antibody as indicated and allowed to incubate on ice during the preparation of the virus. To prepare virus dilutions, stock NL4-3 was diluted to 250 ng ml$^{-1}$ in growth media and subsequently fourfold serially diluted in the assay plate. One hundred microliters of media containing 10,000 cells pre-incubated with antibody were added to wells containing previously diluted virus. Infection was allowed to proceed for 48 hours in a 5% $CO_2$ incubator at 37° C. Before reading the plate, 100 ml of BriteLite reagent (Perkin Elmer) was added to each well, and the plate was incubated for 2 minutes at room temperature. One hundred and twenty microliters of each well was then transferred to an opaque plate and read by VICTOR3 (Wallac 1420 VICTOR3 plate reader, PerkinElmer).

Production of Humanized Mice for In Vivo Challenge

Humanized mice were produced essentially according to the procedure described as follows. Human peripheral mononuclear blood cells (AllCells) were thawed from −80° C., expanded in RPMI medium supplemented with 10% fetal bovine serum, 1% penicillin-streptomycin mix (Mediatech), 1% glutamine (Mediatech), 50 μM β-mercaptoethanol, 10 mM HEPES(Gibco), 13 non-essential amino acids (Gibco), 13 sodium pyruvate (Gibco) and stimulated for T-cell expansion with 5 μg ml$^{-1}$ phytohemagglutinin (Sigma) and 10 ng ml$^{-1}$ human IL-2 (Peprotech) in a 5% $CO_2$ incubator at 37° C. Cells were expanded for 7-13 days before use. For engraftment, 2 million to 4 million cells were injected intraperitoneally into NSG mice in a 300 ml volume of media.

HIV Protection Experiments

One day before HIV challenge, blood samples from each mouse were subjected both to ELISA for antibody quantification and flow cytometry to determine baseline CD4/CD8 ratios. The following day, mice were challenged through either intraperitoneal or intravenous injection of 100 μl containing the specified dose of HIV diluted in PBS. Infected mice were subjected to weekly blood sampling to determine the ratio of CD4 to CD8 cells in the T-lymphocyte subset by flow cytometry.

Flow Cytometry

Blood samples were taken from mice by retro-orbital bleeding and were centrifuged for 5 minutes at 1,150 g in a microcentrifuge to separate plasma from cell pellets. Plasma was removed and frozen for future analysis and cell pellets were re-suspended in 1.1 ml of 1×RBC lysis buffer (Biolegend) and incubated on ice for at least 10 minutes to remove red blood cells. After lysis, samples were pelleted at 1,150 g in a microcentrifuge for 5 minutes at room temperature, and stained with 65 μl of a cocktail containing 5 μl anti-human CD3-FITC, 5 μl anti-human CD4-PE, 5 μl anti-human CD8a-APC antibodies (Biolegend) and 50 μl of phosphate buffered saline supplemented with 2% fetal bovine serum (PBS1). Samples were washed with 1 ml PBS+ and again pelleted at 1,150 g in a microcentrifuge for 5 minutes. Pelleted cells were re-suspended in 200 μl of PBS+ supplemented with 2 μg ml$^{-1}$ propidium iodide (Invitrogen) and analysed on a FACSCalibur flow cytometer (Beckton-Dickinson). Samples were first gated by CD3 expression before determining the ratio of CD4 to CD8 cells within this subset. Samples containing fewer than 20 CD3$^+$ events were excluded from the analysis.

Histological Staining for HIV p24

At the conclusion of the in vivo challenge experiments, spleens were removed from mice and immersed in 10% neutral buffered formalin for 24 hours. After fixation, tissues were removed and placed in 70% ethanol until standard paraffin embedding and processing. Sections (4 mm thick) were then taken and immunohistochemical staining was performed for HIV-p24 detection using the Kal-1 murine monoclonal antibody and standard antigen retrieval techniques. The slides were reviewed by a pathologist (D.S.R.) on an Olympus BX51 light microscope and images obtained using a SPOT Insight Digital Camera (Diagnostic Instruments).

Example 1

Construction and Cloning of Modular AAV Transfer Vectors

To construct the AAV transfer vectors, oligonucleotides encoding the 145-base-pair (bp) AAV2-derived inverted terminal repeat 1 (ITR1) in the 'flip' orientation and ITR2 in the 'flop' orientation flanked by unique restriction sites were synthesized (Integrated DNA Technologies) and annealed before ligation into PBR322 plasmid vector. Subsequently, promoters, transgenes and polyadenylation signals flanked by compatible sites were amplified by PCR and cloned between the ITRs, resulting in a modular AAV transfer vector in which unique combinations of restriction sites flanked each element.

To evaluate the expression potential of various promoters in muscle expression, a series of vectors carrying the luciferase gene driven by a panel of ubiquitous and tissue-specific promoters were made. These vectors were administered intramuscularly via a single injection in the gastrocnemius muscle and luciferase expression was monitored to determine the relative expression potential of each promoter in this target tissue. The cytomegalovirus immediate early promoter (CMV), chimeric chicken-β-actin (CAG), and ubiquitin C (UBC) promoters provided robust muscle expression (FIG. 1A).

A novel synthetic CASI promoter (about 1.05 kb in length) (FIG. 1B) was generated. The CASI promoter consists of the cytomegalovirus immediate early promoter (CMV) followed by a fragment of chicken-β-actin (CAG) promoter containing the transcription initiation site. This fusion is immediately followed by a synthetically designed intron that utilizes consensus splice donor and splice acceptor sequences flanking the enhancer region of the human ubiquitin C (UBC) promoters. In vivo testing demonstrated that the CASI promoter was considerably more active in muscle than the CAG promoter despite being 34% more compact (FIG. 1C). The woodchuck hepatitis virus posttranscriptional regulatory element (WPRE) was then incorporated into the AAV transfer vector, which significantly enhanced expression of transgenes (FIG. 1D).

The efficiencies of various polyadenylation signals were also examined for muscle-derived expression. The SV40 late poly(A), the rabbit beta-globin (RBG) poly(A) and the bovine growth hormone (BGH) poly(A) all demonstrated comparable levels of expression (FIG. 1D).

FIG. 1E shows a schematic illustration of a portion of the muscle-optimized expression vector encoding an IgG1 scaffold into which heavy and light chain V regions derived from monoclonal antibodies could be inserted.

Figure 2:
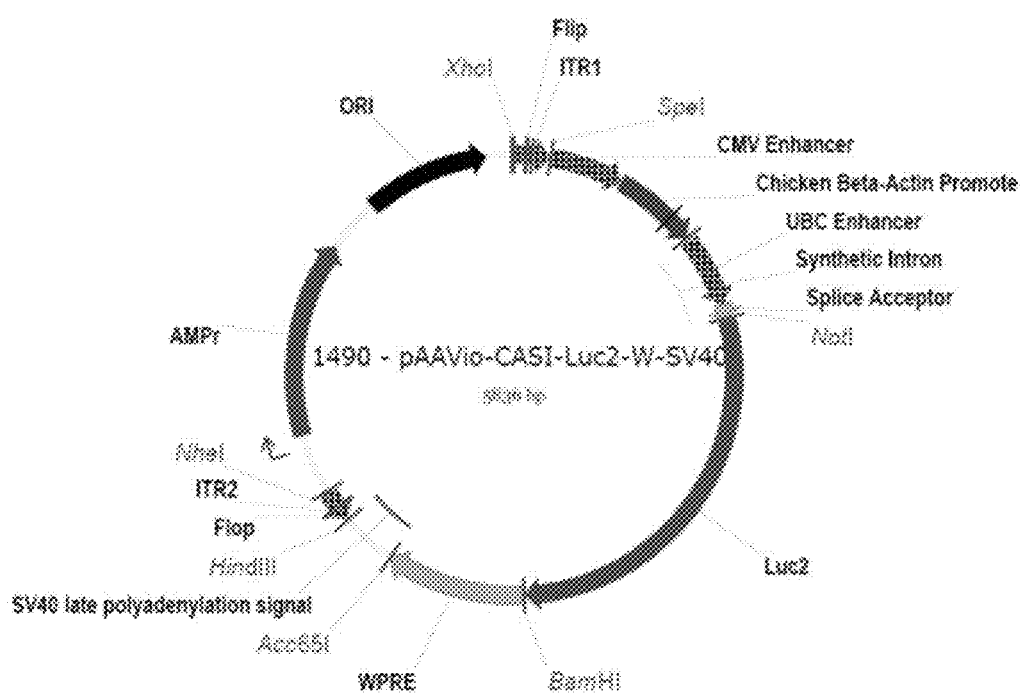
FIG. 2 is a schematic representation of an embodiment of the AAV vector that is within the scope of the present application.

FIG. 2 shows a schematic presentation of the map of a muscle-optimized expression vector with a luciferase transgene inserted. As shown in Supplementary FIG. 2, the vector has unique restriction sites flanking each modular element (e.g., XhoI, SpeI, NodI, BamHT, Acc65I, HindIII, and NheI). In this vector, AAV sequences begin immediately following the XhoI restriction site with a 145 bp "flip"-inverted terminal repeat (ITR) from AAV2 followed by a SpeI restriction site and the CASI promoter. The CASI promoter is followed by a NodI restriction site and one additional C residue following the consensus recognition sequence of GCGGCCGC (SEQ ID NO: 35) cleavage site to mimic a Kozak consensus sequence prior to the ATG of the luciferase transgene. The 3' end of the transgene is terminated with a TAA stop codon followed by one additional A residue prior to the BamHT site. The WPRE element follows this restriction site and continues until an Acc65I restriction site that precedes an SV40 late polyadenylation signal and HindIII restriction site. In addition, a second 145 bp AAV2 "flop"-ITR is located prior to a NheI site.

Example 2

Production and Purification of Recombinant AAV Viruses

Recombinant AAV virus was produced and purified from culture supernatants according to the procedure as described in the following.

293T cells were maintained in DMEM medium supplemented with 10% fetal bovine serum, 1% penicillin-streptomycin mix (Mediatech) and 1% glutamine (Mediatech) in a 5% $CO_2$ incubator at 37° C. Three days before transfection, four 15 cm plates were seeded with $3.75 \times 10^6$ cells each in 25 ml media. Alternatively, $1.875 \times 10^6$ cells can be plated per plate four days before the day of transfection ($7.5 \times 10^6$ cells plated per virus). Two hours before transfection, media was changed to 15 ml of fresh media.

The AAV transfer vector was co-transfected with adenoviral helper vectors (pHELP (Applied Viromics) or pAd-delta-F6) and helper plasmid expressing the Rep and Cap gene products of AAV (pAAV 2/8 SEED) at a ratio of 0.25:1:2 using BioT transfection reagent (Bioland Scientific). The total amount of DNA used per transfection was 80 μg. Five AAV virus collections were performed at 36, 48, 72, 96, and 120 hours after transfection. For each time point, media was filtered through a 0.2 μm filter and 15 ml of fresh media was gently added to the plate.

After collection, approximately 75 ml of 5×PEG solution (40% polyethylene glycol, 2.5M NaCl) was added to the total volume of supernatant collected (~300 ml) and the virus was precipitated on ice for at least 2 hours. Precipitated virus was pelleted at 7,277 g for 30 minutes (Sorvall RC 3B Plus, H-6000A rotor) and re-suspended in 1.37 g $ml^{-1}$ caesium chloride. Resuspended virus was split evenly into two Quick-Seal tubes (Beckman) and spun at 329,738 g at 20° C. for 24 hours (Beckman Coulter, Optima LE-80K, 70Ti rotor). Fractions of 100-200 ml were collected in a 96-well flat-bottom tissue culture plate, and a refractometer was used to quantify the refractive index of 5 ml of each fraction. Wells exhibiting refractive indexes between 1.3755 and 1.3655 were combined and diluted to a final volume of 15 ml using Test Formulation Buffer 2 (TFB2, 100 mM sodium citrate, 10 mM Tris, pH 8). Virus was loaded onto 100 kDa MWCO centrifugal filters (Millipore) and subjected to centrifugation at 500 g at 4° C. until 1 ml retentate remained. Retained virus was then again diluted to 15 ml total volume in TFB2 and this process was repeated such that the virus was washed three times. Final retentate volume was between 500-1000 ml total, which was aliquoted and stored at –80° C.

Example 3

Optimization of the Antibody Transgene

Figure 3:
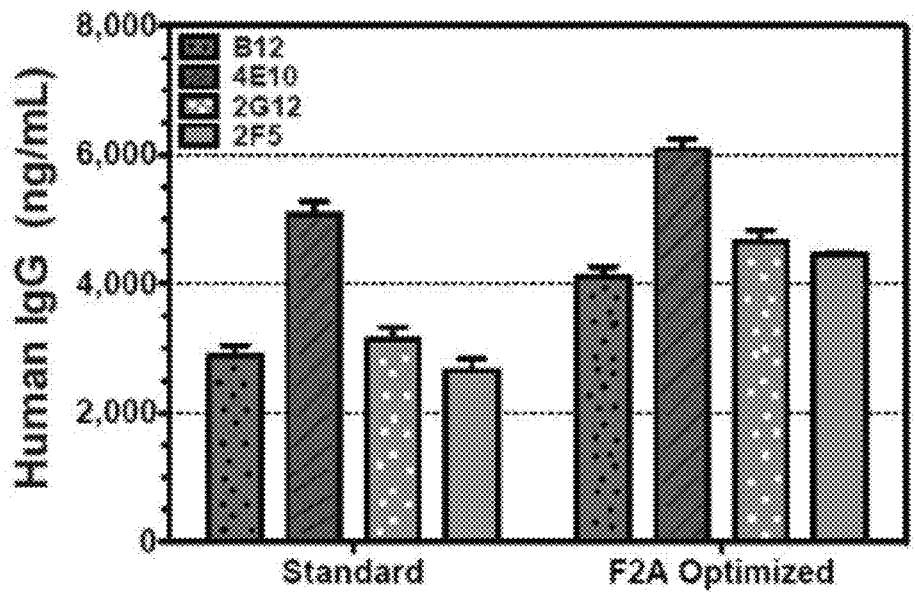
FIG. 3A is a bar graph showing comparison of antibody expression in vitro by ELISA following transfection with vectors carrying the antibody transgene shown above with standard or optimized F2A sequences that include a furin cleavage site.
FIG. 3B is a bar graph showing comparison of 4E10 antibody expression in vitro by ELISA following transfection with vectors carrying 4E10 with natural or human growth hormone (HGH) derived signal peptides fused to the heavy chain gene, the light chain gene or both genes.
FIG. 3C is a bar graph showing comparison of 4E10 antibody expression in vitro by ELISA following transfection with vectors carrying 4E10 in the standard expression cassette or a cassette in which the splice donors and acceptors were mutated to reduce the potential for extraneous splicing.
FIG. 3D is a schematic presentation of an exemplary IgG1 transgene that was optimized for expression in vitro. Highlighted are the heavy and light chain signal sequences ("SS"), the F2A self-processing peptide ("F2A") and the predicted splice donor and acceptor sites (solid lines in the "Heavy Chain Constant Region" and "Kappa Constant").
Figure 3:
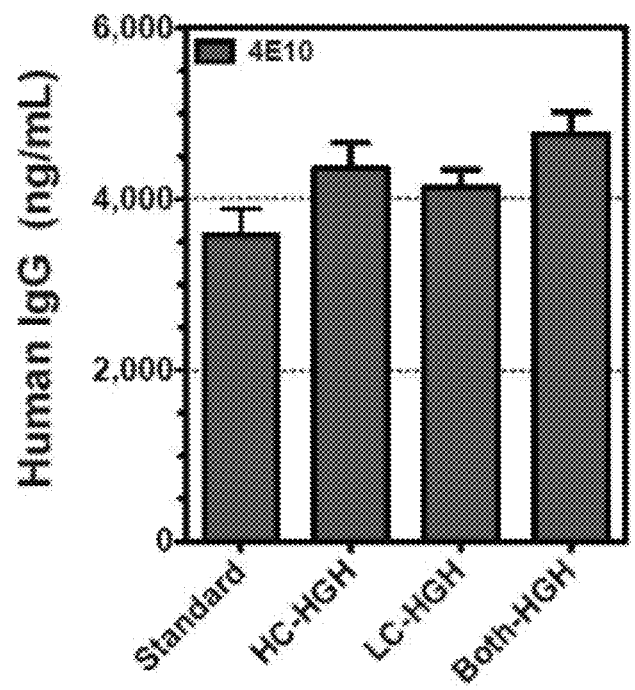
Figure 3:
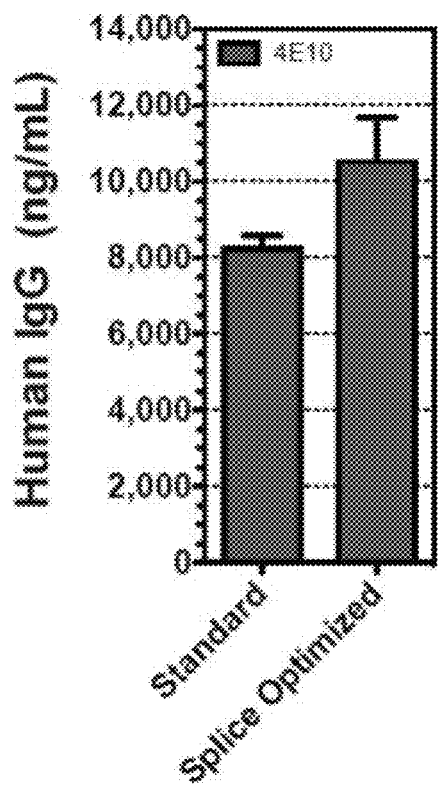
Figure 3:
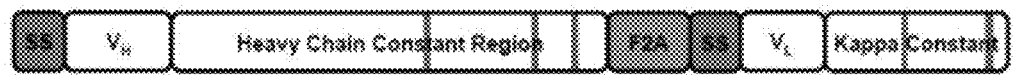
Figure 4:
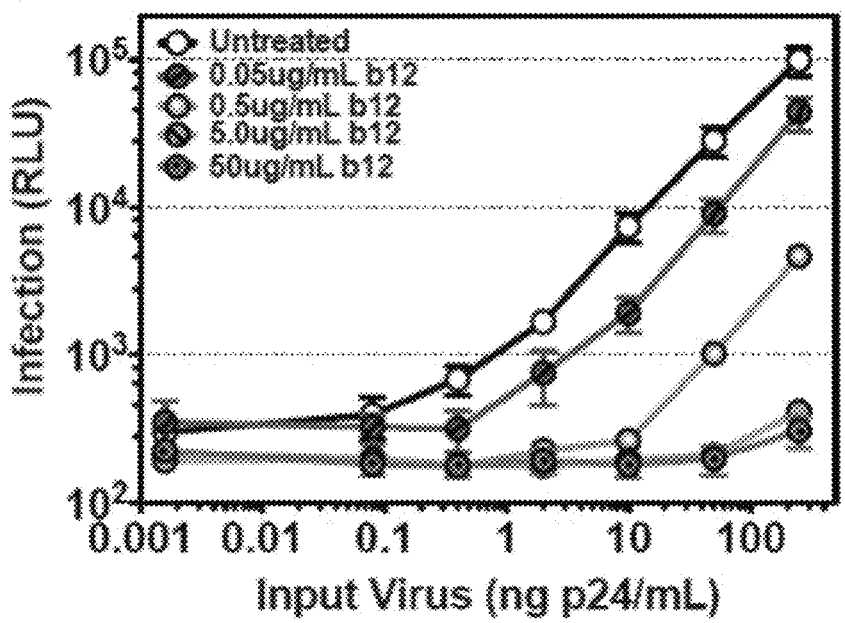
FIG. 4-D shows neutralization of HIV by antibodies expressed from an optimized-expression transgene: b12 (FIG. 4A), 2G12 (FIG. 4B), 4E10 (FIG. 4C) and 2F5 (FIG. 4D) (n=3, RLU=Relative luciferase Units).
Figure 4:
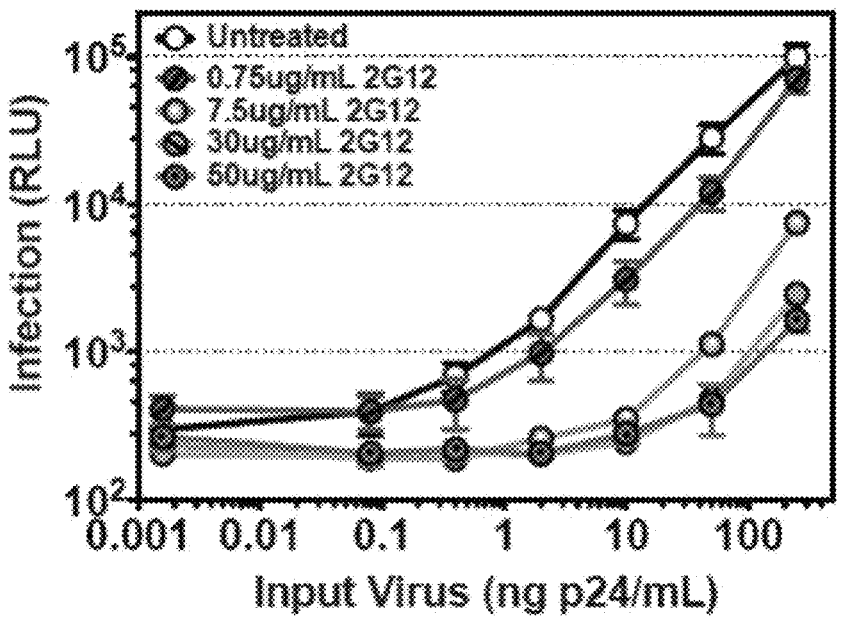
Figure 4:
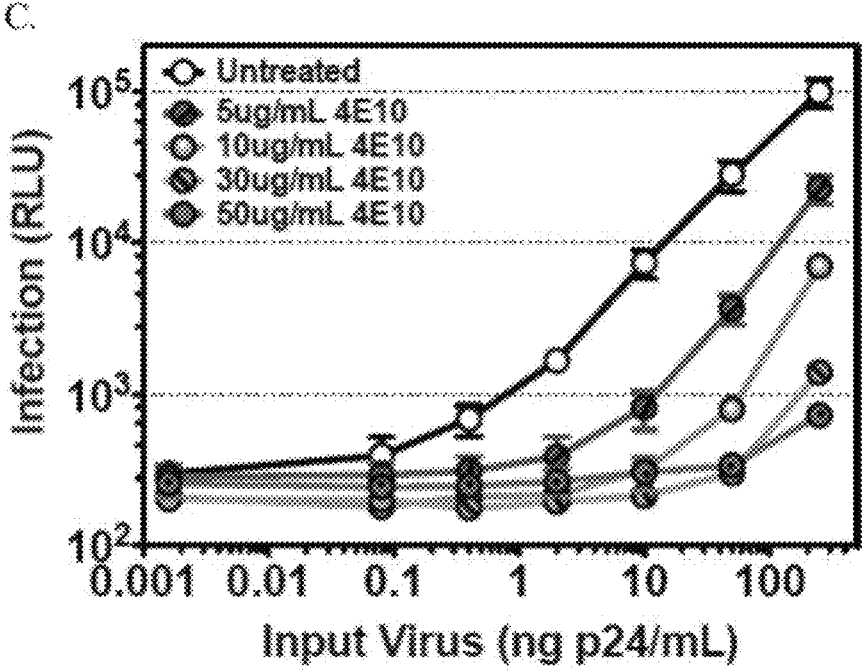
Figure 4:
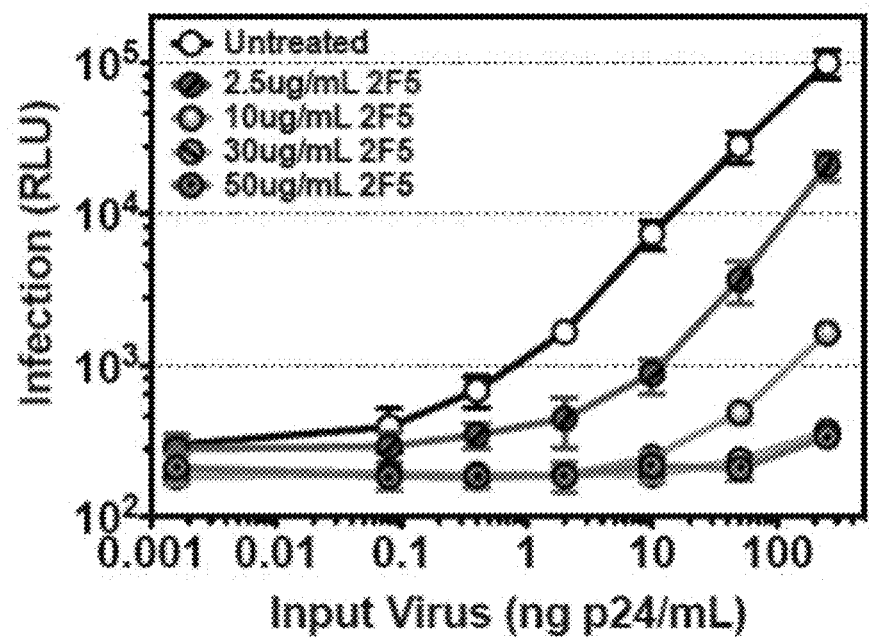

To create an optimal framework for the expression of antibody, the heavy and light chains of several broadly neutralizing HIV antibodies separated by an F2A self-processing peptide sequence were cloned into a mammalian expression vector under the control of the CMV promoter. 293T cells transfected with these vectors demonstrated secretion of human IgG into the culture supernatant that could be detected by ELISA (FIG. 3A). To improve expression, the F2A sequence was re-engineered to better reflect mammalian codon usage and incorporated a furin cleavage site at the N-terminus for optimal processing. Comparison of the vectors with optimized F2A sequence (SEQ ID NO: 9) to the vector with standard F2A sequence (SEQ ID NO: 10) by transfection showed the vectors with optimized F2A sequence produced higher levels of all four antibodies tested.

To improve secretion of the antibody, the endogenous signal sequences was replaced with a codon optimized sequence derived from the human growth hormone (HGH) and created versions of the 4E10 expression vector in which either the heavy chain, the light chain, or both chains were driven by separate HGH signal sequences and compared their expression by transfection. To minimize repetitive sequence in the vectors, two HGH sequences (SEQ ID NOs: 11 and 12) were synthesized which had distinct nucleotide sequences but encoded identical amino acids, and each were used for either the heavy or light chain exclusively. Replacement of the endogenous signal sequences with HGH sequences at either the heavy or light chains resulted in higher levels of antibody production, and signal sequence replacement of both chains yielded the best results (FIG. 3B).

To remove the potential for inappropriate splicing of the transcript encoding the antibody, the sequence was subjected to in silico splice prediction and removed all potential splice donor and acceptor sequences through the use of conservative mutations to the site or, when this was not possible, the surrounding sequences. Improved expression of the 4E10 antibody was observed when placed in this splice-optimized framework (FIG. 3C).

A schematic illustration of the structure of the final antibody transgene is shown in FIG. 3D. As shown in FIG. 3D, the antibody transgene consists of an HGH signal sequence followed by a swappable VH region, a splice-optimized heavy chain constant region, a furin cleavage site linked to an optimized F2A peptide which is fused to a second HGH signal sequence, a swappable VL region, and a spliceoptimized kappa light chain constant region.

To confirm that the above-described optimizations made to improve gene expression did not impact the neutralizing efficacy of the antibodies, several well-studied broadly neutralizing antibodies (e.g., b12, 2G12, 4E10, and 2F5 anti-HIV antibodies) were expressed from the optimized expression vector. The produced antibodies were purified and tested in an in vitro protection assay using TZM-bl luciferase reporter cells. Cells carrying a luciferase gene under the control of HIV-induced transcriptional elements (TZM-bl cells) were incubated with dilutions of each antibody prior to challenge with increasing amounts of HIV. Cells were plated with various concentrations of the antibodies prior to challenge with increasing titers of NL4-3 HIV strain. Two days after challenge, cells were lysed and quantitated for luciferase activity following the addition of luciferin substrate. Robust reduction in TZM-bl cell infection was observed at antibody concentrations that correlated well with the previously established $IC_{50}$ and $IC_{90}$ values for all four antibodies tested against this strain (FIG. 4A-D).

Example 4

In Vivo Expression of Antibody Transgenes

Figure 5:
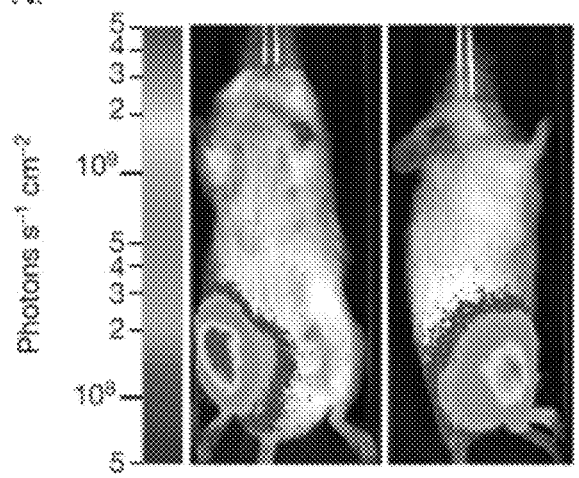
FIG. 5A shows Xenogen images of a representative Rag2/γc mouse 15 weeks after intramuscular injection of $1 \times 10^{10}$ genome copies of AAV2/8 expressing luciferase.
FIG. 5B is a graph showing quantitation of luciferase activity by Xenogen imaging of Rag2$^{-/-}$γc$^{-/-}$ mice receiving intramuscular injection of $1 \times 10^{10}$ or $1 \times 10^{11}$ GC of AAV2/8 encoding luciferase demonstrates long-term dose-dependent expression (n=2).
FIG. 5C is a graph showing concentration of human IgG in circulation as measured by total human IgG ELISA on serum samples taken after intramuscular injection of $1 \times 10^{10}$ or $1 \times 10^{11}$ GC of AAV2/8 expressing 4E10-IgG1 into Rag2$^{-/-}$γc$^{-/-}$ mice (n=2).
Figure 5:
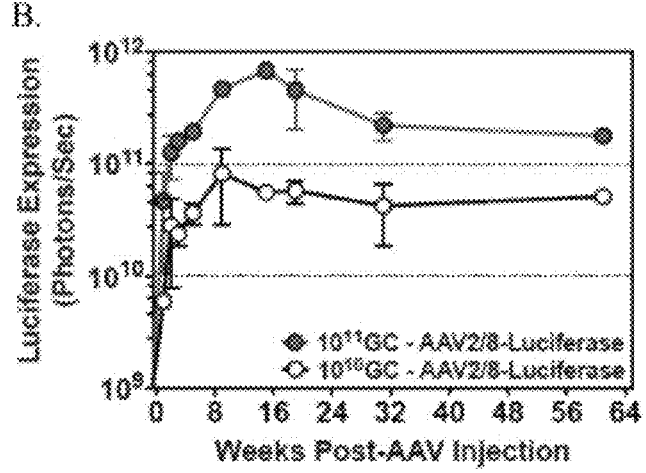
Figure 5:
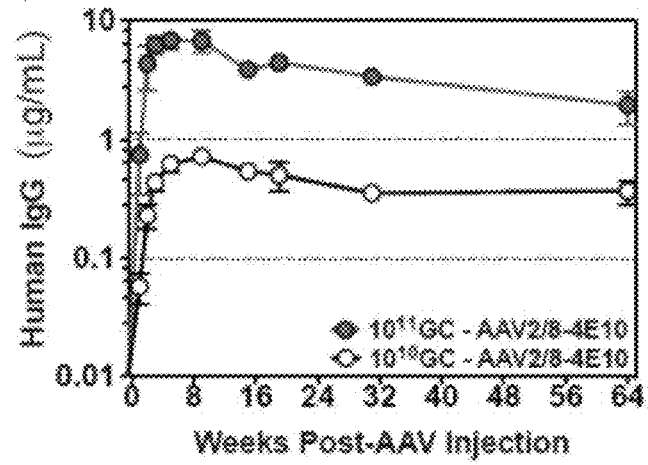

Recombinant AAV viruses with the capsid from serotype 8 that expressed either luciferase or 4E10 HIV neutralizing antibody driven from cytomegalovirus (CMV) promoters were administered to mice through a single injection of the gastrocnemius muscle. The Xenogen images of a representative Rag2/γc mouse 15 weeks after intramuscular injection of $1 \times 10^{10}$ genome copies of AAV2/8 expressing luciferase are shown in (FIG. 5A). Within one week of the administration, either luciferase or antibody gene expression was detectable (FIGS. 5B and 5C, respectively). Expression continued to rise, achieving maximum levels after 12-16 weeks and then decreasing two- to three-fold before stabilizing for the duration of the 64-week study. FIGS. 5B-C show that antibody production is dose-dependent and is maintained for at least 64 weeks.

Figure 6:
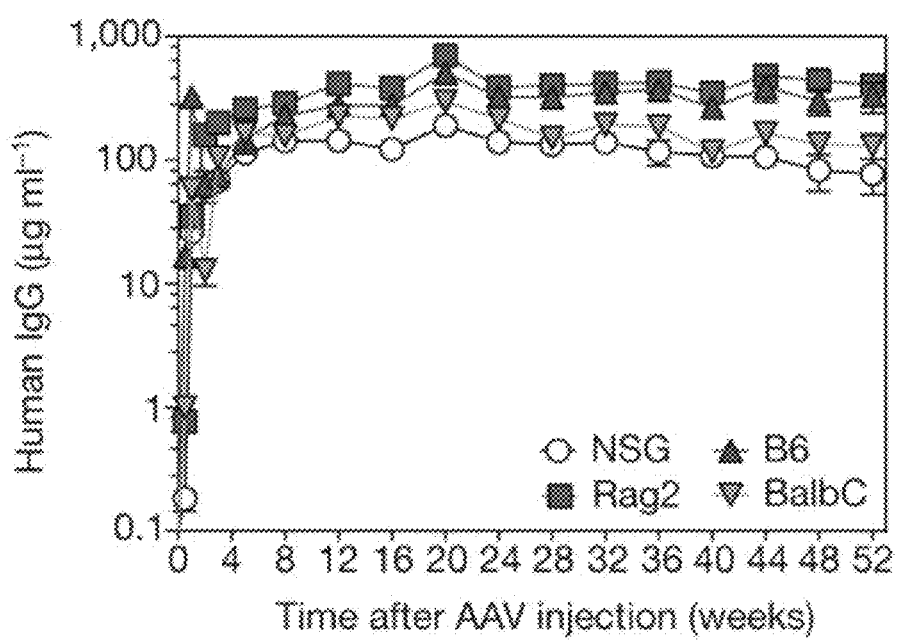
FIG. 6 is a plot showing quantification of human IgG by ELISA after intramuscular injection of $1 \times 10^{11}$ genome copies of the optimized expression vector producing b12-IgG in either immunodeficient NOD/SCID/γc (NSG) and Rag2/γc (Rag2) or immunocompetent C57BL/6 (B6) and Balb/C mice (plot shows mean and standard error, n=4).

The heavy- and light-chain variable regions of the HIV-neutralizing b12 antibody were cloned into the AAV transfer vector, and recombinant AAV stock was produced for intramuscular administration of $1 \times 10^{11}$ genome copies into the gastrocnemius muscle of two immunodeficient and two immunocompetent mouse strains: NOD/SCID/γc (NSG), Rag2/γc (RAG), C57BL/6 (B6) and Balb/C. Mice produced the encoded antibody at serum concentrations that were 100-fold higher than the levels achieved with the nonoptimized vector, and this level of expression persisted for at least 52 weeks (FIG. 6 compared with FIG. 5C). Very limited mouse antibodies were raised against human b12-IgG in B6 mice, whereas Balb/C animals generated detectable mouse antibodies against the transgene that did not appear to impact human IgG levels.

Example 5

Prevention of Loss of CD4 Cells Caused by HIV Challenge

Figure 7:
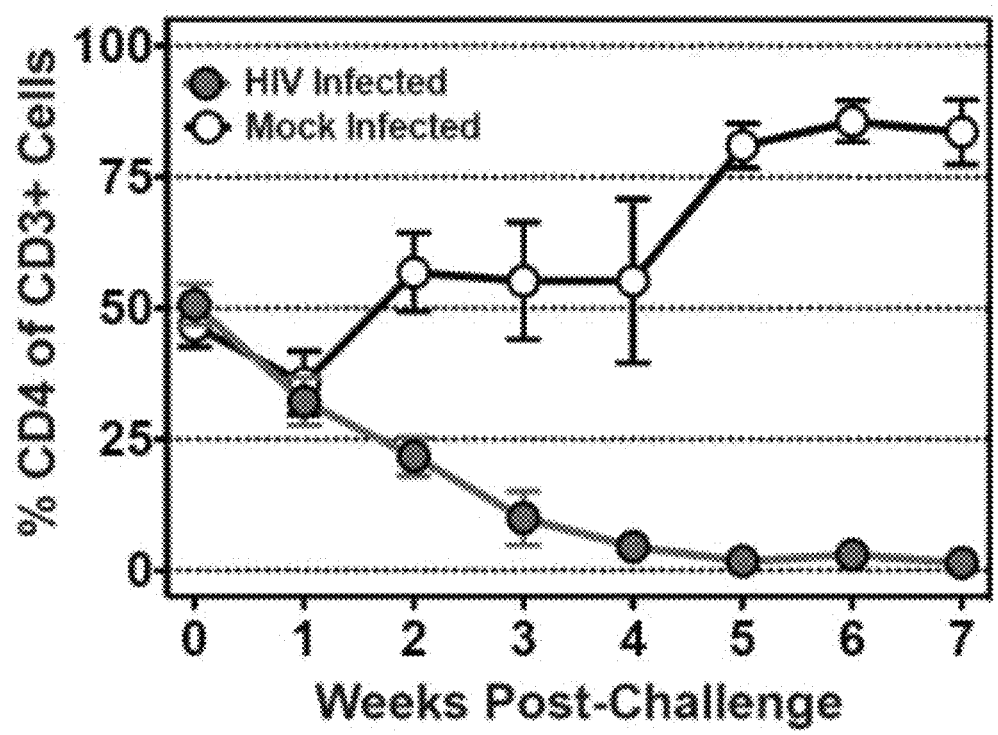
FIG. 7 is a graph showing depletion of CD4 cells in HuPBMC-NSG humanized mice following HIV challenge.

HuPBMC-NSG humanized mice exhibits CD4 cell depletion following challenge with replication competent HIV (20 ng p24 NL4-3, n=4, FIG. 7). This mouse model was used to test ability of the vectors described herein to protect mice from in vivo challenge.

Figure 8:
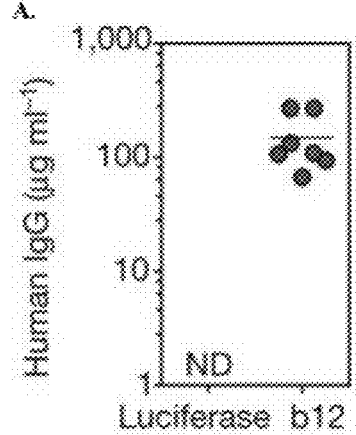
FIG. 8A is graph showing concentration of human IgG in circulation as measured by ELISA on serum samples taken 6 weeks after intramuscular injection of vector expressing either luciferase or b12-IgG (ND, not detected).
FIG. 8B shows depletion of CD4 T cells in humanized mice after intraperitoneal challenge with 10 ng p24 NL4-3 into animals that received AAV2/8 vectors expressing luciferase (left graph) or b12-IgG1 (right graph) 6 weeks earlier (n=6).
Figure 8:
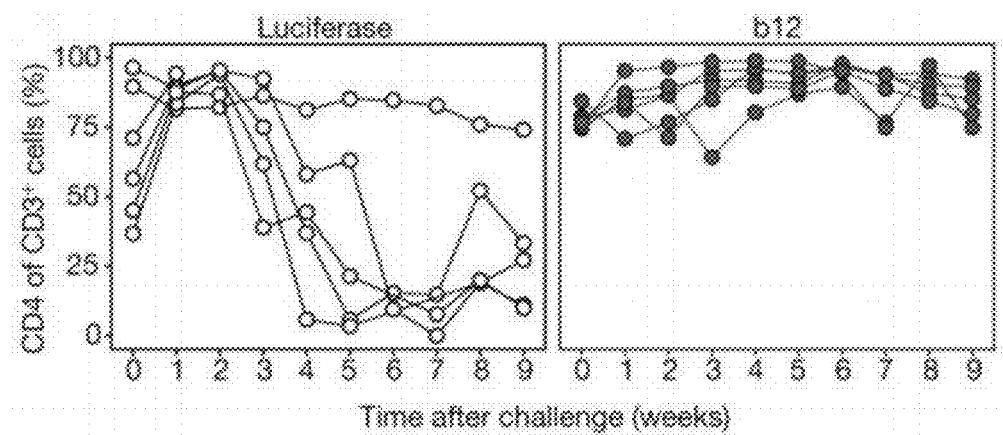

Recombinant AAV viruses expressing either luciferase or b12 antibody were administered to NSG mice, producing stable serum b12 antibody concentrations of approximately 100 μml$^{-1}$ within 6 weeks (FIG. 8A). These mice were adoptively populated with expanded human peripheral blood mononuclear cells (huPBMCs), which engrafted over a period of 2 weeks. Mice were then challenged by intraperitoneal injection of the NL4-3 strain of HIV.

After HIV challenge, most mice expressing luciferase showed dramatic loss of CD4 cells whereas mice expressing b12 antibody showed no CD4 cell depletion (FIG. 8B).

This example demonstrates that the recombinant AAV virus expressing an anti-HIV antibody can protect mice from CD4 cell loss caused by HIV infection.

Example 6

Protection Using Various HIV Neutralizing Antibodies

Figure 9:
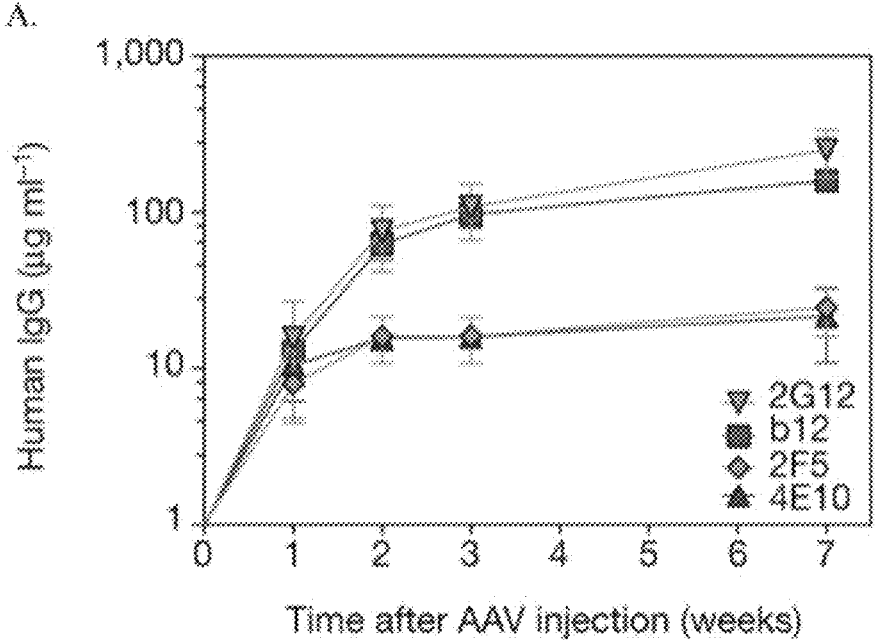
FIG. 9 shows a comparison of protection mediated by various broadly neutralizing HIV antibodies.
Figure 9:
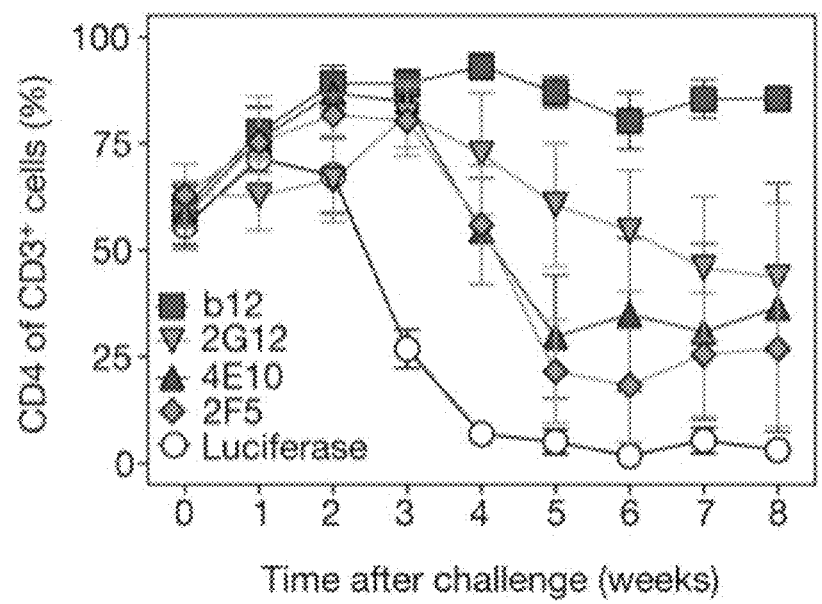
Figure 9:
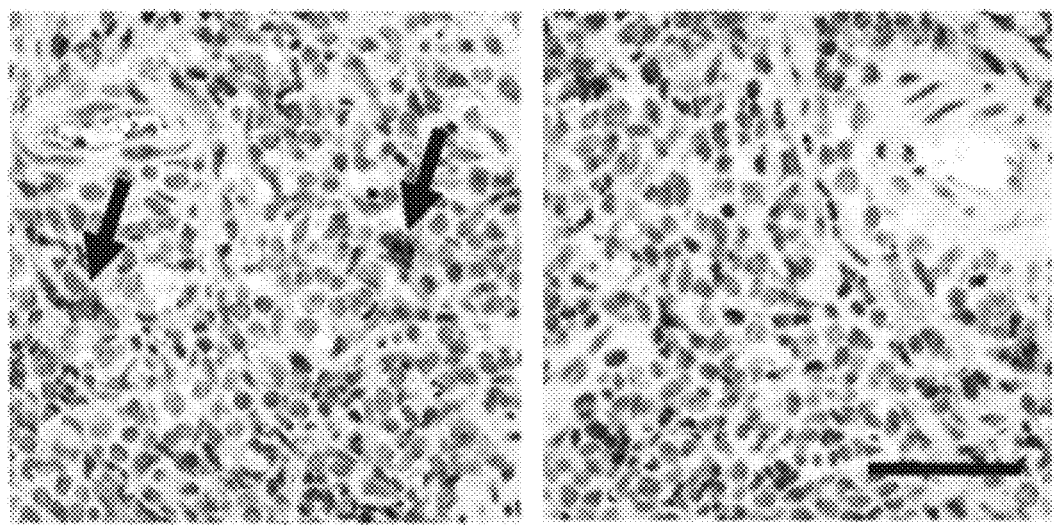
Figure 9:
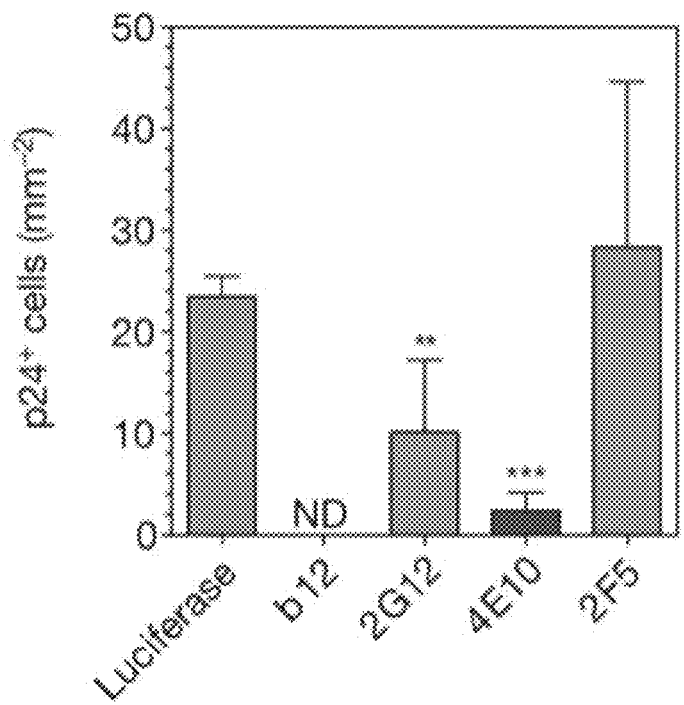

To compare the protective abilities of various broadly neutralizing HIV antibodies, recombinant AAV viruses expressing b12, 2G12, 4E10 and 2F5 were produced and administered to NSG mice, respectively. Seven weeks after administration, NSG mice produced 20-250 μml$^{-1}$ of the indicated antibodies (FIG. 9A). In vivo serum concentrations of each of the HIV antibodies were measured. The results are shown in (FIG. 3A).

Transduced mice were adoptively populated with huPBMCs, challenged by intravenous injection with HIV and sampled weekly to quantify CD4 cell depletion over time (FIG. 9B). As shown in FIG. 9B, animals expressing b12 were completely protected from infection, and those expressing 2G12, 4E10 and 2F5 were partly protected. Groups demonstrating partial protection consisted of animals with delayed CD4 cell depletion as well as animals that maintained high CD4 cell levels throughout the course of the experiment.

Eight weeks after challenge, mice were killed and paraffin-embedded spleen sections underwent immunohistochemical staining for the HIV-expressed p24 antigen to quantify the extent of infection (FIG. 9C). As shown in FIG. 9D, mice expressing b12 had no detectable p24-expressing cells.

Example 7

Determination of the Robustness of Anti-HIV Protection

Figure 10:
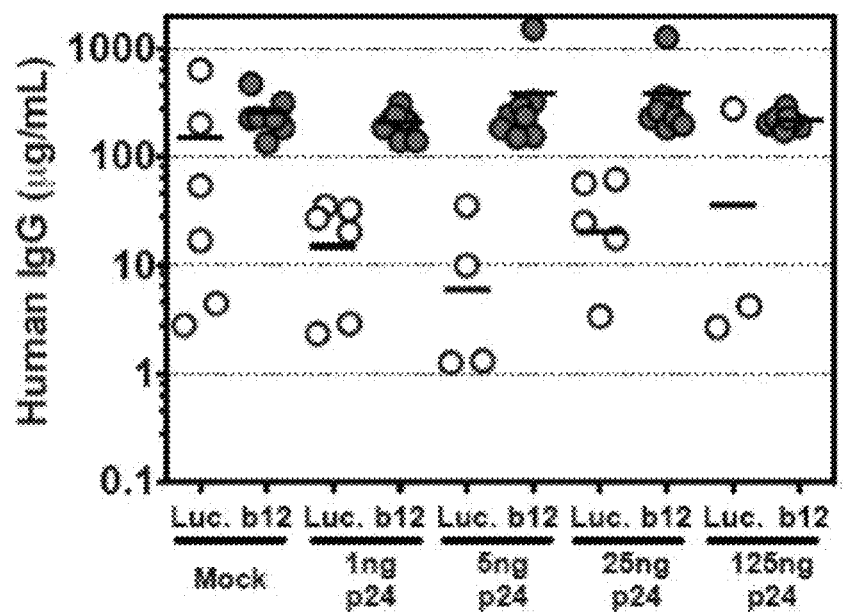
FIG. 10 shows serum concentrations of total human IgG and gp120 binding IgG prior to HIV challenge.
Figure 10:
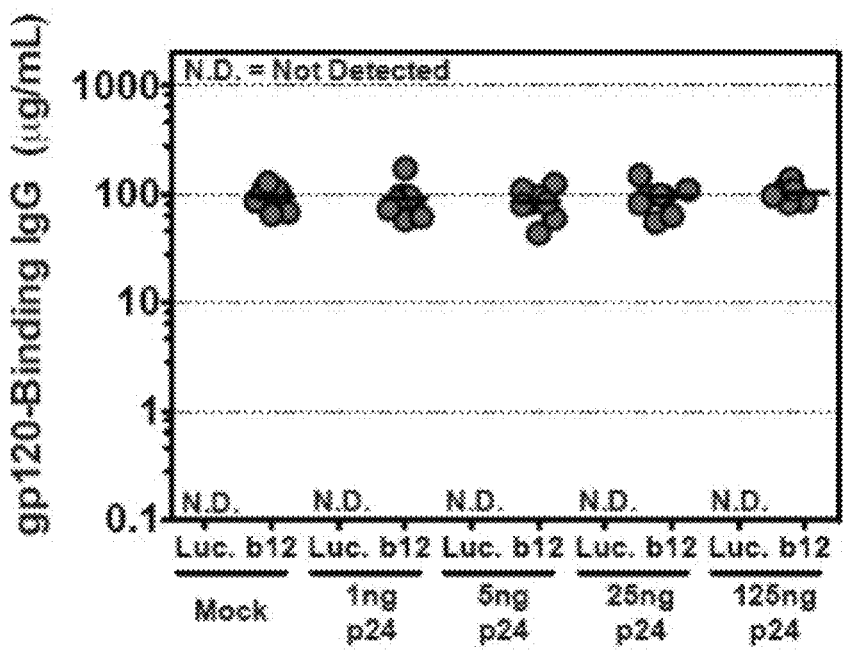

A large cohort of mice expressing b12 antibody were adoptively populated with huPBMCs. Before challenge, all mice expressed high levels of human IgG, presumably owing to engrafted human B-cells (FIG. 10A), but only those receiving the b12-expressing vector produced IgG specific for gp120, which reached 100 μg ml$^{-1}$ (FIG. 10B).

Figure 11:
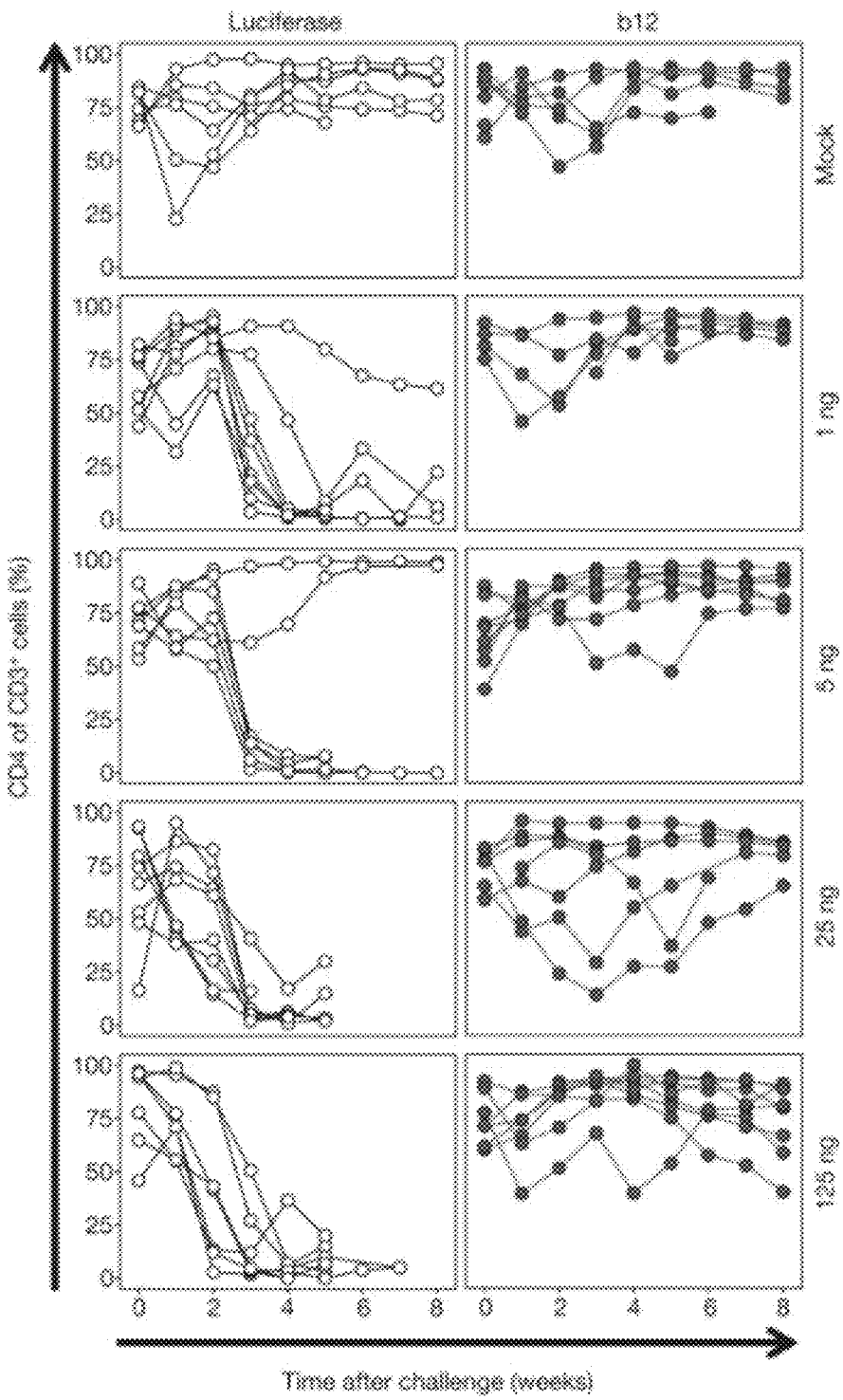
FIG. 11 are graphs showing b12 antibody-mediated CD4 cell protection over time. CD4 cell depletion in huPBMC-NSG humanized mice as a result of intravenous challenge with the dose of NL4-3 indicated on the far right. Mice expressing luciferase (left plots) were susceptible to CD4 cell loss, whereas those expressing b12 (right plots) demonstrated protection from HIV at all doses (n=8).

Mock-infected mice expressing either luciferase or b12 demonstrated consistent high-level CD4 cell engraftment throughout the course of the experiment, showing that transgene toxicity was not contributing to CD4 cell loss (FIG. 11). In contrast, mice expressing luciferase that received 1 ng of HIV experienced rapid and extensive CD4 cell depletion. At higher doses, infection in luciferase expressing mice became more consistent and resulted in depletion of CD4 cells below the level of detection in some cases (25, 125 ng doses). Remarkably, all mice expressing b12 demonstrated protection from CD4 cell loss, despite receiving HIV doses over 100-fold higher than necessary to deplete seven out of eight control animals (FIG. 11).

This example shows that the recombinant AAV virus disclosed herein can be used to provide effective and robust immunoprophylaxis against HIV infection.

Example 8

Expression of b12 Anti-HIV Antibody

Figure 12:
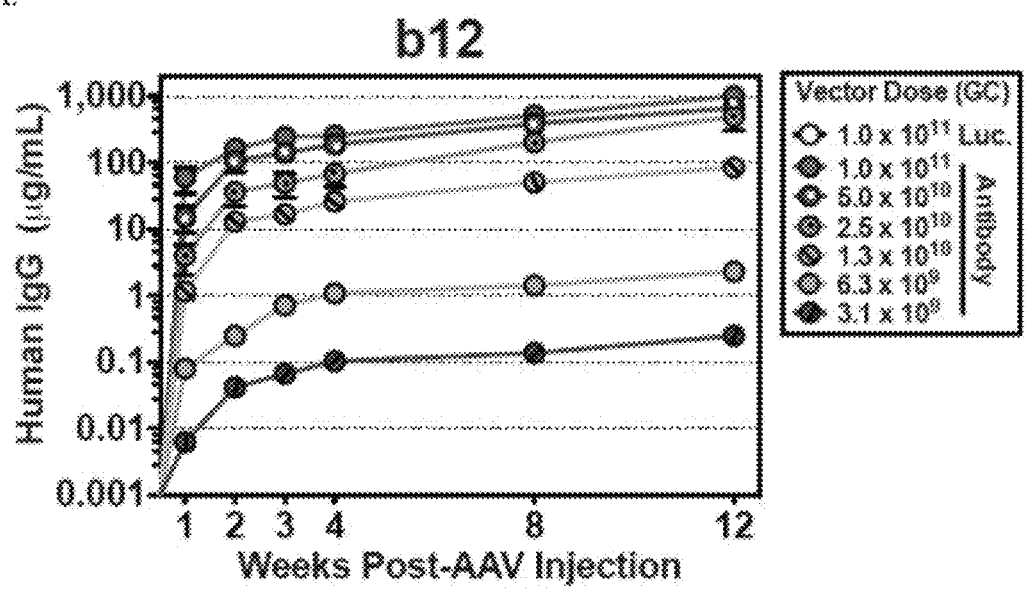
FIG. 12A is a plot showing b12 expression over time as a function of dose as determined by total human IgG ELISA on serum samples taken following AAV administration (n=8). Mice receiving luciferase-expressing vector exhibited no detectable human antibodies (n=12).
FIG. 12B is a graph showing concentration of b12 in serum one day prior to challenge, 3 weeks after adoptive transfer of human PBMCs and 15 weeks after intramuscular administration of the indicated dose of AAV as determined by a gp120-specific ELISA to measure the fraction of antibodies capable of binding HIV (n=8-12).
FIG. 12C is a plot showing CD4 cell depletion in HuPBMC-NSG humanized mice as a result of intravenous challenge with 10 ng of NL4-3 into animals expressing a range of b12 demonstrating the minimum dose of antibody necessary to protect against infection.
Figure 12:
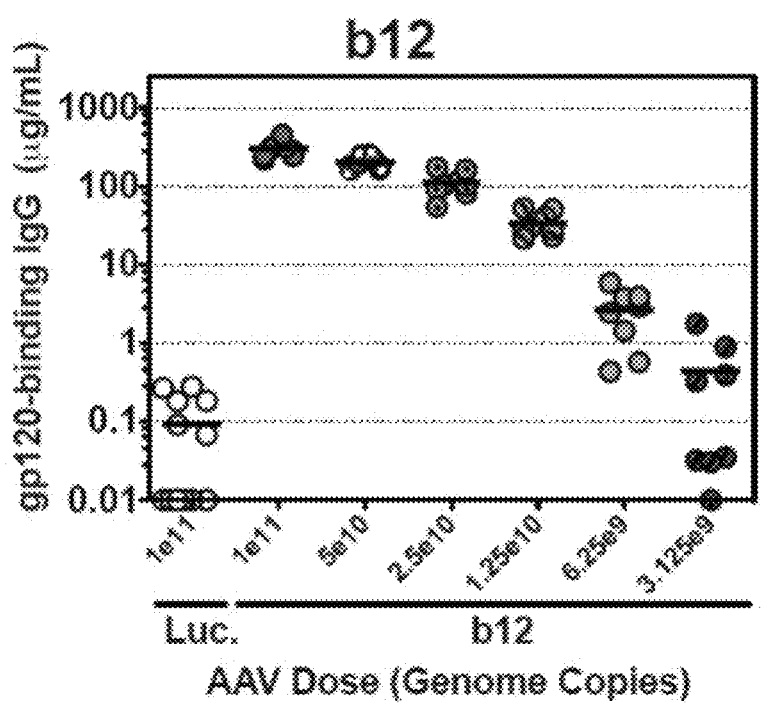
Figure 12:
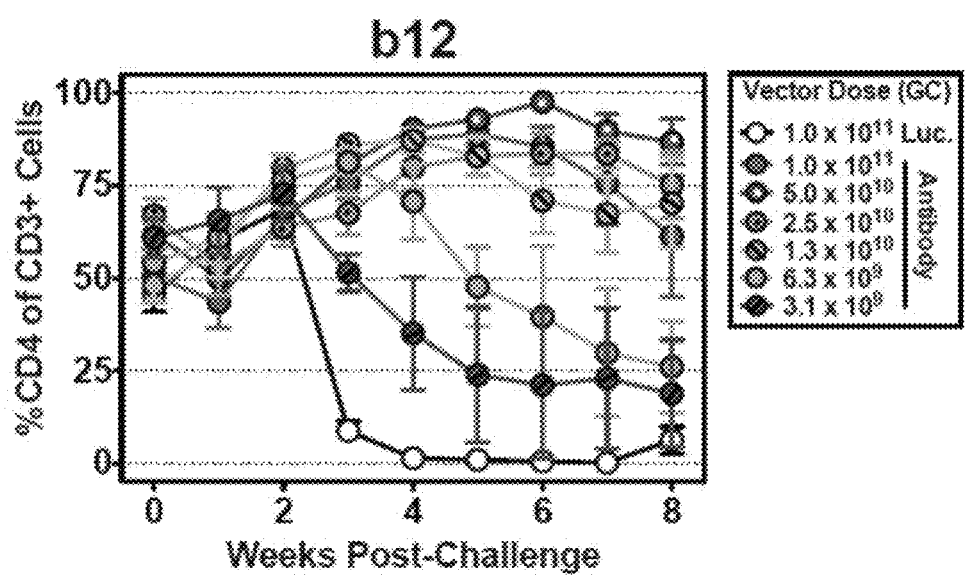

FIG. 12A is a plot showing b12 expression over time as a function of dose as determined by total human IgG ELISA on serum samples taken following AAV administration (n=8).

Mice receiving luciferase-expressing vector exhibited no detectable human antibodies (n=12). FIG. 12B shows concentration of b12 in serum one day prior to challenge, 3 weeks after adoptive transfer of human PBMCs and 15 weeks after intramuscular administration of the indicated dose of AAV as determined by a gp120-specific ELISA to measure the fraction of antibodies capable of binding HIV (n=8-12). FIG. 12C shows CD4 cell depletion in HuPBMC-NSG humanized mice as a result of intravenous challenge with 10 ng of NL4-3 into animals expressing a range of b12 demonstrating the minimum dose of antibody necessary to protect against infection. FIGS. 12A and C show mean and standard error, plot b shows individual animals and mean (n=8-12).

Example 9

Comparison of b12 and VRC01 Antibodies in Anti-HIV Protection

In this examples, b12 antibody was compared with VRC01 antibody, an anti-HIV antibody found to neutralize over 90% of circulating HIV strains in vitro. Decreasing doses of vector expressing either b12 or VRC01 were administered to NSG mice, and expression of the antibodies over time was monitored.

Figure 13:
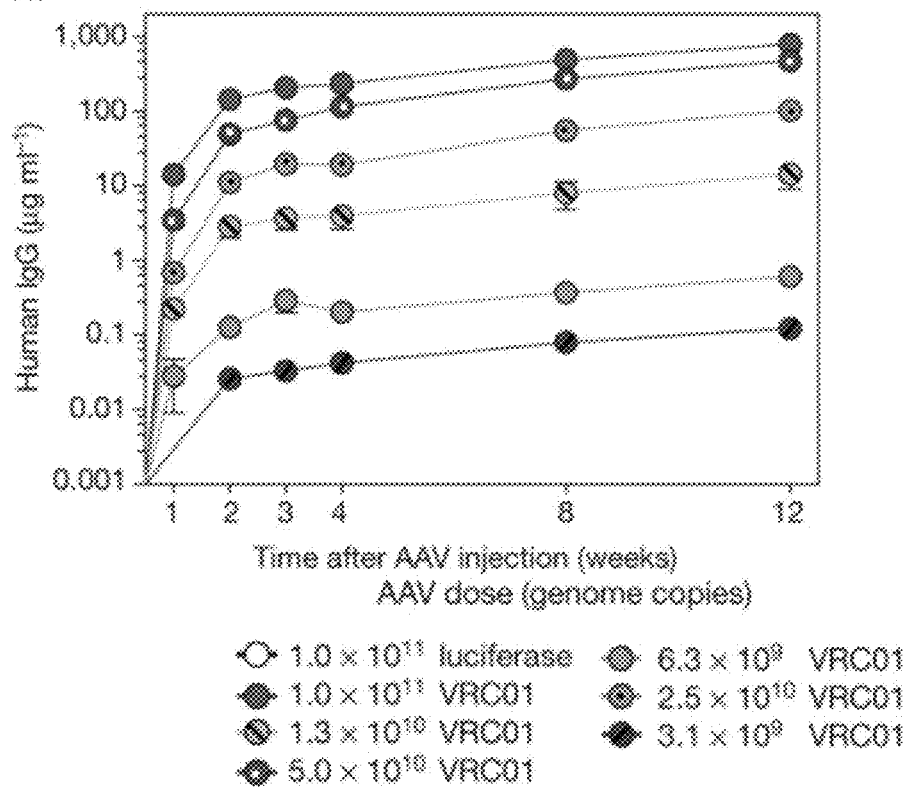
FIG. 13A is a graph showing VRC01 expression over time as a function of dose as determined by total human IgG ELISA on serum samples taken after AAV administration (n=8). Mice receiving luciferase-expressing vector exhibited no detectable human antibodies (n=12).
FIG. 13B is a graph showing concentration of VRC01 in serum 1 day before challenge, 3 weeks after adoptive transfer of human PBMCs and 15 weeks after intramuscular administration of the indicated dose of AAV, as determined by a gp120-specific ELISA to measure the fraction of antibodies capable of binding HIV (n=8-12).
FIG. 13C is a graph showing CD4 cell depletion in huPBMC-NSG humanized mice as a result of intravenous challenge with 10 ng of NL4-3 into animals expressing a range of VRC01, demonstrating the minimum dose of antibody necessary to protect against infection.
Figure 13:
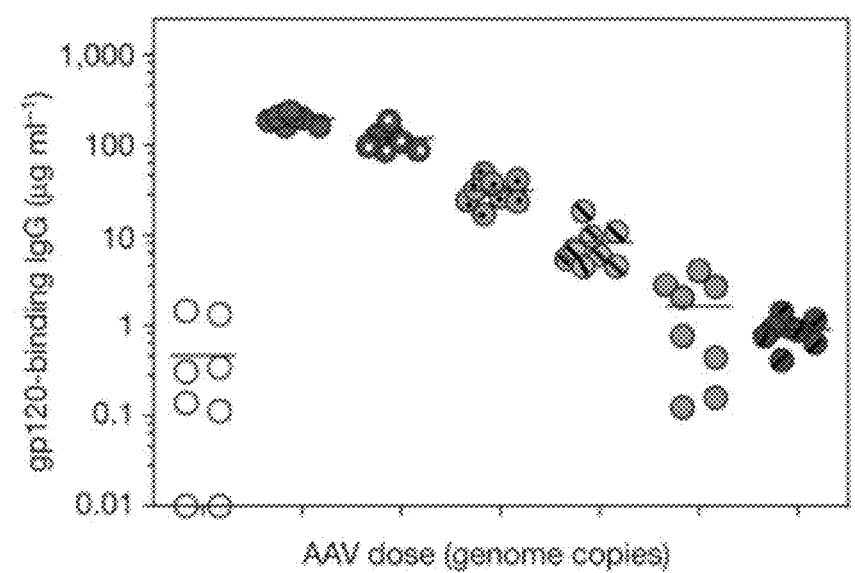
Figure 13:
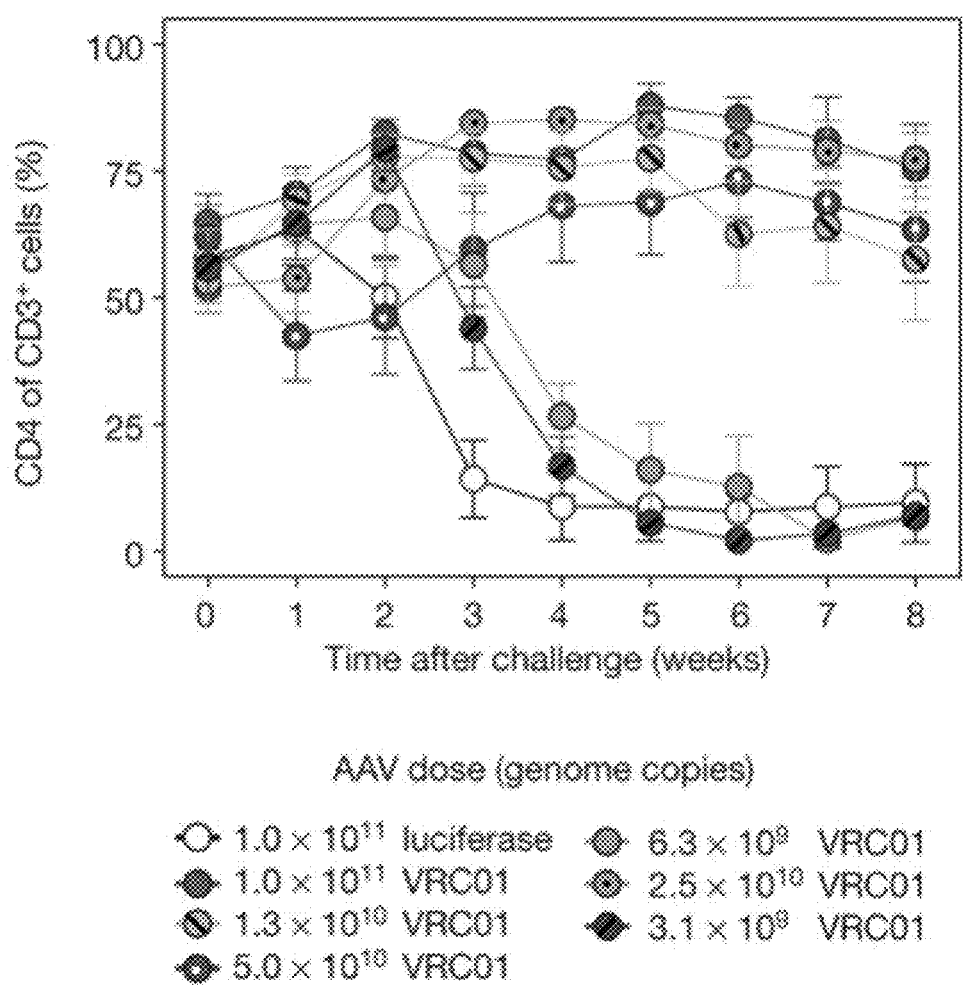

For both antibodies, dose-dependent expression was observed at all time points analysed (FIG. 12A and FIG. 13A). Mice expressing luciferase or antibodies at various levels were adoptively populated with huPBMCs. Just before challenge, a gp120-specific enzyme-linked immunosorbent assay (ELISA) confirmed the effective antibody concentration in each group (FIG. 12B and FIG. 13B). After intravenous challenge with 10 ng of HIV, CD4 cells were monitored to determine the impact of antibody concentration. An average b12 concentration of 34 μg ml$^{-1}$ and VRC01 concentration of 8.3 μg ml protected mice from infection (FIG. 12C and FIG. 13C). Groups expressing lower concentrations of b12 and VRC01 were partly protected, with several animals showing no detectable loss of CD4 cells and others exhibiting delayed CD4 cell depletion.

Example 10

Protection from Influenza Infection

In this example, the AAV vector disclosed herein were used to produce recombinant AAV viruses expressing anti-influenza antibodies, and the recombinant AAV viruses were found to be effective in protecting mice from influenza virus infection.

Experimental Materials and Methods

Influenza Virus Production and Quantification

All influenza viruses used for the mouse infections in this example derived their six internal genes (PB2, PB1, PA, NP, M, and NS) from the A/Puerto Rico/8/1934 (H1N1) strain. The HA and NA genes were derived from the following three strains and given the following name abbreviations:

(1) PR8: the HA and NA derived from A/Puerto Rico/8/1934 (H1N1), a widely used lab-adapted strain.

(2) CA/09: the HA and NA derived from A/California/07/2009 (H1N1), a strain isolated early during the emergence in humans of the 2009 swine-origin H1N1 pandemic.

(3) SI/06: the HA and NA derived from A/Solomon Islands/3/2006 (H1N1), a human seasonal H1N1 vaccine strain.

The influenza viruses were generated using the 8-plasmid bidirectional reverse-genetics system. Briefly, 293T and MDCK cells were maintained in DMEM (Mediatech) supplemented with 10% fetal bovine serum (Omega Scientific), 100 IU/mL penicillin (Mediatech), 100 μg/mL streptomycin (Mediatech), and 1% L-glutamine (Mediatech). 6-well tissue culture dishes (Corning) containing co-cultures of 293T and MDCK cells were co-transfected with 250 ng of each of the 8 plasmids. At 14 hours post-transfection, the media was aspirated, the cells were washed once with PBS, and influenza growth medium plus 3 μg/mL of TPCK-treated trypsin (Sigma-Aldrich) was added to the cells. Influenza growth medium consists of Opti-MEM I (Invitrogen) with 0.01% fetal bovine serum, 0.3% bovine serum albumin (Invitrogen), 100 IU/mL penicillin, 100 μg/mL streptomycin, and 100 μg/mL calcium chloride. After 72 hours, the supernatant was collected and passaged to 15 cm dishes (Corning) containing nearly confluent MDCK cells in influenza growth medium plus 3 μg/mL trypsin. After 72 hours, the viral supernatant was harvested and centrifuged at 2,000×g for 5 minutes. The viral supernatant was removed and aliquoted, and the aliquots were frozen at −80° C.

Plaque Assays

The influenza viruses were quantified by plaque assays on MDCK cells using an Avicel microcrystalline cellulose overlay. Briefly, MDCK cells were seeded into E-well tissue culture dishes. When the cells were 95% confluent, the media was removed and serial 10-fold dilutions of viral inoculum were added to a 1 mL final volume of influenza growth medium. After 40 minutes, the inoculum was removed by aspiration and replaced by 4 ml of influenza growth media with 2.4% Avicel microcrystalline cellulose and 3 μg/ml of TPCK-treated trypsin. The plates were grown undisturbed for 3 days a 37° C. The overlay was then removed by aspiration, the cell layer was washed twice with PBS, and the cells were stained with 0.1% crystal violet in 20% ethanol for 15 minutes. This staining solution was then removed by aspiration, the cells were washed again with PBS, and the plaques were counted visually to determine the viral titer in terms of plaque forming units (PFU).

Mouse Strains

Immunocompetent BALB/cJ (BALB/c) and immunodeficient NOD/SCID/γ$^{-/-}$ (NSG) mice of approximately 4-5 weeks of age were obtained from the Jackson Laboratory (JAX). For experiments involving aged mice, these animals were bred and housed under barrier conditions for the period of time prior to influenza challenge.

Cloning of Influenza Neutralizing Antibodies into AAV Vector

Sequences corresponding to the heavy and light chain variable regions of various influenza antibodies were synthesized (Integrated DNA Technologies) and cloned into an AAV transfer vector containing the IgG1 constant region framework. In some instances, the antibody gene was optimized to improve antibody production in vivo.

AAV Production and Administration to Mice

AAV production and intramuscular injection were performed according to the procedure described as follows. Briefly, 1.2×10$^8$ 293T cells were transfected with 80 μg of the vector encoding the antibody of interest, pHELP (Applied Viromics), and pAAV 2/8 SEED (University of Pennsylvania Vector Core) at a ratio of 0.25:1:2. Supernatant was collected 5 times over the course of 120 hours. Virus was purified by PEG precipitation and cesium chloride fractionation before being diafiltrated, concentrated, and buffer exchanged through 100 k MWCO centrifuge filters (Millipore) into buffer consisting of 100 mM sodium citrate and 10 mM Tris pH 8 prior to aliquoting and storage at −80° C. To quantify aliquots, virus was thawed, treated with DNAse, and titered by qPCR as previously described (13). Briefly, virus titer was determined by quantitative PCR using a standard curve generated from previously-titered, purified, AAV2/8 encoding 4E10 antibody. Infectivity of virus aliquots was confirmed in vitro by transducing 293T cells and quantifying antibody concentration in the cell supernatant by ELISA.

AAV Transduction of Mice and Quantitation of Gene Expression

Prior to intramuscular injection, recombinant AAV viruses were thawed and diluted to the indicated dose with buffer (100 mM sodium citrate, 10 mM Tris pH 8) in a 40 µL volume. Mice were anesthetized by isofluorane inhalation, and viruses were administered as a single injection of 40 uL into the gastrocnemius muscle.

Bioluminescent imaging and was performed using an IVIS 200 instrument essentially as previously described with the following modifications: Bioluminescent images were taken 10 minutes after intraperitoneal injection of 1.5 mg D-luciferin (Gold Biotechnology). The concentration of human IgG in mouse serum was determined by performing ELISAs using a standard curve generated from purified Human IgG/Kappa (Bethyl).

Challenge of Mice with Influenza

Influenza viruses were thawed and diluted in PBS to deliver the indicated dose in a 20 µL volume. Prior to inoculation, mice were weighed and anaesthetized by intraperitoneal injection of 200 µL of a cocktail containing 2 mg of ketamine and 0.2 mg xylazine diluted in PBS. Mice were challenged with influenza by intranasal inoculation with 20 µL of diluted virus, 10 µL per nostril. Infected mice were weighed at the same time each day.

GFP Influenza Virus Production and Quantification

PB1flank-GFP influenza viruses were generated in which GFP is packaged in the PB1 segment according to the methods described in Bloom et al. Science 328:1272 (2010). PB1flank-GFP viruses were grown and assayed in 293T-CMV-PB1 and MDCK-SIAT1-CMV-PB1 cells that supplied the missing PB1 protein in trans, as described in Bloom et al. PB1flank-GFP viruses were generated using the 8-plasmid bidirectional reverse-genetics system, but with the standard PB1 plasmid replaced by pHH-PB1flank-eGFP. For these viruses, the other five internal genes (PB2, PA, NP, M, and NS) were derived from the PR8 strain as for the viruses used in the mouse infections. In addition to viruses with the HA and NA from PR8, CA/09, and SI/06, two additional viruses were used in these assays:

(1) JP/57: the HA and NA derived from A/Japan/305/1957 (H2N2), an early strain from the Asian Flu pandemic.

(2) Viet/04: the HA from A/Vietnam/1203/2004 (H5N1), a highly pathogenic avian influenza strain. The NA for this virus was derived from the lab-adapted A/WSN/1933 (H1N1) strain. The polybasic cleavage site was removed from the HA.

PB1flank-GFP viruses were quantified by flow cytometry. MDCK-SIAT1-CMV-PB1 cells were seeded in 12-well dishes (Corning) at 105 cells per well in 1 mL of influenza growth medium. 8 hours after seeding, viruses were diluted 1:10, 1:100, and 1:1000 in media. Wells were infected with 50 µL of each of these dilutions. Cells were harvested 16.5 h post-infection by incubation with 250 uL of trypsin-EDTA (Invitrogen) for five minutes, removal of trypsin by aspiration, and re-suspension in 250 µL of PBS supplemented with 2% fetal bovine serum and 2 µg/mL propidium iodide (Invitrogen). Samples were analyzed on a FACSCalibur flow cytometer (Beckton-Dickinson), and samples with a percentage of GFP-positive cells between 0.3-3% were used to quantify viral titer. Titer was calculated from the percentage of GFP-positive cells, the dilution factor, and the total count of $10^5$ cells per well.

Neutralization Assays

Neutralization assays were performed using PB1flank-GFP influenza viruses and MDCK-SIAT1-CMV-PB1 cells. 40 µL of influenza growth medium were added to all wells of a flat-bottom 96-well tissue culture dish (Corning), except for Row A, which received 57 µL of media. Mouse sera samples were serially diluted by adding 3 µL of serum to the 57 µL of influenza growth medium in Row A, then performing 1:3 serial dilutions down to Row G, resulting in an initial dilution of 1:20 and final dilution of $1:4.374 \times 10^4$. $2 \times 10^4$ infectious particles of PB1flank-GFP virus (as determined by flow cytometry titering) were added to samples in a 20 µL volume of influenza growth medium. The mixtures of diluted serum and virus were incubated for 1 h in a 5% CO2 incubator at 37° C. After incubation, $2 \times 10^4$ MDCK-SIAT1-CMV-PB1 cells in a 20 µL volume of influenza growth medium were added to all wells for an MOI of 1. A cell-only control, which received naive BALB/c mouse serum and no virus, and a virus control, which received naive BALB/c mouse serum, were included for each virus. Plates were incubated in a 5% $CO_2$ incubator at 37° C. for 18 hours. Post-incubation, 40 µL of 1.5% Triton X-100 (Sigma-Aldrich) in PBS was added to each well to give a final concentration of 0.5% Triton X-100, and plates were incubated at room temperature for 5 minutes. 100 µL of each sample was transferred into opaque 96-well plates (Corning) for reading. GFP fluorescence was quantified using a Safire2 plate reader (Tecan) configured to read from the top with an excitation of 485 nm, emission of 515 nm, 12 nm slit widths for both excitation and emission, gain set to "optimal," an integration time of 500 µs, and 5 reads per well. Baseline fluorescence from the cell-only control was subtracted from all readings. Samples were normalized to the virus control.

Histology

At the conclusion of the in vivo challenge experiments, lungs were removed from mice and half of this tissue was immersed in 10% neutral buffered formalin for 24 hours. Following fixation, tissues were removed from formalin and placed in 70% ethanol until standard paraffin embedding and processing. Four-micron thick sections were then taken, and hematoxylin and eosin staining (H&E) staining was performed. The slides were reviewed by a pathologist (D.S.R.) on an Olympus BX51 light microscope, and images were obtained using a SPOT Insight Digital Camera (Diagnostic Instruments). Inflammation was scored as follows: 0=no to minimal inflammation; 1=occasional infiltrates in bronchioles (less than 10% of bronchioles); 2=easily identified infiltrates in bronchioles (10-50% of bronchioles); 3=easily identified infiltrates in bronchioles with parenchymal infiltrates and/or early patchy fibrosis; 4=>50% of bronchioles with infiltrates, OR 10-50% bronchiole involvement with extensive necrotic epithelium in bronchioles, angionecrosis, or extensive fibrosis. Scoring was done in a blinded fashion and an ordinal scale was assumed for any statistical tests.

Relative Viral Quantification by RT-qPCR

Lung tissue was homogenized in 100 µL PBS. 25 µL of homogenate was used for RNA extraction via TRIzol Reagent (Invitrogen). Purified RNA was re-suspended in nuclease-free water, and RNA concentration was normalized to 150 ng/µL. Real-time RT-qPCR was performed using qScript One-Step SYBR Green qRT-PCR Kit, Rox (Quanta Biosciences) with primers designed against PR8 M and an endogenous control consisting of mouse ribosomal protein L32. Forward-M: CAAGCAGCAGAGGCCATGGA (SEQ ID NO: 36), Reverse-M: GACCAGCACTGGAGCTAGGA (SEQ ID NO: 37), Forward-L32: AAGCGAAACTGGCG-GAAAC (SEQ ID NO: 38), Reverse-L32: TAACCGATGT-TGGGCATCAG (SEQ ID NO: 39). Samples were DNAse-treated using Turbo DNAse kit (Invitrogen) and run in triplicate on an ABI 7300 Real-Time PCR System (Life Technologies) with the following program: 50° C. for 10 minutes, 95° C. for 5 minutes, 40 cycles of 95° C. for 15 seconds and 55° C. for 30 seconds, followed by a melt curve analysis. Each sample was individually normalized by L32 signal to account for variation in input RNA.

Expression of Anti-Influenza Antibody In Vivo

Figure 14:
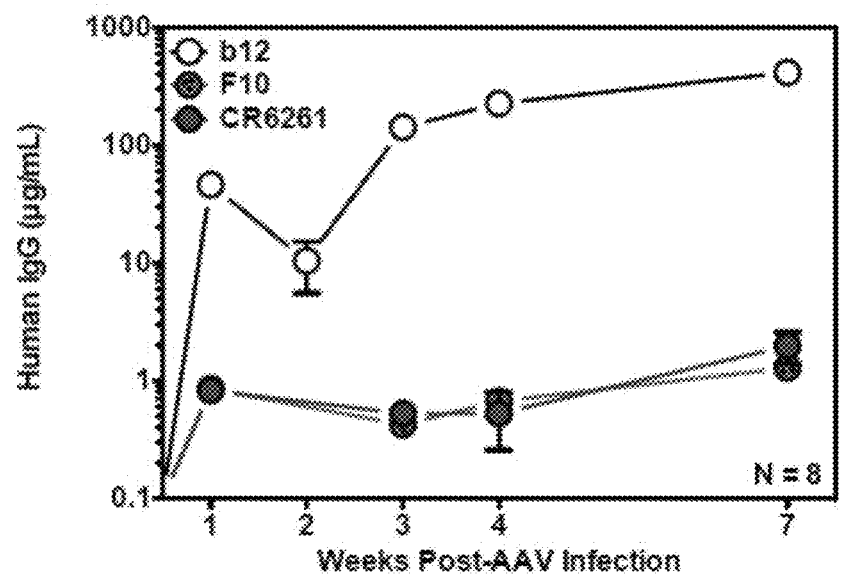
FIG. 14 is a graph showing quantitation of human IgG in serum by ELISA following intramuscular injection of $1\times10^{11}$ genome copies (GC) of recombinant AAV viruses expressing unmodified b12, F10, or CR6261 antibodies in Balb/C mice (plot shows mean and standard error, n=8).

Recombinant AAV viruses expressing unmodified full-length F10 or CR6261 anti-influenza antibody were produced. A single intramuscular injection of $1 \times 10^{11}$ genome copies (GC) of the recombinant AAV virus was administered into the gastrocnemius muscle of Balb/c mice. Serum samples were obtained weekly and human IgG was quantified by ELISA (FIG. 14). Significant expression of the b12 antibody above 100 μg/mL was observed. In contrast, both F10 and CR6261 antibodies demonstrated approximately 1 μg/mL of expression at one week that became undetectable at the following time point prior to slowly rising to several micrograms per mL of serum by week 7.

Figure 15:
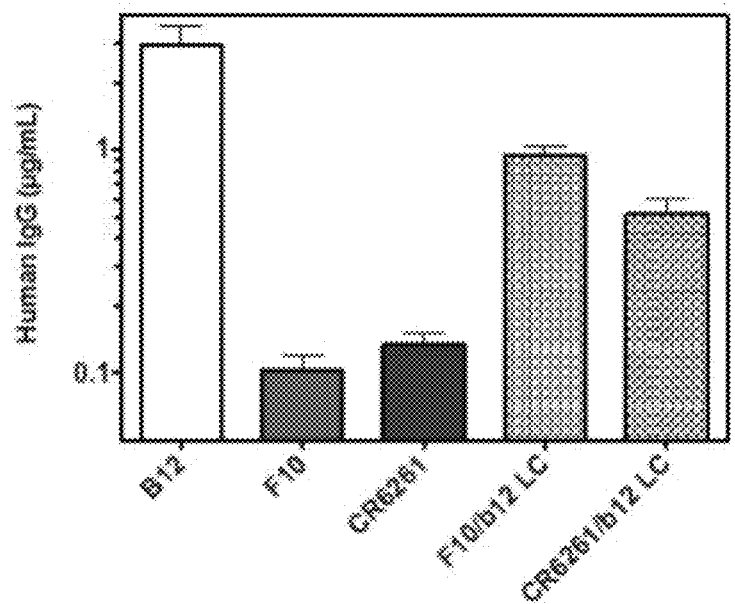
FIG. 15 shows the increased expression of modified F10 and CR6261 antibodies.
Figure 15:
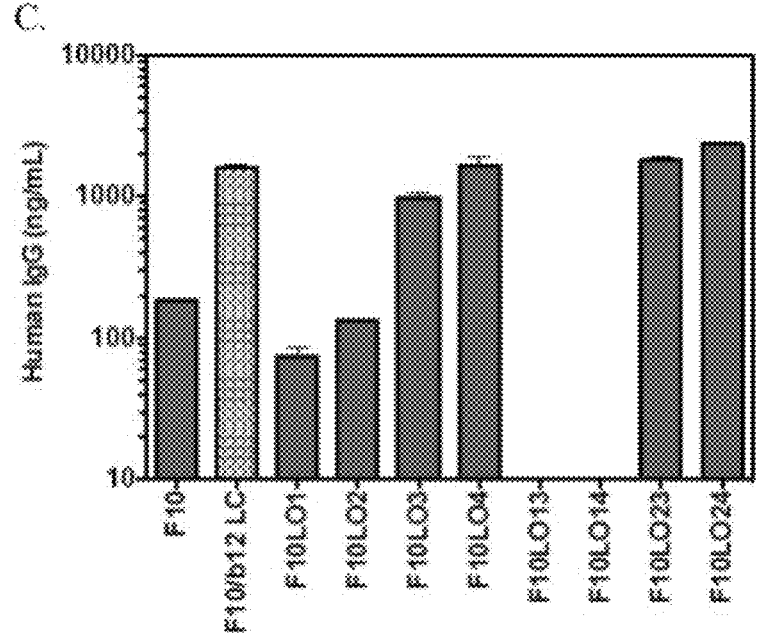
Figure 15:
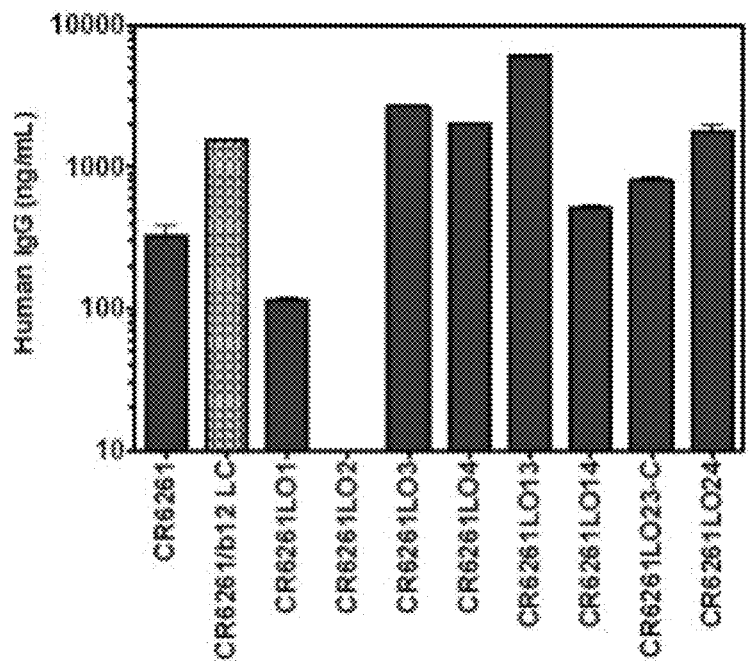

To improve the in vivo expression of F10 and CR6251 antibodies, chimeric antibody constructs in which the light chains of each of the F10 and CR6251 antibodies were replaced with the light chain of b12. Following transfection of 293T cells, substantially higher expression of both antibodies were observed when paired with b12 light chains, indicating that the non-native light chain improved antibody expression (FIG. 15A). To improve expression of the natural light chains, a set of modified light chain variable regions containing 5' and 3' junctional sequences derived from the light chains of either b12 or 4E10 antibodies was created. The modified light chain variable regions used are listed in FIG. 15B. Following transfection of 293T cells, the F10LO24 light chain containing sequences from b12 as well as 4E10 exhibited as much as 12-fold higher expression in vitro (FIG. 15C]). Likewise, transfection of constructs containing CR6261LO13 light chain with sequences from b12 antibody exhibited as much as 20-fold higher expression in vitro (FIG. 15D). These modified antibodies were tested using in vitro neutralization assays, and the results confirmed that antibodies containing modified light chains maintained their ability to neutralize two strains of influenza. In light of the substantially improved antibody expression observed for modified light chains, all subsequent experiments were carried out with the F10LO24 and CR6261LO13 modified sequences and referred to as F10 and CR6261 respectively. The complete variable region sequences used, including the chimeric light chain variable regions, are provided in SEQ ID NOs: 40-43.

Figure 16:
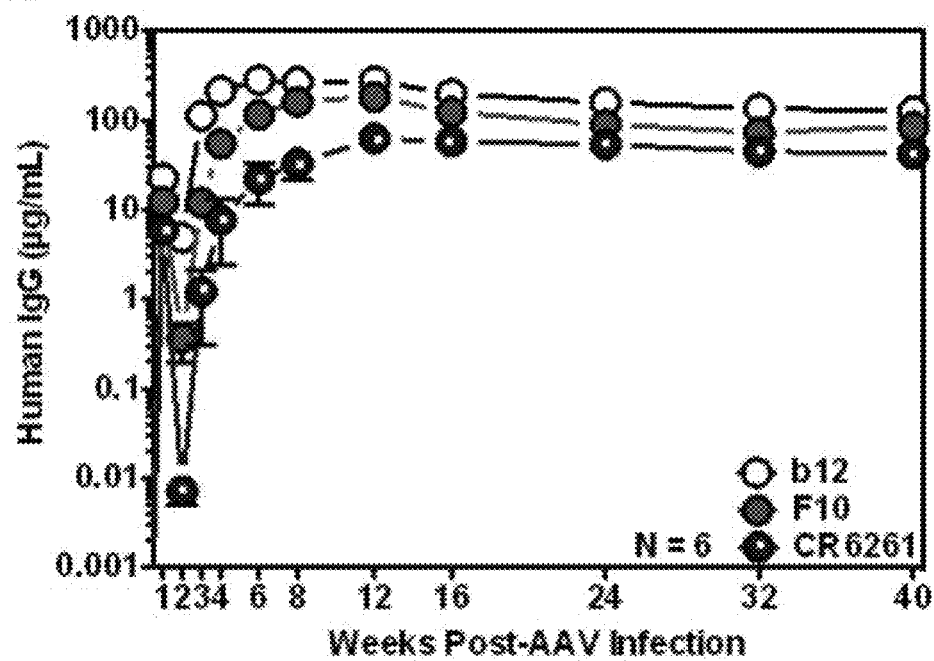
FIG. 16A is a graph showing quantitation of human IgG in serum by ELISA following intramuscular injection of $1\times10^{11}$ GC of the optimized expression vector producing b12, F10, or CR6261 antibodies in Balb/C mice (plot shows mean and standard error, n=6).
FIG. 16B is a plot showing neutralizing activity of sera taken from mice given VIP expressing b12, F10, or CR6261 antibodies as measured against five strains of influenza (PR/8, CA/09, SI/06, VN/04, JP/57) using a GFP reporter assay. Values are calculated as the fold dilution of serum that resulted in 50% neutralization of influenza infection. Dashed line represents the lowest dilution tested (20-fold) and values below this line are extrapolated from the curve fit or are plotted along the axis to represent no detectable neutralization activity.
Figure 16:
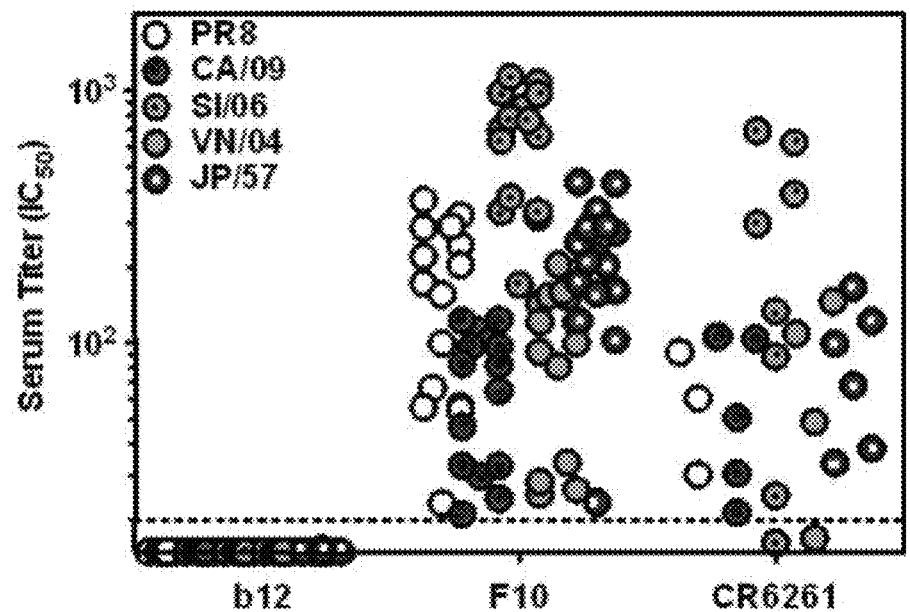

As shown in FIG. 16A, a single intramuscular injection of 1×1011 genome copies (GC) of AAV into BALB/c mice produced detectable antibody within one week of injection. Antibody concentrations transiently declined prior to increasing over the following 6-8 weeks, reaching a plateau between 50-200 μg/mL that was maintained for the duration of the 40 week study.

In Vitro Neutralization Assays

To determine the breadth of neutralizing potential of sera from animals treated with the recombinant AAV viruses, in vitro neutralization assays were performed using GFP-reporter influenza virions containing five diverse hemagglutinins from three different HA subtypes (H1, H2, and H5). As shown in FIG. 16B, sera from mice expressing a negative control antibody (b12, an antibody against HIV) demonstrated no appreciable neutralization of any of the five strains tested. In contrast, sera from animals receiving recombinant AAV viruses expressing either F10 or CR6261 showed significant ability to neutralize all five strains.

In Vivo Protection

Figure 17:
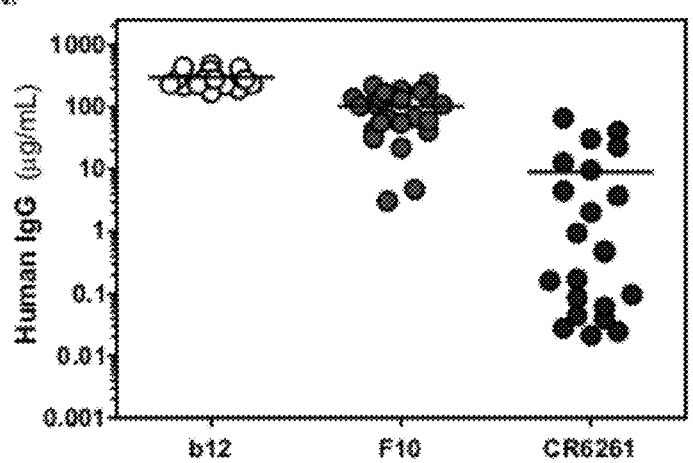
FIG. 17A is a graph showing concentration of human IgG in circulation as measured by total human IgG ELISA in serum samples taken 5 weeks after intramuscular injection of vector expressing b12, F10, or CR6261 and two days prior to viral challenge.
FIG. 17B is a graph showing weight loss observed in Balb/C mice following intranasal challenge with $1\times10^4$ PFU of CA/09 influenza in animals that received VIP expressing control (b12) or F10-IgG (n=8).
FIG. 17C is a graph showing correlation of weight loss 4 days post challenge with CA/09 and CR6261-IgG concentration. d, Weight loss observed in Balb/C mice following intranasal challenge with $5\times10^4$ PFU of SI06 in animals that received VIP expressing control (b12) or F10-IgG (n=8).
FIG. 17D is a graph showing survival rate in Balb/C mice expressing b12 and F10 following intranasal challenge of PR/8.
FIG. 17E is a graph showing weight loss observed in Balb/C mice following intranasal challenge with 1000 PFU of PR/8 in animals that received VIP expressing control (b12) or F10 (n=8).
FIGS. 17F-G are plots showing in vitro neutralization of five strains of influenza (PR/8, CA/09, SI/06, VN/04, JP/57) as detected by GFP reporter assays using serums taken from animals receiving recombinant AAV expressing either b12, F10 or CR6261 following CA/09 (FIG. 17F) or SI06 (FIG. 17G) challenge. Values are calculated as the fold dilution that resulted in 50% neutralization of influenza infection. Dashed line represents the lowest dilution tested (20-fold dilution) and values below this line are extrapolated from the curve fit or are plotted along the axis to represent no detectable neutralization activity.
Figure 17:
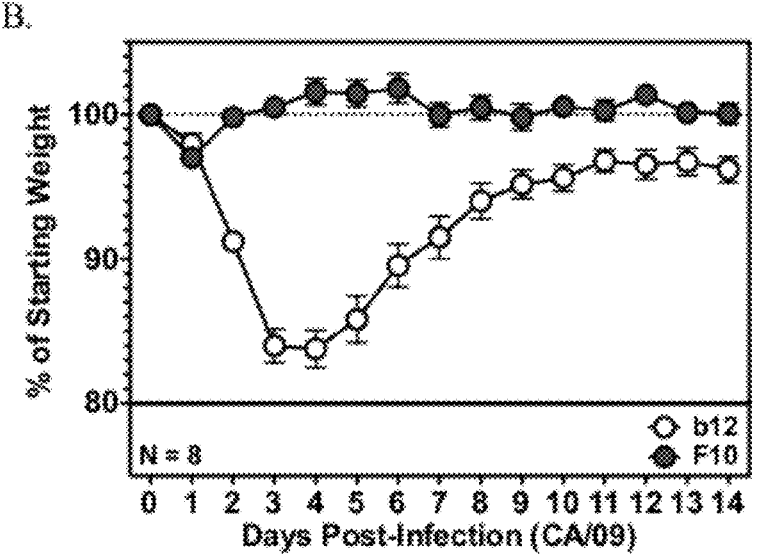
Figure 17:
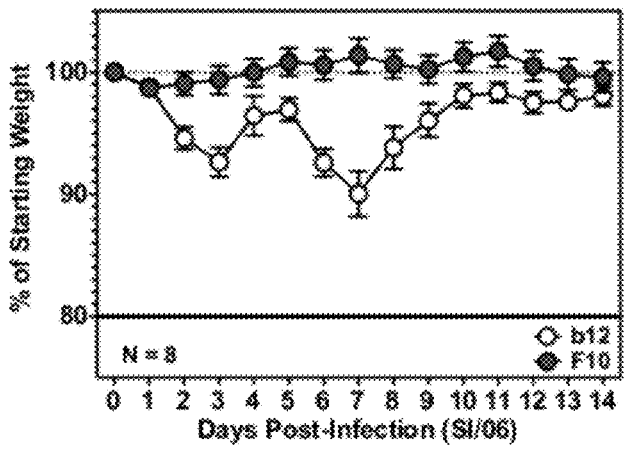
Figure 17:
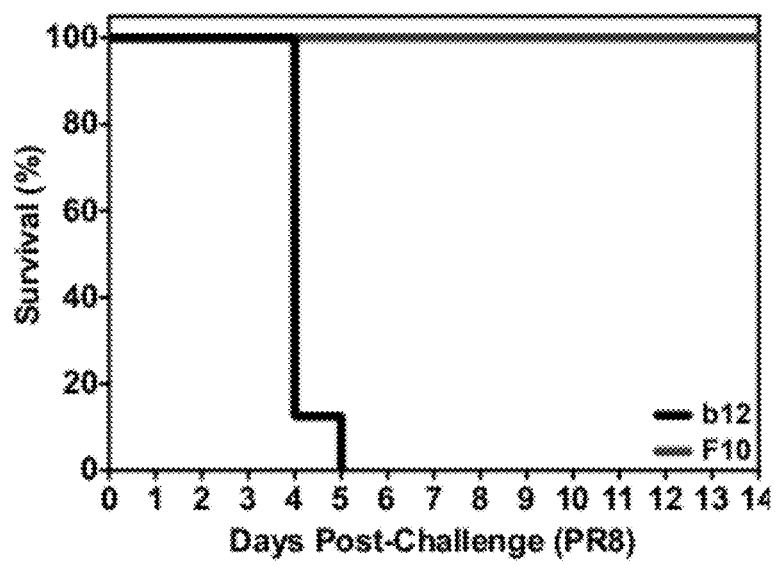
Figure 17:
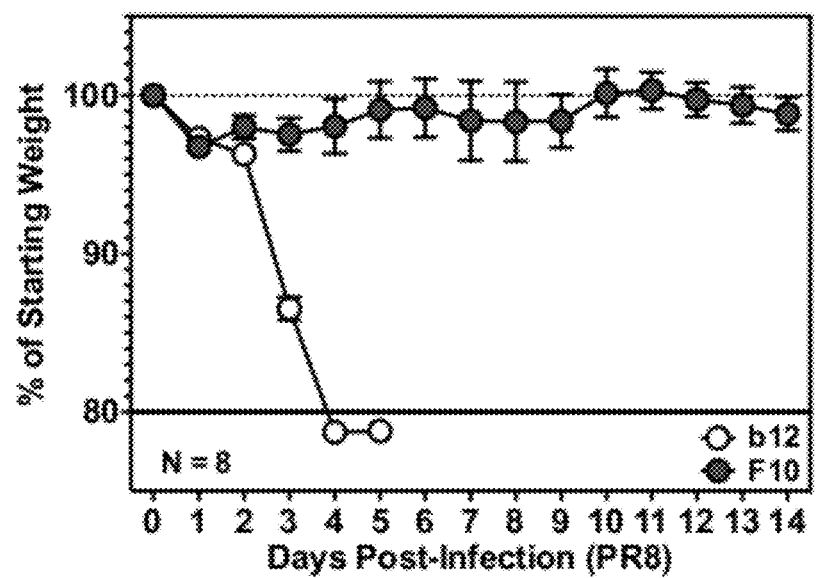
Figure 17:
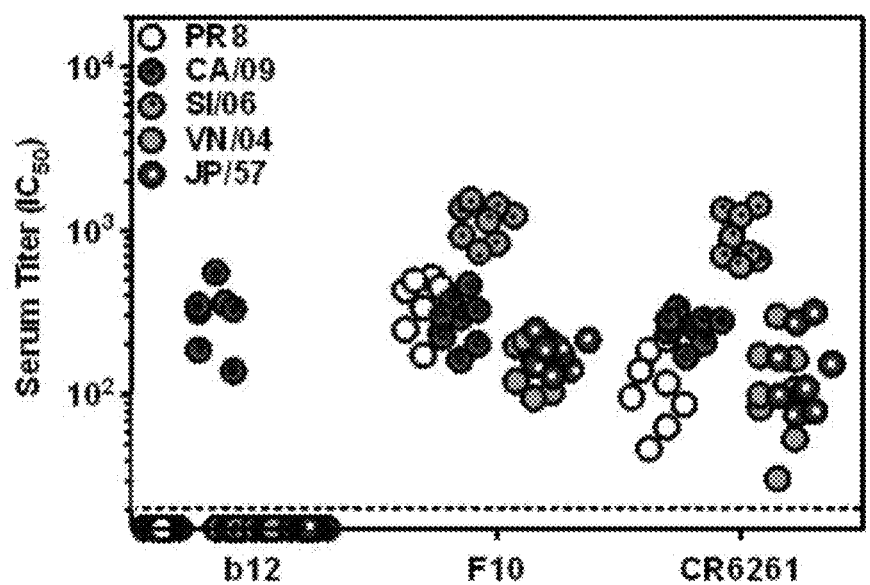
Figure 17:
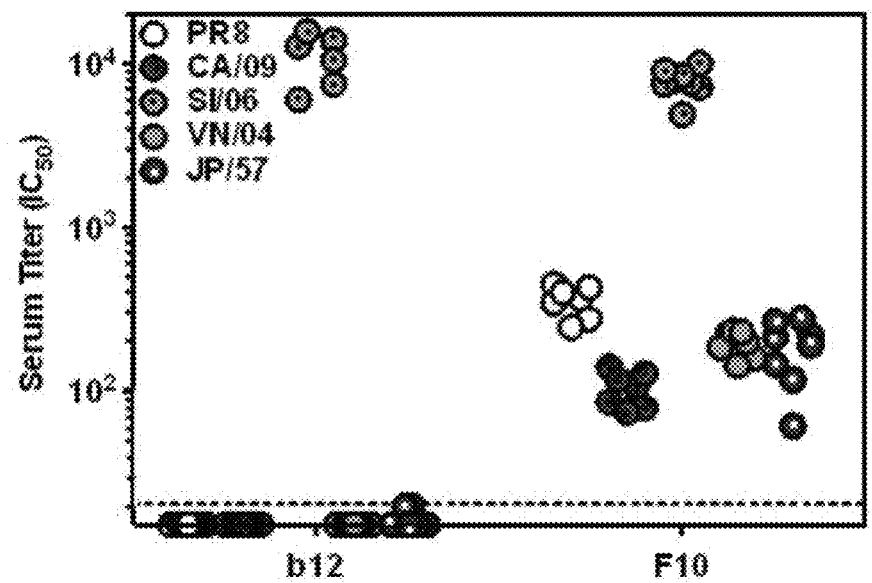

To determine the ability of the recombinant AAV viruses to protect mice from influenza infection, the recombinant viruses were administered to animals and allowed five weeks for antibody expression. Just prior to influenza challenge, approximately 100-200 μg/mL of both b12 and F10 antibodies and a broad range of CR6261 concentrations ranging from 0.1 μg/mL to 100 μg/mL were observed in the circulation of mice (FIG. 17A). Following intranasal administration of the CA/09 strain, a dramatic loss of weight was observed in animals expressing the control b12 antibody, but no appreciable loss in mice expressing F10 antibody (FIG. 17B). Mice expressing CR6261 demonstrated a range of weight loss that was inversely proportional to the serum IgG concentration, suggesting that a minimum serum concentration of approximately 7.5 μg/mL of this antibody was required to prevent illness from CA/09 infection.

To examine the ability of VIP to protect against other strains in vivo, animals expressing b12 control or F10 antibody were challenged with the SI/06 strain (FIG. 17C). Mice expressing the control antibody exhibited weight loss over a period of two weeks. In contrast, mice expressing F10 showed no signs of illness following SI/06 challenge.

To determine the ability of VIP to protect animals from a lethal influenza challenge, 1000 PFU of the mouse-lethal PR/8 strain were intranasally administered to the animals. Mice expressing b12 control experienced a dramatic loss of weight and reached the endpoint of our study within 4 days (FIGS. 17D-E). In contrast, mice expressing F10 showed no significant signs of illness or weight loss, demonstrating that the animals treated with the recombinant AAV viruses were protected against at least three diverse influenza strains.

To determine the impact of CA/09 and SI/06 challenge on the endogenous immune response in influenza-challenged mice, serum samples from such animals were analyzed using neutralization assays. Sera from previously challenged mice expressing the control b12 antibody demonstrated strong neutralizing activity against the challenge strain, but no detectable activity against heterologous strains (FIGS. 17F-G). In contrast, mice treated with recombinant AAV viruses expressing F10 or CR6261 continued to demonstrate broad serum neutralizing activity against all strains tested. Also, while serum neutralizing activity against PR8, VN/04 and JP/57 was not differentially affected by CA/09 or SI/06 challenge, enhanced serum neutralizing activity against the challenge strain was observed in mice treated with the recombinant AAV viruses (Compare FIGS. 17F and 17G). These results suggests that expression of broadly neutralizing antibodies protected against illness, yet still allowed for the formation of additional, even more potent, endogenous humoral immunity.

This example shows that the recombinant AAV virus disclosed herein can be used to provide effective immunoprophylaxis against infection caused by various influenza viruses.

Example 11

Protection from Influenza Infection in Older and Immunocompromised Animals

Recombinant AAV viruses expressing the variable regions from the F10 and CR6261 broadly neutralizing influenza antibodies were produced.

Figure 18:
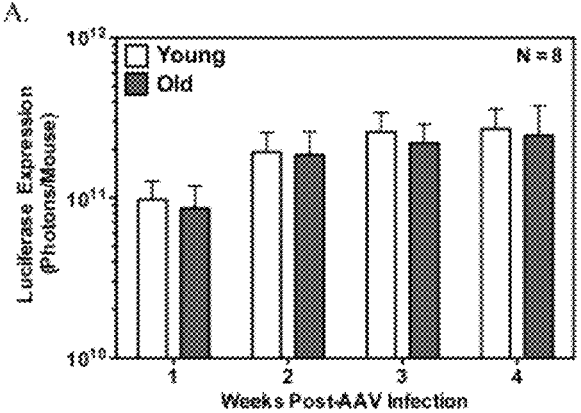
FIG. 18A is a graph showing quantitation of luciferase expression by Xenogen imaging of young (3 month) or old (12 month) NOD/SCID/γc$^{-/-}$ (NSG) mice following intramuscular injection of $1\times10^{11}$ GC of vector expressing luciferase (n=8).
FIG. 18B is a graph showing quantitation of human IgG by ELISA in the serum of young (3 month) or old (12 month) NSG mice following intramuscular injection of $1\times10^{11}$ GC of vector expressing F10-IgG (n=8).
FIG. 18C are graphs showing survival (left) and weight loss (right) of 3 month old NSG mice receiving recombinant AAV expressing luciferase or F10-IgG following intranasal challenge with 1000 PFU of PR/8 influenza (n=6-8).
FIG. 18D are graphs showing survival (left) and weight loss (right) of 12 month old NSG mice receiving recombinant AAV expressing luciferase or F10-IgG following intranasal challenge with 1000 PFU of PR/8 influenza (n=4-6).
FIG. 18E shows hematoxylin and eosin staining of representative lung sections taken from 3 month old NSG mice receiving either luciferase or F10-IgG expressing VIP 5 days post-challenge with 1000 PFU of PR/8 influenza (scale bar=100 microns).
FIG. 18F is a plot showing ordinal score denoting inflammation as quantified by a trained pathologist (0=no inflammation, 5=maximal inflammation).
FIG. 18G is a plot showing quantitation of influenza RNA in lung tissues as a function of time as animals were sacrificed for analysis.
Figure 18:
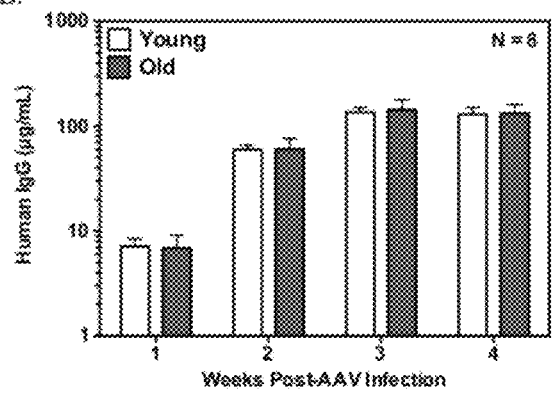
Figure 18:
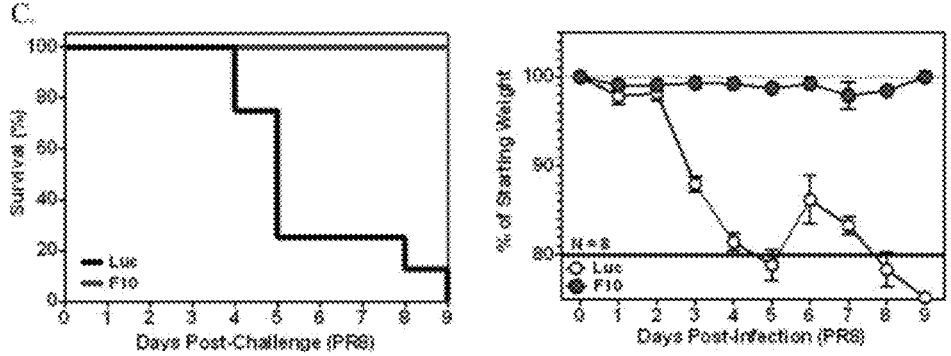
Figure 18:
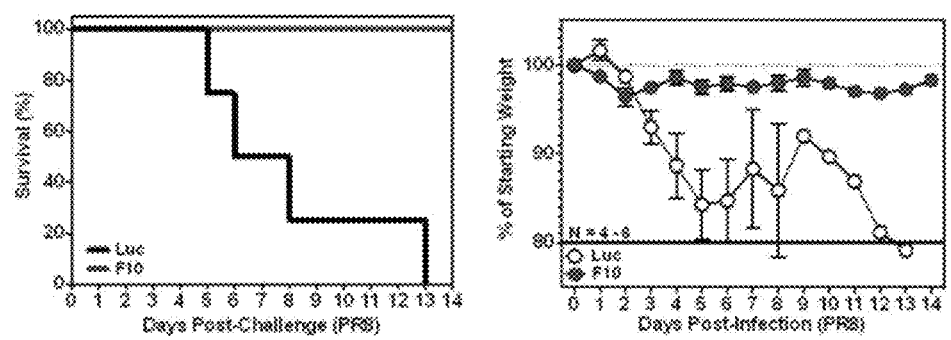
Figure 18:
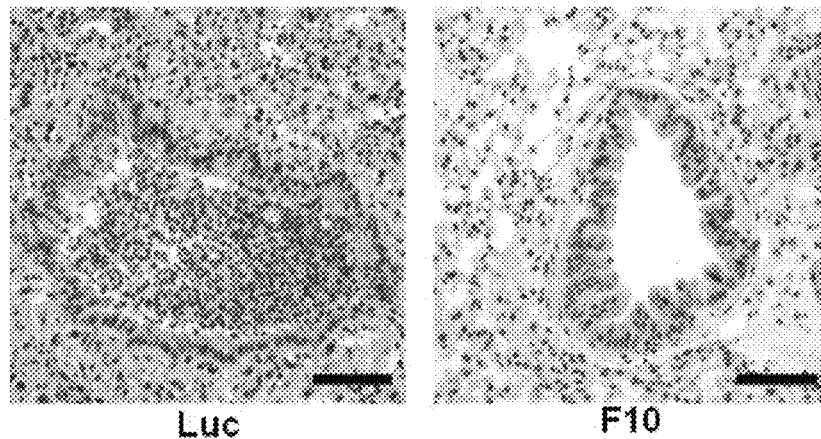
Figure 18:
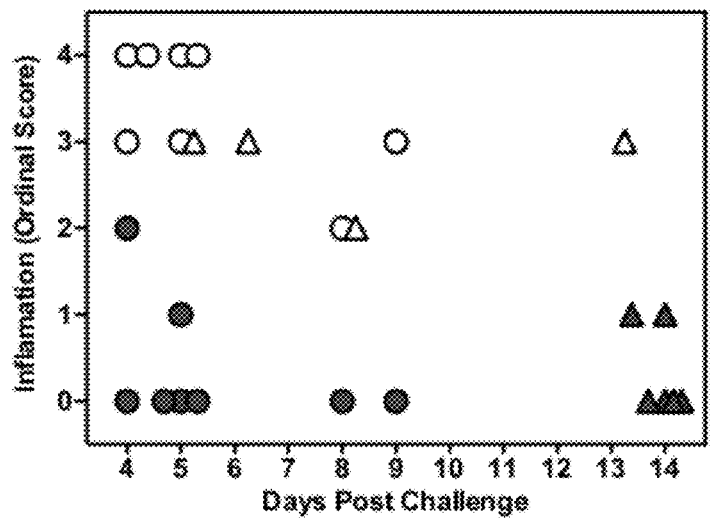
Figure 18:
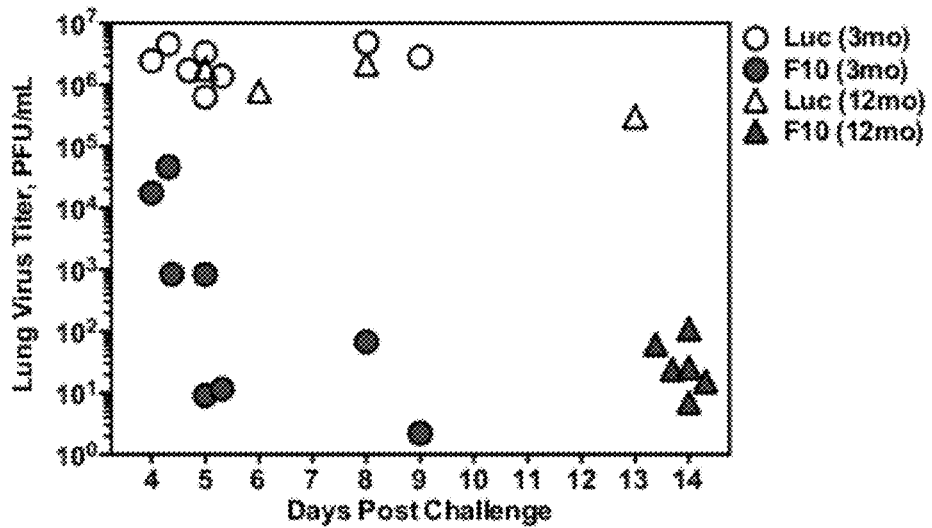

Immunodeficient NOD/SCID/γ$^{-/-}$ (NSG) mice are mice completely lack adaptive immunity and exhibit significantly impaired innate immune responses. The recombinant AAV viruses expressing F10 and CR6261 antibodies were administered at a normalized dose of 5×10$^{12}$ GC per kg to NSG animals that were relatively young (14-19 weeks old) or of an advanced age (46-55 weeks old). Gene expression was quantified over four weeks using Xenogen imaging or ELISA (FIGS. 18A and 18B respectively). Both animal groups demonstrated remarkably similar levels of gene expression at all time points, suggesting that age did not impact the capacity for muscle-based gene expression from AAV. To determine whether the in vivo antibody expression was sufficient to protect these immunocompromised animals from challenge with influenza, 1000 PFU of the lethal PR8 strain was administered to both young and old groups of mice (FIGS. 18C and 18D respectively).

In both cases, illness and weight loss were observed in control mice expressing luciferase, which resulted in death of all such animals over the course of the study. In contrast, both young and old NSG animals expressing F10 were completely protected from influenza-induced weight loss, suggesting that these concentrations of F10 antibody alone were sufficient to protect mice in the absence of an endogenous immune response. To further characterize the extent to which F10 was capable of preventing illness in NSG mice, the animals were sacrificed throughout the period of study and the level of inflammation was scored in histological samples of lung tissue. Infected mice expressing luciferase demonstrated substantial luminal infiltration of the bronchioles five days post-infection (FIG. 18E left). In contrast, animals protected by F10 showed very low levels of inflammation and clear bronchioles consistent with a substantially lower level of pathology in these mice (FIG. 18E right). Scoring of lung inflammation in histological samples over time demonstrated that animals at early time points exhibited the most severe inflammation (FIG. 18F). Mice expressing F10 antibody exhibited significantly less inflammation at all time points analyzed as compared with luciferase control mice.

To directly quantify the ability of the recombinant AAV viruses to control viral replication, we determined the amount of virus in NSG mice by extracting total RNA from lung tissue harvested at the time of sacrifice and measured viral RNA by quantitative RT-PCR. As show in FIG. 18G, lungs from mice expressing luciferase exhibited high viral load throughout the course of the experiment. In contrast, F10-expressing animals analyzed at early time points contained moderate levels of viral RNA that declined substantially over time, as a result of dramatically reduced viral replication in the presence of F10 antibody despite the lack of endogenous adaptive immunity.

Example 12

Protection from HIV Infection in Bone Liver Thymus (BLT) Humanized Mice

The Bone Liver Thymus (BLT) humanized mouse model is a well-established model for prevention of intravaginal HIV infection. The BLT humanized mouse is produced by surgical implantation of fetal tissues into immunodeficient NOD/SCID/γC (NSG) recipients, followed by engraftment of hematopoietic stem cells. These engrafted cells give rise to a complete repertoire of immune cells trained in the mouse that can produce functional immune responses following HIV infection. The BLT model has been found to exhibit significant human cell engraftment of mucosal tissues including vagina and colon and has been shown to support HIV transmission following mucosal exposure to concentrated CCR5-tropic JR-CSF HIV virus. In this example, BLT mice were used to test the ability of the recombinant AAV viruses expressing anti-HIV antibodies to prevent HIV transmission through mucosal routes.

Recombinant AAV viruses expressing VRC01 anti-HIV antibody or luciferase protein were produced according to the methods disclosed herein. To test the efficacy of VRC01 antibody to prevent the transmission of HIV at the mucosal surface, a cohort of BLT animals was produced and the recombinant AAV viruses expressing VRC01 were administered to the BLT mice to generate animals expressing either VRC01 neutralizing antibody at a serum concentration of 100 μg/mL or luciferase protein as a negative control.

Figure 19:
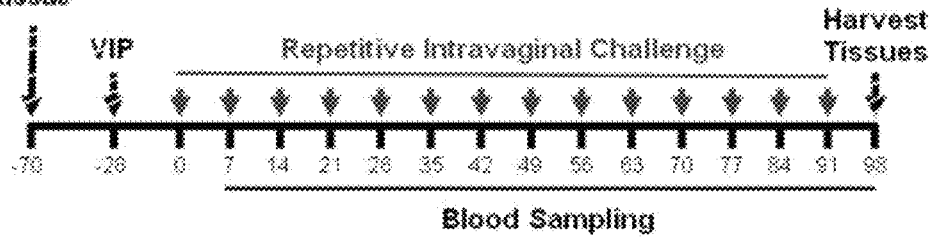
FIG. 19A is a schematic representation of the low-dose mucosal HIV challenge regimen employed in Example 12. Each week, mice were bled and then challenged with 50 ng p24 of JR-CSF by non-abrasive intravaginal administration of inoculum as indicated by the solid arrows.
FIG. 19B is a graph showing CD4 cell depletion in the circulation over time as a result of HIV infection as measured by flow cytometry.
FIG. 19C is a plot showing HIV plasma viral load at time of sacrifice following 13 intravaginal challenges as measured by Abbott RealTime HIV-1 Viral Load qPCR assay. Limit of detection for this assay was 200 copies/mL. Undetectable samples were plotted at the limit of detection.
Figure 19:
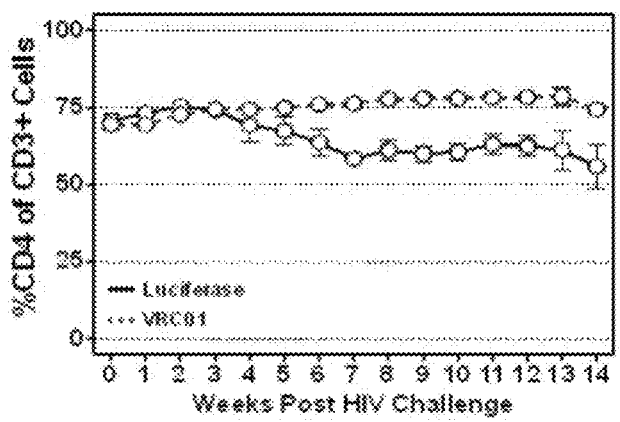
Figure 19:
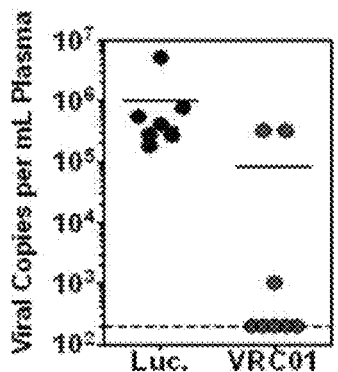

To model the relatively infrequent nature of human mucosal HIV transmission, a low-dose repetitive challenge regimen of weekly non-abrasive vaginal administrations of unconcentrated JR-CSF HIV virus was adopted. A schematic representation of the HIV challenge regimen is shown in FIG. 19A. During a 14-week period, mice were bled and then challenged each week with 50 ng p24 of JR-CSF HIV virus by non-abrasive intravaginal administration of inoculum. CD4 cell levels were measured weekly using flow cytometry (FIG. 19B). As shown in FIG. 17B, there was a modest but statistically significant decline in CD4+ cell level in animals expressing luciferase relative to those producing VRC01. After 13 weeks of repetitive vaginal HIV challenge, HIV plasma viral loads at the time of sacrifice were measured by Abbott RealTime HIV-1 Viral Load qPCR assay (limit of detection for this assay was 200 copies/mL). The results are shown in FIG. 19C, which revealed that while all animals expressing luciferase became infected, only two of the eight mice expressing VRC01 showed significant evidence of viral replication. These results show that the recombinant AAV viruses expressing anti-HIV antibodies can prevent mucosal HIV transmission in BLT mice.

Example 13

Production of Hepatitis C Virus (HCV) Antibodies in FVB Mice

This example illustrates that recombinant AAV viruses can be used to produce high level of HCV antibody in vivo.

Figure 20:
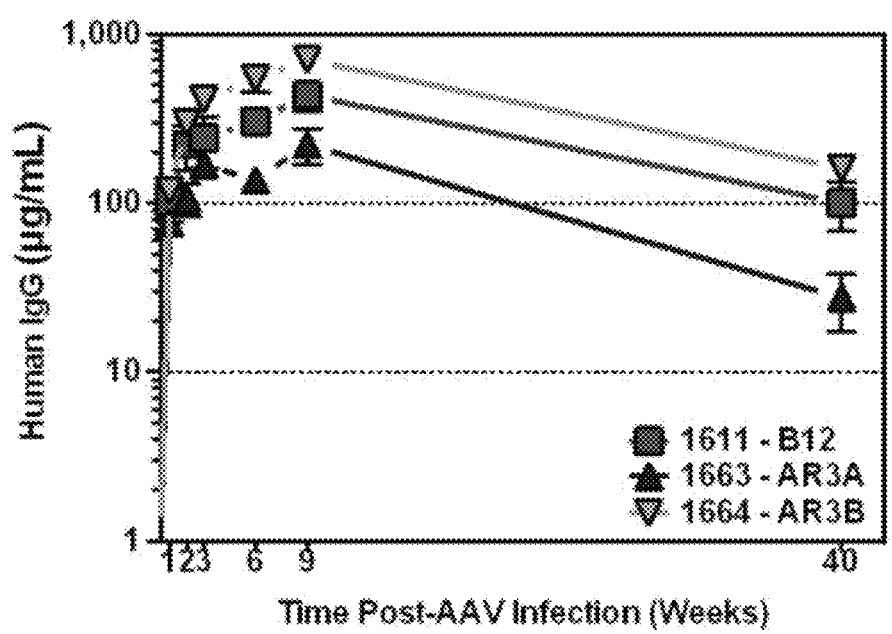
FIG. 20 is a graph showing quantitation of human IgG in serum by ELISA following administration of recombinant AAV viruses expressing B12, AR3A and AR3B antibodies.

AAV vectors comprising coding sequences for B12, AR3A and AR3B antibodies were constructed. The AAV vectors were used to produce recombinant AAV viruses expressing B12, AR3A and ARSB antibodies, respectively. The recombinant AAV viruses were administered to FVB mice. Expression levels of the corresponding antibody in animal serum were measured weekly. The results are shown in FIG. 20. As shown in FIG. 20, significant levels of HCV antibodies have been produced in the animal.

Example 14

Prevention of HIV Infection

This example illustrates immunoprophylaxis of a patient at risk of developing HIV infection.

A recombinant AAV is produced using an AAV transfer vector comprising a polynucleotide encoding an anti-HIV neutralizing antibody. Any known anti-HIV neutralizing antibody can be used, including but not limited to, b12 anti-HIV antibody, 2G12 anti-HIV antibody, 4E10 anti-HIV antibody, 2F5 anti-HIV antibody, and any variant thereof. For example, an AAV transfer vector having the CASI promoter, coding sequences for an anti-HIV neutralizing antibody, WPRE and SV40 poly(A) sequence can be used. Examples of such AAV transfer vectors include the vectors provided in SEQ ID NOs: 17-21 and 24. A patient is identified as being at risk of developing HIV infection and administered an effective amount of the recombinant AAV. The recombinant AAV is administered to the patient by intramuscular injection. The recombinant AAV expresses the anti-HIV antibody in the patient, thereby reducing the risk for the patient to develop HIV injection. The HIV viral load in the patient can be determined at various timepoints after the patient being administered with the recombinant AAV. The appropriate dosage (i.e., the expression level of the anti-HIV antibody) and treatment regimen can be readily determined by skilled artisans based on a number of factors including, but not limited to, the route of administration and the extent of HIV exposure for the patient. The immunoprophylaxis efficacy is evaluated by observing reducing the risk of HIV infection as compared to the patients receiving no AAV treatment.

Example 15

Treatment of Colon Cancer

This example illustrates the treatment of a patient suffering from or at risk of developing colon cancer.

A recombinant AAV is produced using an AAV transfer vector comprising a polynucleotide encoding IMC-C225 antibody (Cetuximab™, an epidermal growth factor receptor (EGFR) antibody). For example, coding sequences for IMC-C225 antibody can be inserted in an AAV transfer vector having the CASI promoter, WPRE and SV40 poly(A) sequence. A patient suffering from or at risk of developing colon cancer is identified and administered an effective amount of the recombinant AAV. The recombinant AAV is administered to the patient by intramuscular injection. The recombinant AAV expresses IMC-C225 antibody in the patient, thereby inhibiting cancer progression in the patient. The appropriate dosage (i.e., the expression level of IMC-C225 antibody) and treatment regimen can be readily determined by skilled artisans based on a number of factors including, but not limited to, the route of administration and the patient's disease state. The treatment efficacy is evaluated by observing delay or slowing of disease progression, amelioration or palliation of the disease state, and remission.

Example 16

Prevention of HCV Infection

This example illustrates immunoprophylaxis of a patient at risk of developing HCV infection.

A recombinant AAV is produced using an AAV transfer vector comprising a polynucleotide encoding an anti-HCV neutralizing antibody. Any known anti-HCV neutralizing antibody can be used, including but not limited to, AR3A anti-HCV antibody, AR3B anti-HCV antibody, AR4A anti-HCV antibody, and any variant thereof. For example, an AAV transfer vector having the CASI promoter, coding sequences for an anti-HCV neutralizing antibody, WPRE and SV40 poly(A) sequence can be used. Examples of such AAV transfer vectors include the vector provided in SEQ ID NO: 22, 23 and 28.

A patient is identified as being at risk of developing HCV infection and administered an effective amount of the recombinant AAV. The recombinant AAV is administered to the patient by intramuscular injection. The recombinant AAV expresses AR3A antibody in the patient, thereby reducing the risk for the patient to develop HCV injection. The appropriate dosage (i.e., the expression level of the anti-HCV antibody) and treatment regimen can be readily determined by skilled artisans based on a number of factors including, but not limited to, the route of administration and the extent of HCV exposure for the patient. The HCV viral load in the patient can be determined at various time points after the patient being administered with the recombinant AAV. The immunoprophylaxis efficacy is evaluated by observing reducing the risk of HCV infection as compared to the patients receiving no AAV treatment.

Example 17

Prevention of Influenza Virus Infection

This example illustrates immunoprophylaxis of a patient at risk of developing influenza virus infection.

A recombinant AAV is produced using an AAV transfer vector comprising a polynucleotide encoding an anti-influenza neutralizing antibody. Any known anti-influenza neutralizing antibody can be used, including but not limited to, F10 anti-influenza antibody, CR6261 anti-influenza antibody, FI6 anti-influenza antibody, TCN32 anti-influenza antibody, and any variant thereof. For example, an AAV transfer vector having the CASI promoter, coding sequences for an anti-influenza neutralizing antibody, WPRE and SV40 poly (A) sequence can be used. Examples of such AAV transfer vectors include the vector provided in SEQ ID NO: 25-27, 29 and 30.

A patient is identified as being at risk of developing influenza infection and administered an effective amount of the recombinant AAV. The recombinant AAV is administered to the patient by intramuscular injection. The recombinant AAV expresses F10 antibody in the patient, thereby reducing the risk for the patient to develop influenza virus injection. The appropriate dosage (i.e., the expression level of the anti-influenza neutralizing antibody) and treatment regimen can be readily determined by skilled artisans based on a number of factors including, but not limited to, the route of administration and the extent of influenza virus exposure for the patient. The influenza viral load in the patient can be determined at various time points after the patient being administered with the recombinant AAV. The immunoprophylaxis efficacy is evaluated by observing reducing the risk of influenza infection as compared to the patients receiving no AAV treatment.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A viral vector, comprising:
   a 5' inverted terminal repeat (ITR) of adeno-associated virus (AAV) and a 3' AAV ITR;
   a synthetic promoter, wherein the promoter comprises a nucleotide sequence having at least 95% sequence identity to the sequence of SEQ ID NO: 1;
   a restriction site downstream of the promoter to allow insertion of a polynucleotide encoding one or more proteins of interest, and
   a posttranscriptional regulatory element downstream of the restriction site,
   wherein the promoter, the restriction site and the posttranscriptional regulatory element are located downstream of the 5' AAV ITR and upstream of the 3' AAV ITR.

2. The viral vector of claim 1, further comprising a polynucleotide inserted at the restriction site and operably linked with the promoter, wherein the polynucleotide comprises a coding region of a protein of interest.

3. The viral vector of claim 2, wherein the polynucleotide comprises a signal peptide-encoding sequence immediately upstream of the coding region of the protein of interest.

4. The viral vector of claim 3, wherein the signal peptide is selected from the group consisting of a signal peptide of interferon, a signal peptide of human growth hormone, a signal peptide of erythropoietin (EPO), a signal peptide of granulocyte colony-stimulating factor (G-CSF), a signal peptide of insulin, and any combination thereof.

5. The viral vector of claim 2, wherein the vector comprises a nucleotide sequence having at least 70% sequence identity to the Kozak consensus sequence.

6. The viral vector of claim 1, wherein the protein of interest is selected from the group consisting of full-length antibodies, growth hormones (GHs), insulin-like growth factors (IGFs), G-CSFs, erythropoietins (EPOs), insulins, antibody Fab fragments, antibody scFV fragments, hemophilia related clotting proteins, dystrophin, lysosomal acid lipase, phenylalanine hydroxylase (PAH), glycogen storage disease-related enzymes, and any variants thereof.

7. The viral vector of claim 1, wherein the protein of interest is a virus neutralizing antibody.

8. The viral vector of claim 7, wherein the virus neutralizing antibody is a neutralizing antibody for a human immunodeficiency virus (HIV), a hepatitis C virus (HCV), or an influenza virus.

9. The viral vector of claim 8, wherein the neutralizing antibody for HIV is selected from the group consisting of b12 anti-HIV antibody, 2G12 anti-HIV antibody, 4E10 anti-HIV antibody, 2F5 anti-HIV antibody, and any variant thereof.

10. The viral vector of claim 8, wherein the neutralizing antibody for HCV is selected from the group consisting AR3A anti-HCV antibody, AR3B anti-HCV antibody, AR4A anti-HCV antibody, and any variant thereof.

11. The viral vector of claim 1, wherein the protein of interest is a neutralizing antibody for malaria.

12. The viral vector of claim 1, wherein the promoter comprises a splice donor, a splice acceptor, or any variant thereof.

13. The viral vector of claim 12, wherein the splice donor comprises a nucleotide sequence having at least 95% sequence identity to the sequence of SEQ ID NO: 5.

14. The viral vector of claim 12, wherein the splice acceptor comprises a nucleotide sequence having at least 95% sequence identity to the sequence of SEQ ID NO: 6.

15. The viral vector of claim 1, wherein the promoter comprises a nucleotide sequence having at least 95% sequence identity to the sequence of any one of SEQ ID NOs: 2-4.

16. The viral vector of claim 1, wherein the posttranscriptional regulatory element is a viral posttranscriptional regulatory element.

17. The viral vector of claim 16, wherein the viral posttranscriptional regulatory element is woodchuck hepatitis virus posttranscriptional regulatory element (WPRE), hepatitis B virus posttranscriptional regulatory element (HBVPRE), RNA transport element (RTE), or any variant thereof.

18. The viral vector of claim 1, further comprising a transcription termination region downstream of the posttranscriptional regulatory element.

19. The viral vector of claim 18, the transcription termination region comprises an SV40 late poly(A) sequence, a rabbit beta-globin poly(A) sequence, a bovine growth hormone poly(A) sequence, or any variant thereof.

20. The viral vector of claim 1, wherein the promoter comprises an intron.

21. The viral vector of claim 20, wherein the intron is a synthetic intron comprising a nucleotide sequence having at least 95% sequence identity to the sequence of SEQ ID NO: 8.

22. The viral vector of claim 2, wherein the polynucleotide comprises a first coding region for the heavy chain variable region of an immunoglobulin and a second coding region for the light chain variable region of the immunoglobulin.

23. The viral vector of claim 22, wherein the first coding region and the second coding region are separated by a 2A sequence.

24. The viral vector of claim 23, wherein the 2A sequence is a foot-and-mouth disease virus 2A (F2A) sequence.

25. The viral vector of claim 22, wherein 5' of the first coding region is fused with a first signal peptide sequence and 5' of the second coding region is fused with a second signal peptide sequence.

26. The viral vector of claim 25, wherein the first signal peptide sequence and the second signal peptide sequence are different.

27. The viral vector of claim 1, wherein the region starting from the 5' ITR and ending at the 3' ITR is at least 2.5 kb.

28. An isolated, synthetic or recombinant polynucleotide, comprising:
a nucleic acid sequence having at least 95% sequence identity to the sequence of SEQ ID NO: 1.

29. The polynucleotide of claim 28, wherein the polynucleotide comprises the nucleotide sequence selected from the group consisting of: SEQ ID NO: 2, SEQ ID NO: 3 and SEQ ID NO: 4.

* * * * *

SEQUENCE LISTING

```
<160> NUMBER OF SEQ ID NOS: 42

<210> SEQ ID NO 1
<211> LENGTH: 1055
<212> TYPE: DNA
<213> ORGANISM: Artificial Sequence
<220> FEATURE:
<223> OTHER INFORMATION: CASI Promoter

<400> SEQUENCE: 1
ggagttccgc gttacataac ttacggtaaa tggcccgcct ggctgaccgc ccaacgaccc      60
ccgcccattg acgtcaataa tgacgtatgt tcccatagta acgccaatag ggactttcca    120
ttgacgtcaa tgggtggagt atttacggta aactgcccac ttggcagtac atcaagtgta    180
tcatatgcca agtacgcccc ctattgacgt caatgacggt aaatggcccg cctggcatta    240
tgcccagtac atgaccttat gggactttcc tacttggcag tacatctacg tattagtcat    300
cgctattacc atggtcgagg tgagcccac gttctgcttc actctcccca tctcccccc      360 ctccccaccc ccaattttgt atttatttat tttttaatta ttttgtgcag cgatggggc      420 ggggggggg ggggcgcgc gccaggcggg gcggggcggg gcgaggggcg gggcggggcg      480
aggcggagag gtgcggcggc agccaatcag agcggcgcgc tccgaaagtt tccttttatg    540
```

```
gcgaggcggc ggcggcggcg gccctataaa aagcgaagcg cgcggcgggc gggagtcgct    600
gcgcgctgcc ttcgccccgt gccccgctcc gccgccgcct cgcgccgccc gccccggctc    660
tgactgaccg cgttactaaa acaggtaagt ccggcctccg cgccgggttt tggcgcctcc    720
cgcgggcgcc cccctcctca cggcgagcgc tgccacgtca gacgaagggc gcagcgagcg    780
tcctgatcct tccgcccgga cgctcaggac agcggcccgc tgctcataag actcggcctt    840
agaaccccag tatcagcaga aggacatttt aggacgggac ttgggtgact ctagggcact    900
ggttttcttt ccagagagcg gaacaggcga ggaaaagtag tcccttctcg gcgattctgc    960
ggagggatct ccgtggggcg gtgaacgccg atgatgcctc tactaaccat gttcatgttt   1020 tcttttttt tctacaggtc ctgggtgacg aacag                              1055

<210> SEQ ID NO 2
<211> LENGTH: 311
<212> TYPE: DNA
<213> ORGANISM: Artificial Sequence
<220> FEATURE:
<223> OTHER INFORMATION: CMV Enhancer

<400> SEQUENCE: 2
ggagttccgc gttacataac ttacggtaaa tggcccgcct ggctgaccgc ccaacgaccc     60
ccgcccattg acgtcaataa tgacgtatgt tcccatagta acgccaatag ggactttcca    120
ttgacgtcaa tgggtggagt atttacggta aactgcccac ttggcagtac atcaagtgta    180
tcatatgcca agtacgcccc ctattgacgt caatgacggt aaatggcccg cctggcatta    240
tgcccagtac atgaccttat gggactttcc tacttggcag tacatctacg tattagtcat    300
cgctattacc a                                                        311

<210> SEQ ID NO 3
<211> LENGTH: 366
<212> TYPE: DNA
<213> ORGANISM: Artificial Sequence
<220> FEATURE:
<223> OTHER INFORMATION: Chicken Beta-Actin Fragment

<400> SEQUENCE: 3
tggtcgaggt gagccccacg ttctgcttca ctctccccat ctcccccccc tccccacccc     60 caatttgta tttatttatt ttttaattat tttgtgcagc gatggggcg ggggggggg     120 ggggcgcgcg ccaggcgggg cggggcgggg cgaggggcgg ggcggggcga ggcggagagg    180
tgcggcggca gccaatcaga gcggcgcgct ccgaaagttt ccttttatgg cgaggcggcg    240
gcggcggcgg ccctataaaa agcgaagcgc gcggcgggcg ggagtcgctg cgcgctgcct    300 tcgcccgtg ccccgctccg ccgccgcctc gcgccgcccg cccggctct gactgaccgc    360 gttact                                                              366

<210> SEQ ID NO 4
<211> LENGTH: 303
<212> TYPE: DNA
<213> ORGANISM: Artificial Sequence
<220> FEATURE:
<223> OTHER INFORMATION: UBC Enhancer

<400> SEQUENCE: 4
ggcctccgcg ccgggttttg gcgcctcccg cgggcgcccc cctcctcacg gcgagcgctg     60
ccacgtcaga cgaagggcgc agcgagcgtc tgatccttc cgcccggacg ctcaggacag    120
cggcccgctg ctcataagac tcggccttag aaccccagta tcagcagaag gacattttag    180
```

```
gacgggactt gggtgactct agggcactgg ttttctttcc agagagcgga acaggcgagg    240
aaaagtagtc ccttctcggc gattctgcgg agggatctcc gtggggcggt gaacgccgat    300
gat                                                                  303
```

<210> SEQ ID NO 5
<211> LENGTH: 15
<212> TYPE: DNA
<213> ORGANISM: Artificial Sequence
<220> FEATURE:
<223> OTHER INFORMATION: Synthetic Splice Donor

<400> SEQUENCE: 5

```
aaaacaggta agtcc                                                     15
```

<210> SEQ ID NO 6
<211> LENGTH: 60
<212> TYPE: DNA
<213> ORGANISM: Artificial Sequence
<220> FEATURE:
<223> OTHER INFORMATION: Synthetic Splice Acceptor

<400> SEQUENCE: 6

```
gcctctacta accatgttca tgttttcttt ttttttctac aggtcctggg tgacgaacag    60
```

<210> SEQ ID NO 7
<211> LENGTH: 592
<212> TYPE: DNA
<213> ORGANISM: Artificial Sequence
<220> FEATURE:
<223> OTHER INFORMATION: WPRE

<400> SEQUENCE: 7

```
taatcaacct ctggattaca aaatttgtga agattgact ggtattctta actatgttgc     60
tccttttacg ctatgtggat acgctgcttt aatgcctttg tatcatgcta ttgcttcccg    120
tatggctttc attttctcct ccttgtataa atcctggttg ctgtctcttt atgaggagtt    180
gtggcccgtt gtcaggcaac gtggcgtggt gtgcactgtg tttgctgacg caaccccac    240 tggttggggc attgccacca cctgtcagct cctttccggg actttcgctt tccccctccc    300
tattgccacg gcggaactca tcgccgcctg ccttgcccgc tgctggacag gggctcggct    360
gttgggcact gacaattccg tggtgttgtc ggggaaatca tcgtcctttc cttggctgct    420
cgcctgtgtt gccacctgga ttctgcgcgg gacgtccttc tgctacgtcc cttcggccct    480
caatccagcg gaccttcctt cccgcggcct gctgccggct ctgcggcctc ttccgcgtct    540
tcgccttcgc cctcagacga gtcggatctc cctttgggcc gcctccccgc ct            592
```

<210> SEQ ID NO 8
<211> LENGTH: 353
<212> TYPE: DNA
<213> ORGANISM: Artificial Sequence
<220> FEATURE:
<223> OTHER INFORMATION: Synthetic Intron

<400> SEQUENCE: 8

```
gtaagtccgg cctccgcgcc gggttttggc gcctcccgcg ggcgcccccc tcctcacggc    60
gagcgctgcc acgtcagacg aagggcgcag cgagcgtcct gatccttccg cccggacgct    120
caggacagcg gcccgctgct cataagactc ggccttagaa ccccagtatc agcagaagga    180
cattttagga cgggacttgg gtgactctag ggcactggtt ttctttccag agagcggaac    240
```
aggcgaggaa aagtagtccc ttctcggcga ttctgcggag ggatctccgt ggggcggtga      300
acgccgatga tgcctctact aaccatgttc atgttttctt ttttttttcta cag            353

<210> SEQ ID NO 9
<211> LENGTH: 84
<212> TYPE: DNA
<213> ORGANISM: Artificial Sequence
<220> FEATURE:
<223> OTHER INFORMATION: F2A Standard - Standard Furin Clevage

<400> SEQUENCE: 9
cgggctaaga gagcaccggt gaaacagact ttgaattttg accttctcaa gttggcggga      60
gacgtggagt ccaacccagg gccc                                             84

<210> SEQ ID NO 10
<211> LENGTH: 96
<212> TYPE: DNA
<213> ORGANISM: Artificial Sequence
<220> FEATURE:
<223> OTHER INFORMATION: F2A Optimized - with modified Furin Clevage
      site

<400> SEQUENCE: 10
cgaaaaagaa gatcaggttc gggtgcgcca gtaaagcaga cattaaactt tgatttgctg      60
aaacttgcag gtgatgtaga gtcaaatcca ggtcca                                96

<210> SEQ ID NO 11
<211> LENGTH: 78
<212> TYPE: DNA
<213> ORGANISM: Artificial Sequence
<220> FEATURE:
<223> OTHER INFORMATION: Variant of HGH Signal Sequence

<400> SEQUENCE: 11
atggcgacgg gttcaagaac ttccctactt cttgcatttg gcctgctttg tttgccgtgg      60
ttacaggagg gctcggca                                                    78

<210> SEQ ID NO 12
<211> LENGTH: 78
<212> TYPE: DNA
<213> ORGANISM: Artificial Sequence
<220> FEATURE:
<223> OTHER INFORMATION: Variant of HGH Signal Sequence

<400> SEQUENCE: 12
atggcaacag ggagccgaac ctctctgctc cttgctttcg ggctcctttg cctaccgtgg      60
ctccaagagg gctcggca                                                    78

<210> SEQ ID NO 13
<211> LENGTH: 5421
<212> TYPE: DNA
<213> ORGANISM: Artificial Sequence
<220> FEATURE:
<223> OTHER INFORMATION: pAAVio-CMV-B12AB-HA-SV40

<400> SEQUENCE: 13
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg      120
gccaactcca tcactagggg ttcctactag tggagttccg cgttacataa cttacggtaa      180
atggcccgcc tggctgaccg cccaacgacc cccgcccatt gacgtcaata atgacgtatg      240

```
ttcccatagt aacgccaata gggactttcc attgacgtca atgggtggag tatttacggt      300
aaactgccca cttggcagta catcaagtgt atcatatgcc aagtacgccc cctattgacg      360
tcaatgacgg taaatggccc gcctggcatt atgcccagta catgacctta tgggactttc      420
ctacttggca gtacatctac gtattagtca tcgctattac catggtgatg cggttttggc      480
agtacatcaa tgggcgtgga tagcggtttg actcacgggg atttccaagt ctccacccca      540
ttgacgtcaa tgggagtttg ttttggcacc aaaatcaacg ggactttcca aaatgtcgta      600
acaactccgc cccattgacg caaatgggcg gtaggcgtgt acggtgggag gtctatataa      660
gcagagctcg tttagtgaac cgtcagatcg cctggagacg ccatccacgc tgttttgacc      720
tccatagaag acaccggcgg ccgccatggc gacgggttca agaacttccc tacttcttgc      780
atttggcctg ctttgtttgc cgtggttaca ggagggctcg gcacaggttc agctggttca      840
gtccggggct gaggtgaaga agcctggggc ctcagtgaag gtttcttgtc aggcttctgg      900
atacagattc agtaactttg ttattcattg ggtgcgccag gccccggac agaggtttga       960 gtggatggga tggatcaatc cttacaacgg aaacaaagaa ttttcagcga agttccagga     1020
cagagtcacc tttaccgcgg acacatccgc gaacacagcc tacatggagt tgaggagcct     1080
caggtctgca gacacggctg tttattattg tgcgagagtg gggccatata gttgggatga     1140
ttctccccag gacaattatt atatggacgt ctggggcaaa gggaccacgg tcatcgtgag     1200
ctcagccagc accaagggcc catcggtctt ccccctggca ccctcctcca agagcacctc     1260
tgggggcaca gcggccctgg gctgcctggt caaggactac ttccccgaac cggtgacggt     1320
gtcgtggaac tcaggcgccc tgaccagcgg cgtgcacacc ttcccggctg tcctacagtc     1380
ctcaggactc tactccctca gcagcgtggt gaccgtgccc tccagcagct gggcaccca     1440 gacctacatc tgcaacgtga atcacaagcc cagcaacacc aaggtggaca gaaagttga     1500 gcccaaatct tgtgacaaaa ctcacacatg cccaccgtgc ccagcacctg aactcctggg     1560
gggaccgtca gtcttcctct tccccccaaa acccaaggac accctcatga tctcccggac     1620
ccctgaggtc acatgcgtgg tggtggacgt gagccacgaa gaccctgagg tcaagttcaa     1680
ctggtatgtt gacggcgtgg aggtgcataa tgccaagaca aagccgcggg aggagcagta     1740
caacagcacg taccgtgtgg tcagcgtcct caccgtcctg caccaggact ggctgaatgg     1800
caaggagtac aagtgcaagg tctccaacaa agccctccca gcccccatcg agaaaaccat     1860
ctccaaagcc aaagggcagc cccgagaacc acaggtgtac accctgcccc catcccggga     1920
tgagctgacc aagaatcaag tcagcctgac ctgcctggtc aaaggcttct atcccagcga     1980
catcgccgtg gagtgggaga gcaatgggca gccggagaac aactacaaga ccacgcctcc     2040
cgtgctggac tccgacggct ccttcttcct ctactcaaaa ctcaccgtgg acaagagcag     2100
gtggcagcag gggaacgtct tctcatgctc cgtgatgcat gaggctctgc acaaccacta     2160
cacgcagaag agcctctccc tgtctccggg taaaagggca aaacgttcgg gttcgggtgc     2220
gccagtaaag cagacattaa actttgattt gctgaaactt gcaggtgatg tagagtcaaa     2280
tccaggtcca atggcaacag ggagccgaac ctctctgctc cttgctttcg ggctcctttg     2340
cctaccgtgg ctcaagagg gctcggcaga atcgttctc acgcagtctc caggcaccct      2400
gtctctgtct ccaggggaaa gagccacctt ctcctgtagg tccagtcaca gcattcgcag     2460
ccgccgcgta gcctggtacc agcacaaacc tggccaggct ccaaggctgg tcatacatgg     2520
tgtttccaat agggcctctg gcatctcaga caggttcagc ggcagtgggt ctgggacaga     2580
cttcactctc accatcacca gagtggagcc tgaagacttt gcactgtact actgtcaggt     2640
```

```
ctatggtgcc tcctcgtaca cttttggcca ggggaccaaa ctggagagga aacgtacggt    2700
ggccgctccc agcgtgttca tcttccctcc ctctgatgaa cagctgaaaa gcggaacagc    2760
cagcgtggtg tgtctgctga caacttcta ccccagagaa gccaaagtgc agtggaaggt    2820
ggacaacgcc ctgcagagcg gaaacagcca ggaaagcgtg acagagcagg attccaagga    2880
ttccacatac agcctgagca gcacactgac actgtccaag gccgactacg agaagcacaa    2940
ggtgtacgcc tgcgaagtga caccaggg actgtcctcc cctgtgacaa agagcttcaa    3000
cagaggagaa tgctacccctt acgacgtacc agactacgca taaaggatcc gaaggtacct    3060
tcgagcagac atgataagat acattgatga gtttggacaa accacaacta gaatgcagtg    3120
aaaaaaatgc tttatttgtg aaatttgtga tgctattgct ttatttgtaa ccattataag    3180
ctgcaataaa caagttaaca acaacaattg cattcatttt atgtttcagg ttcaggggga    3240
gatgtgggag gtttttttaaa gcaagtaaaa cctctacaaa tgtggtaaaa tcaagcttag    3300 gaaccccctag tgatggagtt ggccactccc tctctgcgcg ctcgctcgct cactgaggcc    3360
gggcgaccaa aggtcgcccg acgcccgggc tttgcccggg cggcctcagt gagcgagcga    3420
gcgcgcagag agggagtggc caagctagcg ggcgattaag gaaagggcta gatcattctt    3480
gaagacgaaa gggcctcgtg atacgcctat ttttataggt taatgtcatg ataataatgg    3540
tttcttagac gtcaggtggc acttttcggg gaaatgtgcg cggaacccct atttgtttat    3600
ttttctaaat acattcaaat atgtatccgc tcatgagaca ataaccctga taaatgcttc    3660
aataatattg aaaaaggaag agtatgagta ttcaacattt ccgtgtcgcc cttattccct    3720 ttttttgcggc attttgcctt cctgtttttg ctcacccaga aacgctggtg aaagtaaaag    3780
atgctgaaga tcagttgggt gcacgagtgg gttacatcga actggatctc aacagcggta    3840
agatccttga gagttttcgc cccgaagaac gttttccaat gatgagcact tttaaagttc    3900
tgctatgtgg cgcggtatta tcccgtgttg acgccgggca agagcaactc ggtcgccgca    3960
tacactattc tcagaatgac ttggttgagt actcaccagt cacagaaaag catcttacgg    4020
atggcatgac agtaagagaa ttatgcagtg ctgccataac catgagtgat aacactgcgg    4080
ccaacttact tctgacaacg atcggaggac cgaaggagct aaccgctttt ttgcacaaca    4140
tgggggatca tgtaactcgc cttgatcgtt gggaaccgga gctgaatgaa gccataccaa    4200
acgacgagcg tgacaccacg atgcctgtag caatggcaac aacgttgcgc aaactattaa    4260
ctggcgaact acttactcta gcttcccggc aacaattaat agactggatg gaggcggata    4320
aagttgcagg accacttctg cgctcggccc ttccggctgg ctggtttatt gctgataaat    4380
ctggagccgg tgagcgtggg tctcgcggta tcattgcagc actggggcca gatggtaagc    4440
cctcccgtat cgtagttatc tacacgacgg ggagtcaggc aactatggat gaacgaaata    4500
gacagatcgc tgagataggt gcctcactga ttaagcattg gtaactgtca gaccaagttt    4560
actcatatat actttagatt gatttaaaac ttcatttta atttaaaagg atctaggtga    4620 agatccttttt tgataatctc atgaccaaaa tcccttaacg tgagttttcg ttccactgag    4680
cgtcagaccc cgtagaaaag atcaaaggat cttcttgaga tccttttttt ctgcgcgtaa    4740
tctgctgctt gcaaacaaaa aaaccaccgc taccagcggt ggtttgtttg ccggatcaag    4800
agctaccaac tctttttccg aaggtaactg gcttcagcag agcgcagata ccaaatactg    4860
ttcttctagt gtagccgtag ttaggccacc acttcaagaa ctctgtagca ccgcctacat    4920
acctcgctct gctaatcctg ttaccagtgg ctgctgccag tggcgataag tcgtgtctta    4980
```

-continued

```
ccgggttgga ctcaagacga tagttaccgg ataaggcgca gcggtcgggc tgaacggggg      5040
gttcgtgcac acagcccagc ttggagcgaa cgacctacac cgaactgaga tacctacagc      5100
gtgagctatg agaaagcgcc acgcttcccg aagggagaaa ggcggacagg tatccggtaa      5160
gcggcagggt cggaacagga gagcgcacga gggagcttcc agggggaaac gcctggtatc      5220
tttatagtcc tgtcgggttt cgccacctct gacttgagcg tcgatttttg tgatgctcgt      5280 cagggggggcg gagcctatgg aaaaacgcca gcaacgcggc cttttttacgg ttcctggcct      5340 tttgctggcc ttttgctcac atgtaataaa cacacacaca ccaacaaccg tggttggttg      5400
ttgtgttggt ttattctcga g                                                5421

<210> SEQ ID NO 14
<211> LENGTH: 5836
<212> TYPE: DNA
<213> ORGANISM: Artificial Sequence
<220> FEATURE:
<223> OTHER INFORMATION: pAAVio-CASI-Luc2-W-SV40

<400> SEQUENCE: 14
ttggccactc cctctctgcg cgctcgctcg ctcactgagg ccgggcgacc aaaggtcgcc        60
cgacgcccgg gctttgcccg gcggcctcca gtgagcgagc gagcgcgcag agagggagtg       120
gccaactcca tcactagggg ttcctactag tggagttccg cgttacataa cttacggtaa       180
atggcccgcc tggctgaccg cccaacgacc cccgcccatt gacgtcaata atgacgtatg       240
ttcccatagt aacgccaata gggactttcc attgacgtca atgggtggag tatttacggt       300
aaactgccca cttggcagta catcaagtgt atcatatgcc aagtacgccc cctattgacg       360
tcaatgacgg taaatggccc gcctggcatt atgcccagta catgacctta tgggactttc       420
ctacttggca gtacatctac gtattagtca tcgctattac catggtcgag gtgagcccca       480
cgttctgctt cactctcccc atctcccccc cctccccacc cccaattttg tatttattta       540
ttttttaatt attttgtgca gcgatggggg cggggggggg gggggggcgc gcgccaggcg       600
gggcggggcg gggcgagggg cggggcgggg cgaggcggag aggtgcggcg gcagccaatc       660
agagcggcgc gctccgaaag tttccttttta tggcgaggcg gcggcggcgg cggccctata       720
aaaagcgaag cgcgcggcgg gcgggagtcg ctgcgcgctg ccttcgcccc gtgccccgct       780
ccgccgccgc ctcgcgccgc ccgccccggc tctgactgac cgcgttacta aaacaggtaa       840
gtccggcctc cgcgccgggt tttggcgcct cccgcgggcg cccccctcct cacggcgagc       900
gctgccacgt cagacgaagg cgcagcgag cgtcctgatc cttccgcccg gacgctcagg       960
acagcggccc gctgctcata agactcggcc ttagaacccc agtatcagca gaaggacatt      1020
ttaggacggg acttgggtga ctctagggca ctggttttct ttccagagag cggaacaggc      1080
gaggaaaagt agtcccttct cggcgattct gcggagggat ctccgtgggg cggtgaacgc      1140
cgatgatgcc tctactaacc atgttcatgt tttctttttt tttctacagg tcctgggtga      1200
cgaacaggcg gccgccatgg aagatgccaa aaacattaag aagggcccag cgccattcta      1260
cccactcgaa gacgggaccg ccggcgagca gctgcacaaa gccatgaagc gctacgccct      1320 ggtgccggc accatcgcct ttaccgacgc acatatcgag gtggacatta cctacgccga      1380
gtacttcgag atgagcgttc ggctggcaga agctatgaag cgctatgggc tgaatacaaa      1440
ccatcggatc gtggtgtgca gcgagaatag cttgcagttc ttcatgcccg tgttgggtgc      1500
cctgttcatc ggtgtggctg tggccccagc taacgacatc tacaacgagc gcgagctgct      1560
gaacagcatg ggcatcagcc agcccaccgt cgtattcgtg agcaagaaag ggctgcaaaa      1620
```

```
gatcctcaac gtgcaaaaga agctaccgat catacaaaag atcatcatca tggatagcaa   1680
gaccgactac cagggcttcc aaagcatgta caccttcgtg acttcccatt tgccacccgg   1740
cttcaacgag tacgacttcg tgcccgagag cttcgaccgg acaaaaacca tcgccctgat   1800
catgaacagt agtggcagta ccggattgcc caagggcgta gccctaccgc accgcaccgc   1860
ttgtgtccga ttcagtcatg cccgcgaccc catcttcggc aaccagatca tccccgacac   1920
cgctatcctc agcgtggtgc catttcacca cggcttcggc atgttcacca cgctgggcta   1980
cttgatctgc ggctttcggg tcgtgctcat gtaccgcttc gaggaggagc tattcttgcg   2040
cagcttgcaa gactataaga ttcaatctgc cctgctggtg cccacactat ttagcttctt   2100
cgctaagagc actctcatcg acaagtacga cctaagcaac ttgcacgaga tcgccagcgg   2160
cggggcgccg ctcagcaagg aggtaggtga ggccgtggcc aaacgcttcc acctaccagg   2220
catccgccag ggctacggcc tgacagaaac aaccagcgcc attctgatca cccccgaagg   2280
ggacgacaag cctggcgcag taggcaaggt ggtgcccttc ttcgaggcta aggtggtgga   2340
cttggacacc ggtaagacac tgggtgtgaa ccagcgcggc gagctgtgcg tccgtggccc   2400
catgatcatg agcggctacg ttaacaaccc cgaggctaca aacgctctca tcgacaagga   2460
cggctggctg cacagcggcg acatcgccta ctgggacgag gacgagcact tcttcatcgt   2520
ggaccggctg aagagcctga tcaaatacaa gggctaccag gtagcccag ccgaactgga   2580 gagcatcctg ctgcaacacc ccaacatctt cgacgccggg gtcgccggcc tgcccgacga   2640
cgatgccggc gagctgcccg ccgcagtcgt cgtgctggaa cacggtaaaa ccatgaccga   2700
gaaggagatc gtggactatg tggccagcca ggttacaacc gccaagaagc tgcgcggtgg   2760
tgttgtgttc gtggacgagg tgcctaaagg actgaccggc aagttggacg cccgcaagat   2820
ccgcgagatt ctcattaagg ccaagaaggg cggcaagatc gccgtgtaaa ggatcctaat   2880
caacctctgg attacaaaat ttgtgaaaga ttgactggta ttcttaacta tgttgctcct   2940
tttacgctat gtggatacgc tgctttaatg cctttgtatc atgctattgc ttcccgtatg   3000
gctttcattt tctcctcctt gtataaatcc tggttgctgt ctctttatga ggagttgtgg   3060
cccgttgtca ggcaacgtgg cgtggtgtgc actgtgtttg ctgacgcaac ccccactggt   3120
tggggcattg ccaccacctg tcagctcctt ccgggacttt cgctttcccc cctccctatt   3180
gccacggcgg aactcatcgc cgcctgcctt gcccgctgct ggacagggc tcggctgttg   3240 ggcactgaca attccgtggt gttgtcgggg aaatcatcgt cctttccttg gctgctcgcc   3300
tgtgttgcca cctggattct gcgcgggacg tccttctgct acgtcccttc ggccctcaat   3360
ccagcggacc ttccttcccg cggcctgctg ccggctctgc ggcctcttcc gcgtcttcgc   3420
cttcgccctc agacgagtcg gatctccctt gggccgcct cccgcctgg taccttcgag   3480 cagacatgat aagatacatt gatgagtttg gacaaaccac aactagaatg cagtgaaaaa   3540
aatgctttat ttgtgaaatt tgtgatgcta ttgctttatt tgtaaccatt ataagctgca   3600
ataaacaagt taacaacaac aattgcattc attttatgtt tcaggttcag ggggagatgt   3660
gggaggtttt ttaaagcaag taaaacctct acaaatgtgg taaaatcaag cttaggaacc   3720
cctagtgatg gagttggcca ctccctctct gcgcgctcgc tcgctcactg aggccgggcg   3780
accaaaggtc gcccgacgcc cgggctttgc ccgggcggcc tcagtgagcg agcgagcgcg   3840
cagagaggga gtgccaagc tagcgggcga ttaaggaaag gctagatca ttcttgaaga   3900 cgaaagggcc tcgtgatacg cctatttttta taggttaatg tcatgataat aatggtttct   3960
```

```
tagacgtcag gtggcacttt tcggggaaat gtgcgcggaa ccctatttg tttattttc      4020 taaatacatt caaatatgta tccgctcatg agacaataac cctgataaat gcttcaataa    4080
tattgaaaaa ggaagagtat gagtattcaa catttccgtg tcgcccttat tccctttttt    4140
gcggcatttt gccttcctgt ttttgctcac ccagaaacgc tggtgaaagt aaaagatgct    4200
gaagatcagt tgggtgcacg agtgggttac atcgaactgg atctcaacag cggtaagatc    4260
cttgagagtt ttcgccccga agaacgtttt ccaatgatga gcacttttaa agttctgcta    4320
tgtggcgcgg tattatcccg tgttgacgcc gggcaagagc aactcggtcg ccgcatacac    4380
tattctcaga atgacttggt tgagtactca ccagtcacag aaaagcatct tacgatggc     4440 atgacagtaa gagaattatg cagtgctgcc ataaccatga gtgataacac tgcggccaac    4500
ttacttctga caacgatcgg aggaccgaag gagctaaccg cttttttgca acaacatgggg   4560 gatcatgtaa ctcgccttga tcgttgggaa ccggagctga atgaagccat accaaacgac    4620
gagcgtgaca ccacgatgcc tgtagcaatg gcaacaacgt tgcgcaaact attaactggc    4680
gaactactta ctctagcttc ccggcaacaa ttaatagact ggatggaggc ggataaagtt    4740
gcaggaccac ttctgcgctc ggcccttccg gctggctggt ttattgctga taaatctgga    4800
gccggtgagc gtgggtctcg cggtatcatt gcagcactgg ggccagatgg taagccctcc    4860
cgtatcgtag ttatctacac gacggggagt caggcaacta tggatgaacg aaatagacag    4920
atcgctgaga taggtgcctc actgattaag cattggtaac tgtcagacca agtttactca    4980
tatatacttt agattgattt aaaacttcat ttttaattta aaaggatcta ggtgaagatc    5040
ctttttgata atctcatgac caaaatccct taacgtgagt tttcgttcca ctgagcgtca    5100
gaccccgtag aaaagatcaa aggatcttct tgagatcctt ttttctgcg cgtaatctgc      5160 tgcttgcaaa caaaaaaacc accgctacca gcggtggttt gtttgccgga tcaagagcta    5220
ccaactcttt ttccgaaggt aactggcttc agcagagcgc agataccaaa tactgttctt    5280
ctagtgtagc cgtagttagg ccaccacttc aagaactctg tagcaccgcc tacatacctc    5340
gctctgctaa tcctgttacc agtggctgct gccagtggcg ataagtcgtg tcttaccggg    5400
ttggactcaa gacgatagtt accggataag gcgcagcggt cgggctgaac ggggggttcg    5460
tgcacacagc ccagcttgga gcgaacgacc tacaccgaac tgagatacct acagcgtgag    5520
ctatgagaaa gcgccacgct tcccgaaggg agaaaggcgg acaggtatcc ggtaagcggc    5580
agggtcggaa caggagagcg cacgagggag cttccagggg gaaacgcctg gtatctttat    5640
agtcctgtcg ggtttcgcca cctctgactt gagcgtcgat ttttgtgatg ctcgtcaggg    5700
gggcggagcc tatggaaaaa cgccagcaac gcggcctttt tacggttcct ggccttttgc    5760
tggccttttg ctcacatgta ataaacacac acaccaac aaccgtggtt ggttgttgtg       5820
ttggtttatt ctcgag                                                    5836
```

<210> SEQ ID NO 15
<211> LENGTH: 5730
<212> TYPE: DNA
<213> ORGANISM: Artificial Sequence
<220> FEATURE:
<223> OTHER INFORMATION: pAAVio-CASI-Luc2-W-RBG

<400> SEQUENCE: 15

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg     120
gccaactcca tcactagggg ttcctactag tggagttccg cgttacataa cttacggtaa    180
```

| | |
|---|---|
| atggcccgcc tggctgaccg cccaacgacc cccgcccatt gacgtcaata atgacgtatg | 240 |
| ttcccatagt aacgccaata gggactttcc attgacgtca atgggtggag tatttacggt | 300 |
| aaactgccca cttggcagta catcaagtgt atcatatgcc aagtacgccc cctattgacg | 360 |
| tcaatgacgg taaatggccc gcctggcatt atgcccagta catgacctta tgggactttc | 420 |
| ctacttggca gtacatctac gtattagtca tcgctattac catggtcgag gtgagcccca | 480 |
| cgttctgctt cactctcccc atctcccccc cctcccacc cccaattttg tatttattta | 540 |
| tttttaatt attttgtgca gcgatggggg cggggggggg ggggggcgc gcgccaggcg | 600 |
| gggcggggcg gggcgagggg cggggcgggg cgaggcggag aggtgcggcg gcagccaatc | 660 |
| agagcggcgc gctccgaaag tttccttta tggcgaggcg gcggcggcgg cggccctata | 720 |
| aaaagcgaag cgcgcggcgg gcgggagtcg ctgcgcgctg ccttcgcccc gtgccccgct | 780 |
| ccgccgccgc ctcgcgccgc ccgccccggc tctgactgac cgcgttacta aaacaggtaa | 840 |
| gtccggcctc cgcgccgggt tttggcgcct cccgcgggcg ccccctcct cacgcgagc | 900 |
| gctgccacgt cagacgaagg gcgcagcgag cgtcctgatc cttcgcccg gacgctcagg | 960 |
| acagcggccc gctgctcata agactcggcc ttagaacccc agtatcagca agggacatt | 1020 |
| ttaggacggg acttgggtga ctctagggca ctggttttct ttccagagag cggaacaggc | 1080 |
| gaggaaaagt agtcccttct cggcgattct gcggagggat ctccgtgggg cggtgaacgc | 1140 |
| cgatgatgcc tctactaacc atgttcatgt tttctttttt tttctacagg tcctgggtga | 1200 |
| cgaacaggcg gccgccatgg aagatgccaa aaacattaag aagggcccag cgccattcta | 1260 |
| cccactcgaa gacgggaccg ccggcgagca gctgcacaaa gccatgaagc gctacgccct | 1320 |
| ggtgccggc accatcgcct ttaccgacgc acatatcgag gtggacatta cctacgccga | 1380 |
| gtacttcgag atgagcgttc ggctggcaga agctatgaag cgctatgggc tgaatacaaa | 1440 |
| ccatcggatc gtggtgtgca gcgagaatag cttgcagttc ttcatgcccg tgttgggtgc | 1500 |
| cctgttcatc ggtgtggctg tggccccagc taacgacatc tacaacgagc gcgagctgct | 1560 |
| gaacagcatg gcatcagcc agcccaccgt cgtattcgtg agcaagaaag ggctgcaaaa | 1620 |
| gatcctcaac gtgcaaaaga agctaccgat catacaaaag atcatcatca tggatagcaa | 1680 |
| gaccgactac cagggcttcc aaagcatgta ccttcgtg acttcccatt gccacccgg | 1740 |
| cttcaacgag tacgacttcg tgcccgagag cttcgaccgg acaaaaccca tcgccctgat | 1800 |
| catgaacagt agtggcagta ccggattgcc caagggcgta gccctaccgc accgcaccgc | 1860 |
| ttgtgtccga ttcagtcatg cccgcgaccc catcttcggc aaccagatca tccccgacac | 1920 |
| cgctatcctc agcgtggtgc catttcacca cggcttcggc atgttcacca cgctgggcta | 1980 |
| cttgatctgc ggctttcggg tcgtgctcat gtaccgcttc gaggaggagc tattcttgcg | 2040 |
| cagcttgcaa gactataaga ttcaatctgc cctgctggtg cccacactat ttagcttctt | 2100 |
| cgctaagagc actctcatcg acaagtacga cctaagcaac ttgcacgaga tcgccagcgg | 2160 |
| cggggcgccg ctcagcaagg aggtaggtga ggccgtggcc aaacgcttcc acctaccagg | 2220 |
| catccgccag ggctacggcc tgacagaaac aaccagcgcc attctgatca ccccgaagg | 2280 |
| ggacgacaag cctggcgcag taggcaaggt ggtgcccttc ttcgaggcta aggtggtgga | 2340 |
| cttggacacc ggtaagacac tgggtgtgaa ccagcgcggc gagctgtgcg tccgtggccc | 2400 |
| catgatcatg agcggctacg ttaacaaccc cgaggctaca aacgctctca tcgacaagga | 2460 |
| cggctggctg cacagcggcg acatcgccta ctgggacgag gacgagcact tcttcatcgt | 2520 |

```
ggaccggctg aagagcctga tcaaatacaa gggctaccag gtagccccag ccgaactgga    2580
gagcatcctg ctgcaacacc ccaacatctt cgacgccggg gtcgccggcc tgcccgacga    2640
cgatgccggc gagctgcccg ccgcagtcgt cgtgctggaa cacggtaaaa ccatgaccga    2700
gaaggagatc gtggactatg tggccagcca ggttacaacc gccaagaagc tgcgcggtgg    2760
tgttgtgttc gtggacgagg tgcctaaagg actgaccggc aagttggacg cccgcaagat    2820
ccgcgagatt ctcattaagg ccaagaaggg cggcaagatc gccgtgtaaa ggatcctaat    2880
caacctctgg attacaaaat ttgtgaaaga ttgactggta ttcttaacta tgttgctcct    2940
tttacgctat gtggatacgc tgctttaatg cctttgtatc atgctattgc ttcccgtatg    3000
gctttcattt tctcctcctt gtataaatcc tggttgctgt ctctttatga ggagttgtgg    3060
cccgttgtca ggcaacgtgg cgtggtgtgc actgtgtttg ctgacgcaac ccccactggt    3120
tggggcattg ccaccacctg tcagctcctt tccgggactt tcgctttccc cctccctatt    3180 gccacgcgg aactcatcgc cgcctgcctt gcccgctgct ggacaggggc tcggctgttg    3240
ggcactgaca attccgtggt gttgtcgggg aaatcatcgt cctttccttg gctgctcgcc    3300
tgtgttgcca cctggattct gcgcgggacg tccttctgct acgtcccttc ggccctcaat    3360
ccagcggacc ttccttcccg cggcctgctg ccggctctgc ggcctcttcc gcgtcttcgc    3420
cttcgccctc agacgagtcg gatctccctt gggccgcct cccgcctgg taccgatctt    3480 tttcctctg ccaaaaatta tggggacatc atgaagcccc ttgagcatct gacttctggc    3540
taataaagga aatttatttt cattgcaata gtgtgttgga attttttgtg tctctcactc    3600
gaagcttagg aaccccctagt gatggagttg gccactccct ctctgcgcgc tcgctcgctc    3660
actgaggccg ggcgaccaaa ggtcgcccga cgcccgggct tgcccgggc ggcctcagtg    3720 agcgagcgag cgcgcagaga gggagtggcc aagctagcgg gcgattaagg aaagggctag    3780
atcattcttg aagacgaaag ggcctcgtga tacgcctatt tttataggtt aatgtcatga    3840
taataatggt ttcttagacg tcaggtggca cttttcgggg aaatgtgcgc ggaacccta    3900 tttgtttatt tttctaaata cattcaaata tgtatccgct catgagacaa taaccctgat    3960
aaatgcttca ataatattga aaaggaaga gtatgagtat tcaacatttc cgtgtcgccc    4020 ttattcccctt ttttgcggca ttttgccttc ctgttttttgc tcacccagaa acgctggtga    4080
aagtaaaaga tgctgaagat cagttgggtg cacgagtggg ttacatcgaa ctggatctca    4140
acagcggtaa gatccttgag agtttttcgcc ccgaagaacg ttttccaatg atgagcactt    4200
ttaaagttct gctatgtggc gcggtattat cccgtgttga cgccgggcaa gagcaactcg    4260
gtcgccgcat acactattct cagaatgact tggttgagta ctcaccagtc acagaaaagc    4320
atcttacgga tggcatgaca gtaagagaat tatgcagtgc tgccataacc atgagtgata    4380
acactgcggc caacttactt ctgacaacga tcggaggacc gaaggagcta accgcttttt    4440
tgcacaacat gggggatcat gtaactcgcc ttgatcgttg ggaaccggag ctgaatgaag    4500
ccataccaaa cgacgagcgt gacaccacga tgcctgtagc aatggcaaca acgttgcgca    4560
aactattaac tggcgaacta cttactctag cttcccggca acaattaata gactggatgg    4620
aggcggataa agttgcagga ccacttctgc gctcggccct tccggctggc tggtttattg    4680
ctgataaatc tggagccggt gagcgtgggt ctcgcggtat cattgcagca ctggggccag    4740
atggtaagcc ctcccgtatc gtagttatct acacgacggg gagtcaggca actatggatg    4800
aacgaaatag acagatcgct gagataggtg cctcactgat taagcattgg taactgtcag    4860
accaagttta ctcatatata ctttagattg atttaaaact tcatttttaa tttaaaagga    4920
```

```
tctaggtgaa gatcctttt gataatctca tgaccaaaat cccttaacgt gagtttcgt    4980 tccactgagc gtcagacccc gtagaaaaga tcaaaggatc ttcttgagat ccttttttc    5040 tgcgcgtaat ctgctgcttg caaacaaaaa aaccaccgct accagcggtg gtttgtttgc    5100
cggatcaaga gctaccaact ctttttccga aggtaactgg cttcagcaga gcgcagatac    5160
caaatactgt tcttctagtg tagccgtagt taggccacca cttcaagaac tctgtagcac    5220
cgcctacata cctcgctctg ctaatcctgt taccagtggc tgctgccagt ggcgataagt    5280
cgtgtcttac cgggttggac tcaagacgat agttaccgga taaggcgcag cggtcgggct    5340 gaacggggggg ttcgtgcaca cagcccagct tggagcgaac gacctacacc gaactgagat    5400
acctacagcg tgagctatga gaaagcgcca cgcttcccga agggagaaag gcggacaggt    5460
atccggtaag cggcagggtc ggaacaggag agcgcacgag ggagcttcca gggggaaacg    5520
cctggtatct ttatagtcct gtcgggtttc gccacctctg acttgagcgt cgatttttgt    5580
gatgctcgtc agggggcgg agcctatgga aaaacgccag caacgcggcc ttttacggt     5640 tcctggcctt tgctggcct tttgctcaca tgtaataaac acacacacac caacaaccgt    5700
ggttggttgt tgtgttggtt tattctcgag                                     5730

<210> SEQ ID NO 16
<211> LENGTH: 5818
<212> TYPE: DNA
<213> ORGANISM: Artificial Sequence
<220> FEATURE:
<223> OTHER INFORMATION: pAAVio-CASI-Luc2-W-BGH

<400> SEQUENCE: 16
ttggccactc cctctctgcg cgctcgctcg ctcactgagg ccgggcgacc aaaggtcgcc      60
cgacgcccgg gctttgcccg gcggcctcca gtgagcgagc gagcgcgcag agagggagtg     120
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctcccccc cctccccacc cccaattttg tatttattta    540
ttttttaatt attttgtgca gcgatggggg cgggggggg gggggggcgc gcgccaggcg    600 ggcggggcg gggcgagggg cggggcggg cgaggcggag aggtgcggcg gcagccaatc    660
agagcggcgc gctccgaaag tttccttta tggcgaggcg gcggcggcgg cggccctata    720
aaaagcgaag cgcgcggcgg gcgggagtcg ctgcgcgctg ccttcgcccc gtgccccgct    780
ccgccgccgc ctcgcgccgc ccgccccggc tctgactgac cgcgttacta aaacaggtaa    840
gtccggcctc cgcgccgggt tttggcgcct cccgcgggcg cccccctcct cacggcgagc    900
gctgccacgt cagacgaagg cgcagcgag cgtcctgatc cttccgcccg gacgctcagg    960
acagcggccc gctgctcata agactcggcc ttagaacccc agtatcagca gaaggacatt    1020
ttaggacggg acttgggtga ctctagggca ctggttttct ttccagagag cggaacaggc    1080
gaggaaaagt agtcccttct cggcgattct gcggagggat ctccgtgggg cggtgaacgc    1140
cgatgatgcc tctactaacc atgttcatgt tttcttttt tttctacagg tcctgggtga    1200
```

```
cgaacaggcg gccgccatgg aagatgccaa aaacattaag aagggcccag cgccattcta      1260
cccactcgaa gacgggaccg ccggcgagca gctgcacaaa gccatgaagc gctacgccct      1320
ggtgcccggc accatcgcct ttaccgacgc acatatcgag gtggacatta cctacgccga      1380
gtacttcgag atgagcgttc ggctggcaga agctatgaag cgctatgggc tgaatacaaa      1440
ccatcggatc gtggtgtgca gcgagaatag cttgcagttc ttcatgcccg tgttgggtgc      1500
cctgttcatc ggtgtggctg tggccccagc taacgacatc tacaacgagc gcgagctgct      1560
gaacagcatg ggcatcagcc agcccaccgt cgtattcgtg agcaagaaag ggctgcaaaa      1620
gatcctcaac gtgcaaaaga agctaccgat catacaaaag atcatcatca tggatagcaa      1680
gaccgactac cagggcttcc aaagcatgta caccttcgtg acttcccatt tgccacccgg      1740
cttcaacgag tacgacttcg tgcccgagag cttcgaccgg gacaaaacca tcgccctgat      1800
catgaacagt agtggcagta ccggattgcc caagggcgta gccctaccgc accgcaccgc      1860
ttgtgtccga ttcagtcatg cccgcgaccc catcttcggc aaccagatca tccccgacac      1920
cgctatcctc agcgtggtgc catttcacca cggcttcggc atgttcacca cgctgggcta      1980
cttgatctgc ggctttcggg tcgtgctcat gtaccgcttc gaggaggagc tattcttgcg      2040
cagcttgcaa gactataaga ttcaatctgc cctgctggtg cccacactat ttagcttctt      2100
cgctaagagc actctcatcg acaagtacga cctaagcaac ttgcacgaga tcgccagcgg      2160
cggggcgccg ctcagcaagg aggtaggtga ggccgtggcc aaacgcttcc acctaccagg      2220
catccgccag ggctacggcc tgacagaaac aaccagcgcc attctgatca ccccgaagg      2280 ggacgacaag cctggcgcag taggcaaggt ggtgcccttc ttcgaggcta aggtggtgga      2340
cttggacacc ggtaagacac tgggtgtgaa ccagcgcggc gagctgtgcg tccgtggccc      2400
catgatcatg agcggctacg ttaacaaccc cgaggctaca aacgctctca tcgacaagga      2460
cggctggctg cacagcggcg acatcgccta ctgggacgag gacgagcact tcttcatcgt      2520
ggaccggctg aagagcctga tcaaatacaa gggctaccag gtagccccag ccgaactgga      2580
gagcatcctg ctgcaacacc ccaacatctt cgacgccggg gtcgccggcc tgcccgacga      2640
cgatgccggc gagctgcccg ccgcagtcgt cgtgctggaa cacggtaaaa ccatgaccga      2700
gaaggagatc gtggactatg tggccagcca ggttacaacc gccaagaagc tgcgcggtgg      2760
tgttgtgttc gtggacgagg tgcctaaagg actgaccggc aagttggacg cccgcaagat      2820
ccgcgagatt ctcattaagg ccaagaaggg cggcaagatc gccgtgtaaa ggatcctaat      2880
caacctctgg attacaaaat ttgtgaaaga ttgactggta ttcttaacta tgttgctcct      2940
tttacgctat gtggatacgc tgctttaatg cctttgtatc atgctattgc ttcccgtatg      3000
gctttcattt tctcctcctt gtataaatcc tggttgctgt ctctttatga ggagttgtgg      3060
cccgttgtca ggcaacgtgg cgtggtgtgc actgtgtttg ctgacgcaac ccccactggt      3120
tggggcattg ccaccacctg tcagctcctt ccgggactt tcgctttccc cctccctatt      3180
gccacggcgg aactcatcgc cgcctgcctt gcccgctgct ggacagggc tcggctgttg      3240 ggcactgaca attccgtggt gttgtcgggg aaatcatcgt cctttccttg gctgctcgcc      3300
tgtgttgcca cctggattct gcgcgggacg tccttctgct acgtcccttc ggccctcaat      3360
ccagcggacc ttccttcccg cggcctgctg ccggctctgc ggcctcttcc gcgtcttcgc      3420
cttcgccctc agacgagtcg gatctccctt tgggccgcct ccccgcctgg taccgctcg      3480 actgtgcctt ctagttgcca gccatctgtt gtttgccct cccccgtgcc ttccttgacc      3540
ctggaaggtg ccactcccac tgtcctttcc taataaaatg aggaaattgc atcgcattgt      3600
```

```
ctgagtaggt gtcattctat tctgggggt ggggtggggc aggacagcaa ggggaggat    3660
tgggaagaca atagcaggca tgctggggaa agcttaggaa ccctagtga tggagttggc    3720
cactccctct ctgcgcgctc gctcgctcac tgaggccggg cgaccaaagg tcgcccgacg    3780
cccgggcttt gcccgggcgg cctcagtgag cgagcgagcg cgcagagagg gagtggccaa    3840
gctagcgggc gattaaggaa agggctagat cattcttgaa gacgaagggg cctcgtgata    3900
cgcctatttt tataggttaa tgtcatgata ataatggttt cttagacgtc aggtggcact    3960
tttcggggaa atgtgcgcgg aacccctatt tgtttatttt tctaaataca ttcaaatatg    4020
tatccgctca tgagacaata accctgataa atgcttcaat aatattgaaa aaggaagagt    4080
atgagtattc aacatttccg tgtcgccctt attccctttt ttgcggcatt ttgccttcct    4140
gttttgctc acccagaaac gctggtgaaa gtaaaagatg ctgaagatca gttgggtgca    4200
cgagtgggtt acatcgaact ggatctcaac agcggtaaga tccttgagag ttttcgcccc    4260
gaagaacgtt ttccaatgat gagcactttt aaagttctgc tatgtggcgc ggtattatcc    4320
cgtgttgacg ccgggcaaga gcaactcggt cgccgcatac actattctca gaatgacttg    4380
gttgagtact caccagtcac agaaaagcat cttacggatg gcatgacagt aagagaatta    4440
tgcagtgctg ccataaccat gagtgataac actgcggcca acttacttct gacaacgatc    4500
ggaggaccga aggagctaac cgcttttttg cacaacatgg gggatcatgt aactcgcctt    4560
gatcgttggg aaccggagct gaatgaagcc ataccaaacg acgagcgtga ccaccgatg    4620
cctgtagcaa tggcaacaac gttgcgcaaa ctattaactg gcgaactact tactctagct    4680
tcccggcaac aattaataga ctggatggag gcggataaag ttgcaggacc acttctgcgc    4740
tcggcccttc cggctggctg gtttattgct gataaatctg gagccggtga gcgtgggtct    4800
cgcggtatca ttgcagcact ggggccagat ggtaagccct cccgtatcgt agttatctac    4860
acgacgggga gtcaggcaac tatggatgaa cgaaatagac agatcgctga gataggtgcc    4920
tcactgatta agcattggta actgtcagac caagtttact catatatact ttagattgat    4980
ttaaaacttc attttaatt taaaaggatc taggtgaaga tccttttga taatctcatg    5040
accaaaatcc cttaacgtga gttttcgttc cactgagcgt cagaccccgt agaaaagatc    5100
aaaggatctt cttgagatcc ttttttctg cgcgtaatct gctgcttgca acaaaaaaa    5160
ccaccgctac cagcggtggt ttgtttgccg gatcaagagc taccaactct ttttccgaag    5220
gtaactggct tcagcagagc gcagatacca aatactgttc ttctagtgta gccgtagtta    5280
ggccaccact tcaagaactc tgtagcaccg cctacatacc tcgctctgct aatcctgtta    5340
ccagtggctg ctgccagtgg cgataagtcg tgtcttaccg ggttggactc aagacgatag    5400
ttaccggata aggcgcagcg gtcgggctga acggggggtt cgtgcacaca gcccagcttg    5460
gagcgaacga cctacaccga actgagatac ctacagcgtg agctatgaga aagcgccacg    5520
cttcccgaag ggagaaaggc ggacaggtat ccggtaagcg gcagggtcgg aacaggagag    5580
cgcacgaggg agcttccagg gggaaacgcc tggtatcttt atagtcctgt cgggtttcgc    5640
cacctctgac ttgagcgtcg atttttgtga tgctcgtcag ggggggcggag cctatgaaa    5700
aacgccagca acgcggcctt tttacggttc ctggcctttt gctggccttt tgctcacatg    5760
taataaacac acacacacca acaaccgtgg ttggttgttg tgttggttta ttctcgag     5818
```

<210> SEQ ID NO 17
<211> LENGTH: 6481
<212> TYPE: DNA

<213> ORGANISM: Artificial Sequence
<220> FEATURE:
<223> OTHER INFORMATION: pAAVio-CASI-B12AB-HA-W-SV40

<400> SEQUENCE: 17

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctactag tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtcgag gtgagcccca     480
cgttctgctt cactctcccc atctcccccc cctccccacc cccaattttg tatttattta     540
ttttttaatt attttgtgca gcgatggggg cggggggggg ggggggcgc gcgccaggcg     600
gggcggggcg gggcgagggg cggggcgggg cgaggcggag aggtgcggcg gcagccaatc     660
agagcggcgc gctccgaaag tttccttttta tggcgaggcg gcggcggcgg cggccctata     720
aaaagcgaag cgcgcggcgg gcgggagtcg ctgcgcgctg ccttcgcccc gtgccccgct     780
ccgccgccgc ctcgcgccgc ccgccccggc tctgactgac cgcgttacta aaacaggtaa     840
gtccggcctc cgcgccgggt tttggcgcct cccgcgggcg cccccctcct cacggcgagc     900
gctgccacgt cagacgaagg cgcagcgag cgtcctgatc cttccgcccg gacgctcagg     960
acagcggccc gctgctcata agactcggcc ttagaacccc agtatcagca gaaggacatt    1020
ttaggacggg acttgggtga ctctaggca ctggttttct tccagagag cggaacaggc    1080
gaggaaaagt agtcccttct cggcgattct gcggagggat ctccgtgggg cggtgaacgc    1140
cgatgatgcc tctactaacc atgttcatgt tttctttttt tttctacagg tcctgggtga    1200
cgaacaggcg gccgccatgg cgacgggttc aagaacttcc ctacttcttg catttggcct    1260
gctttgtttg ccgtgttac aggagggctc ggcacaggtt cagctggttc agtccggggc    1320
tgaggtgaag aagcctgggg cctcagtgaa ggtttcttgt caggcttctg gatacagatt    1380
cagtaacttt gttattcatt gggtgcgcca ggcccccgga cagaggtttg agtggatggg    1440
atggatcaat ccttacaacg gaaacaaaga attttcagcg aagttccagg acagagtcac    1500
ctttaccgcg gacacatccg cgaacacagc ctacatggag ttgaggagcc tcaggtctgc    1560
agacacggct gtttattatt gtgcgagagt ggggccatat agttgggatg attctcccca    1620
ggacaattat tatatggacg tctggggcaa agggaccacg gtcatcgtga gctcagccag    1680
caccaagggc ccatcggtct tccccctggc accctcctcc aagagcacct ctggggggcac    1740
agcggccctg ggctgcctgg tcaaggacta cttccccgaa ccggtgacgg tgtcgtggaa    1800
ctcaggcgcc ctgaccagcg gcgtgcacac cttcccggct gtcctacagt cctcaggact    1860
ctactccctc agcagcgtgg tgaccgtgcc ctccagcagc ttgggcaccc agacctacat    1920
ctgcaacgta atcacaagc ccagcaacac caaggtggac aagaaagttg agcccaaatc    1980
ttgtgacaaa actcacacat gcccaccgtg cccagcacct gaactcctgg ggggaccgtc    2040
agtcttcctc ttccccccaa aacccaagga caccctcatg atctcccgga cccctgaggt    2100
cacatgcgtg gtggtggacg tgagccacga agaccctgag gtcaagttca actggtatgt    2160
tgacggcgtg gaggtgcata atgccaagac aaagccgcgg gaggagcagt acaacagcac    2220
```

-continued

```
gtaccgtgtg gtcagcgtcc tcaccgtcct gcaccaggac tggctgaatg caaggagta    2280 caagtgcaag gtctccaaca aagccctccc agccccatc gagaaaacca tctccaaagc    2340
caaagggcag ccccgagaac acaggtgta cccctgccc ccatcccggg atgagctgac     2400
caagaatcaa gtcagcctga cctgcctggt caaaggcttc tatcccagcg acatcgccgt   2460
ggagtgggag agcaatgggc agccggagaa caactacaag accacgcctc ccgtgctgga   2520
ctccgacggc tccttcttcc tctactcaaa actcaccgtg gacaagagca ggtggcagca   2580
ggggaacgtc ttctcatgct ccgtgatgca tgaggctctg cacaaccact acacgcagaa   2640
gagcctctcc ctgtctccgg gtaaaagggc aaaacgttcg ggttcgggtg cgccagtaaa   2700
gcagacatta aactttgatt tgctgaaact tgcaggtgat gtagagtcaa atccaggtcc   2760
aatggcaaca gggagccgaa cctctctgct ccttgctttc gggctccttt gcctaccgtg   2820
gctccaagag ggctcggcag agatcgttct cacgcagtct ccaggcaccc tgtctctgtc   2880
tccaggggaa agagccacct tctcctgtag gtccagtcac agcattcgca gccgccgcgt   2940
agcctggtac cagcacaaac ctggccaggc tccaaggctg gtcatacatg gtgtttccaa   3000
tagggcctct ggcatctcag acaggttcag cggcagtggg tctgggacag acttcactct   3060
caccatcacc agagtggagc ctgaagactt tgcactgtac tactgtcagg tctatggtgc   3120
ctcctcgtac acttttggcc aggggaccaa actggagagg aaacgtacgg tggccgctcc   3180
cagcgtgttc atcttccctc cctctgatga acagctgaaa agcggaacag ccagcgtggt   3240
gtgtctgctg aacaacttct accccagaga agccaaagtg cagtggaagg tggacaacgc   3300
cctgcagagc ggaaacagcc aggaaagcgt gacagagcag gattccaagg attccacata   3360
cagcctgagc agcacactga cactgtccaa ggccgactac gagaagcaca aggtgtacgc   3420
ctgcgaagtg acacaccagg gactgtcctc ccctgtgaca aagagcttca acagaggaga   3480 atgctacccct tacgacgtac cagactacgc ataaaggatc ctaatcaacc tctggattac   3540
aaaatttgtg aaagattgac tggtattctt aactatgttg ctccttttac gctatgtgga    3600
tacgctgctt taatgccttt gtatcatgct attgcttccc gtatggcttt cattttctcc    3660
tccttgtata aatcctggtt gctgtctctt tatgaggagt tgtggcccgt tgtcaggcaa    3720
cgtggcgtgg tgtgcactgt gtttgctgac gcaacccca ctggttgggg cattgccacc     3780
acctgtcagc tcctttccgg gactttcgct ttccccctcc ctattgccac ggcggaactc    3840
atcgccgcct gccttgcccg ctgctggaca ggggctcggc tgttgggcac tgacaattcc    3900
gtggtgttgt cggggaaatc atcgtccttt ccttggctgc tcgcctgtgt tgccacctgg    3960
attctgcgcg gacgtccttc tgctacgtc ccttcggccc tcaatccagc ggaccttcct    4020
tcccgcggcc tgctgccggc tctgcggcct cttccgcgtc ttcgccttcg ccctcagacg   4080
agtcggatct ccctttgggc cgcctccccg cctggtacct tcgagcagac atgataagat   4140
acattgatga gtttggacaa accacaacta gaatgcagtg aaaaaaatgc tttatttgtg   4200
aaatttgtga tgctattgct ttatttgtaa ccattataag ctgcaataaa caagttaaca   4260
acaacaattg cattcatttt atgtttcagg ttcaggggga gatgtgggag gtttttaaa    4320 gcaagtaaaa cctctacaaa tgtggtaaaa tcaagcttag gaacccctag tgatggagtt   4380
ggccactccc tctctgcgcg ctcgctcgct cactgaggcc gggcgaccaa aggtcgcccg   4440
acgcccggga tttgcccggg cggcctcagt gagcgagcga gcgcgcagag agggagtggc   4500
caagctagcg ggcgattaag gaaagggcta gatcattctt gaagacgaaa gggcctcgtg   4560
```

| atacgcctat | ttttataggt | taatgtcatg | ataataatgg | tttcttagac | gtcaggtggc | 4620 |
| acttttcggg | gaaatgtgcg | cggaacccct | atttgtttat | ttttctaaat | acattcaaat | 4680 |
| atgtatccgc | tcatgagaca | ataaccctga | taaatgcttc | aataatattg | aaaaaggaag | 4740 |
| agtatgagta | ttcaacattt | ccgtgtcgcc | cttattccct | tttttgcggc | attttgcctt | 4800 |
| cctgttttttg | ctcacccaga | aacgctggtg | aaagtaaaag | atgctgaaga | tcagttgggt | 4860 |
| gcacgagtgg | gttacatcga | actggatctc | aacagcggta | agatccttga | gagttttcgc | 4920 |
| cccgaagaac | gttttccaat | gatgagcact | tttaaagttc | tgctatgtgg | cgcggtatta | 4980 |
| tcccgtgttg | acgccgggca | agagcaactc | ggtcgccgca | tacactattc | tcagaatgac | 5040 |
| ttggttgagt | actcaccagt | cacagaaaag | catcttacgg | atggcatgac | agtaagagaa | 5100 |
| ttatgcagtg | ctgccataac | catgagtgat | aacactgcgg | ccaacttact | tctgacaacg | 5160 |
| atcggaggac | cgaaggagct | aaccgctttt | ttgcacaaca | tgggggatca | tgtaactcgc | 5220 |
| cttgatcgtt | gggaaccgga | gctgaatgaa | gccataccaa | acgacgagcg | tgacaccacg | 5280 |
| atgcctgtag | caatggcaac | aacgttgcgc | aaactattaa | ctggcgaact | acttactcta | 5340 |
| gcttcccggc | aacaattaat | agactggatg | gaggcggata | aagttgcagg | accacttctg | 5400 |
| cgctcggccc | ttccggctgg | ctggtttatt | gctgataaat | ctggagccgg | tgagcgtggg | 5460 |
| tctcgcggta | tcattgcagc | actggggcca | gatggtaagc | cctcccgtat | cgtagttatc | 5520 |
| tacacgacgg | ggagtcaggc | aactatggat | gaacgaaata | gacagatcgc | tgagataggt | 5580 |
| gcctcactga | ttaagcattg | gtaactgtca | gaccaagttt | actcatatat | actttagatt | 5640 |
| gatttaaaac | ttcatttttta | atttaaaagg | atctaggtga | agatcctttt | tgataatctc | 5700 |
| atgaccaaaa | tcccttaacg | tgagttttcg | ttccactgag | cgtcagaccc | cgtagaaaag | 5760 |
| atcaaaggat | cttcttgaga | tccttttttt | ctgcgcgtaa | tctgctgctt | gcaaacaaaa | 5820 |
| aaaccaccgc | taccagcggt | ggtttgtttg | ccggatcaag | agctaccaac | tcttttttccg | 5880 |
| aaggtaactg | gcttcagcag | agcgcagata | ccaaatactg | ttcttctagt | gtagccgtag | 5940 |
| ttaggccacc | acttcaagaa | ctctgtagca | ccgcctacat | acctcgctct | gctaatcctg | 6000 |
| ttaccagtgg | ctgctgccag | tggcgataag | tcgtgtctta | ccgggttgga | ctcaagacga | 6060 |
| tagttaccgg | ataaggcgca | gcggtcgggc | tgaacggggg | gttcgtgcac | acagcccagc | 6120 |
| ttggagcgaa | cgacctacac | cgaactgaga | tacctacagc | gtgagctatg | agaaagcgcc | 6180 |
| acgcttcccg | aagggagaaa | ggcggacagg | tatccggtaa | gcggcagggt | cggaacagga | 6240 |
| gagcgcacga | gggagcttcc | agggggaaac | gcctggtatc | tttatagtcc | tgtcgggttt | 6300 |
| cgccacctct | gacttgagcg | tcgatttttg | tgatgctcgt | caggggggcg | gagcctatgg | 6360 |
| aaaaacgcca | gcaacgcggc | ctttttacgg | ttcctggcct | tttgctggcc | ttttgctcac | 6420 |
| atgtaataaa | cacacacaca | ccaacaaccg | tggttggttg | ttgtgttggt | ttattctcga | 6480 |
| g | | | | | | 6481 |

<210> SEQ ID NO 18
<211> LENGTH: 6493
<212> TYPE: DNA
<213> ORGANISM: Artificial Sequence
<220> FEATURE:
<223> OTHER INFORMATION: pAAVio-CASI-4E10AB-V5-W-SV40

<400> SEQUENCE: 18

| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |

```
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctcccccc cctccccacc cccaattttg tatttattta    540 tttttttaatt attttgtgca gcgatggggg cggggggggg gggggggcgc gcgccaggcg    600
gggcggggcg gggcgagggg cggggcgggg cgaggcggag aggtgcggcg gcagccaatc    660
agagcggcgc gctccgaaag tttccttttta tggcgaggcg gcggcggcgg cggccctata    720
aaaagcgaag cgcgcggcgg gcgggagtcg ctgcgcgctg ccttcgcccc gtgccccgct    780
ccgccgccgc ctcgcgccgc ccgccccggc tctgactgac cgcgttacta aaacaggtaa    840
gtccggcctc cgcgccgggt tttggcgcct cccgcgggcg cccccctcct cacggcgagc    900
gctgccacgt cagacgaagg cgcagcgag cgtcctgatc cttccgcccg gacgctcagg    960
acagcggccc gctgctcata agactcggcc ttagaacccc agtatcagca gaaggacatt    1020
ttaggacggg acttgggtga ctctagggca ctggttttct ttccagagag cggaacaggc    1080
gaggaaaagt agtcccttct cggcgattct gcggagggat ctccgtgggg cggtgaacgc    1140
cgatgatgcc tctactaacc atgttcatgt tttcttttttt tttctacagg tcctgggtga    1200
cgaacaggcg gccgccatgg cgacgggttc aagaacttcc ctacttcttg catttggcct    1260
gctttgtttg ccgtggttac aggagggctc ggcagtgcag ctggtgcaga gcggagccga    1320
ggtgaagagg cccggcagca gcgtgaccgt gagctgcaag gccagcggcg gcagcttcag    1380
cacctacgcc ctgagctggg tgcggcaggc tcctggaagg ggcctcgaat ggatgggcgg    1440
cgtgatcccc ctgctgacca tcaccaacta cgcccccagg ttccagggcc ggatcaccat    1500
caccgccgac agaagcacca gcaccgccta cctggaactg aacagcctgc ggcccgagga    1560
caccgccgtg tactactgcg ccagagaggg caccaccggc tggggctggc tgggcaagcc    1620
catcggcgcc ttcgcccact ggggccaggg caccctggtg accgtgtcca gcgccagcac    1680
caagggccca tcggtcttcc ccctggcacc ctcctccaag agcacctctg ggggcacagc    1740
ggccctgggc tgcctggtca aggactactt ccccgaaccg gtgacggtgt cgtggaactc    1800
aggcgccctg accagcggcg tgcacacctt cccggctgtc ctacagtcct caggactcta    1860
ctccctcagc agcgtggtga ccgtgccctc cagcagcttg ggcacccaga cctacatctg    1920
caacgtgaat cacaagccca gcaacaccaa ggtggacaag aaagttgagc ccaaatcttg    1980
tgacaaaact cacacatgcc caccgtgccc agcacctgaa ctcctggggg gaccgtcagt    2040
cttcctcttc cccccaaaac ccaaggacac cctcatgatc tcccggaccc ctgaggtcac    2100
atgcgtggtg gtggacgtga gccacgaaga ccctgaggtc aagttcaact ggtatgttga    2160
cggcgtggag gtgcataatg ccaagacaaa gccgcgggag gagcagtaca acagcacgta    2220
ccgtgtggtc agcgtcctca ccgtcctgca ccaggactgg ctgaatggca aggagtacaa    2280
gtgcaaggtc tccaacaaag ccctcccagc ccccatcgag aaaaccatct ccaaagccaa    2340
agggcagccc cgagaaccac aggtgtacac cctgccccca tcccgggatg agctgaccaa    2400
gaatcaagtc agcctgacct gcctggtcaa aggcttctat cccagcgaca tcgccgtgga    2460
```

```
gtgggagagc aatgggcagc cggagaacaa ctacaagacc acgcctcccg tgctggactc    2520
cgacggctcc ttcttcctct actcaaaact caccgtggac aagagcaggt ggcagcaggg    2580
gaacgtcttc tcatgctccg tgatgcatga ggctctgcac aaccactaca cgcagaagag    2640
cctctccctg tctccgggta aagggcaaa acgttcgggt tcgggtgcgc cagtaaagca    2700
gacattaaac tttgatttgc tgaaacttgc aggtgatgta gagtcaaatc caggtccaat    2760
ggcaacaggg agccgaacct ctctgctcct tgctttcggg ctccttttgcc taccgtggct    2820
ccaagagggc tcggcagaga tcgtgctgac ccagagcccc ggcacccaga gcctgagccc    2880
tggcgagcgg gccaccctga gctgccgggc cagccagagc gtgggcaaca caagctggc    2940
ctggtatcag cagagacccg gccaggcccc caggctgctg atctacggcg cctcctctag    3000
gcctagcggc gtggccgacc ggtttagcgg cagcggctcc ggcaccgact tcaccctgac    3060
catcagccgg ctggaacccg aggacttcgc cgtgtactac tgccagcagt acggccagag    3120
cctgtccacc ttcggccagg gcaccaaggt ggaggtgaag cggaccgtgg ccgctcccag    3180
cgtgttcatc ttccctccct ctgatgaaca gctgaaaagc ggaacagcca gcgtggtgtg    3240
tctgctgaac aacttctacc ccagagaagc caaagtgcag tggaaggtgg acaacgccct    3300
gcagagcgga aacagccagg aaagcgtgac agagcaggat tccaaggatt ccacatacag    3360
cctgagcagc acactgacac tgtccaaggc cgactacgag aagcacaagg tgtacgcctg    3420
cgaagtgaca caccagggac tgtcctcccc tgtgacaaag agcttcaaca gaggagaatg    3480
cggcaagcct atccctaacc ctctcctcgg tctcgattct acgtaaagga tcctaatcaa    3540
cctctggatt acaaaatttg tgaaagattg actggtattc ttaactatgt tgctcctttt    3600
acgctatgtg gatacgctgc tttaatgcct ttgtatcatg ctattgcttc ccgtatggct    3660
ttcattttct cctccttgta taaatcctgg ttgctgtctc tttatgagga gttgtggccc    3720
gttgtcaggc aacgtggcgt ggtgtgcact gtgtttgctg acgcaacccc cactggttgg    3780
ggcattgcca ccacctgtca gctcctttcc gggactttcg cttccccct ccctattgcc    3840
acggcggaac tcatcgccgc ctgccttgcc cgctgctgga caggggctcg gctgttgggc    3900
actgacaatt ccgtggtgtt gtcggggaaa tcatcgtcct ttccttggct gctcgcctgt    3960
gttgccacct ggattctgcg cgggacgtcc ttctgctacg tcccttcggc cctcaatcca    4020
gcggaccttc cttcccgcgg cctgctgccg gctctgcggc ctcttccgcg tcttcgcctt    4080
cgccctcaga cgagtcggat ctccctttgg gccgcctccc cgcctggtac cttcgagcag    4140
acatgataag atacattgat gagtttggac aaaccacaac tagaatgcag tgaaaaaaat    4200
gctttatttg tgaaatttgt gatgctattg ctttatttgt aaccattata agctgcaata    4260
aacaagttaa caacaacaat tgcattcatt ttatgtttca ggttcagggg gagatgtggg    4320
aggttttta aagcaagtaa aacctctaca atgtgtaa aatcaagctt aggaacccct    4380
agtgatggag ttggccactc cctctctgcg cgctcgctcg ctcactgagg ccgggcgacc    4440
aaaggtcgcc cgacgcccgg gctttgcccg ggcggcctca gtgagcgagc gagcgcgcag    4500
agagggagtg gccaagctag cgggcgatta aggaagggc tagatcattc ttgaagacga    4560
aagggcctcg tgatacgcct atttttatag gttaatgtca tgataataat ggtttcttag    4620
acgtcaggtg cacttttcg gggaaatgtg cgcggaaccc ctatttgttt attttttctaa    4680
atacattcaa atatgtatcc gctcatgaga caataaccct gataaatgct tcaataatat    4740
tgaaaaagga agagtatgag tattcaacat ttccgtgtcg cccttattcc cttttttgcg    4800
gcattttgcc ttcctgtttt tgctcaccca gaaacgctgg tgaaagtaaa agatgctgaa    4860
```

```
gatcagttgg gtgcacgagt gggttacatc gaactggatc tcaacagcgg taagatcctt    4920
gagagttttc gccccgaaga acgttttcca atgatgagca cttttaaagt tctgctatgt    4980
ggcgcggtat tatcccgtgt tgacgccggg caagagcaac tcggtcgccg catacactat    5040
tctcagaatg acttggttga gtactcacca gtcacagaaa agcatcttac ggatggcatg    5100
acagtaagag aattatgcag tgctgccata accatgagtg ataacactgc ggccaactta    5160
cttctgacaa cgatcggagg accgaaggag ctaaccgctt ttttgcacaa catgggggat    5220
catgtaactc gccttgatcg ttgggaaccg gagctgaatg aagccatacc aaacgacgag    5280
cgtgacacca cgatgcctgt agcaatggca acaacgttgc gcaaactatt aactggcgaa    5340
ctacttactc tagcttcccg gcaacaatta atagactgga tggaggcgga taaagttgca    5400
ggaccacttc tgcgctcggc ccttccggct ggctggttta ttgctgataa atctggagcc    5460
ggtgagcgtg ggtctcgcgg tatcattgca gcactggggc cagatggtaa gccctcccgt    5520
atcgtagtta tctacacgac ggggagtcag gcaactatgg atgaacgaaa tagacagatc    5580
gctgagatag gtgcctcact gattaagcat tggtaactgt cagaccaagt ttactcatat    5640
atactttaga ttgatttaaa acttcatttt taatttaaaa ggatctaggt gaagatcctt    5700
tttgataatc tcatgaccaa aatcccttaa cgtgagtttt cgttccactg agcgtcagac    5760
cccgtagaaa agatcaaagg atcttcttga gatcctttt ttctgcgcgt aatctgctgc    5820
ttgcaaacaa aaaaaccacc gctaccagcg gtggtttgtt tgccggatca agagctacca    5880 actcttttc cgaaggtaac tggcttcagc agagcgcaga taccaaatac tgttcttcta    5940
gtgtagccgt agttaggcca ccacttcaag aactctgtag caccgcctac atacctcgct    6000
ctgctaatcc tgttaccagt ggctgctgcc agtggcgata gtcgtgtct taccgggttg    6060 gactcaagac gatagttacc ggataaggcg cagcggtcgg gctgaacggg gggttcgtgc    6120
acacagccca gcttggagcg aacgacctac accgaactga gatacctaca gcgtgagcta    6180
tgagaaagcg ccacgcttcc cgaagggaga aaggcggaca ggtatccggt aagcggcagg    6240
gtcggaacag gagagcgcac gagggagctt ccaggggaa acgcctggta tctttatagt    6300
cctgtcgggt ttcgccacct ctgacttgag cgtcgatttt tgtgatgctc gtcagggggg    6360
cggagcctat ggaaaaacgc cagcaacgcg gcctttttac ggttcctggc cttttgctgg    6420
ccttttgctc acatgtaata aacacacaca caccaacaac cgtggttggt tgttgtgttg    6480
gtttattctc gag    6493
```

<210> SEQ ID NO 19
<211> LENGTH: 6469
<212> TYPE: DNA
<213> ORGANISM: Artificial Sequence
<220> FEATURE:
<223> OTHER INFORMATION: pAAVio-CASI-2G12AB-Myc-W-SV40

<400> SEQUENCE: 19

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
```

```
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctcccccc cctccccacc cccaattttg tatttattta    540
tttttaatt attttgtgca gcgatggggg cggggggggg ggggggcgc gcgccaggcg     600
ggcggggcg gggcgagggg cggggcgggg cgaggcggag aggtgcggcg gcagccaatc     660
agagcggcgc gctccgaaag tttccttta tggcgaggcg gcggcggcgg cggccctata    720
aaaagcgaag cgcgcggcgg gcgggagtcg ctgcgcgctg ccttcgcccc gtgcccgct    780
ccgccgccgc ctcgcgccgc ccgccccggc tctgactgac cgcgttacta aaacaggtaa    840
gtccggcctc cgcgccgggt tttggcgcct cccgcgggcg cccccctcct cacggcgagc    900
gctgccacgt cagacgaagg gcgcagcgag cgtcctgatc cttccgcccg gacgctcagg    960
acagcggccc gctgctcata agactcggcc ttagaacccc agtatcagca gaaggacatt   1020
ttaggacggg acttgggtga ctctagggca ctggtttttct ttccagagag cggaacaggc   1080
gaggaaaagt agtcccttct cggcgattct gcggagggat ctccgtgggg cggtgaacgc   1140
cgatgatgcc tctactaacc atgttcatgt tttcttttt tttctacagg tcctgggtga   1200
cgaacaggcg gccgccatgg cgacgggttc aagaacttcc ctacttcttg catttggcct   1260
gctttgtttg ccgtggttac aggagggctc ggcagaggtg caacttttag agtctggcgg   1320
cggcctggtc aaggcgggag gttccctcat actctcctgt ggagtctcta attttagaat   1380
ctctgcccat accatgaatt gggtccgccg ggttccaggg gggggctgg agtgggtcgc    1440
ttccattagt acgagttcca cttatagaga ctatgcagac gctgtgaagg gccgattcac   1500
cgtttccaga gacgacctcg aagactttgt gtatttgcaa atgcacaaaa tgagagtcga   1560
agacacggct atttattact gcgccagaaa gggatctgac agactaagcg acaacgatcc   1620
ttttgatgcc tggggcccag ggacagtggt caccgtctct ccagccagca ccaagggccc   1680
atcggtcttc cccctggcac cctcctccaa gagcacctct gggggcacag cggccctggg   1740
ctgcctggtc aaggactact ccccgaacc ggtgacggtg tcgtggaact caggcgccct    1800
gaccagcggc gtgcacacct tcccggctgt cctacagtcc tcaggactct actccctcag   1860
cagcgtggtg accgtgccct ccagcagctt gggcacccag acctacatct gcaacgtgaa   1920
tcacaagccc agcaacacca aggtggacaa gaaagttgag cccaaatctt gtgacaaaac   1980
tcacacatgc ccaccgtgcc cagcacctga actcctgggg ggaccgtcag tcttcctctt   2040
cccccaaaa cccaaggaca ccctcatgat ctcccggacc cctgaggtca catgcgtggt   2100
ggtggacgtg agccacgaag accctgaggt caagttcaac tggtatgttg acggcgtgga   2160
ggtgcataat gccaagacaa agccgcggga ggagcagtac aacagcacgt accgtgtggt   2220
cagcgtcctc accgtcctgc accaggactg gctgaatggc aaggagtaca agtgcaaggt   2280
ctccaacaaa gccctcccag cccccatcga gaaaaccatc tccaaagcca aagggcagcc   2340
ccgagaacca caggtgtaca ccctgccccc atcccgggat gagctgacca agaatcaagt   2400
cagcctgacc tgcctggtca aaggcttcta tcccagcgac atcgccgtgg agtgggagag   2460
caatgggcag ccggagaaca actacaagac cacgcctccc gtgctggact ccgacggctc   2520
cttcttcctc tactcaaaac tcaccgtgga caagagcagg tggcagcagg ggaacgtctt   2580
ctcatgctcc gtgatgcatg aggctctgca caaccactac acgcagaaga gcctctccct   2640
gtctccgggt aaaagggcaa aacgttcggg ttcgggtgcg ccagtaaagc agacattaaa   2700
ctttgatttg ctgaaacttg caggtgatgt agagtcaaat ccaggtccaa tggcaacagg   2760
```

```
gagccgaacc tctctgctcc ttgctttcgg gctcctttgc ctaccgtggc tccaagaggg    2820
ctcggcagaa attgagctca cccagtctcc ttccaccctg tctgcatctg tcggagacac    2880
aatcaccatc acttgccggg ccagtcagag tattgaaacc tggttggcct ggtatcagca    2940
gaagccaggg aaagccccaa aactcctaat ctacaaggcg tctactttaa aaactggagt    3000
cccgtcaaga ttcagcggca gtggatctgg aacagagttc actcttacca tcagtggcct    3060
gcagttcgat gactttgcaa cttatcactg tcagcactat gctggttatt cagccacttt    3120
tggccaggga accagggtgg agatcaaacg tacggtggcc gctcccagcg tgttcatctt    3180
ccctccctct gatgaacagc tgaaaagcgg aacagccagc gtggtgtgtc tgctgaacaa    3240
cttctacccc agagaagcca aagtgcagtg gaaggtggac aacgccctgc agagcggaaa    3300
cagccaggaa agcgtgacag agcaggattc caaggattcc acatacagcc tgagcagcac    3360
actgacactg tccaaggccg actacgagaa gcacaaggtg tacgcctgcg aagtgacaca    3420
ccagggactg tcctcccctg tgacaaagag cttcaacaga ggagaatgcg aacaaaaact    3480
catctcagaa gaggatctgt aaaggatcct aatcaacctc tggattacaa atttgtgaa    3540 agattgactg gtattcttaa ctatgttgct ccttttacgc tatgtggata cgctgcttta    3600
atgcctttgt atcatgctat tgcttcccgt atggctttca ttttctcctc cttgtataaa    3660
tcctggttgc tgtctcttta tgaggagttg tggcccgttg tcaggcaacg tggcgtggtg    3720
tgcactgtgt ttgctgacgc aaccccact ggttggggca ttgccaccac ctgtcagctc    3780
ctttccggga ctttcgcttt ccccctccct attgccacgg cggaactcat cgccgcctgc    3840
cttgcccgct gctggacagg ggctcggctg ttgggcactg acaattccgt ggtgttgtcg    3900
gggaaatcat cgtcctttcc ttggctgctc gcctgtgttg ccacctggat tctgcgcggg    3960
acgtccttct gctacgtccc ttcggccctc aatccagcgg accttccttc ccgcggcctg    4020
ctgccggctc tgcggcctct tccgcgtctt cgccttcgcc ctcagacgag tcggatctcc    4080
ctttgggccg cctccccgcc tggtaccttc gagcagacat gataagatac attgatgagt    4140
ttggacaaac cacaactaga atgcagtgaa aaaaatgctt tatttgtgaa atttgtgatg    4200
ctattgcttt atttgtaacc attataagct gcaataaaca agttaacaac aacaattgca    4260
ttcattttat gtttcaggtt caggggagga tgtgggaggt tttttaaagc aagtaaaacc    4320
tctacaaatg tggtaaaatc aagcttagga accctagtg atggagttgg ccactccctc    4380
tctgcgcgct cgctcgctca ctgaggccgg gcgaccaaag gtcgcccgac gcccgggctt    4440
tgcccgggcg gcctcagtga gcgagcgagc gcgcagagag ggagtggcca agctagcggg    4500
cgattaagga aagggctaga tcattcttga agacgaaagg gcctcgtgat acgcctattt    4560
ttataggtta atgtcatgat aataatggtt tcttagacgt caggtggcac ttttcgggga    4620
aatgtgcgcg gaacccctat ttgtttattt ttctaaatac attcaaatat gtatccgctc    4680
atgagacaat aaccctgata aatgcttcaa taatattgaa aaaggaagag tatgagtatt    4740
caacatttcc gtgtcgccct tattccctt tttgcggcat tttgccttcc tgtttttgct    4800
cacccagaaa cgctggtgaa agtaaaagat gctgaagatc agttgggtgc acgagtgggt    4860
tacatcgaac tggatctcaa cagcggtaag atccttgaga gttttcgccc cgaagaacgt    4920
tttccaatga tgagcacttt taaagttctg ctatgtggcg cggtattatc ccgtgttgac    4980
gccgggcaag agcaactcgg tcgccgcata cactattctc agaatgactt ggttgagtac    5040
tcaccagtca cagaaaagca tcttacggat ggcatgacag taagagaatt atgcagtgct    5100
```

```
gccataacca tgagtgataa cactgcggcc aacttacttc tgacaacgat cggaggaccg    5160
aaggagctaa ccgcttttt gcacaacatg ggggatcatg taactcgcct tgatcgttgg    5220
gaaccggagc tgaatgaagc cataccaaac gacgagcgtg acaccacgat gcctgtagca    5280
atggcaacaa cgttgcgcaa actattaact ggcgaactac ttactctagc ttcccggcaa    5340
caattaatag actggatgga ggcggataaa gttgcaggac cacttctgcg ctcggccctt    5400
ccggctggct ggtttattgc tgataaatct ggagccggtg agcgtgggtc tcgcggtatc    5460
attgcagcac tggggccaga tggtaagccc tcccgtatcg tagttatcta cacgacgggg    5520
agtcaggcaa ctatggatga acgaaataga cagatcgctg agataggtgc ctcactgatt    5580
aagcattggt aactgtcaga ccaagtttac tcatatatac tttagattga tttaaaactt    5640 cattttttaat ttaaaaggat ctaggtgaag atccttttg ataatctcat gaccaaaatc    5700
ccttaacgtg agttttcgtt ccactgagcg tcagaccccg tagaaaagat caaaggatct    5760
tcttgagatc ctttttttct gcgcgtaatc tgctgcttgc aaacaaaaaa accaccgcta    5820
ccagcggtgg tttgtttgcc ggatcaagag ctaccaactc ttttccgaa ggtaactggc    5880 ttcagcagag cgcagatacc aaatactgtt cttctagtgt agccgtagtt aggccaccac    5940
ttcaagaact ctgtagcacc gcctacatac ctcgctctgc taatcctgtt accagtggct    6000
gctgccagtg gcgataagtc gtgtcttacc gggttggact caagacgata gttaccggat    6060
aaggcgcagc ggtcgggctg aacggggggt tcgtgcacac agcccagctt ggagcgaacg    6120
acctacaccg aactgagata cctacagcgt gagctatgag aaagcgccac gcttcccgaa    6180
gggagaaagg cggacaggta tccggtaagc ggcagggtcg gaacaggaga gcgcacgagg    6240
gagcttccag ggggaaacgc ctggtatctt tatagtcctg tcgggtttcg ccacctctga    6300
cttgagcgtc gatttttgtg atgctcgtca ggggggcgga gcctatggaa aaacgccagc    6360
aacgcggcct ttttacggtt cctggccttt tgctggcctt ttgctcacat gtaataaaca    6420
cacacacacc aacaaccgtg gttggttgtt gtgttggttt attctcgag               6469
```

<210> SEQ ID NO 20
<211> LENGTH: 6502
<212> TYPE: DNA
<213> ORGANISM: Artificial Sequence
<220> FEATURE:
<223> OTHER INFORMATION: pAAVio-CASI-2F5AB-T7-W-SV40

<400> SEQUENCE: 20

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctactag tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtcgag gtgagcccca     480
cgttctgctt cactctcccc atctcccccc cctccccacc cccaattttg tatttattta     540
ttttttaatt attttgtgca gcgatggggg cgggggggg gggggggcgc gcgccaggcg     600
gggcggggcg gggcgagggg cggggcgggg cgaggcggag aggtgcggcg gcagccaatc     660
agagcggcgc gctccgaaag tttccttta tggcgaggcg gcggcggcgg cggccctata     720
```

```
aaaagcgaag cgcgcggcgg gcgggagtcg ctgcgcgctg ccttcgcccc gtgcccgct      780
ccgccgccgc ctcgcgccgc ccgccccggc tctgactgac cgcgttacta aaacaggtaa      840
gtccggcctc cgcgccgggt tttggcgcct cccgcgggcg ccccctcct cacggcgagc       900
gctgccacgt cagacgaagg gcgcagcgag cgtcctgatc cttccgcccg gacgctcagg      960
acagcggccc gctgctcata agactcggcc ttagaacccc agtatcagca gaaggacatt     1020
ttaggacggg acttgggtga ctctagggca ctggttttct ttccagagag cggaacaggc     1080
gaggaaaagt agtcccttct cggcgattct gcggagggat ctccgtgggg cggtgaacgc     1140
cgatgatgcc tctactaacc atgttcatgt tttcttttt tttctacagg tcctgggtga      1200
cgaacaggcg gccgccatgg cgacgggttc aagaacttcc ctacttcttg catttggcct     1260
gctttgtttg ccgtggttac aggagggctc ggcacaccgg atcaccctga aagagagcgg     1320
cccctcccctg gtcaagccca cccagaccct gaccctgaca tgcagcttca gcggcttcag    1380
cctgagcgac ttcggcgtgg gcgtgggctg gatcaggcag ccccctggca aggccctgga    1440
atggctggcc atcatctaca gcgacgacga caagcggtac agcccagcc tgaacacccg      1500
gctgaccatc accaaggaca ccagcaagaa ccaggtggtg ctggtgatga ccagagtgag    1560
ccccgtggac accgccacct acttttgcgc ccaccgcaga ggccccacca ccctgttcgg     1620
cgtgcccatc gccagaggcc ctgtgaacgc catggacgtg tggggccagg gcatcaccgt    1680
gaccatcagc agcacatcca ccagggccc atcggtcttc ccctggcac cctcctccaa      1740
gagcacctct gggggcacag cggccctggg ctgcctggtc aaggactact ccccgaacc     1800
ggtgacggtg tcgtggaact caggcgccct gaccagcggc gtgcacacct tcccggctgt    1860
cctacagtcc tcaggactct actccctcag cagcgtggtg accgtgccct ccagcagctt    1920
gggcacccag acctacatct gcaacgtgaa tcacaagccc agcaacacca aggtggacaa    1980
gaaagttgag cccaaatctt gtgacaaaac tcacacatgc ccaccgtgcc cagcacctga   2040
actcctgggg ggaccgtcag tcttcctctt ccccccaaaa cccaaggaca ccctcatgat    2100
ctcccggacc cctgaggtca catgcgtggt ggtggacgtg agccacgaag accctgaggt   2160
caagttcaac tggtatgttg acggcgtgga ggtgcataat gccaagacaa agccgcggga   2220
ggagcagtac aacagcacgt accgtgtggt cagcgtcctc accgtcctgc accaggactg    2280
gctgaatggc aaggagtaca agtgcaaggt ctccaacaaa gccctcccag cccccatcga    2340
gaaaaccatc tccaaagcca agggcagcc ccgagaacca caggtgtaca ccctgccccc     2400
atcccgggat gagctgacca gaatcaagt cagcctgacc tgcctggtca aaggcttcta     2460
tcccagcgac atcgccgtgg agtgggagag caatgggcag ccggagaaca actacaagac    2520
cacgcctccc gtgctggact ccgacggctc cttcttcctc tactcaaaac tcaccgtgga    2580
caagagcagg tggcagcagg ggaacgtctt ctcatgctcc gtgatgcatg aggctctgca    2640
caaccactac acgcagaaga gcctctcctc gtctccgggt aaaagggcaa acgttcggg    2700
ttcgggtgcg ccagtaaagc agacattaaa ctttgatttg ctgaaacttg caggtgatgt    2760
agagtcaaat ccaggtccaa tggcaacagg gagccgaacc tctctgctcc ttgctttcgg    2820
gctcctttgc ctaccgtggc tccaagaggg ctcggcagcc ctgcagctga cccagagccc    2880
cagcagcctg agcgccagcg tgggcgaccg gatcaccatc acctgccggg ccagccaggg    2940
cgtgacaagc gccctggcct ggtacaggca gaagcccggc agccccctc agctgctgat    3000
ctacgacgcc agctccctgg aaagcggcgt gcccagccgg tttagcggca gcggctccgg    3060
```

```
caccgagttc accctgacca tcagcaccct gcggcccgag gacttcgcca cctactactg    3120
ccagcagctg cacttctacc cccacacctt tggcggcgga acccgggtgg acgtgcggag    3180
aaccgtggcc gctcccagcg tgttcatctt ccctccctct gatgaacagc tgaaaagcgg    3240
aacagccagc gtggtgtgtc tgctgaacaa cttctacccc agagaagcca agtgcagtg    3300 gaaggtggac aacgccctgc agagcggaaa cagccaggaa agcgtgacag agcaggattc    3360
caaggattcc acatacagcc tgagcagcac actgacactg tccaaggccg actacgagaa    3420
gcacaaggtg tacgcctgcg aagtgacaca ccagggactg tcctcccctg tgacaaagag    3480
cttcaacaga ggagaatgca tggctagcat gactggtgga cagcaaatgg gttaaaggat    3540
cctaatcaac ctctggatta caaaatttgt gaaagattga ctggtattct taactatgtt    3600
gctcctttta cgctatgtgg atacgctgct ttaatgcctt tgtatcatgc tattgcttcc    3660
cgtatggctt tcattttctc ctccttgtat aaatcctggt tgctgtctct ttatgaggag    3720
ttgtggcccg ttgtcaggca acgtggcgtg gtgtgcactg tgtttgctga cgcaaccccc    3780
actggttggg gcattgccac cacctgtcag ctcctttccg ggactttcgc tttcccctc    3840 cctattgcca cggcggaact catcgccgcc tgccttgccc gctgctggac aggggctcgg    3900
ctgttgggca ctgacaattc cgtggtgttg tcggggaaat catcgtcctt ccttggctg    3960 ctcgcctgtg ttgccacctg gattctgcgc gggacgtcct tctgctacgt cccttcggcc    4020
ctcaatccag cggaccttcc ttcccgcggc ctgctgccgg ctctgcggcc tcttccgcgt    4080
cttcgccttc gccctcagac gagtcggatc tccctttggg ccgcctcccc gcctggtacc    4140
ttcgagcaga catgataaga tacattgatg agtttggaca aaccacaact agaatgcagt    4200
gaaaaaaatg ctttatttgt gaaatttgtg atgctattgc tttatttgta accattataa    4260
gctgcaataa acaagttaac aacaacaatt gcattcattt tatgtttcag gttcaggggg    4320
agatgtggga ggttttttaa agcaagtaaa acctctacaa atgtggtaaa atcaagctta    4380 ggaacccta gtgatggagt tggccactcc ctctctgcgc gctcgctcgc tcactgaggc    4440
cgggcgacca aggtcgcccg acgcccgggc tttgcccgg gcggcctcag tgagcgagcg    4500
agcgcgcaga gagggagtgg ccaagctagc gggcgattaa ggaaagggct agatcattct    4560
tgaagacgaa agggcctcgt gatacgccta ttttttatagg ttaatgtcat gataataatg    4620
gtttcttaga cgtcaggtgg cacttttcgg ggaaatgtgc gcggaacccc tatttgttta    4680
tttttctaaa tacattcaaa tatgtatccg ctcatgagac aataaccctg ataaatgctt    4740
caataatatt gaaaaggaa gagtatgagt attcaacatt tccgtgtcgc ccttattccc    4800
ttttttgcgg cattttgcct tcctgttttt gctcacccag aaacgctggt gaaagtaaaa    4860
gatgctgaag atcagttggg tgcacgagtg ggttacatcg aactggatct caacagcggt    4920
aagatccttg agagttttcg ccccgaagaa cgttttccaa tgatgagcac ttttaaagtt    4980
ctgctatgtg gcgcggtatt atcccgtgtt gacgccggc aagagcaact cggtcgccgc    5040
atacactatt ctcagaatga cttggttgag tactcaccag tcacagaaaa gcatcttacg    5100
gatggcatga cagtaagaga attatgcagt gctgccataa ccatgagtga taacactgcg    5160
gccaacttac ttctgacaac gatcggagga ccgaaggagc taaccgcttt tttgcacaac    5220 atggggatc atgtaactcg ccttgatcgt tgggaaccgg agctgaatga agccatacca    5280
aacgacgagc gtgacaccac gatgcctgta gcaatggcaa caacgttgcg caaactatta    5340
actggcgaac tacttactct agcttcccgg caacaattaa tagactggat ggaggcggat    5400
aaagttgcag gaccacttct gcgctcggcc cttccggctg gctggtttat tgctgataaa    5460
```

-continued

```
tctggagccg gtgagcgtgg gtctcgcggt atcattgcag cactgggcc agatggtaag      5520 ccctcccgta tcgtagttat ctacacgacg gggagtcagg caactatgga tgaacgaaat    5580
agacagatcg ctgagatagg tgcctcactg attaagcatt ggtaactgtc agaccaagtt    5640
tactcatata ctttagat tgattaaaa cttcattttt aatttaaaag gatctaggtg       5700
aagatccttt tgataatct catgaccaaa atcccttaac gtgagttttc gttccactga     5760
gcgtcagacc ccgtagaaaa gatcaaagga tcttcttgag atcctttttt tctgcgcgta    5820
atctgctgct tgcaaacaaa aaaaccaccg ctaccagcgg tggtttgttt gccggatcaa    5880
gagctaccaa ctcttttcc gaaggtaact ggcttcagca gagcgcagat accaaatact     5940
gttcttctag tgtagccgta gttaggccac cacttcaaga actctgtagc accgcctaca    6000
tacctcgctc tgctaatcct gttaccagtg gctgctgcca gtggcgataa gtcgtgtctt    6060
accgggttgg actcaagacg atagttaccg gataaggcgc agcggtcggg ctgaacgggg    6120
ggttcgtgca cacagcccag cttggagcga acgacctaca ccgaactgag atacctacag    6180
cgtgagctat gagaaagcgc cacgcttccc gaagggagaa aggcggacag gtatccggta    6240
agcggcaggg tcggaacagg agagcgcacg agggagcttc cagggggaaa cgcctggtat    6300
ctttatagtc ctgtcgggtt tcgccacctc tgacttgagc gtcgattttt gtgatgctcg    6360
tcaggggggc ggagcctatg gaaaaacgcc agcaacgcgg ccttttacg gttcctggcc     6420 ttttgctggc cttttgctca catgtaataa acacacacac accaacaacc gtggttggtt    6480
gttgtgttgg tttattctcg ag                                              6502
```

<210> SEQ ID NO 21
<211> LENGTH: 6450
<212> TYPE: DNA
<213> ORGANISM: Artificial Sequence
<220> FEATURE:
<223> OTHER INFORMATION: pAAVio-CASI-B12ABK-W-SV40

<400> SEQUENCE: 21

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctcccccc cctccccacc cccaattttg tatttattta    540
ttttttaatt attttgtgca gcgatggggg cggggggggg ggggcgcg cgccaggcgg      600 ggcggggcgg ggcgaggggc ggggcgggc gaggcggaga ggtgcggcgg cagccaatca    660
gagcggcgcg ctccgaaagt ttccttttat ggcgaggcgg cggcggcggc ggccctataa   720
aaagcgaagc gcgcggcggg cgggagtcgc tgcgcgctgc cttcgccccg tgccccgctc    780
cgccgccgcc tcgcgccgcc cgccccggct ctgactgacc gcgttactaa acaggtaag    840 tccgcctcc gcgccgggtt ttggcgcctc ccgcgggcgc ccccctcctc acggcgagcg    900
ctgccacgtc agacgaaggg cgcagcgagc gtcctgatcc ttccgcccgg acgctcagga    960
```

```
cagcggcccg ctgctcataa gactcggcct tagaaccccca gtatcagcag aaggacattt    1020
taggacggga cttgggtgac tctagggcac tggttttctt tccagagagc ggaacaggcg    1080
aggaaaagta gtcccttctc ggcgattctg cggagggatc tccgtggggc ggtgaacgcc    1140
gatgatgcct ctactaacca tgttcatgtt ttcttttttt ttctacaggt cctgggtgac    1200
gaacaggcgg ccgccatggc gacgggttca agaacttccc tacttcttgc atttggcctg    1260
ctttgtttgc cgtggttaca ggagggctcg gcacaggttc agctggttca gtccggggct    1320
gaggtgaaga agcctggggc ctcagtgaag gtttcttgtc aggcttctgg atacagattc    1380
agtaactttg ttattcattg ggtgcgccag gcccccggac agaggtttga gtggatggga    1440
tggatcaatc cttacaacgg aaacaaagaa ttttcagcga agttccagga cagagtcacc    1500
tttaccgcgg acacatccgc gaacacagcc tacatggagt tgaggagcct caggtctgca    1560
gacacggctg tttattattg tgcgagagtg gggccatata gttgggatga ttctccccag    1620
gacaattatt atatggacgt ctggggcaaa gggaccacgg tcatcgtgag ctcagccagc    1680
accaagggcc catcggtctt ccccctggca ccctcctcca agagcacctc tgggggcaca    1740
gcggccctgg gctgcctggt caaggactac ttccccgaac cggtgacggt gtcgtggaac    1800
tcaggcgccc tgaccagcgg cgtgcacacc ttcccggctg tcctacagtc ctcaggactc    1860
tactccctca gcagcgtggt gaccgtgccc tccagcagct tgggcaccca gacctacatc    1920
tgcaacgtga atcacaagcc cagcaacacc aaggtggaca gaaagttga gcccaaatct    1980 tgtgacaaaa ctcacacatg cccaccgtgc ccagcacctg aactcctggg gggaccgtca    2040
gtcttcctct tccccccaaa acccaaggac accctcatga tctcccggac ccctgaggtc    2100
acatgcgtgg tggtggacgt gagccacgaa gaccctgagg tcaagttcaa ctggtatgtt    2160
gacggcgtga aggtgcataa tgccaagaca aagccgcggg aggagcagta caacagcacg    2220
taccgtgtgg tcagcgtcct caccgtcctg caccaggact ggctgaatgg caaggagtac    2280
aagtgcaagg tctccaacaa agccctccca gcccccatcg agaaaaccat ctccaaagcc    2340
aaagggcagc cccgagaacc acaggtgtac accctgcccc catcccggga tgagctgacc    2400
aagaatcaag tcagcctgac ctgcctggtc aaaggcttct atcccagcga catcgccgtg    2460
gagtgggaga gcaatgggca gccggagaac aactacaaga ccacgcctcc cgtgctggac    2520
tccgacggct ccttcttcct ctactcaaaa ctcaccgtgg acaagagcag gtggcagcag    2580
gggaacgtct tctcatgctc cgtgatgcat gaggctctgc acaaccacta cacgcagaag    2640
agcctctccc tgtctccggg tcgaaaaaga agatcaggtt cgggtgcgcc agtaaagcag    2700
acattaaact ttgatttgct gaaacttgca ggtgatgtag agtcaaatcc aggtccaatg    2760
gcaacaggga gccgaacctc tctgctcctt gctttcgggc tcctttgcct accgtggctc    2820
caagagggct cggcagagat cgttctcacg cagtctccag gcaccctgtc tctgtctcca    2880
ggggaaagag ccaccttctc ctgtaggtcc agtcacagca ttcgcagccg ccgcgtagcc    2940
tggtaccagc acaaacctgg ccaggctcca aggctggtca tacatggtgt ttccaatagg    3000
gcctctggca tctcagacag gttcagcggc agtgggtctg ggacagactt cactctcacc    3060
atcaccagag tggagcctga agactttgca ctgtactact gtcaggtcta tggtgcctcc    3120
tcgtacactt ttggccaggg gaccaaactg gagaggaaac gtacggtggc cgctcccagc    3180
gtgttcatct tccctccctc tgatgaacag ctgaaaagcg aaacagccag cgtggtgtgt    3240
ctgctgaaca acttctaccc cagagaagcc aaagtgcagt ggaaggtgga caacgccctg    3300
cagagcggaa acagccagga aagcgtgaca gagcaggatt ccaaggattc cacatacagc    3360
```

```
ctgagcagca cactgacact gtccaaggcc gactacgaga agcacaaggt gtacgcctgc    3420
gaagtgacac accagggact gtcctcccct gtgacaaaga gcttcaacag aggagaatgc    3480
taaaggatcc taatcaacct ctggattaca aaatttgtga agattgact ggtattctta    3540 actatgttgc tccttttacg ctatgtggat acgctgcttt aatgcctttg tatcatgcta    3600
ttgcttcccg tatggctttc attttctcct ccttgtataa atcctggttg ctgtctcttt    3660
atgaggagtt gtggcccgtt gtcaggcaac gtggcgtggt gtgcactgtg tttgctgacg    3720
caacccccac tggttggggc attgccacca cctgtcagct cctttccggg actttcgctt    3780 tcccctccc tattgccacg gcggaactca tcgccgcctg ccttgcccgc tgctggacag    3840
gggctcggct gttgggcact gacaattccg tggtgttgtc ggggaaatca tcgtcctttc    3900
cttggctgct cgcctgtgtt gccacctgga ttctgcgcgg acgtccttc tgctacgtcc     3960 cttcggccct caatccagcg gaccttcctt cccgcggcct gctgccggct ctgcggcctc    4020
ttccgcgtct tcgccttcgc cctcagacga gtcggatctc cctttgggcc gcctccccgc    4080
ctggtacctt cgagcagaca tgataagata cattgatgag tttggacaaa ccacaactag    4140
aatgcagtga aaaaaatgct ttatttgtga aatttgtgat gctattgctt tatttgtaac    4200
cattataagc tgcaataaac aagttaacaa caacaattgc attcatttta tgtttcaggt    4260 tcaggggag atgtgggagg tttttttaaag caagtaaaac ctctacaaat gtggtaaaat    4320
caagcttagg aacccctagt gatggagttg gccactccct ctctgcgcgc tcgctcgctc    4380
actgaggccg ggcgaccaaa ggtcgcccga cgcccgggct ttgcccgggc ggcctcagtg    4440
agcgagcgag cgcgcagaga gggagtggcc aagctagcgg gcgattaagg aaagggctag    4500
atcattcttg aagacgaaag ggcctcgtga tacgcctatt tttataggtt aatgtcatga    4560
taataatggt ttcttagacg tcaggtggca cttttcgggg aaatgtgcgc ggaacccta    4620 tttgtttatt tttctaaata cattcaaata tgtatccgct catgagacaa taaccctgat    4680
aaatgcttca ataatattga aaaggaaga gtatgagtat tcaacatttc cgtgtcgccc    4740
ttattccctt ttttgcggca ttttgccttc ctgttttgc tcacccagaa acgctggtga    4800
aagtaaaaga tgctgaagat cagttgggtg cacgagtggg ttacatcgaa ctggatctca    4860
acagcggtaa gatccttgag agttttcgcc ccgaagaacg ttttccaatg atgagcactt    4920
ttaaagttct gctatgtggc gcggtattat cccgtgttga cgccgggcaa gagcaactcg    4980
gtcgccgcat acactattct cagaatgact tggttgagta ctcaccagtc acagaaaagc    5040
atcttacgga tggcatgaca gtaagagaat tatgcagtgc tgccataacc atgagtgata    5100
acactgcggc caacttactt ctgacaacga tcggaggacc gaaggagcta accgcttttt    5160
tgcacaacat gggggatcat gtaactcgcc ttgatcgttg ggaaccggag ctgaatgaag    5220
ccataccaaa cgacgagcgt gacaccacga tgcctgtagc aatggcaaca acgttgcgca    5280
aactattaac tggcgaacta cttactctag cttcccggca acaattaata gactggatgg    5340
aggcggataa agttgcagga ccacttctgc gctcggccct tccggctggc tggtttattg    5400
ctgataaatc tggagccggt gagcgtgggt ctcgcggtat cattgcagca ctggggccag    5460
atggtaagcc ctcccgtatc gtagttatct acacgacggg gagtcaggca actatggatg    5520
aacgaaatag acagatcgct gagataggtg cctcactgat taagcattgg taactgtcag    5580
accaagttta ctcatatata ctttagattg atttaaaact tcatttttaa tttaaaagga    5640
tctaggtgaa gatccttttt gataatctca tgaccaaaat cccttaacgt gagttttcgt    5700
```

```
tccactgagc gtcagacccc gtagaaaaga tcaaaggatc ttcttgagat cctttttttc   5760
tgcgcgtaat ctgctgcttg caaacaaaaa aaccaccgct accagcggtg gtttgtttgc   5820
cggatcaaga gctaccaact cttttttccga aggtaactgg cttcagcaga gcgcagatac   5880
caaatactgt tcttctagtg tagccgtagt taggccacca cttcaagaac tctgtagcac   5940
cgcctacata cctcgctctg ctaatcctgt taccagtggc tgctgccagt ggcgataagt   6000
cgtgtcttac cgggttggac tcaagacgat agttaccgga taaggcgcag cggtcgggct   6060
gaacggggggg ttcgtgcaca cagcccagct tggagcgaac gacctacacc gaactgagat   6120
acctacagcg tgagctatga gaaagcgcca cgcttcccga agggagaaag gcggacaggt   6180
atccggtaag cggcagggtc ggaacaggag agcgcacgag ggagcttcca gggggaaacg   6240
cctggtatct ttatagtcct gtcgggtttc gccacctctg acttgagcgt cgatttttgt   6300
gatgctcgtc aggggggcgg agcctatgga aaaacgccag caacgcggcc ttttacggt   6360
tcctggcctt tgctggcct tttgctcaca tgtaataaac acacacacac caacaaccgt   6420
ggttggttgt tgtgttggtt tattctcgag                                    6450
```

<210> SEQ ID NO 22
<211> LENGTH: 6456
<212> TYPE: DNA
<213> ORGANISM: Artificial Sequence
<220> FEATURE:
<223> OTHER INFORMATION: pAAVio-CASI-AR3AABK-W-SV40

<400> SEQUENCE: 22

```
ttggccactc cctctctgcg cgctcgctcg ctcactgagg ccgggcgacc aaaggtcgcc     60
cgacgcccgg gctttgcccg ggcggcctca gtgagcgagc gagcgcgcag agagggagtg   120
gccaactcca tcactagggg ttcctactag tggagttccg cgttacataa cttacggtaa   180
atggcccgcc tggctgaccg cccaacgacc cccgcccatt gacgtcaata atgacgtatg   240
ttcccatagt aacgccaata gggactttcc attgacgtca atgggtggag tatttacggt   300
aaactgccca cttggcagta catcaagtgt atcatatgcc aagtacgccc cctattgacg   360
tcaatgacgg taaatggccc gcctggcatt atgcccagta catgacctta tgggactttc   420
ctacttggca gtacatctac gtattagtca tcgctattac catggtcgag gtgagcccca   480
cgttctgctt cactctcccc atctcccccc cctccccacc cccaattttg tatttattta   540
ttttttaatt attttgtgca gcgatggggg cggggggggg gggggcgcg cgccaggcgg   600
ggcggggcgg ggcgagggc ggggcgggc gaggcgaga ggtgcggcgg cagccaatca   660
gagcggcgcg ctccgaaagt ttcctttat ggcgaggcgg cggcggcggc ggccctataa   720
aaagcgaagc gcgcggcggg cgggagtcgc tgcgcgctgc cttcgccccg tgccccgctc   780
cgccgccgcc tcgcgccgcc cgccccggct ctgactgacc gcgttactaa aacaggtaag   840
tccggcctcc gcgccgggtt ttggcgcctc ccgcgggcgc ccccctcctc acggcgagcg   900
ctgccacgtc agacgaaggg cgcagcgagc gtcctgatcc ttccgcccgg acgctcagga   960
cagcggcccg ctgctcataa gactcggcct tagaaccccca gtatcagcag aaggacattt   1020
taggacggga cttgggtgac tctagggcac tggttttctt tccagagagc ggaacaggcg   1080
aggaaaagta gtcccttctc ggcgattctg cggagggatc tccgtggggc ggtgaacgcc   1140
gatgatgcct ctactaacca tgttcatgtt tcttttttttt ttctacaggt cctgggtgac   1200
gaacaggcg ccgccatggc gacggggtca agaacttccc tacttcttgc atttggcctg   1260
ctttgtttgc cgtggttaca ggagggctcg gcagaggttc agctgctcga gcagtctggg   1320
```

```
gctgaggtga agacgcctgg gtcctcggtg agggtctcct gcaggcctcc tggaggcaac       1380
ttcaacagtt atagtataaa ctgggtccga caggcccctg acacggcct tgagtgggtg        1440 gggactttca tccctatgtt tggaacctca agtacgcgc agaagtttca ggggagagtc        1500
acgattaccg cggacgggtc ctcgggcacc gcttacatgg acctgaacag cctgagatct      1560
gacgacacgg ccttttacta ctgtgtgcgt cctgaaacgc ccagatattg tagtggcggt      1620
ttctgctatg tgaatttga caactggggc caggaaccc tggtcaccgt ctcctctgcc        1680
agcaccaagg gcccatcggt cttccccctg gcaccctcct ccaagagcac ctctgggggc      1740
acagcggccc tgggctgcct ggtcaaggac tacttccccg aaccggtgac ggtgtcgtgg      1800
aactcaggcg ccctgaccag cggcgtgcac accttcccgg ctgtcctaca gtcctcagga     1860
ctctactccc tcagcagcgt ggtgaccgtg ccctccagca gcttgggcac ccagacctac      1920
atctgcaacg tgaatcacaa gcccagcaac accaaggtgg acaagaaagt tgagcccaaa     1980
tcttgtgaca aaactcacac atgcccaccg tgcccagcac ctgaactcct ggggggaccg      2040
tcagtcttcc tcttccccccc aaaacccaag gacaccctca tgatctcccg gacccctgag    2100
gtcacatgcg tggtggtgga cgtgagccac gaagaccctg aggtcaagtt caactggtat     2160
gttgacggcg tggaggtgca taatgccaag acaaagccgc gggaggagca gtacaacagc     2220
acgtaccgtg tggtcagcgt cctcaccgtc ctgcaccagg actggctgaa tggcaaggag     2280
tacaagtgca aggtctccaa caaagccctc ccagccccca tcgagaaaac catctccaaa    2340
gccaaagggc agccccgaga accacaggtg tacaccctgc ccccatcccg ggatgagctg    2400
accaagaatc aagtcagcct gacctgcctg gtcaaaggct tctatcccag cgacatcgcc    2460
gtggagtggg agagcaatgg gcagccggag aacaactaca agaccacgcc tcccgtgctg    2520
gactccgacg gctccttctt cctctactca aaactcaccg tggacaagag caggtggcag     2580
caggggaacg tcttctcatg ctccgtgatg catgaggctc tgcacaacca ctacacgcag    2640
aagagcctct ccctgtctcc gggtcgaaaa agaagatcag gttcgggtgc gccagtaaag     2700
cagacattaa actttgattt gctgaaactt gcaggtgatg tagagtcaaa tccaggtcca    2760
atggcaacag ggagccgaac ctctctgctc cttgctttcg ggctcctttg cctaccgtgg     2820
ctccaagagg gctcggcaga gatcgagctc acactcacgc agtctccagg caccctgtct    2880
ttgtctccag gggaaagagc caccctctcc tgcagggcca gtcagagtgt tagcggcagc    2940
tacttagcct ggtaccagca gaaacctggc caggctccca ggctcctcat ctatggtgca    3000
tccaacaggg ccactggcat cccacacagg ttcagtggca gtgggtctgg gacagacttc    3060
actctcacca tcagcagact ggagcctgag gattttgcag tgtattactg tcagcagtat     3120
ggttcctcac cgacgttcgg ccaggggacc agggtgaca tcaaacgaac agtgccgct       3180 cccagcgtgt tcatcttccc tccctctgat gaacagctga aaagcggaac agccagcgtg    3240
gtgtgtctgc tgaacaactt ctaccccaga gaagccaaag tcagtggaa ggtggacaac     3300 gccctgcaga gcggaaacag ccaggaaagc gtgacagagc aggattccaa ggattccaca    3360
tacagcctga gcagcacact gacactgtcc aaggccgact acgagaagca caaggtgtac    3420
gcctgcgaag tgacacacca gggactgtcc tcccctgtga caagagctt caacagagga     3480 gaatgctaaa ggatcctaat caacctctgg attacaaaat ttgtgaaaga ttgactggta    3540
ttcttaacta tgttgctcct tttacgctat gtggatacgc tgctttaatg cctttgtatc    3600
atgctattgc ttcccgtatg ctttcatttt tctcctcctt gtataaatcc tggttgctgt    3660
```

```
ctctttatga ggagttgtgg cccgttgtca ggcaacgtgg cgtggtgtgc actgtgtttg   3720
ctgacgcaac ccccactggt tgggcattg ccaccacctg tcagctcctt tccgggactt   3780
tcgctttccc cctccctatt gccacggcgg aactcatcgc cgcctgcctt gcccgctgct   3840
ggacaggggc tcggctgttg ggcactgaca attccgtggt gttgtcgggg aaatcatcgt   3900
cctttccttg gctgctcgcc tgtgttgcca cctggattct gcgcgggacg tccttctgct   3960
acgtcccttc ggccctcaat ccagcggacc ttccttcccg cggcctgctg ccggctctgc   4020
ggcctcttcc gcgtcttcgc cttcgccctc agacgagtcg gatctcccct tgggccgcct   4080
ccccgcctgg taccttcgag cagacatgat aagatacatt gatgagtttg acaaaccac    4140 aactagaatg cagtgaaaaa aatgctttat ttgtgaaatt tgtgatgcta ttgctttatt   4200
tgtaaccatt ataagctgca ataaacaagt taacaacaac aattgcattc attttatgtt   4260
tcaggttcag ggggagatgt gggaggtttt ttaaagcaag taaaacctct acaaatgtgg   4320
taaaatcaag cttaggaacc cctagtgatg gagttggcca ctccctctct gcgcgctcgc   4380
tcgctcactg aggccgggcg accaaaggtc gcccgacgcc cgggctttgc ccgggcggcc   4440
tcagtgagcg agcgagcgcg cagagaggga gtggccaagc tagcgggcga ttaaggaaag   4500
ggctagatca ttcttgaaga cgaaagggcc tcgtgatacg cctatttta taggttaatg    4560 tcatgataat aatggtttct tagacgtcag gtggcacttt tcggggaaat gtgcgcggaa   4620
cccctatttg tttattttc taaatacatt caaatatgta tccgctcatg agacaataac    4680
cctgataaat gcttcaataa tattgaaaaa ggaagagtat gagtattcaa catttccgtg   4740
tcgcccttat tcccttttt gcggcatttt gccttcctgt ttttgctcac ccagaaacgc    4800
tggtgaaagt aaaagatgct gaagatcagt tgggtgcacg agtgggttac atcgaactgg   4860
atctcaacag cggtaagatc cttgagagtt ttcgccccga agaacgtttt ccaatgatga   4920
gcacttttaa agttctgcta tgtggcgcgg tattatcccg tgttgacgcc gggcaagagc   4980
aactcggtcg ccgcatacac tattctcaga atgacttggt tgagtactca ccagtcacag   5040
aaaagcatct tacggatggc atgacagtaa gagaattatg cagtgctgcc ataaccatga   5100
gtgataacac tgcggccaac ttacttctga caacgatcgg aggaccgaag gagctaaccg   5160
cttttttgca caacatgggg gatcatgtaa ctcgccttga tcgttgggaa ccggagctga   5220
atgaagccat accaaacgac gagcgtgaca ccacgatgcc tgtagcaatg gcaacaacgt   5280
tgcgcaaact attaactggc gaactactta ctctagcttc ccggcaacaa ttaatagact   5340
ggatggaggc ggataaagtt gcaggaccac ttctgcgctc ggcccttccg gctggctggt   5400
ttattgctga taaatctgga gccggtgagc gtgggtctcg cggtatcatt gcagcactgg   5460
ggccagatgg taagccctcc cgtatcgtag ttatctacac gacggggagt caggcaacta   5520
tggatgaacg aaatagacag atcgctgaga taggtgcctc actgattaag cattggtaac   5580
tgtcagacca gtttactca tatatacttt agattgattt aaaacttcat ttttaattta    5640
aaaggatcta ggtgaagatc cttttgata atctcatgac caaaatccct aacgtgagt    5700 tttcgttcca ctgagcgtca gaccccgtag aaaagatcaa aggatcttct tgagatcctt   5760 ttttttctgcg cgtaatctgc tgcttgcaaa caaaaaaacc accgctacca gcggtggttt   5820
gtttgccgga tcaagagcta ccaactcttt ttccgaaggt aactggcttc agcagagcgc   5880
agataccaaa tactgttctt ctagtgtagc cgtagttagg ccaccacttc aagaactctg   5940
tagcaccgcc tacatacctc gctctgctaa tcctgttacc agtggctgct gccagtggcg   6000
ataagtcgtg tcttaccggg ttggactcaa gacgatagtt accggataag cgcagcggt    6060
```

```
cgggctgaac gggggttcg tgcacacagc ccagcttgga gcgaacgacc tacaccgaac    6120
tgagatacct acagcgtgag ctatgagaaa gcgccacgct tcccgaaggg agaaaggcgg    6180
acaggtatcc ggtaagcggc agggtcggaa caggagagcg cacgagggag cttccagggg    6240
gaaacgcctg gtatctttat agtcctgtcg ggtttcgcca cctctgactt gagcgtcgat    6300
ttttgtgatg ctcgtcaggg gggcggagcc tatggaaaaa cgccagcaac gcggcctttt    6360
tacggttcct ggccttttgc tggccttttg ctcacatgta ataaacacac acacaccaac    6420
aaccgtggtt ggttgttgtg ttggtttatt ctcgag                              6456
```

<210> SEQ ID NO 23
<211> LENGTH: 6453
<212> TYPE: DNA
<213> ORGANISM: Artificial Sequence
<220> FEATURE:
<223> OTHER INFORMATION: pAAVio-CASI-AR3BABK-W-SV40

<400> SEQUENCE: 23

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctcccccc cctccccacc cccaattttg tatttattta    540 tttttttaatt attttgtgca gcgatggggg cggggggggg ggggggcgcg cgccaggcgg    600
ggcggggcgg ggcgaggggc ggggcgggc gaggcggaga ggtgcggcgg cagccaatca    660
gagcggcgcg ctccgaaagt ttcctttttat ggcgaggcgg cggcggcggc ggccctataa    720
aaagcgaagc gcgcggcggg cgggagtcgc tgcgcgctgc cttcgccccg tgccccgctc    780
cgccgccgcc tcgcgccgcc cgccccggct ctgactgacc gcgttactaa aacaggtaag    840
tccggcctcc gcgccgggtt ttggcgcctc ccgcgggcgc ccccctcctc acggcgagcg    900
ctgccacgtc agacgaaggg cgcagcgagc gtcctgatcc ttccgcccgg acgctcagga    960
cagcggcccc ctgctcataa gactcggcct tagaacccca gtatcagcag aaggacatt    1020 taggacggga cttgggtgac tctagggcac tggttttctt tccagagagc ggaacaggcg    1080
aggaaaagta gtcccttctc ggcgattctg cggagggatc tccgtggggc ggtgaacgcc    1140
gatgatgcct ctactaacca tgttcatgtt ttctttttt ttctacaggt cctgggtgac    1200
gaacaggcgg ccgccatggc gacgggttca agaacttccc tacttcttgc atttggcctg    1260
ctttgtttgc cgtggttaca ggagggctcg gcagaggttc agctgctcga gcagtctggg    1320
cctgaggtga agaagcctgg gtcgtcggtg aaggtctcct gcaaggattc tggagacacc    1380
ttcaacgaac ctgtcacctg ggtgcgacag gcccctggac aaggccttga gtggatcgga    1440
ggaatcatcc ctgcgtttgg tgtgacaaag tacgcacaga aattccaggg ccgagtcatc    1500
atttccgcgg acgcatctac ggccacggcc tatttggagc tgagcagtct gagatctgaa    1560
gacacggccg tctattactg tgcgaaagtt ggcctgcggg gcattgtaat ggttggggc    1620
```

```
ctggcgatga actggctcga cccctggggc cagggaaccc aagtcaccgt ctcctctgcc   1680
agcaccaagg gccatcggt cttcccctg gcaccctcct ccaagagcac ctctgggggc    1740
acagcggccc tgggctgcct ggtcaaggac tacttccccg aaccggtgac ggtgtcgtgg  1800
aactcaggcg ccctgaccag cggcgtgcac accttcccgg ctgtcctaca gtcctcagga  1860
ctctactccc tcagcagcgt ggtgaccgtg ccctccagca gcttgggcac ccagacctac  1920
atctgcaacg tgaatcacaa gcccagcaac accaaggtgg acaagaaagt tgagcccaaa  1980
tcttgtgaca aaactcacac atgcccaccg tgcccagcac ctgaactcct ggggggaccg  2040
tcagtcttcc tcttcccccc aaaacccaag gacaccctca tgatctcccg gacccctgag  2100
gtcacatgcg tggtggtgga cgtgagccac gaagaccctg aggtcaagtt caactggtat  2160
gttgacggcg tggaggtgca taatgccaag acaaagccgc gggaggagca gtacaacagc  2220
acgtaccgtg tggtcagcgt cctcaccgtc ctgcaccagg actggctgaa tggcaaggag  2280
tacaagtgca aggtctccaa caaagccctc ccagccccca tcgagaaaac catctccaaa  2340
gccaaagggc agccccgaga accacaggtg tacaccctgc ccccatcccg ggatgagctg  2400
accaagaatc aagtcagcct gacctgcctg gtcaaaggct tctatcccag cgacatcgcc  2460
gtggagtggg agagcaatgg gcagccggag aacaactaca agaccacgcc tcccgtgctg  2520
gactccgacg gctccttctt cctctactca aaactcaccg tggacaagag caggtggcag  2580
caggggaacg tcttctcatg ctccgtgatg catgaggctc tgcacaacca ctacacgcag  2640
aagagcctct ccctgtctcc gggtcgaaaa agaagatcag gttcgggtgc gccagtaaag  2700
cagacattaa actttgattt gctgaaactt gcaggtgatg tagagtcaaa tccaggtcca  2760
atggcaacag ggagccgaac ctctctgctc cttgctttcg ggctcctttg cctaccgtgg  2820
ctccaagagg gctcggcaga gatcgagctc actcagtctc caggcaccct gtctttgtct  2880
ccaggggaaa gagccaccct ctcctgcagg gccagtcaga gtgttagcag cagctactta  2940
gcctggtacc agcagaaacc tggccaggct cccaggctcc tcatctatgg tgcatccagc  3000
agggccactg gcatcccaga caggttcagt ggcagtgggt ctgggacaga cttcactctc  3060
accatcagca gactggagcc tgaagatttt gcagtgtatt actgtcagca gtatggtagc  3120
tcacctcaga cgttcggcca agggaccaag gtggaaatca aacgaacagt ggccgctccc  3180
agcgtgttca tcttccctcc ctctgatgaa cagctgaaaa gcggaacagc cagcgtggtg  3240
tgtctgctga caacttcta ccccagagaa gccaaagtgc agtggaaggt ggacaacgcc  3300
ctgcagagcg gaaacagcca ggaaagcgtg acagagcagg attccaagga ttccacatac  3360
agcctgagca gcacactgac actgtccaag gccgactacg agaagcacaa ggtgtacgcc  3420
tgcgaagtga cacaccaggg actgtcctcc cctgtgacaa agagcttcaa cagaggagaa  3480
tgctaaagga tcctaatcaa cctctggatt acaaaatttg tgaaagattg actggtattc  3540
ttaactatgt tgctcctttt acgctatgtg gatacgctgc tttaatgcct ttgtatcatg  3600
ctattgcttc ccgtatggct ttcattttct cctccttgta taaatcctgg ttgctgtctc  3660
tttatgagga gttgtggccc gttgtcaggc aacgtggcgt ggtgtgcact gtgtttgctg  3720
acgcaacccc cactggttgg ggcattgcca ccacctgtca gctcctttcc gggactttcg  3780
ctttccccct ccctattgcc acggcggaac tcatcgccgc ctgccttgcc cgctgctgga  3840
caggggctcg gctgttgggc actgacaatt ccgtggtgtt gtcggggaaa tcatcgtcct  3900
ttccttggct gctcgcctgt gttgccacct ggattctgcg cggacgtcc ttctgctacg   3960
tcccttcggc cctcaatcca gcggaccttc cttcccgcgg cctgctgccg gctctgcggc  4020
```

```
ctcttccgcg tcttcgcctt cgccctcaga cgagtcggat ctcccttggg gccgcctccc    4080
cgcctggtac cttcgagcag acatgataag atacattgat gagtttggac aaaccacaac    4140
tagaatgcag tgaaaaaaat gctttatttg tgaaatttgt gatgctattg ctttatttgt    4200
aaccattata agctgcaata aacaagttaa caacaacaat tgcattcatt ttatgtttca    4260
ggttcagggg gagatgtggg aggtttttta aagcaagtaa aacctctaca aatgtggtaa    4320
aatcaagctt aggaacccct agtgatggag ttggccactc cctctctgcg cgctcgctcg    4380
ctcactgagg ccgggcgacc aaaggtcgcc cgacgcccgg gctttgcccg gcggcctca    4440
gtgagcgagc gagcgcgcag agagggagtg gccaagctag cgggcgatta aggaaagggc    4500
tagatcattc ttgaagacga aagggcctcg tgatacgcct attttatag gttaatgtca    4560
tgataataat ggtttcttag acgtcaggtg gcacttttcg gggaaatgtg cgcggaaccc    4620
ctatttgttt atttttctaa atacattcaa atatgtatcc gctcatgaga caataaccct    4680
gataaatgct tcaataatat tgaaaaagga agagtatgag tattcaacat ttccgtgtcg    4740
cccttattcc cttttttgcg gcattttgcc ttcctgtttt tgctcaccca gaaacgctgg    4800
tgaaagtaaa agatgctgaa gatcagttgg gtgcacgagt gggttacatc gaactggatc    4860
tcaacagcgg taagatcctt gagagttttc gccccgaaga acgttttcca atgatgagca    4920
cttttaaagt tctgctatgt ggcgcggtat tatcccgtgt tgacgccggg caagagcaac    4980
tcggtcgccg catacactat tctcagaatg acttggttga gtactcacca gtcacagaaa    5040
agcatcttac ggatggcatg acagtaagag aattatgcag tgctgccata accatgagtg    5100
ataacactgc ggccaactta cttctgacaa cgatcggagg accgaaggag ctaaccgctt    5160
ttttgcacaa catgggggat catgtaactc gccttgatcg ttgggaaccg gagctgaatg    5220
aagccatacc aaacgacgag cgtgacacca cgatgcctgt agcaatggca acaacgttgc    5280
gcaaactatt aactggcgaa ctacttactc tagcttcccg gcaacaatta atagactgga    5340
tggaggcgga taaagttgca ggaccacttc tgcgctcggc ccttccggct ggctggttta    5400
ttgctgataa atctggagcc ggtgagcgtg ggtctcgcgg tatcattgca gcactggggc    5460
cagatggtaa gccctcccgt atcgtagtta tctacacgac ggggagtcag gcaactatgg    5520
atgaacgaaa tagacagatc gctgagatag gtgcctcact gattaagcat tggtaactgt    5580
cagaccaagt ttactcatat atactttaga ttgatttaaa acttcatttt taatttaaaa    5640
ggatctaggt gaagatcctt tttgataatc tcatgaccaa aatcccttaa cgtgagtttt    5700
cgttccactg agcgtcagac cccgtagaaa agatcaaagg atcttcttga gatccttttt    5760
ttctgcgcgt aatctgctgc ttgcaaacaa aaaaaccacc gctaccagcg gtggtttgtt    5820
tgccggatca agagctacca actctttttc cgaaggtaac tggcttcagc agagcgcaga    5880
taccaaatac tgttcttcta gtgtagccgt agttaggcca ccacttcaag aactctgtag    5940
caccgcctac atacctcgct ctgctaatcc tgttaccagt ggctgctgcc agtggcgata    6000
agtcgtgtct taccgggttg gactcaagac gatagttacc ggataaggcg cagcggtcgg    6060
gctgaacggg gggttcgtgc acacagccca gcttggagcg aacgacctac accgaactga    6120
gatacctaca gcgtgagcta tgagaaagcg ccacgcttcc cgaagggaga aaggcggaca    6180
ggtatccggt aagcggcagg gtcggaacag gagagcgcac gagggagctt ccaggggaa    6240
acgcctggta tctttatagt cctgtcgggt ttcgccacct ctgacttgag cgtcgatttt    6300
tgtgatgctc gtcaggggg cggagcctat ggaaaaacgc cagcaacgcg gcctttttac    6360
```

```
ggttcctggc cttttgctgg cctttgctc acatgtaata acacacaca caccaacaac    6420 cgtggttggt tgttgtgttg gtttattctc gag                               6453

<210> SEQ ID NO 24
<211> LENGTH: 6418
<212> TYPE: DNA
<213> ORGANISM: Artificial Sequence
<220> FEATURE:
<223> OTHER INFORMATION: pAAVio-CASI-VRC01ABK-W-SV40

<400> SEQUENCE: 24
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctccccc cctccccacc cccaattttg tatttattta    540
ttttttaatt attttgtgca gcgatggggg cggggggggg gggggggcgc gcgccaggcg    600 ggcggggcg gggcgagggg cggggcgggg cgaggcggag aggtgcggcg gcagccaatc    660
agagcggcgc gctccgaaag tttccttta tggcgaggcg gcggcggcgg cggccctata    720
aaaagcgaag cgcgcggcgg gcgggagtcg ctgcgcgctg ccttcgcccc gtgccccgct    780
ccgccgccgc ctcgcgccgc ccgccccggc tctgactgac cgcgttacta aaacaggtaa    840
gtccggcctc cgcgccgggt tttggcgcct cccgcgggcg cccccctcct cacggcgagc    900
gctgccacgt cagacgaagg cgcagcgag cgtcctgatc cttccgcccg gacgctcagg    960
acagcggccc gctgctcata agactcggcc ttagaacccc agtatcagca gaaggacatt   1020
ttaggacggg acttgggtga ctctaggca ctggttttct ttccagagag cggaacaggc   1080
gaggaaaagt agtcccttct cggcgattct gcggagggat ctccgtgggg cggtgaacgc   1140
cgatgatgcc tctactaacc atgttcatgt tttcttttt tttctacagg tcctgggtga   1200
cgaacaggcg gccgccatgg cgacgggttc aagaacttcc ctacttcttg catttggcct   1260
gctttgtttg ccgtggttac aggagggctc ggcacaggtg cagctggtgc agtctggagg   1320
tcagatgaag aagcctggcg agtcgatgag aatttcttgt cgggcttctg gatatgaatt   1380
tattgattgt acgctaaatt ggattcgtct ggccccgga aaaaggcctg agtggatggg   1440
atggctgaag cctcggggg gggccgtcaa ctacgcacgt ccacttcagg gcagagtgac   1500
catgactcga gacgtttatt ccgacacagc ctttttggag ctgcgctcgt tgacagtaga   1560
cgacacggcc gtctactttt gtactagggg aaaaaactgt gattacaatt gggacttcga   1620
acactggggc cggggcaccc cggtcatcgt ctcatcaccg agcaccaagg gcccatcggt   1680
cttccccctg gcaccctcct ccaagagcac ctctgggggc acagcggccc tgggctgcct   1740
ggtcaaggac tacttccccg aaccggtgac ggtgtcgtgg aactcaggcg ccctgaccag   1800
cggcgtgcac accttcccgg ctgtcctaca gtcctcagga ctctactccc tcagcagcgt   1860
ggtgaccgtg ccctccagca gcttgggcac ccagacctac atctgcaacg tgaatcacaa   1920
gcccagcaac accaaggtgg acaagaaagt tgagcccaaa tcttgtgaca aaactcacac   1980
```

```
atgcccaccg tgcccagcac ctgaactcct gggggggaccg tcagtcttcc tcttccccc       2040 aaaacccaag gacaccctca tgatctcccg gaccectgag gtcacatgeg tggtggtgga       2100 cgtgagccac gaagacectg aggtcaagtt caactggtat gttgacggcg tggaggtgca       2160
taatgccaag acaaagccgc gggaggagca gtacaacagc acgtaccgtg tggtcagcgt       2220
cctcaccgtc ctgcaccagg actggctgaa tggcaaggag tacaagtgca aggtctccaa       2280
caaagccctc ccagccccca tcgagaaaac catctccaaa gccaagggc agccccgaga        2340 accacaggtg tacaccctgc ccccatcccg ggatgagctg accaagaatc aagtcagcct       2400
gacctgcctg gtcaaaggct tctatcccag cgacatcgcc gtggagtggg agagcaatgg       2460
gcagccggag aacaactaca agaccacgcc tcccgtgctg gactccgacg gctccttctt      2520
cctctactca aaactcaccg tggacaagag caggtggcag caggggaacg tcttctcatg      2580
ctccgtgatg catgaggctc tgcacaacca ctacacgcag aagagcctct ccctgtctcc      2640
gggtcgaaaa agaagatcag gttcgggtgc gccagtaaag cagacattaa actttgattt     2700
gctgaaactt gcaggtgatg tagagtcaaa tccaggtcca atggcaacag ggagccgaac     2760
ctctctgctc cttgctttcg ggctccttg cctaccgtgg ctccaagagg gctcggcaga     2820
aattgtgttg acacagtctc caggcaccct gtctttgtct ccaggggaaa cagccatcat     2880
ctcttgtcgg accagtcagt atggttcctt agcctggtat caacagaggc ccggccaggc     2940
ccccaggctc gtcatctatt cgggctctac tcgggccgct ggcatcccag acaggttcag     3000
cggcagtcgg tggggccag actacaatct caccatcagc aacctggagt cgggagattt     3060
tggtgtttat tattgccagc agtatgaatt ttttggccag gggaccaagg tccaggtcga    3120
cattaaacgt acggtggccg ctcccagcgt gttcatcttc cctccctctg atgaacagct    3180
gaaaagcgga acagccagcg tggtgtgtct gctgaacaac ttctacccca gagaagccaa   3240
agtgcagtgg aaggtggaca acgccctgca gagcggaaac agccaggaaa gcgtgacaga   3300
gcaggattcc aaggattcca catacagcct gagcagcaca ctgacactgt ccaaggccga   3360
ctacgagaag cacaaggtgt acgcctgcga agtgacacac cagggactgt cctcccctgt   3420
gacaaagagc ttcaacagag gagaatgcta aaggatccta atcaacctct ggattacaaa   3480
atttgtgaaa gattgactgg tattcttaac tatgttgctc cttttacgct atgtggatac    3540
gctgctttaa tgcctttgta tcatgctatt gcttcccgta tggctttcat ttctcctcc    3600 ttgtataaat cctggttgct gtctctttat gaggagttgt ggcccgttgt caggcaacgt   3660
ggcgtggtgt gcactgtgtt tgctgacgca acccccactg gttggggcat tgccaccacc   3720
tgtcagctcc tttccgggac tttcgctttc ccctcccta ttgccacggc ggaactcatc    3780
gccgcctgcc ttgcccgctg ctggacaggg gctcggctgt tgggcactga caattccgtg    3840
gtgttgtcgg ggaaatcatc gtcctttcct tggctgctcg cctgtgttgc cacctggatt    3900
ctgcgcggga cgtccttctg ctacgtccct tcggccctca atccagcgga ccttccttcc    3960
cgcggcctgc tgccggctct gcggcctctt ccgcgtcttc gccttcgccc tcagacgagt    4020
cggatctccc tttgggccgc ctccccgcct ggtaccttcg agcagacatg ataagataca    4080
ttgatgagtt tggacaaacc acaactagaa tgcagtgaaa aaaatgcttt atttgtgaaa    4140
tttgtgatgc tattgcttta tttgtaacca ttataagctg caataaacaa gttaacaaca    4200
acaattgcat tcattttatg tttcaggttc agggggagat gtgggaggtt ttttaaagca    4260
agtaaaacct ctacaaatgt ggtaaaatca agcttaggaa cccctagtga tggagttggc    4320
```

```
cactccctct ctgcgcgctc gctcgctcac tgaggccggg cgaccaaagg tcgcccgacg    4380
cccgggcttt gcccgggcgg cctcagtgag cgagcgagcg cgcagagagg gagtggccaa    4440
gctagcgggc gattaaggaa agggctagat cattcttgaa gacgaaaggg cctcgtgata    4500
cgcctatttt tataggttaa tgtcatgata ataatggttt cttagacgtc aggtggcact    4560
tttcggggaa atgtgcgcgg aacccctatt tgtttatttt tctaaataca ttcaaatatg    4620
tatccgctca tgagacaata accctgataa atgcttcaat aatattgaaa aaggaagagt    4680
atgagtattc aacatttccg tgtcgccctt attccctttt ttgcggcatt ttgccttcct    4740 gttttttgctc acccagaaac gctggtgaaa gtaaaagatg ctgaagatca gttgggtgca    4800
cgagtgggtt acatcgaact ggatctcaac agcggtaaga tccttgagag ttttcgcccc    4860
gaagaacgtt ttccaatgat gagcactttt aaagttctgc tatgtggcgc ggtattatcc    4920
cgtgttgacg ccgggcaaga gcaactcggt cgccgcatac actattctca gaatgacttg    4980
gttgagtact caccagtcac agaaaagcat cttacggatg gcatgacagt aagagaatta    5040
tgcagtgctg ccataaccat gagtgataac actgcggcca acttacttct gacaacgatc    5100
ggaggaccga aggagctaac cgcttttttg cacaacatgg gggatcatgt aactcgcctt    5160
gatcgttggg aaccggagct gaatgaagcc ataccaaacg acgagcgtga ccacacgatg    5220
cctgtagcaa tggcaacaac gttgcgcaaa ctattaactg gcgaactact tactctagct    5280
tcccggcaac aattaataga ctggatggag gcggataaag ttgcaggacc acttctgcgc    5340
tcggcccttc cggctggctg gtttattgct gataaatctg gagccggtga gcgtgggtct    5400
cgcggtatca ttgcagcact ggggccagat ggtaagccct cccgtatcgt agttatctac    5460
acgacgggga gtcaggcaac tatggatgaa cgaaatagac agatcgctga gataggtgcc    5520
tcactgatta gcattggta actgtcagac caagtttact catatatact ttagattgat    5580
ttaaaacttc attttttaatt taaaaggatc taggtgaaga tcctttttga taatctcatg    5640
accaaaatcc cttaacgtga gttttcgttc cactgagcgt cagacccgt agaaaagatc    5700 aaaggatctt cttgagatcc ttttttttctg cgcgtaatct gctgcttgca acaaaaaaa    5760 ccaccgctac cagcggtggt ttgtttgccg gatcaagagc taccaactct ttttccgaag    5820
gtaactggct tcagcagagc gcagatacca aatactgttc ttctagtgta gccgtagtta    5880
ggccaccact tcaagaactc tgtagcaccg cctacatacc tcgctctgct aatcctgtta    5940
ccagtggctg ctgccagtgg cgataagtcg tgtcttaccg ggttggactc aagacgatag    6000
ttaccggata aggcgcagcg gtcgggctga acggggggtt cgtgcacaca gcccagcttg    6060
gagcgaacga cctacaccga actgagatac ctacagcgtg agctatgaga aagcgccacg    6120
cttcccgaag ggagaaaggc ggacaggtat ccggtaagcg gcagggtcgg aacaggagag    6180
cgcacgaggg agcttccagg gggaaacgcc tggtatcttt atagtcctgt cgggtttcgc    6240
cacctctgac ttgagcgtcg atttttgtga tgctcgtcag gggggcggag cctatggaaa    6300
aacgccagca acgcggcctt tttacggttc ctggccttt gctggccttt tgctcacatg    6360
taataaacac acacacacca acaaccgtgg ttggttgttg tgttggttta ttctcgag     6418
```

<210> SEQ ID NO 25
<211> LENGTH: 6427
<212> TYPE: DNA
<213> ORGANISM: Artificial Sequence
<220> FEATURE:
<223> OTHER INFORMATION: pAAVio-CASI-TCN32OptABK-W-SV40

<400> SEQUENCE: 25

```
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcctactag tggagttccg cgttacataa cttacggtaa   180
atggcccgcc tggctgaccg cccaacgacc cccgcccatt gacgtcaata atgacgtatg   240
ttcccatagt aacgccaata gggactttcc attgacgtca atgggtggag tatttacggt   300
aaactgccca cttggcagta catcaagtgt atcatatgcc aagtacgccc cctattgacg   360
tcaatgacgg taaatggccc gcctggcatt atgcccagta catgacctta tgggactttc   420
ctacttggca gtacatctac gtattagtca tcgctattac catggtcgag gtgagcccca   480
cgttctgctt cactctcccc atctcccccc cctccccacc cccaattttg tatttattta   540
ttttttaatt attttgtgca gcgatggggg cggggggggg ggggggcgc gcgccaggcg   600
ggcggggcg gggcgagggg cggggcgggg cgaggcggag aggtgcggcg gcagccaatc   660
agagcggcgc gctccgaaag tttcctttta tggcgaggcg gcggcggcgg cggccctata   720
aaaagcgaag cgcgcggcgg gcgggagtcg ctgcgcgctg ccttcgcccc gtgccccgct   780
ccgccgccgc ctcgcgccgc ccgccccggc tctgactgac cgcgttacta aaacaggtaa   840
gtccggcctc cgcgccgggt tttggcgcct cccgcgggcg cccccctcct cacggcgagc   900
gctgccacgt cagacgaagg gcgcagcgag cgtcctgatc cttccgcccg gacgctcagg   960
acagcggccc gctgctcata agactcggcc ttagaacccc agtatcagca gaaggacatt  1020
ttaggacggg acttgggtga ctctagggca ctggttttct ttccagagag cggaacaggc  1080
gaggaaaagt agtcccttct cggcgattct gcggagggat ctccgtgggg cggtgaacgc  1140
cgatgatgcc tctactaacc atgttcatgt tttctttttt tttctacagg tcctgggtga  1200
cgaacaggcg gccgccatgg cgacgggttc aagaacttcc ctacttcttg catttggcct  1260
gctttgtttg ccgtggttac aggagggctc ggcacaagtt cagttgcagg agtcaggtcc  1320
gggattagtc aaaccttctg aaactctttc cctaacctgt accgtctcag gttcctctat  1380
ttcaaactac tattggagtt ggattagaca aagcccgggc aaagggctgg aatggatagg  1440
ttttatttat tacggggaa atacaaaata taatccaagt ttgaaaagca gagttactat  1500
ttcccaagac acttcaaaaa gtcaagtttc acttacaatg agttcagtga cagcggctga  1560
aagtgcagtg tatttctgtg cgagagcaag ttgttcggga ggatattgta tattggacta  1620
ctggggtcag ggaactttag ttactgtgag ctcagccagc accaagggcc catcggtctt  1680
ccccctggca ccctcctcca agagcacctc tgggggcaca gcggccctgg gctgcctggt  1740
caaggactac ttccccgaac cggtgacggt gtcgtggaac tcaggcgccc tgaccagcgg  1800
cgtgcacacc ttcccggctg tcctacagtc ctcaggactc tactccctca gcagcgtggt  1860
gaccgtgccc tccagcagct tgggcaccca gacctacatc tgcaacgtga atcacaagcc  1920
cagcaacacc aaggtggaca gaaagttga gcccaaatct tgtgacaaaa ctcacacatg  1980
cccaccgtgc ccagcacctg aactcctggg ggaccgtca gtcttcctct tccccccaaa  2040
acccaaggac accctcatga tctcccggac ccctgaggtc acatgcgtgg tggtggacgt  2100
gagccacgaa gaccctgagg tcaagttcaa ctggtatgtt gacggcgtgg aggtgcataa  2160
tgccaagaca aagccgcggg aggagcagta caacagcacg taccgtgtgg tcagcgtcct  2220
caccgtcctg caccaggact ggctgaatgg caaggagtac aagtgcaagg tctccaacaa  2280
agccctccca gcccccatcg agaaaaccat ctccaaagcc aaagggcagc cccgagaacc  2340
```

```
acaggtgtac accctgcccc catcccggga tgagctgacc aagaatcaag tcagcctgac    2400
ctgcctggtc aaaggcttct atcccagcga catcgccgtg gagtgggaga gcaatgggca    2460
gccggagaac aactacaaga ccacgcctcc cgtgctggac tccgacggct ccttcttcct    2520
ctactcaaaa ctcaccgtgg acaagagcag gtggcagcag gggaacgtct tctcatgctc    2580
cgtgatgcat gaggctctgc acaaccacta cacgcagaag agcctctccc tgtctccggg    2640
tcgaaaaaga agatcaggtt cgggtgcgcc agtaaagcag acattaaaact ttgatttgct    2700 gaaacttgca ggtgatgtag agtcaaatcc aggtccaatg gcaacaggga gccgaacctc    2760
tctgctcctt gctttcgggc tcctttgcct accgtggctc caagagggct cggcagacat    2820
acaaatgaca caaagcccaa gttctctaag tgcatcagtg ggggatcgag tgacaattac    2880
ttgtagggct tcccagaaca tatacaaata cttaaactgg tatcaacaac gcccgggaaa    2940
agcaccaaag ggtcttattt ccgcggcttc aggcctgcag tctggcgtcc cttcccggtt    3000
ttctggctca ggctcaggca cggattttac tctgaccata acctctctac agccggagga    3060
ttttgcgact tattattgcc aacaatctta ctctcctcct ctcacatttg gtggtgggac    3120
gagggtagag attaaacgaa cagtggccgc tcccagcgtg ttcatcttcc ctccctctga    3180
tgaacagctg aaaagcggaa cagccagcgt ggtgtgtctg ctgaacaact tctaccccag    3240
agaagccaaa gtgcagtgga aggtggacaa cgccctgcag agcggaaaca gccaggaaag    3300
cgtgacagag caggattcca aggattccac atacagcctg agcagcacac tgacactgtc    3360
caaggccgac tacgagaagc acaaggtgta cgcctgcgaa gtgacacacc agggactgtc    3420
ctcccctgtg acaaagagct caacagagg agaatgctaa aggatcctaa tcaacctctg    3480
gattacaaaa tttgtgaaag attgactggt attcttaact atgttgctcc ttttacgcta    3540
tgtggatacg ctgctttaat gcctttgtat catgctattg cttcccgtat ggctttcatt    3600
ttctcctcct tgtataaatc ctggttgctg tctctttatg aggagttgtg gcccgttgtc    3660
aggcaacgtg gcgtggtgtg cactgtgttt gctgacgcaa ccccccactgg ttggggcatt    3720 gccaccacct gtcagctcct ttccgggact ttcgctttcc ccctccctat tgccacggcg    3780
gaactcatcg ccgcctgcct tgcccgctgc tggacagggg ctcggctgtt gggcactgac    3840
aattccgtgg tgttgtcggg gaaatcatcg tcctttcctt ggctgctcgc ctgtgttgcc    3900
acctggattc tgcgcgggac gtccttctgc tacgtccctt cggccctcaa tccagcggac    3960
cttccttccc gcggcctgct gccggctctg cggcctcttc cgcgtcttcg ccttcgccct    4020
cagacgagtc ggatctccct ttgggccgcc tccccgcctg gtaccttcga gcagacatga    4080
taagatacat tgatgagttt ggacaaacca aactagaat gcagtgaaaa aaatgcttta    4140
tttgtgaaat ttgtgatgct attgctttat ttgtaaccat tataagctgc aataaacaag    4200
ttaacaacaa caattgcatt catttttatgt ttcaggttca gggggagatg tgggaggttt    4260
tttaaagcaa gtaaacctc tacaaatgtg gtaaaatcaa gcttaggaac ccctagtgat    4320
ggagttggcc actccctctc tgcgcgctcg ctcgctcact gaggccgggc gaccaaaggt    4380
cgcccgacgc ccgggctttg cccgggcggc ctcagtgagc gagcgagcgc gcagagaggg    4440
agtggccaag ctagcgggcg attaaggaaa gggctagatc attcttgaag acgaaagggc    4500
ctcgtgatac gcctattttt ataggttaat gtcatgataa taatggtttc ttagacgtca    4560
ggtggcactt ttcggggaaa tgtgcgcgga accctatttt gtttattttt ctaaatacat    4620
tcaaatatgt atccgctcat gagacaataa ccctgataaa tgcttcaata atattgaaaa    4680
aggaagagta tgagtattca acatttccgt gtcgccctta ttcccttttt tgcggcattt    4740
```

```
tgccttcctg tttttgctca cccagaaacg ctggtgaaag taaaagatgc tgaagatcag    4800
ttgggtgcac gagtgggtta catcgaactg gatctcaaca gcggtaagat ccttgagagt    4860
tttcgccccg aagaacgttt tccaatgatg agcactttta aagttctgct atgtggcgcg    4920
gtattatccc gtgttgacgc cgggcaagag caactcggtc gccgcataca ctattctcag    4980
aatgacttgg ttgagtactc accagtcaca gaaaagcatc ttacggatgg catgacagta    5040
agagaattat gcagtgctgc cataaccatg agtgataaca ctgcggccaa cttacttctg    5100
acaacgatcg gaggaccgaa ggagctaacc gcttttttgc acaacatggg gatcatgta    5160 actcgccttg atcgttggga accggagctg aatgaagcca taccaaacga cgagcgtgac    5220
accacgatgc ctgtagcaat ggcaacaacg ttgcgcaaac tattaactgg cgaactactt    5280
actctagctt cccggcaaca attaatagac tggatggagg cggataaagt tgcaggacca    5340
cttctgcgct cggcccttcc ggctggctgg tttattgctg ataaatctgg agccggtgag    5400
cgtgggtctc gcggtatcat tgcagcactg gggccagatg gtaagccctc ccgtatcgta    5460
gttatctaca cgacggggag tcaggcaact atggatgaac gaaatagaca gatcgctgag    5520
ataggtgcct cactgattaa gcattggtaa ctgtcagacc aagtttactc atatatactt    5580
tagattgatt taaaacttca ttttttaattt aaaaggatct aggtgaagat cctttttgat    5640
aatctcatga ccaaaatccc ttaacgtgag ttttcgttcc actgagcgtc agaccccgta    5700
gaaaagatca aggatcttc ttgagatcct ttttttctgc gcgtaatctg ctgcttgcaa    5760
acaaaaaaac caccgctacc agcggtggtt tgtttgccgg atcaagagct accaactctt    5820
tttccgaagg taactggctt cagcagagcg cagataccaa atactgttct tctagtgtag    5880
ccgtagttag gccaccactt caagaactct gtagcaccgc ctacatacct cgctctgcta    5940
atcctgttac cagtggctgc tgccagtggc gataagtcgt gtcttaccgg gttggactca    6000
agacgatagt taccggataa ggcgcagcgg tcgggctgaa cggggggttc gtgcacacag    6060
cccagcttgg agcgaacgac ctacaccgaa ctgagatacc tacagcgtga gctatgagaa    6120
agcgccacgc ttcccgaagg gagaaaggcg gacaggtatc cggtaagcgg cagggtcgga    6180
acaggagagc gcacgaggga gcttccaggg ggaaacgcct ggtatcttta tagtcctgtc    6240
gggtttcgcc acctctgact tgagcgtcga ttttttgtgat gctcgtcagg ggggcggagc    6300
ctatggaaaa acgccagcaa cgcggccttt ttacggttcc tggccttttg ctggcctttt    6360
gctcacatgt aataaacaca cacacaccaa caaccgtggt tggttgttgt gttggtttat    6420
tctcgag                                                             6427
```

<210> SEQ ID NO 26
<211> LENGTH: 6442
<212> TYPE: DNA
<213> ORGANISM: Artificial Sequence
<220> FEATURE:
<223> OTHER INFORMATION: pAAVio-CASI-CR6261LO13-W-SV40

<400> SEQUENCE: 26

```
ttggccactc cctctctgcg cgctcgctcg ctcactgagg ccgggcgacc aaaggtcgcc      60
cgacgcccgg gctttgcccg gcggcctca gtgagcgagc gagcgcgcag agaggagtg       120 gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
```

```
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctccccc cctcccacc cccaattttg tatttattta    540
ttttttaatt attttgtgca gcgatggggg cggggggggg ggggggcgc gcgccaggcg    600
gggcggggcg gggcgagggg cggggcgggg cgaggcggag aggtgcggcg gcagccaatc    660
agagcggcgc gctccgaaag tttccttta tggcgaggcg gcggcggcgg cggccctata    720
aaaagcgaag cgcgcggcgg gcgggagtcg ctgcgcgctg ccttcgcccc gtgcccgct    780
ccgccgccgc ctcgcgccgc ccgccccggc tctgactgac cgcgttacta aaacaggtaa    840
gtccggcctc cgcgcggggt tttggcgcct cccgcgggcg ccccctcct cacggcgagc    900
gctgccacgt cagacgaagg gcgcagcgag cgtcctgatc cttcgcccg gacgctcagg    960
acagcggccc gctgctcata agactcggcc ttagaacccc agtatcagca gaaggacatt   1020
ttaggacggg acttgggtga ctctagggca ctggtttct ttccagagag cggaacaggc   1080
gaggaaaagt agtcccttct cggcgattct gcggagggat ctccgtgggg cggtgaacgc   1140
cgatgatgcc tctactaacc atgttcatgt tttctttttt tttctacagg tcctgggtga   1200
cgaacaggcg ccgccatgg cgacgggttc aagaacttcc ctacttcttg catttggcct   1260
gctttgtttg ccgtggttac aggagggctc ggcagaagtc caactcgtgg aatccggagc   1320
cgaggttaaa aagcccggct ccagcgtgaa agtctcttgc aaagcaagcg gtgggccgtt   1380
tcgatcatac gcgatatcat gggtccggca ggcacctgga caggggcccg aatggatggg   1440
aggcataatc ccaatctttg ggaccacgaa gtatgccccg aaattccagg gtagggtcac   1500
tatcaccgct gacgacttcg ccggaaccgt ctatatggaa cttccagcc tgcgcagcga   1560
ggacaccgca atgtattact gcgcaaaaca catgggatac caagtgagag agaccatgga   1620
tgtgtgggc aagggtacta ctgtgaccgt gagctcagcc agcaccaagg gcccatcggt   1680
cttccccctg gcaccctcct ccaagagcac ctctgggggc acagcggccc tgggctgcct   1740
ggtcaaggac tacttcccg aaccggtgac ggtgtcgtgg aactcaggcg ccctgaccag   1800
cggcgtgcac accttcccgg ctgtcctaca gtcctcagga ctctactccc tcagcagcgt   1860
ggtgaccgtg ccctccagca gcttgggcac ccagacctac atctgcaacg tgaatcacaa   1920
gcccagcaac accaaggtgg acaagaaagt tgagcccaaa tcttgtgaca aaactcacac   1980
atgcccaccg tgcccagcac ctgaactcct gggggaccg tcagtcttcc tcttcccccc   2040
aaaacccaag gacaccctca tgatctcccg gacccctgag gtcacatgcg tggtggtgga   2100
cgtgagccac gaagaccctg aggtcaagtt caactggtat gttgacggcg tggaggtgca   2160
taatgccaag acaaagccgc gggaggagca gtacaacagc acgtaccgtg tggtcagcgt   2220
cctcaccgtc ctgcaccagg actggctgaa tggcaaggag tacaagtgca aggtctccaa   2280
caaagccctc ccagccccca tcgagaaaac catctccaaa gccaaagggc agccccgaga   2340
accacaggtg tacaccctgc ccccatcccg ggatgagctg accaagaatc aagtcagcct   2400
gacctgcctg gtcaaaggct tctatcccag cgacatcgcc gtggagtggg agagcaatgg   2460
gcagccggag aacaactaca agaccacgcc tcccgtgctg gactccgacg gctccttctt   2520
cctctactca aaactcaccg tggacaagag caggtggcag caggggaacg tcttctcatg   2580
ctccgtgatg catgaggctc tgcacaacca ctacacgcag aagagcctct ccctgtctcc   2640
gggtcgaaaa agaagatcag gttcgggtgc gccagtaaag cagacattaa actttgattt   2700
```

```
gctgaaactt gcaggtgatg tagagtcaaa tccaggtcca atggcaacag ggagccgaac    2760
ctctctgctc cttgctttcg ggctcctttg cctaccgtgg ctccaagagg gctcggcaga    2820
gatcgttctc acgcagtctc catccgtatc tgcagccccg ggacagaaag tgacaatttc    2880
atgctctggg tcctcatcca acatcggaaa tgactacgtt agttggtacc aacagctccc    2940
tgggaccgcg ccaaaactgc tgatttatga caacaacaag aggccaagtg gcatccccga    3000
caggttttcc ggctcaaagt ccggcacttc agcaacactg gcatcacgg gtctgcaaac    3060 aggcgatgag gcaaactact attgcgcaac ctgggacagg agaccgaccg cttatgttgt    3120
gttcggcggc gggactaagc tggagaggaa acgtacggtg gccgctccca gcgtgttcat    3180
cttccctccc tctgatgaac agctgaaaag cggaacagcc agcgtggtgt gtctgctgaa    3240
caacttctac cccagagaag ccaaagtgca gtggaaggtg gacaacgccc tgcagagcgg    3300
aaacagccag gaaagcgtga cagagcagga ttccaaggat tccacataca gcctgagcag    3360
cacactgaca ctgtccaagg ccgactacga gaagcacaag gtgtacgcct gcgaagtgac    3420
acaccaggga ctgtcctccc ctgtgacaaa gagcttcaac agaggagaat gctaaaggat    3480
cctaatcaac ctctggatta caaaatttgt gaaagattga ctggtattct taactatgtt    3540
gctcctttta cgctatgtgg atacgctgct ttaatgcctt tgtatcatgc tattgcttcc    3600
cgtatggctt tcattttctc ctccttgtat aaatcctggt tgctgtctct ttatgaggag    3660
ttgtggcccg ttgtcaggca acgtggcgtg gtgtgcactg tgtttgctga cgcaaccccc    3720
actggttggg gcattgccac cacctgtcag ctcctttccg ggactttcgc tttccccctc    3780
cctattgcca cggcggaact catcgccgcc tgccttgccc gctgctggac aggggctcgg    3840
ctgttgggca ctgacaattc cgtggtgttg tcggggaaat catcgtcctt ccttggctg    3900 ctcgcctgtg ttgccacctg gattctgcgc gggacgtcct tctgctacgt cccttcggcc    3960
ctcaatccag cggaccttcc ttcccgcggc ctgctgccgg ctctgcggcc tcttccgcgt    4020
cttcgccttc gccctcagac gagtcggatc tccctttggg ccgcctcccc gcctggtacc    4080
ttcgagcaga catgataaga tacattgatg agtttggaca aaccacaact agaatgcagt    4140
gaaaaaaatg ctttatttgt gaaatttgtg atgctattgc tttatttgta accattataa    4200
gctgcaataa acaagttaac aacaacaatt gcattcattt tatgtttcag gttcagggggg    4260 agatgtggga ggttttttaa agcaagtaaa acctctacaa atgtggtaaa atcaagctta    4320 ggaacccta gtgatggagt tggccactcc ctctctgcgc gctcgctcgc tcactgaggc    4380
cgggcgacca aaggtcgccc gacgcccggg ctttgcccgg gcggcctcag tgagcgagcg    4440
agcgcgcaga gagggagtgg ccaagctagc gggcgattaa ggaaagggct agatcattct    4500
tgaagacgaa agggcctcgt gatacgccta ttttatagg ttaatgtcat gataataatg    4560
gtttcttaga cgtcaggtgg cacttttcgg ggaaatgtgc gcggaacccc tatttgttta    4620
tttttctaaa tacattcaaa tatgtatccg ctcatgagac aataaccctg ataaatgctt    4680
caataatatt gaaaaaggaa gagtatgagt attcaacatt tccgtgtcgc ccttattccc    4740
ttttttgcgg cattttgcct tcctgttttt gctcacccag aaacgctggt gaaagtaaaa    4800
gatgctgaag atcagttggg tgcacgagtg ggttacatcg aactggatct caacagcggt    4860
aagatccttg agagttttcg ccccgaagaa cgttttccaa tgatgagcac ttttaaagtt    4920
ctgctatgtg gcgcggtatt atcccgtgtt gacgccgggc aagagcaact cggtcgccgc    4980
atacactatt ctcagaatga cttggttgag tactcaccag tcacagaaaa gcatcttacg    5040
```

| gatggcatga cagtaagaga attatgcagt gctgccataa ccatgagtga taacactgcg | 5100 |
| gccaacttac ttctgacaac gatcggagga ccgaaggagc taaccgcttt tttgcacaac | 5160 |
| atgggggatc atgtaactcg ccttgatcgt tgggaaccgg agctgaatga agccatacca | 5220 |
| aacgacgagc gtgacaccac gatgcctgta gcaatggcaa caacgttgcg caaactatta | 5280 |
| actggcgaac tacttactct agcttcccgg caacaattaa tagactggat ggaggcggat | 5340 |
| aaagttgcag gaccacttct cgctcggcc cttccggctg gctggtttat tgctgataaa | 5400 |
| tctggagccg gtgagcgtgg gtctcgcggt atcattgcag cactggggcc agatggtaag | 5460 |
| ccctcccgta tcgtagttat ctacacgacg gggagtcagg caactatgga tgaacgaaat | 5520 |
| agacagatcg ctgagatagg tgcctcactg attaagcatt ggtaactgtc agaccaagtt | 5580 |
| tactcatata tactttagat tgatttaaaa cttcattttt aatttaaaag gatctaggtg | 5640 |
| aagatccttt ttgataatct catgaccaaa atcccttaac gtgagttttc gttccactga | 5700 |
| gcgtcagacc ccgtagaaaa gatcaaagga tcttcttgag atcctttttt tctgcgcgta | 5760 |
| atctgctgct tgcaaacaaa aaaaccaccg ctaccagcgg tggtttgttt gccggatcaa | 5820 |
| gagctaccaa ctcttttcc gaaggtaact ggcttcagca gagcgcagat accaaatact | 5880 |
| gttcttctag tgtagccgta gttaggccac cacttcaaga actctgtagc accgcctaca | 5940 |
| tacctcgctc tgctaatcct gttaccagtg gctgctgcca gtggcgataa gtcgtgtctt | 6000 |
| accgggttgg actcaagacg atagttaccg gataaggcgc agcggtcggg ctgaacgggg | 6060 |
| ggttcgtgca cacagcccag cttggagcga acgacctaca ccgaactgag atacctacag | 6120 |
| cgtgagctat gagaaagcgc cacgcttccc gaagggagaa aggcggacag gtatccggta | 6180 |
| agcggcaggg tcggaacagg agagcgcacg agggagcttc caggggggaaa cgcctggtat | 6240 |
| ctttatagtc ctgtcgggtt tcgccacctc tgacttgagc gtcgattttt gtgatgctcg | 6300 |
| tcaggggggc ggagcctatg gaaaaacgcc agcaacgcgg cctttttacg gttcctggcc | 6360 |
| ttttgctggc cttttgctca catgtaataa acacacacac accaacaacc gtggttggtt | 6420 |
| gttgtgttgg tttattctcg ag | 6442 |

<210> SEQ ID NO 27
<211> LENGTH: 6451
<212> TYPE: DNA
<213> ORGANISM: Artificial Sequence
<220> FEATURE:
<223> OTHER INFORMATION: pAAVio-CASI-F10LO24-W-SV40

<400> SEQUENCE: 27

| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctactag tggagttccg cgttacataa cttacggtaa | 180 |
| atggcccgcc tggctgaccg cccaacgacc cccgcccatt gacgtcaata atgacgtatg | 240 |
| ttcccatagt aacgccaata gggactttcc attgacgtca atgggtggag tatttacggt | 300 |
| aaactgccca cttggcagta catcaagtgt atcatatgcc aagtacgccc cctattgacg | 360 |
| tcaatgacgg taaatggccc gcctggcatt atgcccagta catgacctta tgggactttc | 420 |
| ctacttggca gtacatctac gtattagtca tcgctattac catggtcgag gtgagcccca | 480 |
| cgttctgctt cactctcccc atctcccccc cctccccacc cccaattttg tatttattta | 540 |
| ttttttaatt attttgtgca gcgatggggg cggggggggg ggggggggcgc gcgccaggcg | 600 |
| gggcggggcg gggcgagggg cggggcgggg cgaggcggag aggtgcggcg gcagccaatc | 660 |

```
agagcggcgc gctccgaaag tttccttta tggcgaggcg gcggcggcgg cggccctata     720
aaaagcgaag cgcgcggcgg gcgggagtcg ctgcgcgctg ccttcgcccc gtgcccgct     780
ccgccgccgc ctcgcgccgc ccgccccggc tctgactgac cgcgttacta aaacaggtaa    840
gtccggcctc cgcgccgggt tttggcgcct cccgcgggcg ccccctcct cacggcgagc    900
gctgccacgt cagacgaagg gcgcagcgag cgtcctgatc cttccgcccg gacgctcagg    960
acagcggccc gctgctcata agactcggcc ttagaacccc agtatcagca gaaggacatt   1020
ttaggacggg acttgggtga ctctagggca ctggtttct ttccagagag cggaacaggc   1080
gaggaaaagt agtcccttct cggcgattct gcggagggat ctccgtgggg cggtgaacgc   1140
cgatgatgcc tctactaacc atgttcatgt tttcttttt ttctacagg tcctgggtga   1200
cgaacaggcg gccgccatgg cgacgggttc aagaacttcc ctacttcttg catttggcct   1260
gctttgtttg ccgtggttac aggagggctc ggcacaggtt cagcttgtcc aatcgggtgc   1320
ggaggtcaag aagccgggct catcagtcaa agtatcttgc acttcttctg aagttacgtt   1380
cagctctttc gctatatcgt gggtgagaca agcaccgggc cagggattag agtggttggg   1440
aggcatttca cctatgtttg gcactcctaa ttacgcacag aaatttcaag gcagggttac   1500
tatcacagcc gaccaatcca cacgaactgc atatatggac ttgcgaagtt tgaggtctga   1560
agacactgcg gtatattact gcgcccgaag tccttcatac atttgttcgg gaggtacttg   1620
cgtgtttgac cattggggtc agggaacttt agttactgtg agctcagcca gcaccaaggg   1680
cccatcggtc ttccccctgg caccctcctc caagagcacc tctggggca cagcggccct   1740
gggctgcctg gtcaaggact acttccccga accggtgacg gtgtcgtgga actcaggcgc   1800
cctgaccagc ggcgtgcaca ccttcccggc tgtcctacag tcctcaggac tctactccct   1860
cagcagcgtg gtgaccgtgc cctccagcag cttgggcacc cagacctaca tctgcaacgt   1920
gaatcacaag cccagcaaca ccaaggtgga caagaaagtt gagcccaaat cttgtgacaa   1980
aactcacaca tgcccaccgt gcccagcacc tgaactcctg gggggaccgt cagtcttcct   2040
cttcccccca aaacccaagg acaccctcat gatctcccgg acccctgagg tcacatgcgt   2100
ggtggtggac gtgagccacg aagaccctga ggtcaagttc aactggtatg ttgacggcgt   2160
ggaggtgcat aatgccaaga caaagccgcg ggaggagcag tacaacagca cgtaccgtgt   2220
ggtcagcgtc ctcaccgtcc tgcaccagga ctggctgaat ggcaaggagt acaagtgcaa   2280
ggtctccaac aaagccctcc cagcccccat cgagaaaacc atctccaaag ccaaagggca   2340
gccccgagaa ccacaggtgt acaccctgcc cccatcccgg gatgagctga ccaagaatca   2400
agtcagcctg acctgcctgg tcaaaggctt ctatcccagc gacatcgccg tggagtggga   2460
gagcaatggg cagccggaga acaactacaa gaccacgcct cccgtgctgg actccgacgg   2520
ctccttcttc ctctactcaa aactcaccgt ggacaagagc aggtggcagc aggggaacgt   2580
cttctcatgc tccgtgatgc atgaggctct gcacaaccac tacacgcaga agagcctctc   2640
cctgtctccg ggtcgaaaaa gaagatcagg ttcgggtgcg ccagtaaagc agacattaaa   2700
ctttgatttg ctgaaacttg caggtgatgt agagtcaaat ccaggtccaa tggcaacagg   2760
gagccgaacc tctctgctcc ttgctttcgg gctcctttgc ctaccgtggc tccaagaggg   2820
ctcggcagag atcgttctca cgcagtctcc aggcaccctg tctctgtctc cagggaaag   2880
agccaccttc tcctgcacag gcaatagtaa taatgtgggg aatcagggag cagcatggtt   2940
acagcaacat caaggacatc ccccgaaact gctttcctat cgtaacaacg accgcccgtc   3000
```

```
gggaatctcg gaacgttttt ctgcgtcacg ttcaggcaac actgcctcgc tgactataac    3060
tggcttacag cctgaagacg aagcagacta ctattgttca acttgggatt cttctctgtc    3120
tgcggttgtg tttggcggcg gcacaaaagt ggaggtgaag cggaccgtgg ccgctcccag    3180
cgtgttcatc ttccctccct ctgatgaaca gctgaaaagc ggaacagcca gcgtggtgtg    3240
tctgctgaac aacttctacc ccagagaagc caaagtgcag tggaaggtgg acaacgccct    3300
gcagagcgga aacagccagg aaagcgtgac agagcaggat ccaaggatt ccacatacag    3360 cctgagcagc acactgacac tgtccaaggc cgactacgag aagcacaagg tgtacgcctg    3420
cgaagtgaca caccagggac tgtcctcccc tgtgacaaag agcttcaaca gaggagaatg    3480
ctaaaggatc ctaatcaacc tctggattac aaaatttgtg aaagattgac tggtattctt    3540
aactatgttg ctccttttac gctatgtgga tacgctgctt taatgccttt gtatcatgct    3600
attgcttccc gtatggcttt cattttctcc tccttgtata atcctggtt gctgtctctt    3660 tatgaggagt tgtggcccgt tgtcaggcaa cgtggcgtgg tgtgcactgt gtttgctgac    3720 gcaacccca ctggttgggg cattgccacc acctgtcagc tcctttccgg acttttcgct     3780 ttcccctcc ctattgccac ggcggaactc atcgccgcct gccttgcccg ctgctggaca     3840
ggggctcggc tgttgggcac tgacaattcc gtggtgttgt cggggaaatc atcgtccttt    3900
ccttggctgc tcgcctgtgt tgccacctgg attctgcgcg ggacgtcctt ctgctacgtc    3960
ccttcggccc tcaatccagc ggaccttcct tcccgcggcc tgctgccggc tctgcggcct    4020
cttccgcgtc ttcgccttcg ccctcagacg agtcggatct ccctttgggc cgcctccccg    4080
cctggtacct tcgagcagac atgataagat acattgatga gtttggacaa accacaacta    4140
gaatgcagtg aaaaaaatgc tttatttgtg aaatttgtga tgctattgct ttatttgtaa    4200
ccattataag ctgcaataaa caagttaaca acaacaattg cattcatttt atgtttcagg    4260
ttcaggggga gatgtgggag gttttttaaa gcaagtaaaa cctctacaaa tgtggtaaaa    4320
tcaagcttag gaaccctag tgatggagtt ggccactccc tctctgcgcg ctcgctcgct     4380
cactgaggcc gggcgaccaa aggtcgcccg acgcccgggc tttgcccggg cggcctcagt    4440
gagcgagcga gcgcgcagag agggagtggc caagctagcg ggcgattaag gaaagggcta    4500
gatcattctt gaagacgaaa gggcctcgtg atacgcctat ttttataggt taatgtcatg    4560
ataataatgg tttcttagac gtcaggtggc acttttcggg gaaatgtgcg cggaacccct    4620
atttgtttat ttttctaaat acattcaaat atgtatccgc tcatgagaca ataaccctga    4680
taaatgcttc aataatattg aaaaaggaag agtatgagta ttcaacattt ccgtgtcgcc    4740
cttattccct tttttgcggc attttgcctt cctgtttttg ctcacccaga aacgctggtg    4800
aaagtaaaag atgctgaaga tcagttgggt gcacgagtgg gttacatcga actggatctc    4860
aacagcggta agatccttga gagttttcgc cccgaagaac gttttccaat gatgagcact    4920
tttaaagttc tgctatgtgg cgcggtatta cccgtgttg acgccgggca agagcaactc     4980
ggtcgccgca tacactattc tcagaatgac ttggttgagt actcaccagt cacagaaaag    5040
catcttacgg atggcatgac agtaagagaa ttatgcagtg ctgccataac catgagtgat    5100
aacactgcgg ccaacttact tctgacaacg atcggaggac cgaaggagct aaccgctttt    5160
ttgcacaaca tgggggatca tgtaactcgc cttgatcgtt gggaaccgga gctgaatgaa    5220
gccataccaa acgacgagcg tgacaccacg atgcctgtag caatggcaac aacgttgcgc    5280
aaactattaa ctggcgaact acttactcta gcttcccggc aacaattaat agactggatg    5340
gaggcggata aagttgcagg accacttctg cgctcggccc ttccggctgg ctggtttatt    5400
```

```
gctgataaat ctggagccgg tgagcgtggg tctcgcggta tcattgcagc actgggccca    5460
gatggtaagc cctcccgtat cgtagttatc tacacgacgg ggagtcaggc aactatggat    5520
gaacgaaata gacagatcgc tgagataggt gcctcactga ttaagcattg gtaactgtca    5580
gaccaagttt actcatatat actttagatt gatttaaaac ttcattttta atttaaaagg    5640
atctaggtga agatccttt tgataatctc atgaccaaaa tcccttaacg tgagttttcg     5700
ttccactgag cgtcagaccc cgtagaaaag atcaaaggat cttcttgaga tcctttttt   5760 ctgcgcgtaa tctgctgctt gcaaacaaaa aaaccaccgc taccagcggt ggtttgtttg    5820
ccggatcaag agctaccaac tctttttccg aaggtaactg gcttcagcag agcgcagata    5880
ccaaatactg ttcttctagt gtagccgtag ttaggccacc acttcaagaa ctctgtagca    5940
ccgcctacat acctcgctct gctaatcctg ttaccagtgg ctgctgccag tggcgataag    6000
tcgtgtctta ccgggttgga ctcaagacga tagttaccgg ataaggcgca gcggtcgggc    6060
tgaacggggg gttcgtgcac acagcccagc ttggagcgaa cgacctacac cgaactgaga    6120
tacctacagc gtgagctatg agaaagcgcc acgcttcccg aagggagaaa ggcggacagg    6180
tatccggtaa gcggcagggt cggaacagga gagcgcacga gggagcttcc agggggaaac    6240
gcctggtatc tttatagtcc tgtcgggttt cgccacctct gacttgagcg tcgatttttg    6300
tgatgctcgt caggggggcg gagcctatgg aaaaacgcca gcaacgcggc ctttttacgg    6360
ttcctggcct tttgctggcc ttttgctcac atgtaataaa cacacacaca ccaacaaccg    6420
tggttggttg ttgtgttggt ttattctcga g                                   6451

<210> SEQ ID NO 28
<211> LENGTH: 6502
<212> TYPE: DNA
<213> ORGANISM: Artificial Sequence
<220> FEATURE:
<223> OTHER INFORMATION: pAAVio-CASI-AR4AABK-W-SV40

<400> SEQUENCE: 28
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg    120
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctcccccc cctccccacc cccaattttg tatttattta    540 tttttaatt attttgtgca gcgatggggg cggggggggg ggggggcgc gcgccaggcg    600 gggcggggcg gggcgagggg cggggcgggg cgaggcggag aggtgcggcg gcagccaatc    660
agagcggcgc gctccgaaag tttccttta tggcgaggcg gcggcggcgg cggccctata    720
aaaagcgaag cgcgcggcgg gcgggagtcg ctgcgcgctg ccttcgcccc gtgccccgct    780
ccgccgccgc ctcgcgccgc ccgccccggc tctgactgac cgcgttacta aaacaggtaa    840
gtccggcctc cgcgccgggt tttggcgcct cccgcgggcg cccccctcct cacgcgcagc    900
gctgccacgt cagacgaagg cgcagcgagc gtcctgatcc cttccgcccg gacgctcagg    960
```

-continued

| | |
|---|---|
| acagcggccc gctgctcata agactcggcc ttagaacccc agtatcagca gaaggacatt | 1020 |
| ttaggacggg acttgggtga ctctagggca ctggttttct ttccagagag cggaacaggc | 1080 |
| gaggaaaagt agtcccttct cggcgattct gcggagggat ctccgtgggg cggtgaacgc | 1140 |
| cgatgatgcc tctactaacc atgttcatgt tttctttttt tttctacagg tcctgggtga | 1200 |
| cgaacaggcg gccgccatgg cgacgggttc aagaacttcc ctacttcttg catttggcct | 1260 |
| gctttgtttg ccgtggttac aggagggctc ggcagaggtt cagctgctcg agcagtctgg | 1320 |
| gccagaggtg aaaaagcccg ggattctct gaggatctcc tgtaagatgt ctggagacag | 1380 |
| tttagtcacc acttggatcg gctgggtgcg ccagaagccc gggcaaggcc tggagtggat | 1440 |
| ggggatcatc aatcctggtg actcttctac caacatctat cctggtgact ctgccacgcg | 1500 |
| atatggcccg tccttccaag gccaggtcac catctcaatc gacaagtcca ccagcaccgc | 1560 |
| gtacctgcag tggaacaatg tgaaggcctc ggacaccggc atttattact gtgcgagaca | 1620 |
| tgtccccgta ccaatctccg ggactttttct ttggagagag cgggaaatgc atgatttcgg | 1680 |
| ctactttgac gactggggcc agggaaccct ggtcatcgtc tcctcagcca gcaccaaggg | 1740 |
| cccatcggtc ttccccctgg caccctcctc aagagcacc tctgggggca gcggccct | 1800 |
| gggctgcctg gtcaaggact acttccccga accggtgacg gtgtcgtgga actcaggcgc | 1860 |
| cctgaccagc ggcgtgcaca ccttcccggc tgtcctacag tcctcaggac tctactccct | 1920 |
| cagcagcgtg gtgaccgtgc cctccagcag cttgggcacc cagacctaca tctgcaacgt | 1980 |
| gaatcacaag cccagcaaca ccaaggtgga caagaaagtt gagcccaaat cttgtgacaa | 2040 |
| aactcacaca tgcccaccgt gcccagcacc tgaactcctg ggggaccgt cagtcttcct | 2100 |
| cttcccccca aaacccaagg acaccctcat gatctcccgg acccctgagg tcacatgcgt | 2160 |
| ggtggtggac gtgagccacg aagaccctga ggtcaagttc aactggtatg ttgacggcgt | 2220 |
| ggaggtgcat aatgccaaga caaagccgcg ggaggagcag tacaacagca cgtaccgtgt | 2280 |
| ggtcagcgtc ctcaccgtcc tgcaccagga ctggctgaat ggcaaggagt acaagtgcaa | 2340 |
| ggtctccaac aaagccctcc cagcccccat cgagaaaacc atctccaaag ccaaagggca | 2400 |
| gccccgagaa ccacaggtgt acaccctgcc cccatcccgg gatgagctga ccaagaatca | 2460 |
| agtcagcctg acctgcctgg tcaaaggctt ctatcccagc gacatcgccg tggagtggga | 2520 |
| gagcaatggg cagccggaga caactacaa gaccacgcct cccgtgctgg actccgacgg | 2580 |
| ctccttcttc ctctactcaa aactcaccgt ggacaagagc aggtggcagc aggggaacgt | 2640 |
| cttctcatgc tccgtgatgc atgaggctct gcacaaccac tacacgcaga agagcctctc | 2700 |
| cctgtctccg ggtcgaaaaa gaagatcagg ttcgggtgcg ccagtaaagc agacattaaa | 2760 |
| cttttgatttg ctgaaacttg caggtgatgt agagtcaaat ccaggtccaa tggcaacagg | 2820 |
| gagccgaacc tctctgctcc ttgctttcgg gctcctttgc ctaccgtggc tccaagaggg | 2880 |
| ctcggcagag ctcacactca cgcagtctcc aggcaccctg tctttgtctc caggggaaag | 2940 |
| agccacccctc tcctgcaggg ccagtcagag tgttagcaac aactacttag cctggtacca | 3000 |
| gcagaaacct ggccaggctc ccaggctcct catctatggt gcatccagca gggccactgg | 3060 |
| catcccagac aggttcagtg gcagtgggtc tgggacaggc ttcactctca tcatcagcag | 3120 |
| actggagcct gaagattttg cagtgtatta ctgtcagcag tatggtagct cttcgatcac | 3180 |
| cttcggccaa gggacacgac tggagattaa acgaactgtg ccgctccca gcgtgttcat | 3240 |
| cttccctccc tctgatgaac agctgaaaag cggaacagcc agcgtggtgt gtctgctgaa | 3300 |
| caacttctac cccagagaag ccaaagtgca gtggaaggtg gacaacgccc tgcagagcgg | 3360 |

```
aaacagccag gaaagcgtga cagagcagga ttccaaggat tccacataca gcctgagcag   3420
cacactgaca ctgtccaagg ccgactacga gaagcacaag gtgtacgcct gcgaagtgac   3480
acaccaggga ctgtcctccc ctgtgacaaa gagcttcaac agaggagaat gctaaaggat   3540
cctaatcaac ctctggatta caaaatttgt gaaagattga ctggtattct taactatgtt   3600 gctccttttta cgctatgtgg atacgctgct ttaatgcctt tgtatcatgc tattgcttcc   3660
cgtatggctt tcattttctc ctccttgtat aaatcctggt tgctgtctct ttatgaggag   3720
ttgtggcccg ttgtcaggca acgtggcgtg gtgtgcactg tgtttgctga cgcaaccccc   3780
actggttggg gcattgccac cacctgtcag ctccttttccg ggactttcgc tttccccctc   3840
cctattgcca cggcggaact catcgccgcc tgccttgccc gctgctggac aggggctcgg   3900
ctgttgggca ctgacaattc cgtggtgttg tcggggaaat catcgtcctt tccttggctg   3960
ctcgcctgtg ttgccacctg gattctgcgc gggacgtcct tctgctacgt cccttcggcc   4020
ctcaatccag cggaccttcc ttcccgcggc ctgctgccgg ctctgcggcc tcttccgcgt   4080
cttcgccttc gccctcagac gagtcggatc tccctttggg ccgcctcccc gcctggtacc   4140
ttcgagcaga catgataaga tacattgatg agtttggaca aaccacaact agaatgcagt   4200
gaaaaaaatg ctttatttgt gaaatttgtg atgctattgc tttatttgta accattataa   4260
gctgcaataa acaagttaac aacaacaatt gcattcattt tatgtttcag gttcaggggg   4320
agatgtggga ggttttttaa agcaagtaaa acctctacaa atgtggtaaa atcaagctta   4380
ggaaccccta gtgatggagt tggccactcc ctctctgcgc gctcgctcgc tcactgaggc   4440
cgggcgacca aaggtcgccc gacgcccggg ctttgcccgg gcggcctcag tgagcgagcg   4500
agcgcgcaga gagggagtgg ccaagctagc gggcgattaa ggaaagggct agatcattct   4560
tgaagacgaa agggcctcgt gatacgccta ttttttatagg ttaatgtcat gataataatg   4620
gtttcttaga cgtcaggtgg cacttttcgg ggaaatgtgc gcggaacccc tatttgttta   4680
tttttctaaa tacattcaaa tatgtatccg ctcatgagac aataaccctg ataaatgctt   4740
caataatatt gaaaaaggaa gagtatgagt attcaacatt tccgtgtcgc ccttattccc   4800
ttttttgcgg cattttgcct tcctgttttt gctcacccag aaacgctggt gaaagtaaaa   4860
gatgctgaag atcagttggg tgcacgagtg ggttacatcg aactggatct caacagcggt   4920
aagatccttg agagttttcg ccccgaagaa cgttttccaa tgatgagcac ttttaaagtt   4980
ctgctatgtg gcgcggtatt atcccgtgtt gacgccgggc aagagcaact cggtcgccgc   5040
atacactatt ctcagaatga cttggttgag tactcaccag tcacagaaaa gcatcttacg   5100
gatggcatga cagtaagaga attatgcagt gctgccataa ccatgagtga taacactgcg   5160
gccaacttac ttctgacaac gatcggagga ccgaaggagc taaccgcttt tttgcacaac   5220 atggggatc atgtaactcg ccttgatcgt tgggaaccgg agctgaatga agccatacca   5280
aacgacgagc gtgacaccac gatgcctgta gcaatggcaa caacgttgcg caaactatta   5340
actggcgaac tacttactct agcttcccgg caacaattaa tagactggat ggaggcggat   5400
aaagttgcag gaccacttct gcgctcggcc cttccggctg gctggtttat tgctgataaa   5460
tctggagccg gtgagcgtgg gtctcgcggt atcattgcag cactggggcc agatggtaag   5520
ccctcccgta tcgtagttat ctacacgacg gggagtcagg caactatgga tgaacgaaat   5580
agacagatcg ctgagatagg tgcctcactg attaagcatt ggtaactgtc agaccaagtt   5640
tactcatata ctttagat tgatttaaaa cttcattttt aatttaaaag gatctaggtg   5700
```

```
aagatccttt ttgataatct catgaccaaa atcccttaac gtgagttttc gttccactga    5760
gcgtcagacc ccgtagaaaa gatcaaagga tcttcttgag atccttttt tctgcgcgta    5820
atctgctgct tgcaaacaaa aaaccaccg ctaccagcgg tggtttgttt gccggatcaa    5880
gagctaccaa ctctttttcc gaaggtaact ggcttcagca gagcgcagat accaaatact    5940
gttcttctag tgtagccgta gttaggccac cacttcaaga actctgtagc accgcctaca    6000
tacctcgctc tgctaatcct gttaccagtg gctgctgcca gtggcgataa gtcgtgtctt    6060
accgggttgg actcaagacg atagttaccg gataaggcgc agcggtcggg ctgaacgggg    6120
ggttcgtgca cacagcccag cttggagcga acgacctaca ccgaactgag atacctacag    6180
cgtgagctat gagaaagcgc cacgcttccc gaagggagaa aggcggacag gtatccggta    6240
agcggcaggg tcggaacagg agagcgcacg agggagcttc caggggaaa cgcctggtat    6300
ctttatagtc ctgtcgggtt cgccaccctc tgacttgagc gtcgattttt gtgatgctcg    6360
tcaggggggc ggagcctatg gaaaaacgcc agcaacgcgg cctttttacg gttcctggcc    6420
ttttgctggc cttttgctca catgtaataa acacacacac accaacaacc gtggttggtt    6480
gttgtgttgg tttattctcg ag                                            6502
```

<210> SEQ ID NO 29
<211> LENGTH: 6465
<212> TYPE: DNA
<213> ORGANISM: Artificial Sequence
<220> FEATURE:
<223> OTHER INFORMATION: pAAVio-CASI-FI6ABK-W-SV40

<400> SEQUENCE: 29

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctactag tggagttccg cgttacataa cttacggtaa    180
atggcccgcc tggctgaccg cccaacgacc cccgcccatt gacgtcaata atgacgtatg    240
ttcccatagt aacgccaata gggactttcc attgacgtca atgggtggag tatttacggt    300
aaactgccca cttggcagta catcaagtgt atcatatgcc aagtacgccc cctattgacg    360
tcaatgacgg taaatggccc gcctggcatt atgcccagta catgacctta tgggactttc    420
ctacttggca gtacatctac gtattagtca tcgctattac catggtcgag gtgagcccca    480
cgttctgctt cactctcccc atctcccccc cctccccacc cccaattttg tatttattta    540
ttttttaatt attttgtgca gcgatggggg cggggggggg ggggggcgcg cgccaggcgg    600
ggcggggcgg ggcgagggc ggggcgggc gaggcggaga ggtgcggcgg cagccaatca    660
gagcggcgcg ctccgaaagt ttccttttat ggcgaggcgg cggcggcggc ggccctataa    720
aaagcgaagc gcgcggcggg cgggagtcgc tgcgcgctgc cttcgccccg tgccccgctc    780
cgccgccgcc tcgcgccgcc cgccccggct ctgactgacc gcgttactaa acaggtaag    840
tccggcctcc gcgccgggtt ttggcgcctc ccgcgggcgc ccccctcctc acggcgagcg    900
ctgccacgtc agacgaaggg cgcagcgagc gtcctgatcc ttccgcccgg acgctcagga    960
cagcggcccg ctgctcataa gactcggcct tagaacccca gtatcagcag aaggacattt   1020
taggacggga cttgggtgac tctagggcac tggttttctt ccagagagc ggaacaggcg   1080
aggaaaagta gtcccttctc ggcgattctg cggagggatc tccgtggggc ggtgaacgcc   1140
gatgatgcct ctactaacca tgttcatgtt ttcttttttt ttctacaggt cctgggtgac   1200
gaacaggcgg ccgccatggc gacgggttca agaacttccc tacttcttgc atttggcctg   1260
```

| | |
|---|---|
| ctttgtttgc cgtggttaca ggagggctcg gcacaggttc agctggttca gtccggggg | 1320 |
| ggtgtcgtcc aaccgggtag aagcctacgc ttatcctgtg tcgcctccgg tttcactttt | 1380 |
| tccacttacg ctatgcattg ggtcaggcaa gccccggca gaggcttaga atgggtggct | 1440 |
| gtcatttcct acgacggcaa ttacaaatac tatgccgata gcgtaaaggg aaggtttagc | 1500 |
| atatcaaggg ataatagcaa taacactctg catctggaaa tgaacaccct acgcacagag | 1560 |
| gacacagcac tctattattg tgcaaaggat tctcagctcc gttctctgct ctactttgag | 1620 |
| tggctctcac aagggtattt tgacccttgg ggacagggaa ctctcgtaac cgtgacctct | 1680 |
| gccagcacca agggcccatc ggtcttcccc ctggcaccct cctccaagag cacctctggg | 1740 |
| ggcacagcgg ccctgggctg cctggtcaag gactacttcc ccgaaccggt gacggtgtcg | 1800 |
| tggaactcag gcgccctgac cagcggcgtg cacaccttcc cggctgtcct acagtcctca | 1860 |
| ggactctact ccctcagcag cgtggtgacc gtgccctcca gcagcttggg cacccagacc | 1920 |
| tacatctgca acgtgaatca caagcccagc aacaccaagg tggacaagaa agttgagccc | 1980 |
| aaatcttgtg acaaaactca cacatgccca ccgtgcccag cacctgaact cctgggggga | 2040 |
| ccgtcagtct tcctcttccc cccaaaaccc aaggacaccc tcatgatctc ccggacccct | 2100 |
| gaggtcacat gcgtggtggt ggacgtgagc cacgaagacc ctgaggtcaa gttcaactgg | 2160 |
| tatgttgacg gcgtggaggt gcataatgcc aagacaaagc cgcgggagga gcagtacaac | 2220 |
| agcacgtacc gtgtggtcag cgtcctcacc gtcctgcacc aggactggct gaatggcaag | 2280 |
| gagtacaagt gcaaggtctc caacaaagcc ctcccagccc ccatcgagaa aaccatctcc | 2340 |
| aaagccaaag ggcagccccg agaaccacag gtgtacaccc tgcccccatc ccgggatgag | 2400 |
| ctgaccaaga atcaagtcag cctgacctgc ctggtcaaag gcttctatcc cagcgacatc | 2460 |
| gccgtggagt gggagagcaa tgggcagccg gagaacaact acaagaccac gcctcccgtg | 2520 |
| ctggactccg acggctcctt cttcctctac tcaaaactca ccgtggacaa gagcaggtgg | 2580 |
| cagcagggga acgtcttctc atgctccgtg atgcatgagg ctctgcacaa ccactacacg | 2640 |
| cagaagagcc tctccctgtc tccgggtcga aaaagaagat caggttcggg tgcgccagta | 2700 |
| aagcagacat taaactttga tttgctgaaa cttgcaggtg atgtagagtc aaatccaggt | 2760 |
| ccaatggcaa cagggagccg aacctctctg ctccttgctt tcgggctcct ttgcctaccg | 2820 |
| tggctccaag agggctcggc agacatacag atgacacagt cccctgacag tcttgcagtc | 2880 |
| tctctgggtg ctagagcaac tatcaactgt aaaagcagtc agtcagtaac ctttaactac | 2940 |
| aaaaactacc tagcgtggta tcagcaaaaa cccggtcagc cccccaaagt tttaattat | 3000 |
| tgggcaagtg cgagagaaag tggtgtgcct gatagattca gcgggtcagg gtctggcaca | 3060 |
| gatttcactc tcacgatttc aagtttgcag gcagaggatg tcgccgttta ctactgccaa | 3120 |
| cagcactaca ggacaccccc caccttcggg caaggcacta agtcgaaat caaacgtacg | 3180 |
| gtggccgctc ccagcgtgtt catcttccct ccctctgatg aacagctgaa agcggaaca | 3240 |
| gccagcgtgg tgtgtctgct gaacaacttc taccccagag aagccaaagt gcagtggaag | 3300 |
| gtggacaacg ccctgcagag cggaaacagc caggaaagcg tgacagagca ggattccaag | 3360 |
| gattccacat acagcctgag cagcacactg acactgtcca aggccgacta cgagaagcac | 3420 |
| aaggtgtacg cctgcgaagt gacacaccag ggactgtcct ccctgtgac aaagagcttc | 3480 |
| aacagaggag aatgctaaag gatcctaatc aacctctgga ttacaaaatt tgtgaaagat | 3540 |
| tgactggtat tcttaactat gttgctcctt ttacgctatg tggatacgct gctttaatgc | 3600 |

```
ctttgtatca tgctattgct tcccgtatgg ctttcatttt ctcctccttg tataaatcct   3660
ggttgctgtc tctttatgag gagttgtggc ccgttgtcag gcaacgtggc gtggtgtgca   3720
ctgtgtttgc tgacgcaacc cccactggtt ggggcattgc caccacctgt cagctccttt   3780
ccgggacttt cgcttttcccc ctccctattg ccacggcgga actcatcgcc gcctgccttg   3840
cccgctgctg gacaggggct cggctgttgg gcactgacaa ttccgtggtg ttgtcgggga   3900
aatcatcgtc ctttccttgg ctgctcgcct gtgttgccac ctggattctg cgcgggacgt   3960
ccttctgcta cgtcccttcg gccctcaatc cagcggacct tccttcccgc ggcctgctgc   4020
cggctctgcg gcctcttccg cgtcttcgcc ttcgccctca gacgagtcgg atctcccttt   4080
gggccgcctc cccgcctggt accttcgagc agacatgata agatacattg atgagtttgg   4140
acaaaccaca actagaatgc agtgaaaaaa atgctttatt tgtgaaattt gtgatgctat   4200
tgctttattt gtaaccatta taagctgcaa taaacaagtt aacaacaaca attgcattca   4260
ttttatgttt caggttcagg gggagatgtg ggaggttttt taaagcaagt aaaacctcta   4320
caaatgtggt aaaatcaagc ttaggaaccc ctagtgatgg agttggccac tccctctctg   4380
cgcgctcgct cgctcactga ggccgggcga ccaaaggtcg cccgacgccc gggctttgcc   4440
cgggcggcct cagtgagcga gcgagcgcgc agagagggag tggccaagct agcgggcgat   4500
taaggaaagg gctagatcat tcttgaagac gaaagggcct cgtgatacgc ctatttttat   4560
aggttaatgt catgataata atggtttctt agacgtcagg tggcactttt cggggaaatg   4620
tgcgcggaac ccctatttgt ttatttttct aaatacattc aaatatgtat ccgctcatga   4680
gacaataacc ctgataaatg cttcaataat attgaaaaag gaagagtatg agtattcaac   4740
atttccgtgt cgcccttatt cccttttttg cggcattttg ccttcctgtt tttgctcacc   4800
cagaaacgct ggtgaaagta aaagatgctg aagatcagtt gggtgcacga gtgggttaca   4860
tcgaactgga tctcaacagc ggtaagatcc ttgagagttt cgccccgaa gaacgttttc   4920 caatgatgag cacttttaaa gttctgctat gtggcgcggt attatcccgt gttgacgccg   4980
ggcaagagca actcggtcgc cgcatacact attctcagaa tgacttggtt gagtactcac   5040
cagtcacaga aaagcatctt acggatggca tgacagtaag agaattatgc agtgctgcca   5100
taaccatgag tgataacact gcggccaact tacttctgac aacgatcgga ggaccgaagg   5160
agctaaccgc ttttttgcac aacatggggg atcatgtaac tcgccttgat cgttgggaac   5220
cggagctgaa tgaagccata ccaaacgacg agcgtgacac cacgatgcct gtagcaatgg   5280
caacaacgtt gcgcaaacta ttaactggcg aactacttac tctagcttcc cggcaacaat   5340
taatagactg gatggaggcg gataaagttg caggaccact tctgcgctcg gcccttccgg   5400
ctggctggtt tattgctgat aaatctggag ccggtgagcg tgggtctcgc ggtatcattg   5460
cagcactggg gccagatggt aagccctccc gtatcgtagt tatctacacg acggggagtc   5520
aggcaactat ggatgaacga aatagacaga tcgctgagat aggtgcctca ctgattaagc   5580
attggtaact gtcagaccaa gtttactcat atatacttta gattgattta aaacttcatt   5640
tttaatttaa aaggatctag gtgaagatcc ttttgataa tctcatgacc aaaatccctt   5700
aacgtgagtt ttcgttccac tgagcgtcag accccgtaga aaagatcaaa ggatcttctt   5760
gagatccttt ttttctgcgc gtaatctgct gcttgcaaac aaaaaaacca ccgctaccag   5820
cggtggtttg tttgccggat caagagctac caactctttt tccgaaggta actggcttca   5880
gcagagcgca gataccaaat actgttcttc tagtgtagcc gtagttaggc caccacttca   5940
agaactctgt agcaccgcct acatacctcg ctctgctaat cctgttacca gtggctgctg   6000
```

| | |
|---|---|
| ccagtggcga taagtcgtgt cttaccgggt tggactcaag acgatagtta ccggataagg | 6060 |
| cgcagcggtc gggctgaacg gggggttcgt gcacacagcc cagcttggag cgaacgacct | 6120 |
| acaccgaact gagataccta cagcgtgagc tatgagaaag cgccacgctt cccgaaggga | 6180 |
| gaaaggcgga caggtatccg gtaagcggca gggtcggaac aggagagcgc acgagggagc | 6240 |
| ttccaggggg aaacgcctgg tatctttata gtcctgtcgg gtttcgccac ctctgacttg | 6300 |
| agcgtcgatt tttgtgatgc tcgtcagggg gcggagcct atggaaaaac gccagcaacg | 6360 |
| cggccttttt acggttcctg gccttttgct ggccttttgc tcacatgtaa taaacacaca | 6420 |
| cacaccaaca accgtggttg gttgttgtgt tggtttattc tcgag | 6465 |

```
<210> SEQ ID NO 30
<211> LENGTH: 6465
<212> TYPE: DNA
<213> ORGANISM: Artificial Sequence
<220> FEATURE:
<223> OTHER INFORMATION: pAAVio-CASI-FI6v3ABK-W-SV40

<400> SEQUENCE: 30
```

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctactag tggagttccg cgttacataa cttacggtaa | 180 |
| atggcccgcc tggctgaccg cccaacgacc cccgcccatt gacgtcaata atgacgtatg | 240 |
| ttcccatagt aacgccaata gggactttcc attgacgtca atgggtggag tatttacggt | 300 |
| aaactgccca cttggcagta catcaagtgt atcatatgcc aagtacgccc cctattgacg | 360 |
| tcaatgacgg taaatggccc gcctggcatt atgcccagta catgacctta tgggactttc | 420 |
| ctacttggca gtacatctac gtattagtca tcgctattac catggtcgag gtgagcccca | 480 |
| cgttctgctt cactctcccc atctcccccc cctccccacc cccaattttg tatttattta | 540 |
| ttttttaatt attttgtgca gcgatggggg cggggggggg gggggcgcg cgccaggcgg | 600 |
| ggcggggcgg ggcgaggggc ggggcgggc gaggcggaga ggtgcggcgg cagccaatca | 660 |
| gagcggcgcg ctccgaaagt ttccttttat ggcgaggcgg cggcggcggc ggccctataa | 720 |
| aaagcgaagc gcgcggcggg cgggagtcgc tgcgcgctgc cttcgccccg tgccccgctc | 780 |
| cgccgccgcc tcgcgccgcc cgccccggct ctgactgacc gcgttactaa acaggtaag | 840 |
| tccggcctcc gcgccgggtt ttggcgcctc ccgcgggcgc cccctcctc acggcgagcg | 900 |
| ctgccacgtc agacgaaggg cgcagcgagc gtcctgatcc ttccgcccgg acgctcagga | 960 |
| cagcggcccg ctgctcataa gactcggcct tagaacccca gtatcagcag aaggacattt | 1020 |
| taggacggga cttgggtgac tctagggcac tggttttctt tccagagagc ggaacaggcg | 1080 |
| aggaaaagta gtcccttctc ggcgattctg cggagggatc tccgtggggc ggtgaacgcc | 1140 |
| gatgatgcct ctactaacca tgttcatgtt tctttttttt ttctacaggt cctgggtgac | 1200 |
| gaacaggcgg ccgccatggc gacgggttca agaacttccc tacttcttgc atttggcctg | 1260 |
| ctttgtttgc cgtggttaca ggagggctcg gcacaggttc agctggttga agtgggggc | 1320 |
| ggagtggttc agcccggtag aagcctgcga ttatcttgtg ccgccagcgg ctttacattt | 1380 |
| agcacatacg caatgcactg ggttcggcaa gcacccggca aaggattgga gtgggtggca | 1440 |
| gtaattagtt atgacgctaa ctacaagtat tacgccgatt ccgtgaaggg aagatttacg | 1500 |
| attagcagac acaacagcaa gaatacattg tatctgcaaa tgaatagtct gcgtgcagag | 1560 |
| gatacagcag tctactattg tgccaaagac agccaactcc gtagcctgct atactttgag | 1620 |

```
tggctttcgc agggatactt tgattattgg ggacagggca ctctggttac agtgagctca    1680
gccagcacca agggcccatc ggtcttcccc ctggcaccct cctccaagag cacctctggg    1740
ggcacagcgg ccctgggctg cctggtcaag gactacttcc ccgaaccggt gacggtgtcg    1800
tggaactcag gcgccctgac cagcggcgtg cacaccttcc cggctgtcct acagtcctca    1860
ggactctact ccctcagcag cgtggtgacc gtgccctcca gcagcttggg cacccagacc    1920
tacatctgca acgtgaatca caagcccagc aacaccaagg tggacaagaa agttgagccc    1980
aaatcttgtg acaaaactca cacatgccca ccgtgcccag cacctgaact cctggggggga   2040 ccgtcagtct tcctcttccc cccaaaaccc aaggacaccc tcatgatctc ccggacccct    2100
gaggtcacat gcgtggtggt ggacgtgagc cacgaagacc ctgaggtcaa gttcaactgg    2160
tatgttgacg gcgtggaggt gcataatgcc aagacaaagc cgcgggagga gcagtacaac    2220
agcacgtacc gtgtggtcag cgtcctcacc gtcctgcacc aggactggct gaatggcaag    2280
gagtacaagt gcaaggtctc caacaaagcc ctcccagccc ccatcgagaa aaccatctcc    2340
aaagccaaag ggcagccccg agaaccacag gtgtacaccc tgcccccatc ccgggatgag    2400
ctgaccaaga atcaagtcag cctgacctgc ctggtcaaag gcttctatcc cagcgacatc    2460
gccgtggagt gggagagcaa tgggcagccg gagaacaact acaagaccac gcctcccgtg    2520
ctggactccg acggctcctt cttcctctac tcaaaactca ccgtggacaa gagcaggtgg    2580
cagcagggga acgtcttctc atgctccgtg atgcatgagg ctctgcacaa ccactacacg    2640
cagaagagcc tctccctgtc tccgggtcga aaagaagat  caggttcggg tgcgccagta    2700
aagcagacat taaactttga tttgctgaaa cttgcaggtg atgtagagtc aaatccaggt    2760
ccaatggcaa cagggagccg aacctctctg ctccttgctt tcgggctcct ttgcctaccg    2820
tggctccaag agggctcggc agacatcgtg atgacacaaa gccccgatag ccttgccgtt    2880
agtttagggg aaagggcgac tatcaactgc aaatcttcac agtccgttac cttaactac    2940 aagaactatc tcgcttggta tcagcaaaaa ccgggtcagc cacccaagtt gttgatttat    3000
tgggcatcaa caagagaaag tggtgtgcct gaccgttttt cagggtctgg ctctggaact    3060
gatttcacgc ttacaatcag ttcgcttcaa gccgaagatg tggctgtgta ttattgccaa    3120
cagcactata gaactcctcc cacttttggt caagggacaa aggtggagat taaacgtacg    3180
gtggccgctc ccagcgtgtt catcttccct ccctctgatg aacagctgaa agcggaaca    3240 gccagcgtgg tgtgtctgct gaacaacttc taccccagag aagccaaagt gcagtggaag    3300
gtggacaacg ccctgcagag cggaaacagc caggaaagcg tgacagagca ggattccaag    3360
gattccacat acagcctgag cagcacactg acactgtcca aggccgacta cgagaagcac    3420
aaggtgtacg cctgcgaagt gacacaccag ggactgtcct ccctgtgac  aaagagcttc    3480 aacagaggag aatgctaaag gatcctaatc aacctctgga ttacaaaatt tgtgaaagat    3540
tgactggtat tcttaactat gttgctcctt ttacgctatg tggatacgct gctttaatgc    3600
ctttgtatca tgctattgct tcccgtatgg ctttcatttt ctcctccttg tataaatcct    3660
ggttgctgtc tctttatgag gagttgtggc ccgttgtcag caacgtggc  gtggtgtgca    3720 ctgtgtttgc tgacgcaacc cccactggtt ggggcattgc caccacctgt cagctccttt    3780
ccgggacttt cgctttcccc ctccctattg ccacggcgga actcatcgcc gcctgccttg    3840
cccgctgctg gacaggggct cggctgttgg gcactgacaa ttccgtggtg ttgtcgggga    3900
aatcatcgtc ctttccttgg ctgctcgcct gtgttgccac ctggattctg cgcgggacgt    3960
ccttctgcta cgtcccttcg gccctcaatc cagcggacct tccttcccgc ggcctgctgc    4020
```

```
cggctctgcg gcctcttccg cgtcttcgcc ttcgccctca gacgagtcgg atctcccttt    4080
gggccgcctc cccgcctggt accttcgagc agacatgata agatacattg atgagtttgg    4140
acaaaccaca actagaatgc agtgaaaaaa atgctttatt tgtgaaattt gtgatgctat    4200
tgctttattt gtaaccatta taagctgcaa taaacaagtt aacaacaaca attgcattca    4260
ttttatgttt caggttcagg gggagatgtg ggaggttttt taaagcaagt aaaacctcta    4320
caaatgtggt aaaatcaagc ttaggaaccc ctagtgatgg agttggccac tccctctctg    4380
cgcgctcgct cgctcactga ggccgggcga ccaaaggtcg cccgacgccc gggctttgcc    4440
cgggcggcct cagtgagcga gcgagcgcgc agagagggag tggccaagct agcgggcgat    4500
taaggaaagg gctagatcat tcttgaagac gaaagggcct cgtgatacgc ctatttttat    4560
aggttaatgt catgataata atggtttctt agacgtcagg tggcactttt cggggaaatg    4620
tgcgcggaac ccctatttgt ttattttttct aaatacattc aaatatgtat ccgctcatga    4680
gacaataacc ctgataaatg cttcaataat attgaaaaag gaagagtatg agtattcaac    4740
atttccgtgt cgcccttatt cccttttttg cggcattttg ccttcctgtt tttgctcacc    4800
cagaaacgct ggtgaaagta aaagatgctg aagatcagtt gggtgcacga gtgggttaca    4860
tcgaactgga tctcaacagc ggtaagatcc ttgagagttt tcgccccgaa gaacgttttc    4920
caatgatgag cacttttaaa gttctgctat gtggcgcggt attatcccgt gttgacgccg    4980
ggcaagagca actcggtcgc cgcatacact attctcagaa tgacttggtt gagtactcac    5040
cagtcacaga aaagcatctt acggatggca tgacagtaag agaattatgc agtgctgcca    5100
taaccatgag tgataacact gcggccaact tacttctgac aacgatcgga ggaccgaagg    5160
agctaaccgc ttttttgcac aacatggggg atcatgtaac tcgccttgat cgttgggaac    5220
cggagctgaa tgaagccata ccaaacgacg agcgtgacac cacgatgcct gtagcaatgg    5280
caacaacgtt gcgcaaacta ttaactggcg aactacttac tctagcttcc cggcaacaat    5340
taatagactg gatggaggcg gataaagttg caggaccact tctgcgctcg gcccttccgg    5400
ctggctggtt tattgctgat aaatctggag ccggtgagcg tgggtctcgc ggtatcattg    5460
cagcactggg gccagatggt aagccctccc gtatcgtagt tatctacacg acggggagtc    5520
aggcaactat ggatgaacga atagacaga tcgctgagat aggtgcctca ctgattaagc    5580
attggtaact gtcagaccaa gtttactcat atatacttta gattgattta aaacttcatt    5640
tttaatttaa aaggatctag gtgaagatcc ttttttgataa tctcatgacc aaaatccctt    5700
aacgtgagtt ttcgttccac tgagcgtcag accccgtaga aagatcaaa ggatcttctt    5760 gagatccttt ttttctgcgc gtaatctgct gcttgcaaac aaaaaaacca ccgctaccag    5820
cggtggtttg tttgccggat caagagctac caactctttt tccgaaggta actggcttca    5880
gcagagcgca gataccaaat actgttcttc tagtgtagcc gtagttaggc caccacttca    5940
agaactctgt agcaccgcct acatacctcg ctctgctaat cctgttacca gtggctgctg    6000
ccagtggcga taagtcgtgt cttaccgggt tggactcaag acgatagtta ccggataagg    6060
cgcagcggtc gggctgaacg gggggttcgt gcacacagcc cagcttggag cgaacgacct    6120
acaccgaact gagataccta cagcgtgagc tatgagaaag cgccacgctt cccgaaggga    6180
gaaaggcgga caggtatccg gtaagcggca gggtcggaac aggagagcgc acagggggagc    6240 ttccaggggg aaacgcctgg tatctttata gtcctgtcgg gtttcgccac ctctgacttg    6300
agcgtcgatt tttgtgatgc tcgtcagggg ggcggagcct atggaaaaac gccagcaacg    6360
```

```
cggccttttt acggttcctg ccttttgct ggccttttgc tcacatgtaa taaacacaca      6420
cacaccaaca accgtggttg gttgttgtgt tggtttattc tcgag                     6465
```

<210> SEQ ID NO 31
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 31

```
aacgccaata gggactttcc                                                    20
```

<210> SEQ ID NO 32
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 32

```
gggcgtactt ggcatatgat                                                    20
```

<210> SEQ ID NO 33
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 33

```
acgtgcaaaa gaagctaccg                                                    20
```

<210> SEQ ID NO 34
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 34

```
aatgggaagt cacgaaggtg                                                    20
```

<210> SEQ ID NO 35
<211> LENGTH: 8
<212> TYPE: DNA
<213> ORGANISM: Artificial Sequence
<220> FEATURE:
<223> OTHER INFORMATION: Consensus recognition sequence

<400> SEQUENCE: 35

```
gcggccgc                                                                  8
```

<210> SEQ ID NO 36
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 36

```
caagcagcag aggccatgga                                                    20
```

```
<210> SEQ ID NO 37
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 37
gaccagcact ggagctagga                                                   20

<210> SEQ ID NO 38
<211> LENGTH: 19
<212> TYPE: DNA
<213> ORGANISM: Artificial Sequence
<220> FEATURE:
<223> OTHER INFORMATION: Synthetic nucleic acid

<400> SEQUENCE: 38
aagcgaaact ggcggaaac                                                    19

<210> SEQ ID NO 39
<211> LENGTH: 20
<212> TYPE: DNA
<213> ORGANISM: Artificial Sequence
<220> FEATURE:
<223> OTHER INFORMATION: Synthetic nucleic acid

<400> SEQUENCE: 39
taaccgatgt tgggcatcag                                                   20

<210> SEQ ID NO 40
<211> LENGTH: 4183
<212> TYPE: DNA
<213> ORGANISM: Artificial Sequence
<220> FEATURE:
<223> OTHER INFORMATION: pAAVio-CASI-W-SV40

<400> SEQUENCE: 40
ttggccactc cctctctgcg cgctcgctcg ctcactgagg ccgggcgacc aaaggtcgcc        60
cgacgcccgg gctttgcccg ggcggcctca gtgagcgagc gagcgcgcag agagggagtg       120
gccaactcca tcactagggg ttcctactag tggagttccg cgttacataa cttacggtaa       180
atggcccgcc tggctgaccg cccaacgacc cccgcccatt gacgtcaata atgacgtatg       240
ttcccatagt aacgccaata gggactttcc attgacgtca atgggtggag tatttacggt       300
aaactgccca cttggcagta catcaagtgt atcatatgcc aagtacgccc cctattgacg       360
tcaatgacgg taaatggccc gcctggcatt atgcccagta catgacctta tgggactttc       420
ctacttggca gtacatctac gtattagtca tcgctattac catggtcgag gtgagcccca       480
cgttctgctt cactctcccc atctcccccc cctccccacc cccaattttg tatttattta       540 tttttaatt attttgtgca gcgatggggg cggggggggg gggggggcgc gcgccaggcg       600
gggcggggcg gggcgagggg cggggcgggg cgaggcggag aggtgcggcg gcagccaatc       660
agagcggcgc gctccgaaag tttccttttta tggcgaggcg gcggcggcgg cggccctata       720
aaaagcgaag cgcgcggcgg gcgggagtcg ctgcgcgctg ccttcgcccc gtgccccgct       780
ccgccgccgc ctcgcgccgc ccgccccggc tctgactgac cgcgttacta aacaggtaa       840 gtccggcctc cgcgccgggt tttggcgcct cccgcgggcg cccccctcct cacggcgagc       900
gctgccacgt cagacgaagg cgcagcgagc cgtcctgatc cttccgcccg gacgctcagg       960
acagcggccc gctgctcata agactcggcc ttagaacccc agtatcagca gaaggacatt      1020
```

```
ttaggacggg acttgggtga ctctagggca ctggttttct ttccagagag cggaacaggc    1080
gaggaaaagt agtcccttct cggcgattct gcggagggat ctccgtgggg cggtgaacgc    1140
cgatgatgcc tctactaacc atgttcatgt tttcttttt tttctacagg tcctgggtga    1200
cgaacaggcg gccgccagga tcctaatcaa cctctggatt acaaaatttg tgaaagattg    1260
actggtattc ttaactatgt tgctcctttt acgctatgtg gatacgctgc tttaatgcct    1320
ttgtatcatg ctattgcttc ccgtatggct ttcattttct cctccttgta taaatcctgg    1380
ttgctgtctc tttatgagga gttgtggccc gttgtcaggc aacgtggcgt ggtgtgcact    1440
gtgtttgctg acgcaacccc cactggttgg ggcattgcca ccacctgtca gctccttttcc   1500
gggactttcg ctttccccct ccctattgcc acggcggaac tcatcgccgc ctgccttgcc    1560
cgctgctgga caggggctcg gctgttgggc actgacaatt ccgtggtgtt gtcggggaaa    1620
tcatcgtcct ttccttggct gctcgcctgt gttgccacct ggattctgcg cgggacgtcc    1680
ttctgctacg tcccttcggc cctcaatcca gcggaccttc cttcccgcgg cctgctgccg    1740
gctctgcggc ctcttccgcg tcttcgcctt cgccctcaga cgagtcggat ctcccttttgg   1800
gccgcctccc cgcctggtac cttcgagcag acatgataag atacattgat gagtttggac    1860
aaaccacaac tagaatgcag tgaaaaaaat gctttatttg tgaaatttgt gatgctattg    1920
ctttatttgt aaccattata agctgcaata acaagttaa caacaacaat tgcattcatt     1980
ttatgtttca ggttcagggg gagatgtggg aggttttta aagcaagtaa aacctctaca     2040
aatgtggtaa aatcaagctt aggaacccct agtgatggag ttggccactc cctctctgcg    2100
cgctcgctcg ctcactgagg ccgggcgacc aaaggtcgcc cgacgcccgg gctttgcccg    2160
ggcggcctca gtgagcgagc gagcgcgcag agagggagtg gccaagctag cgggcgatta    2220
aggaaagggc tagatcattc ttgaagacga aagggcctcg tgatacgcct atttttatag    2280
gttaatgtca tgataataat ggtttcttag acgtcaggtg gcacttttcg gggaaatgtg    2340
cgcggaaccc ctatttgttt atttttctaa atacattcaa atatgtatcc gctcatgaga    2400
caataaccct gataaatgct tcaataatat tgaaaaagga agagtatgag tattcaacat    2460
ttccgtgtcg cccttattcc cttttttgcg gcattttgcc ttcctgtttt tgctcaccca    2520
gaaacgctgg tgaaagtaaa agatgctgaa gatcagttgg gtgcacgagt gggttacatc    2580
gaactggatc tcaacagcgg taagatcctt gagagttttc gccccgaaga acgttttcca    2640
atgatgagca cttttaaagt tctgctatgt ggcgcggtat tatcccgtgt tgacgccggg    2700
caagagcaac tcggtcgccg catacactat tctcagaatg acttggttga gtactcacca    2760
gtcacagaaa agcatcttac ggatggcatg acagtaagag aattatgcag tgctgccata    2820
accatgagtg ataacactgc ggccaactta cttctgacaa cgatcggagg accgaaggag    2880
ctaaccgctt ttttgcacaa catgggggat catgtaactc gccttgatcg ttgggaaccg    2940
gagctgaatg aagccatacc aaacgacgag cgtgacacca cgatgcctgt agcaatggca    3000
acaacgttgc gcaaactatt aactggcgaa ctacttactc tagcttcccg gcaacaatta    3060
atagactgga tggaggcgga taaagttgca ggaccacttc tgcgctcggc ccttccggct    3120
ggctggttta ttgctgataa atctggagcc ggtgagcgtg gtctcgcgg tatcattgca      3180
gcactggggc cagatggtaa gccctcccgt atcgtagtta tctacacgac ggggagtcag    3240
gcaactatgg atgaacgaaa tagacagatc gctgagatag gtgcctcact gattaagcat    3300
tggtaactgt cagaccaagt ttactcatat atactttaga ttgatttaaa acttcatttt    3360
taatttaaaa ggatctaggt gaagatcctt tttgataatc tcatgaccaa aatcccttaa    3420
```

```
cgtgagtttt cgttccactg agcgtcagac cccgtagaaa agatcaaagg atcttcttga    3480
gatccttttt ttctgcgcgt aatctgctgc ttgcaaacaa aaaaaccacc gctaccagcg    3540
gtggtttgtt tgccggatca agagctacca actcttttc cgaaggtaac tggcttcagc     3600
agagcgcaga taccaaatac tgttcttcta gtgtagccgt agttaggcca ccacttcaag    3660
aactctgtag caccgcctac atacctcgct ctgctaatcc tgttaccagt ggctgctgcc    3720
agtggcgata agtcgtgtct taccgggttg gactcaagac gatagttacc ggataaggcg    3780
cagcggtcgg gctgaacggg gggttcgtgc acacagccca gcttggagcg aacgacctac    3840
accgaactga gatacctaca gcgtgagcta tgagaaagcg ccacgcttcc cgaagggaga    3900
aaggcggaca ggtatccggt aagcggcagg gtcggaacag gagagcgcac gagggagctt    3960 ccaggggaa acgcctggta tctttatagt cctgtcgggt ttcgccacct ctgacttgag     4020
cgtcgatttt tgtgatgctc gtcagggggg cggagcctat ggaaaaacgc cagcaacgcg    4080
gcctttttac ggttcctggc cttttgctgg ccttttgctc acatgtaata aacacacaca    4140
caccaacaac cgtggttggt tgttgtgttg gtttattctc gag                      4183
```

<210> SEQ ID NO 41
<211> LENGTH: 9
<212> TYPE: DNA
<213> ORGANISM: Artificial Sequence
<220> FEATURE:
<223> OTHER INFORMATION: synthetic nucleic acid

<400> SEQUENCE: 41

```
gccgccatg                                                                9
```

<210> SEQ ID NO 42
<211> LENGTH: 12
<212> TYPE: DNA
<213> ORGANISM: Artificial Sequence
<220> FEATURE:
<223> OTHER INFORMATION: Synthetic nucleic acid

<400> SEQUENCE: 42

```
gcggccgcca tg                                                           12
```